Figure 2A:
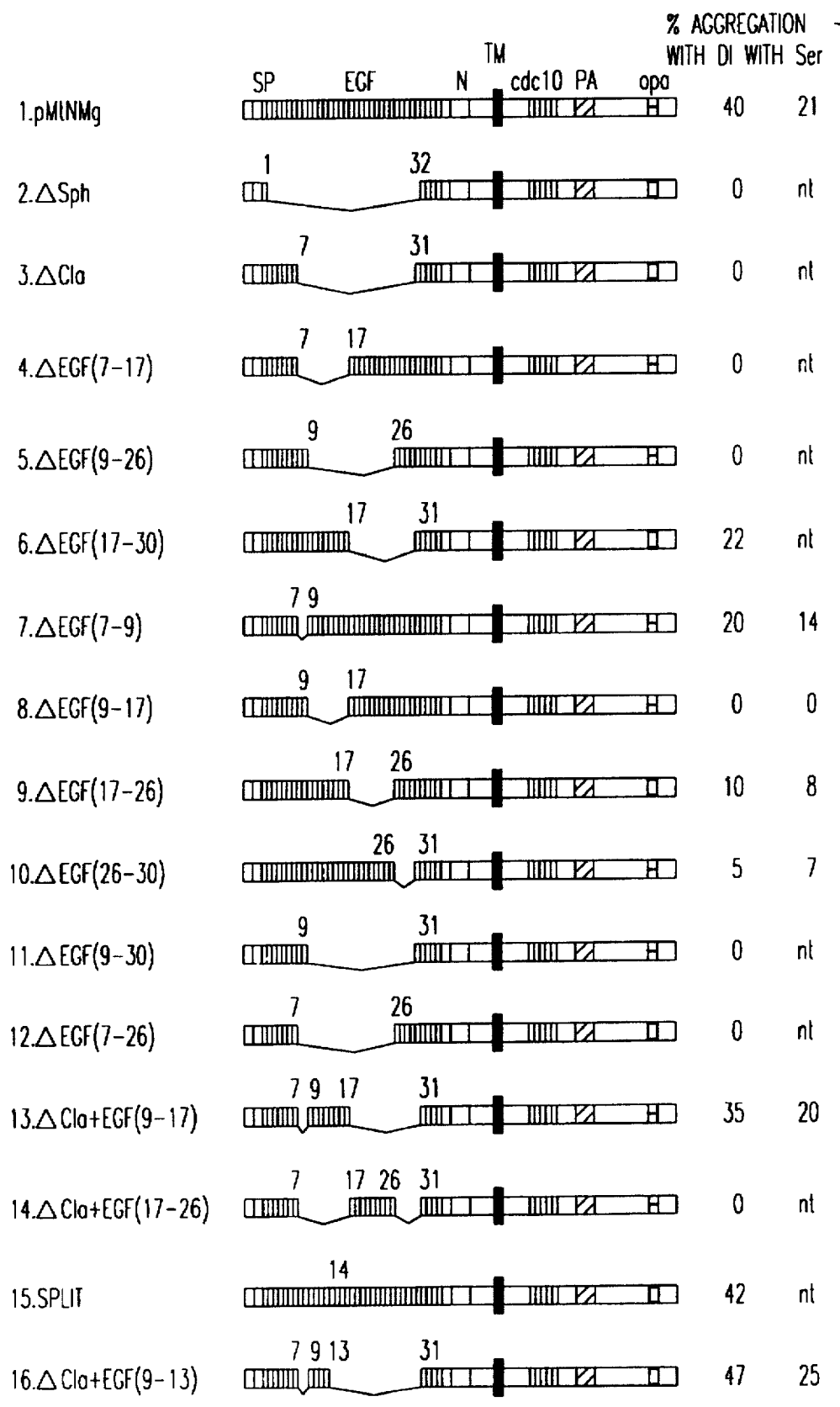

United States Patent [19]
Artavanis-Tsakonas et al.

[11] Patent Number: 5,786,158
[45] Date of Patent: Jul. 28, 1998

[54] THERAPEUTIC AND DIAGNOSTIC METHODS AND COMPOSITIONS BASED ON NOTCH PROTEINS AND NUCLEIC ACIDS

[75] Inventors: Spyridon Artavanis-Tsakonas, Hamden, Conn.; Richard Grant Fehon, Durham, N.C.; Panayiotis Zagouras; Christine Marie Blaumueller, both of New Haven, Conn.

[73] Assignee: Yale University, New Haven, Conn.

[21] Appl. No.: 83,590

[22] Filed: Jun. 25, 1993

Related U.S. Application Data

[63] Continuation-in-part of Ser. No. 955,012, Sep. 30, 1992, abandoned, and a continuation-in-part of Ser. No. 879,038, Apr. 30, 1992, abandoned.

[51] Int. Cl.$^6$ .................... G01N 33/574; G01N 33/53
[52] U.S. Cl. .................... 435/7.23; 435/7.1; 435/7.92; 436/63; 436/64; 436/813; 436/815; 436/811
[58] Field of Search .................... 435/7.23, 7.1, 435/7.92; 436/63, 64, 813, 815, 811

[56] References Cited

U.S. PATENT DOCUMENTS

| | | | |
|---|---|---|---|
| 5,115,096 | 5/1992 | Shoyab et al. | 530/322 |
| 5,132,212 | 7/1992 | Kirsch et al. | 435/69.4 |
| 5,264,557 | 11/1993 | Salomon et al. | 530/399 |

FOREIGN PATENT DOCUMENTS

WO 92/19734  11/1992  WIPO.

OTHER PUBLICATIONS

Welshons, 1965, Analysis of a gene is Drosophila with variations, the genes of microorganisms and those of Drosophila are much the same, Science 150:1122–1129.

Portin, 1975, Allelic negative complementation at the abruptex locus of Drosophila melanogaster, Genetics 81:121–133.

Morita et al., 1984, Derivates of blood coagulation factor IX contain a high affinity $Ca^{2+}$–binding site that lacks γ–carboxyglutamic acid, J. Biol. Chem. 259:5698–5704.

Sugo et al., 1984, Calcium–binding properties of bovine factor X lacking the γ–carboxyglutamic acid–containing region, J. Biol. Chem. 259:5705–5710.

Lindsley and Zinn, 1985, Drosophila Information Service 62:86.

Südhof et al. 1985, The LDL receptor gene: a mosaic of exons shared with different proteins, Science 228:815–822.

Doe and Goodman, 1985, Early events in insect neurogenesis. II. The role of cell interactions and cell lineage in the determination of neuronal precursor cells, Dev. Biol. 111:206–219.

Vässin et al., 1985, Genetic interactions in early neurogenesis if Drosophila melanogaster, J. Neurogenet. 2:291–308.
Wharton et al., 1985, Nucleotide sequence from the neurogenic locus Notch implies a gene product that shares homology with proteins containing EGF–like repeats, Cell 43:567–581.

Kidd et al., 1965 Sequence of the Notch Iocus of Drosophila melanogaster: relationship of the encoded protein to mammalian clotting and growth factors, Mol. Cell. Biol. 6:3094–3108.

Breeden and Nasmyth, 1987, Similarity between cell–cycle genes of budding yeast and fission yeast and the Notch gene of Drosophila Nature 329:651–654.

Appella et al., 1987, The receptor–binding sequence of urokinase. A biological function for the growth–factor module of proteases, J. Biol. Chem. 262:4437–4440.

Knust et al., 1987, EGF homologous sequences encoded in the genome of Drosophila melanogaster, and their relation to neurogenic genes, EMBO J. 6(3):761–766.

Suzuki et al., 1987, Structure and expression of human thrombomodulin, a thrombin receptor on endothelium acting as a cofactor for protein C activation, EMBO J. 6(7):1891–1897.

Hartley et al., 1987, The embryonic expression of the Notch locus of Drosophila melanogaster and the implcations of point mutations in the extracellular EGF–like domain of the predicted protein, EMBO J. 6(11):3407–3417.

Reynolds et al., 1987, Analysis of DNA surrounding the breakpoints of chromosomal translocations involving the βT cell receptor gene in human lymphoblastic neoplasms, Cell 50:107–117.

Vässin et al., 1987, The neurogenic gene Delta of Drosophila melanogasteris expressed in neurogenic territories and endcodes a putative transmembrane protein with EGF–like repeats, EMBO J. 6:3431–3440.

Kelley et al., 1987, Mutations altering the structure of epidermal growth factor–like coding sequences at the Drosophila Notch locus, Cell 51:539–548.

Kopczynski et al., 1988, Delta, a Drosophila neurogenic gene, is transcriptionally complex and encodes a protein related to blood coagulation factors and epidermal growth factor of vertebrates, Genes & Dev. 2:1723–1735.

Kopczynski and Muskavitch, 1989, Complex spatio–temporal accumulation of alternative transcripts from the neurogenic gene Delta during Drosophila embryogensis, Development 107:623–636.

Rees et al., 1988, The role of β–hydroxyaspartate and adjacent carboxylate residues in the first EGF domain of human factor IX, EMBO J. 7(7):2053–2061.

Furie and Furie, 1988, The molecular basis of blood coagulation, Cell 53:505–518.

Artavanis–Tsakonas, 1988, DNA, differentiation & development, Trends in Genetics 4:95–100.

(List continued on next page.)

Primary Examiner—Toni R. Scheiner
Attorney, Agent, or Firm—Pennie & Edmonds LLP

[57] ABSTRACT

The present invention relates to diagnostic methods and compositions for detection of malignancy or nervous system disorders based on the level of Notch proteins or nucleic acids. Therapeutic methods and methods of inhibiting Notch expression are also provided.

9 Claims, 68 Drawing Sheets

OTHER PUBLICATIONS

Kurosawa et al., 1988, A 10-kDa cyanogen bromide fragment from the epidermal growth factor homology domain of rabbit thrombomodulin contains the primary thrombin binding site, J. Biol. Chem. 263(13):5993–5996.

Yochem et al., 1988, The Caenorhabditis elegans lin –12 gene encodes a transmembrane protein with overall similarity to Drosophila Notch, Nature 335:547–550.

Rothberg et al., 1988, slit : An EGF–homologous locus of D. melanogaster involved in the development of the embryonic central nervous system, Cell 55:1047–1059.

Kidd et al., 1989, Structure and distribution of the Notch protein in developing Drosophila, Genes & Dev. 3:1113–1129.

Johansen et al., 1989, The Notch gene product is a glycoprotein expressed on the cell surface of both epidermal and neuronal precursor cells during Drosophila development, J. Cell Biol. 109:2427–2440.

Shepard et al., 1989, A tripartite interaction among alleles of Notch, Delta,and Enhancer of split during imaginal development of Drosophila melanogaste , Genetics 122:429–438.

Alton et al., 1989, Molecular genetics of Delta , a locus required for ectodermal differentiation in Drosophila , Dev. Genet. 10:261–272.

Handford et al., 1990, The first EGF–like domain from human factor IX contains a high–affinity calcium binding site, EMBO J. 9:475–480.

Fehon et al., 1990, Molecular interactions between the protein products of the neurogenic loci Notch and Delta , two EGF–homologous genes in Drosophila, Cell 61:523–534.

Coffman et al., 1990, Xotch, the Xenopus homolog of Drosophila Notch , Science 249:1438–1441.

Palka et al., 1990, Neurogenic and antineurogenic effects from modifications at the Notch locus, Develop. 109:167–175.

Xu et al., 1990, The Notch Locus and the egenetic circuitry involved in early Drosophila neurogenesis, Genes & Dev. 4:464–475.

Weinmaster et al., 1991, A homolog of Drosophila Notch expressed during mammalian development, Develop. 113:199–205.

Fehon et al., 1991, Complex spatial and temporal regulation of Notch expression during embryonic and imaginal development of Drosophila , implications for Notch function, J. Cell Biol. 113:657–669.

Coffman et al., 1993, "Expression of an extracellular deletion of xotch diverts cell fate in xenopus embryos", Cell 73:659–671.

Adams et al., 1991, Science 252:1651–1656.

Stifani et al., 1992, Nature Genetics 2(2):119–127.

Weinmaster et al., 1992, Development 116(4):931–941.

Croce, 1987, "Role of Chromosome Translocations in Human Neoplasia", Cell 49:155–156.

Borrow and Solomon, 1992, "Molecular Analysis of the t(15;17) translocation in acute promyelocytic leukaemia", Bailliere 's Clinical Hematology 5(4):833–856.

Jhappan et al., 1992, "Expression of an activated Notch–related int–3 transgene interferes with cell differentiation and induces neoplastic transformation in mammary and salivary glands", Genes & Dev. 6:345–355.

Robbins et al., 1992, "Mouse mammary tumor gene int–3: a member of the notch gene family transforms mammary epithelial cells", J. Viol. 66:2594–2599.

Campos–Ortega and Knust, 1990, "Molecular analysis of a cellular decision during embryonic development of Drocophila melasnogaster : epidermogenesis or neurogensis", Eur. J. Biochem. 190:1–10.

De Celis et al., 1993, "Genetic and molecular characterization of a Notch mutation in its Deta– and Serrate–binding domain in Drosophila ", Proc. Natl. Acad. Sci. USA 90:4037–4041.

Greenspan, 1990, "The Notch gene, adhesion, and developmental fate in the Drosophila embryo, "New Biologist 2(7):595–600.

Rebay et al., 1991, "Specific EGF repeats of Notch mediate interactions with Delta and Serrate: implications for Notch as a multifunctional receptor, "Cell 67:687–699.

Robbins et al., 1992, "Mouse mammary tumor gene int–3: a member of the notch gene family transforms mammary epithelial cells, " Biol. Abstr. 93(11):AB–465 (Abstr. 122736).

Ellisen, L.W., et al., Cell , vol.66, pp. 649–661, Aug. 23, 1991.

```
GAATTCGGAG GAATTATTCA AAACATAAAC ACAATAAACA ATTTGAGTAG TTGCCGCACA    60

CACACACACA CACAGCCCGT GGATTATTAC ACTAAAAGCG ACACTCAATC CAAAAAATCA   120

GCAACAAAAA CATCAATAAA C ATG CAT TGG ATT AAA TGT TTA TTA ACA GCA   171
                         Met His Trp Ile Lys Cys Leu Leu Thr Ala
                          1               5                   10

TTC ATT TGC TTC ACA GTC ATC GTG CAG GTT CAC AGT TCC GGC AGC TTT   219
Phe Ile Cys Phe Thr Val Ile Val Gln Val His Ser Ser Gly Ser Phe
             15                  20                  25

GAG TTG CGC CTG AAG TAC TTC AGC AAC GAT CAC GGG CGG GAC AAC GAG   267
Glu Leu Arg Leu Lys Tyr Phe Ser Asn Asp His Gly Arg Asp Asn Glu
             30                  35                  40

GGT CGC TGC TGC AGC GGG GAG TCG GAC GGA GCG ACG GGC AAG TGC CTG   315
Gly Arg Cys Cys Ser Gly Glu Ser Asp Gly Ala Thr Gly Lys Cys Leu
             45                  50                  55

GGC AGC TGC AAG ACG CGG TTT CGC GTC TGC CTA AAG CAC TAC CAG GCC   363
Gly Ser Cys Lys Thr Arg Phe Arg Val Cys Leu Lys His Tyr Gln Ala
             60                  65                  70

ACC ATC GAC ACC ACC TCC CAG TGC ACC TAC GGG GAC GTG ATC ACG CCC   411
Thr Ile Asp Thr Thr Ser Gln Cys Thr Tyr Gly Asp Val Ile Thr Pro
 75              80                  85                  90

ATT CTC GGC GAG AAC TCG GTC AAT CTG ACC GAC GCC CAG CGC TTC CAG   459
Ile Leu Gly Glu Asn Ser Val Asn Leu Thr Asp Ala Gln Arg Phe Gln
                 95                  100                 105

AAC AAG GGC TTC ACG AAT CCC ATC CAG TTC CCC TTC TCG TTC TCA TGG   507
Asn Lys Gly Phe Thr Asn Pro Ile Gln Phe Pro Phe Ser Phe Ser Trp
             110                 115                 120
```

FIG.1A

```
CCG GGT ACC TTC TCG CTG ATC GTC GAG GCC TGG CAT GAT ACG AAC AAT      555
Pro Gly Thr Phe Ser Leu Ile Val Glu Ala Trp His Asp Thr Asn Asn
        125             130             135

AGC GGC AAT GCG CGA ACC AAC AAG CTC CTC ATC CAG CGA CTC TTG GTG      603
Ser Gly Asn Ala Arg Thr Asn Lys Leu Leu Ile Gln Arg Leu Leu Val
        140             145             150

CAG CAG GTA CTG GAG GTG TCC TCC GAA TGG AAG ACG AAC AAG TCG GAA      651
Gln Gln Val Leu Glu Val Ser Ser Glu Trp Lys Thr Asn Lys Ser Glu
155             160             165             170

TCG CAG TAC ACG TCG CTG GAG TAC GAT TTC CGT GTC ACC TGC GAT CTC      699
Ser Gln Tyr Thr Ser Leu Glu Tyr Asp Phe Arg Val Thr Cys Asp Leu
            175             180             185

AAC TAC TAC GGA TCC GGC TGT GCC AAG TTC TGC CGG CCC CGC GAC GAT      747
Asn Tyr Tyr Gly Ser Gly Cys Ala Lys Phe Cys Arg Pro Arg Asp Asp
            190             195             200

TCA TTT GGA CAC TCG ACT TGC TCG GAG ACG GGC GAA ATT ATC TGT TTG      795
Ser Phe Gly His Ser Thr Cys Ser Glu Thr Gly Glu Ile Ile Cys Leu
            205             210             215

ACC GGA TGG CAG GGC GAT TAC TGT CAC ATA CCC AAA TGC GCC AAA GGC      843
Thr Gly Trp Gln Gly Asp Tyr Cys His Ile Pro Lys Cys Ala Lys Gly
        220             225             230

TGT GAA CAT GGA CAT TGC GAC AAA CCC AAT CAA TGC GTT TGC CAA CTG      891
Cys Glu His Gly His Cys Asp Lys Pro Asn Gln Cys Val Cys Gln Leu
235             240             245             250

GGC TGG AAG GGA GCC TTG TGC AAC GAG TGC GTT CTG GAA CCG AAC TGC      939
Gly Trp Lys Gly Ala Leu Cys Asn Glu Cys Val Leu Glu Pro Asn Cys
        255             260             265
```

FIG.1B

```
ATC CAT GGC ACC TGC AAC AAA CCC TGG ACT TGC ATC TGC AAC GAG GGT      987
Ile His Gly Thr Cys Asn Lys Pro Trp Thr Cys Ile Cys Asn Glu Gly
        270             275             280

TGG GGA GGC TTG TAC TGC AAC CAG GAT CTG AAC TAC TGC ACC AAC CAC     1035
Trp Gly Gly Leu Tyr Cys Asn Gln Asp Leu Asn Tyr Cys Thr Asn His
        285             290             295

AGA CCC TGC AAG AAT GGC GGA ACC TGC TTC AAC ACC GGC GAG GGA TTG     1083
Arg Pro Cys Lys Asn Gly Gly Thr Cys Phe Asn Thr Gly Glu Gly Leu
        300             305             310

TAC ACA TGC AAA TGC GCT CCA GGA TAC AGT GGT GAT GAT TGC GAA AAT     1131
Tyr Thr Cys Lys Cys Ala Pro Gly Tyr Ser Gly Asp Asp Cys Glu Asn
315             320             325             330

GAG ATC TAC TCC TGC GAT GCC GAT GTC AAT CCC TGC CAG AAT GGT GGT     1179
Glu Ile Tyr Ser Cys Asp Ala Asp Val Asn Pro Cys Gln Asn Gly Gly
        335             340             345

ACC TGC ATC GAT GAG CCG CAC ACA AAA ACC GGC TAC AAG TGT CAT TGC     1227
Thr Cys Ile Asp Glu Pro His Thr Lys Thr Gly Tyr Lys Cys His Cys
        350             355             360

GCC AAC GGC TGG AGC GGA AAG ATG TGC GAG GAG AAA GTG CTC ACG TGT     1275
Ala Asn Gly Trp Ser Gly Lys Met Cys Glu Glu Lys Val Leu Thr Cys
        365             370             375

TCG GAC AAA CCC TGT CAT CAG GGA ATC TGC CGC AAC GTT CGT CCT GGC     1323
Ser Asp Lys Pro Cys His Gln Gly Ile Cys Arg Asn Val Arg Pro Gly
        380             385             390

TTG GGA AGC AAG GGT CAG GGC TAC CAG TGC GAA TGT CCC ATT GGC TAC     1371
Leu Gly Ser Lys Gly Gln Gly Tyr Gln Cys Glu Cys Pro Ile Gly Tyr
395             400             405             410
```

FIG.1C

```
AGC GGA CCC AAC TGC GAT CTC CAG CTG GAC AAC TGC AGT CCG AAT CCA      1419
Ser Gly Pro Asn Cys Asp Leu Gln Leu Asp Asn Cys Ser Pro Asn Pro
                415                 420                 425

TGC ATA AAC GGT GGA AGC TGT CAG CCG AGC GGA AAG TGT ATT TGC CCA      1467
Cys Ile Asn Gly Gly Ser Cys Gln Pro Ser Gly Lys Cys Ile Cys Pro
                430                 435                 440

GCG GGA TTT TCG GGA ACG AGA TGC GAG ACC AAC ATT GAC GAT TGT CTT      1515
Ala Gly Phe Ser Gly Thr Arg Cys Glu Thr Asn Ile Asp Asp Cys Leu
                445                 450                 455

GGC CAC CAG TGC GAG AAC GGA GGC ACC TGC ATA GAT ATG GTC AAC CAA      1563
Gly His Gln Cys Glu Asn Gly Gly Thr Cys Ile Asp Met Val Asn Gln
            460                 465                 470

TAT CGC TGC CAA TGC GTT CCC GGT TTC CAT GGC ACC CAC TGT AGT AGC      1611
Tyr Arg Cys Gln Cys Val Pro Gly Phe His Gly Thr His Cys Ser Ser
475                 480                 485                 490

AAA GTT GAC TTG TGC CTC ATC AGA CCG TGT GCC AAT GGA GGA ACC TGC      1659
Lys Val Asp Leu Cys Leu Ile Arg Pro Cys Ala Asn Gly Gly Thr Cys
                495                 500                 505

TTG AAT CTC AAC AAC GAT TAC CAG TGC ACC TGT CGT GCG GGA TTT ACT      1707
Leu Asn Leu Asn Asn Asp Tyr Gln Cys Thr Cys Arg Ala Gly Phe Thr
                510                 515                 520

GGC AAG GAT TGC TCT GTG GAC ATC GAT GAG TGC AGC AGT GGA CCC TGT      1755
Gly Lys Asp Cys Ser Val Asp Ile Asp Glu Cys Ser Ser Gly Pro Cys
                525                 530                 535

CAT AAC GGC GGC ACT TGC ATG AAC CGC GTC AAT TCG TTC GAA TGC GTG      1803
His Asn Gly Gly Thr Cys Met Asn Arg Val Asn Ser Phe Glu Cys Val
            540                 545                 550
```

FIG.1D

```
TGT GCC AAT GGT TTC AGG GGC AAG CAG TGC GAT GAG GAG TCC TAC GAT         1851
Cys Ala Asn Gly Phe Arg Gly Lys Gln Cys Asp Glu Glu Ser Tyr Asp
555                 560                 565                 570

TCG GTG ACC TTC GAT GCC CAC CAA TAT GGA GCG ACC ACA CAA GCG AGA         1899
Ser Val Thr Phe Asp Ala His Gln Tyr Gly Ala Thr Thr Gln Ala Arg
                575                 580                 585

GCC GAT GGT TTG ACC AAT GCC CAG GTA GTC CTA ATT GCT GTT TTC TCC         1947
Ala Asp Gly Leu Thr Asn Ala Gln Val Val Leu Ile Ala Val Phe Ser
                590                 595                 600

GTT GCG ATG CCT TTG GTG GCG GTT ATT GCG GCG TGC GTG GTC TTC TGC         1995
Val Ala Met Pro Leu Val Ala Val Ile Ala Ala Cys Val Val Phe Cys
                605                 610                 615

ATG AAG CGC AAG CGT AAG CGT GCT CAG GAA AAG GAC GAC GCG GAG GCC         2043
Met Lys Arg Lys Arg Lys Arg Ala Gln Glu Lys Asp Asp Ala Glu Ala
620                 625                 630

AGG AAG CAG AAC GAA CAG AAT GCG GTG GCC ACA ATG CAT CAC AAT GGC         2091
Arg Lys Gln Asn Glu Gln Asn Ala Val Ala Thr Met His His Asn Gly
635                 640                 645                 650

AGT GGG GTG GGT GTA GCT TTG GCT TCA GCC TCT CTG GGC GGC AAA ACT         2139
Ser Gly Val Gly Val Ala Leu Ala Ser Ala Ser Leu Gly Gly Lys Thr
                655                 660                 665

GGC AGC AAC AGC GGT CTC ACC TTC GAT GGC GGC AAC CCG AAT ATC ATC         2187
Gly Ser Asn Ser Gly Leu Thr Phe Asp Gly Gly Asn Pro Asn Ile Ile
                670                 675                 680

AAA AAC ACC TGG GAC AAG TCG GTC AAC AAC ATT TGT GCC TCA GCA GCA         2235
Lys Asn Thr Trp Asp Lys Ser Val Asn Asn Ile Cys Ala Ser Ala Ala
                685                 690                 695
```

FIG.1E

```
GCA GCG GCG GCG GCG GCA GCA GCG GCG GAC GAG TGT CTC ATG TAC GGC      2283
Ala Ala Ala Ala Ala Ala Ala Ala Ala Asp Glu Cys Leu Met Tyr Gly
    700                 705                 710

GGA TAT GTG GCC TCG GTG GCG GAT AAC AAC AAT GCC AAC TCA GAC TTT      2331
Gly Tyr Val Ala Ser Val Ala Asp Asn Asn Asn Ala Asn Ser Asp Phe
715                 720                 725                 730

TGT GTG GCT CCG CTA CAA AGA GCC AAG TCG CAA AAG CAA CTC AAC ACC      2379
Cys Val Ala Pro Leu Gln Arg Ala Lys Ser Gln Lys Gln Leu Asn Thr
                735                 740                 745

GAT CCC ACG CTC ATG CAC CGC GGT TCG CCG GCA GGC AGC TCA GCC AAG      2427
Asp Pro Thr Leu Met His Arg Gly Ser Pro Ala Gly Ser Ser Ala Lys
            750                 755                 760

GGA GCG TCT GGC GGA GGA CCG GGA GCG GCG GAG GGC AAG AGG ATC TCT      2475
Gly Ala Ser Gly Gly Gly Pro Gly Ala Ala Glu Gly Lys Arg Ile Ser
        765                 770                 775

GTT TTA GGC GAG GGT TCC TAC TGT AGC CAG CGT TGG CCC TCG TTG GCG      2523
Val Leu Gly Glu Gly Ser Tyr Cys Ser Gln Arg Trp Pro Ser Leu Ala
    780                 785                 790

GCG GCG GGA GTG GCC GGA GCC TGT TCA TCC CAG CTA ATG GCT GCA GCT      2571
Ala Ala Gly Val Ala Gly Ala Cys Ser Ser Gln Leu Met Ala Ala Ala
795                 800                 805                 810

TCG GCA GCG GGC AGC GGA GCG GGG ACG GCG CAA CAG CAG CGA TCC GTG      2619
Ser Ala Ala Gly Ser Gly Ala Gly Thr Ala Gln Gln Gln Arg Ser Val
                815                 820                 825

GTC TGC GGC ACT CCG CAT ATG TAACTCCAAA AATCCGGAAG GGCTCCTGGT         2670
Val Cys Gly Thr Pro His Met
                830
AAATCCGGAG AAATCCGCAT GGAGGAGCTG ACAGCACATA CACAAAGAAA AGACTGGGTT   2730
GGGTTCAAAA TGTGAGAGAG ACGCCAAAAT GTTGTTGTTG ATTGAAGCAG TTTAGTCGTC   2790
ACGAAAAATG AAAAATCTGT AACAGGCATA ACTCGTAAAC TCCCTAAAAA ATTTGTATAG   2850
TAATTAGCAA AGCTGTGACC CAGCCGTTTC GATCCCGAAT TC                      2892
```

FIG.1F

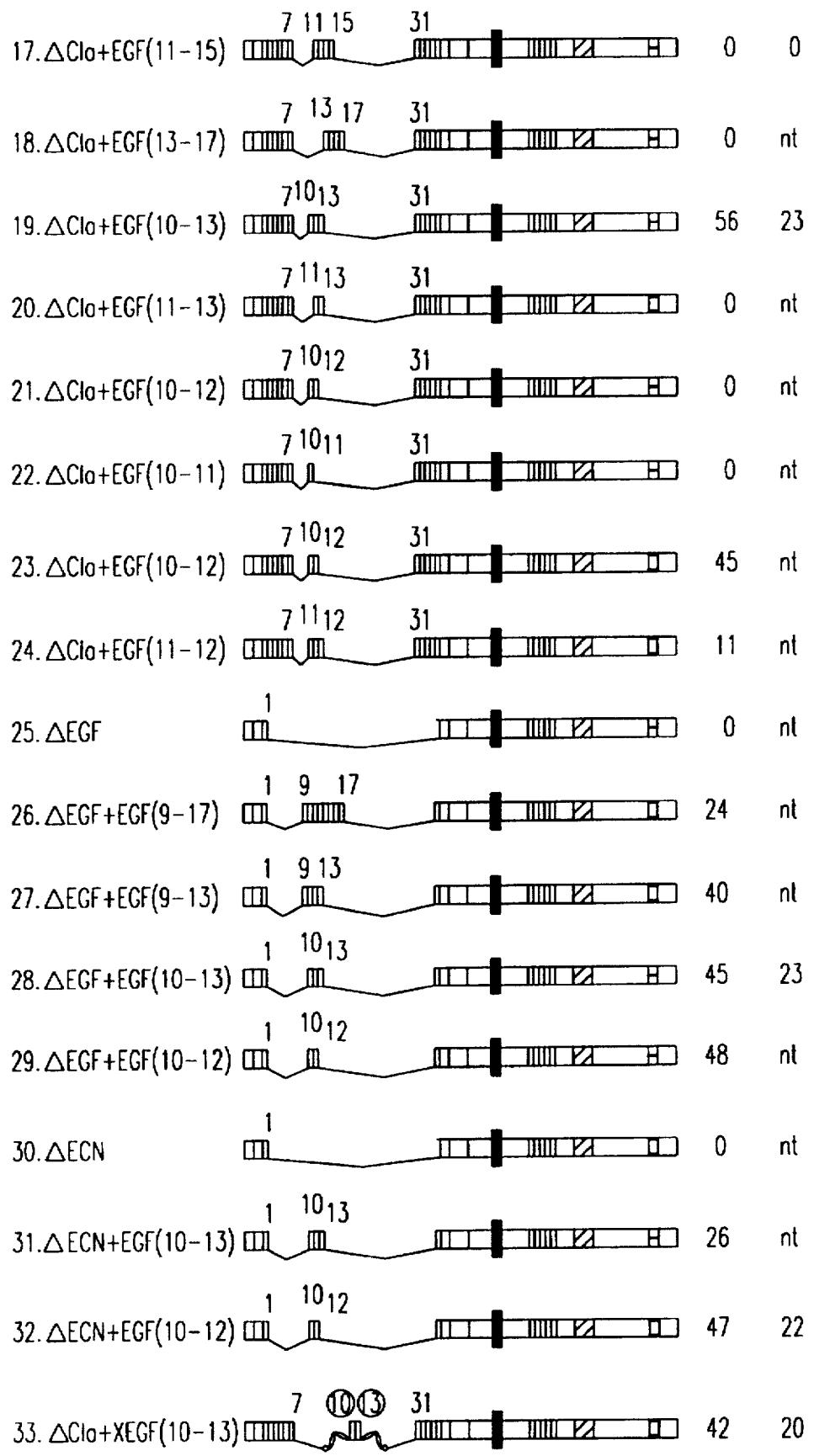

FIG. 5A

```
  1  CCGAGTCGAGCCCGTGCTTCGAGGGTGATGAGCCCTTTTCTGTCAACGCTAAAGATC
121  AAGCACATACTAAGGTCCATATAAATAATAATAATAATTGTGTGTGATAACACATTAT
241  GGCCGTTATTCAGCTATCCAGAGTCAAGTGTAGTGTGCAAAATAGAAACAAACAAGGCA
361  CAATCCAGAGTGAATCCGAAACAAACTCCATCTAGATCGCCAACCAGCATCACGCTCGCA

481  TCGTCGTTGGAGTCAACAATAGAATCAGCAGACAGCCTGGAATGTCCAAGAAGACGGCG
     SerSerLeuGluSerThrIleGluSerAlaAspSerLeuGlyMetSerLysLysThrAla

601  CGGCGATTGTCGATCATTAAAGTCTGCCTGCAACTTAATTGCTTAATTTAATTACTGTTA
     ArgAspCysArgSerLeuLysSerAlaCysAsnLeuIleAlaLeuIleLeuIleLeuLeu

721  AACAGCCATCTACTCAACGGCTATTGCTGCGGCATGCCAGCGGAACTTAGGGCCACCAAG
     AsnSerHisLeuLeuAsnGlyTyrCysCysGlyMetProAlaGluLeuArgAlaThrLys

841  ACGAGCAGGGTGCCAGCATATCCACGGGCTGTTCGTTGGCAAGGCCACCACCAAGATA
     ThrGluGlnGlyAlaSerIleSerThrGlyCysSerPheGlyAsnAlaThrThrLysIle
                                                    #2

961  ACGTTTCGTTGGACGAAGTCGTTTACGCTGATACTGAGCAGGCGTTGGATATGTACAACACA
     ThrPheArgTrpThrLysSerPheThrLeuIleLeuGlnAlaLeuAspMetTyrAsnThr

1081 TCGCCGGAGTGGAAGACGCTGGACCACATCGGGGAACGCGGAGCGGAATCACCTACCGTGTC
     SerProGluTrpLysThrLeuAspHisIleGlyArgAsnAlaArgIleThrTyrArgVal
        #3

1201 GACGATCAGTTCGGTCACTACCCTGCGGCTCCGAGGGTCAGAAGCTCGCCTGAATGGC
     AspAspGlnPheGlyHisTyrAlaCysGlySerGluGlyGlnLysGlyLeuCysLeuAsnGly
```

```
TACAAAACATCAGGCGCCTATCAAGTGGAAGTGTCAAGTGTGAACAAAAACAAAAACGAGAG     13
CCAAACAAAACCAAACAAAACGAAGGCAAAGTGGAGAAAATGATACAGCATCCAGAGTAC
CCAAAATCTGCATACATGGGCTAATTAAGGCTGCCAGCGAATTTACATTTGTGTGGTGC
AACGCCCCCAGAAGTGTACAAAATGTTTAGGAAACATTTTCGGCGAAAACCAGTCGTCG
                   MetPheArgLysHisPheArgArgLysProAlaThrSer        53

ACAAAAAGGCAGGTCCGAGGCATCGGGTACCCAAAATCGCGACCCTGCCATCGACGATC
ThrLysArgGlnArgProArgHisArgValProLysIleAlaThrLeuProSerThrIle     93
                                                 ‾‾‾‾‾‾‾‾‾
GTCCATAAGATATCCGGCAGCTGGTAACTTCGAGCTGGAAATATTAGAAATCTCAAATACC
ValHisLysIleSerAlaAlaGlyAsnPheGluLeuGluIleLeuGluIleSerAsnThr     133
‾‾‾‾‾‾‾‾‾‾‾‾‾‾‾‾‾‾‾‾‾          #1
ACGATAGGCTGCTGCCATGCACGACGCATTCCGCTGTGCCTGAAGGAGTACCAGACC
ThrIleGlyCysSerProCysThrThrAlaPheArgLeuCysLeuLysGluTyrGlnThr    173
                             ‾‾‾‾‾‾‾‾‾‾‾‾‾‾‾‾‾‾‾‾‾‾‾‾‾‾
CTGGGTGGCTCCAGTTTTGTGCTCAGCGATCCGGGTGTGGGAGCCATTGTGCTGCCCTTT
LeuGlyGlySerSerPheValLeuSerAspProGlyValGlyAlaIleValLeuProPhe    213

TCCTATCCAGATGCCGAGAGGTTAATTGAGGAAACATCATACTCGGGCGTGATACTGCCG
SerTyrProAspAlaGluArgLeuIleGluGluThrSerTyrSerGlyValIleLeuPro    253
                                                          #4
CGGGTGCAATGCGCCGTTACCTACTACACAACGACCTTGTGCCGTCGCGG
ArgValGlnCysAlaValThrTyrTyrAsnThrThrCysThrPheCysArgProArg      253
                                        ‾‾‾‾‾‾‾‾‾‾‾‾‾‾‾‾
TGGCAGGGGTCAACTGCGAGGAGGCCATATGCAAGGGCTGCGACCCCGTCCACGGC
TrpGlnGlyValAsnCysGluGluAlaIleCysLysAlaGlyCysAspProValHisGly    293
```

FIG.5B

```
  1 GAATTCCGCT GGGAGAATGG TCTGAGCTAC CTGCCCGTCC TGCTGGGGCA TCAATGGCAA
 61 GTGGGGAAAG CCACACTGGG CAAACGGGCC AGGCCATTTC TGGAATGTGG TACATGGTGG
121 GCAGGGGGCC CGCAACAGCT GGAGGGCAGG TGGACTGAGG CTGGGGATCC CCCGCTGGTT
181 GGGCAATACT GCCTTTACCC ATGAGCTGGA AAGTCACAAT GGGGGGCAAG GGCTCCCGAG
241 GGTGGTTATG TGCTTCCTTC AGGTGGC
```

FIG.8A

```
  1 GAATTCCTTC CATTATACGT GACTTTTCTG AAACTGTAGC CACCCTAGTG TCTCTAACTC
 61 CCTCTGGAGT TTGTCAGCTT TGGTCTTTTC AAAGAGCAGG CTCTCTTCAA GCTCCTTAAT
121 GCGGGCATGC TCCAGTTTGG TCTGCGTCTC AAGATCACCT TTGGTAATTG ATTCTTCTTC
181 AACCCGGAAC TGAAGGCTGG CTCTCACCCT CTAGGCAGAG CAGGAATTCC GAGGTGGATG
241 TGTTAGATGT GAATGTCCGT GGCCCAGATG GCTGCACCCC ATTGATGTTG GCTTCTCTCC
301 GAGGAGGCAG CTCAGATTTG AGTGATGAAG ATGAAGATGC AGAGGACTGT TCTGCTAACA
361 TCATCACAGA CTTGGTCTAC CAGGGTGCCA GCCTCCAGAC CAGACAGACC GGACTGGTGA
421 GATGGCCCTG CACCTTGCAG CCCGCTACTC ACGGGCTGAT GCTGCCAAGC GTCTCCTGGA
481 TGCAGGTGCA GATGCCAATG CCCAGGACAA CATGGGCCGC TGTCCACTCC ATGCTGCAGT
541 GGCACGTGAT GCCAAGGTGT ATTCAGATCT GTTA
```

FIG.8B

```
  1 TCCAGATTCT GATTCGCAAC CGAGTAACTG ATCTAGATGC CAGGATGAAT GATGGTACTA
 61 CACCCCTGAT CCTGGCTGCC CGCCTGGCTG TGGAGGGAAT GGTGGCAGAA CTGATCAACT
121 GCCAAGCGGA TGTGAATGCA GTGGATGACC ATGGAAAATC TGCTCTTCAC TGGGCAGCTG
181 CTGTCAATAA TGTGGAGGCA ACTCTTTTGT TGTTGAAAAA TGGGGCCAAC CGAGACATGC
241 AGGACAACAA GGAAGAGACA CCTCTGTTTC TTGCTGCCCG GGAGGAGCTA TAAGC
```

FIG.8C

```
  1 GAATTCCATT CAGGAGGAAA GGGTGGGGAG AGAAGCAGGC ACCCACTTTC CCGTGGCTGG
 61 ACTCGTTCCC AGGTGGCTCC ACCGGCAGCT GTGACCGCCG CAGGTGGGGG CGGAGTGCCA
121 TTCAGAAAAT TCCAGAAAAG CCCTACCCCA ACTCGGACGG CAACGTCACA CCCGTGGGTA
181 GCAACTGGCA CACAAACAGC CAGCGTGTCT GGGGCACGGG GGGATGGCAC CCCCTGCAGG
241 CAGAGCTG
```

FIG.9A

```
  1 CTAAAGGGAA CAAAAGCNGG AGCTCCACCG CGGGCGGCNC NGCTCTAGAA CTAGTGGANN
 61 NCCCGGGCTG CAGGAATTCC GGCGGACTGG GCTCGGGCTC AGAGCGGCGC TGTGGAAGAG
121 ATTCTAGACC GGGAGAACAA GCGAATGGCT GACAGCTGGC CTCCAAAGTC ACCAGGCTCA
181 AATCGCTCGC CCTGGACATC GAGGGATGCA GAGGATCAGA ACCGGTACCT GGATGGCATG
241 ACTCGGATTT ACAAGCATGA CCAGCCTGCT TACAGGGAGC GTGANNTTTT CACATGCAGT
301 CGACAGACAC GAGCTCTATG CAT
```

FIG.9B

```
          *         10          *         20          *         30          *         40          *
        TGC CAG GAG GAC GCG GGC AAC AAG GTC TGC AGC CTG CAG AAC AAC
         C   Q   E   D   A   G   N   K   V   C   S   L   Q   N   N

50         *         60          *         70          *         80          *         90          *
        CAC GCG TGC GGC TGG GAC GGT GAC TGC TCC CTC AAC TTC AAT GAC
         H   A   C   G   W   D   G   D   C   S   L   N   F   N   D

*        100          *        110          *        120          *        130          *        140          *
        CCC TGG AAG AAC TGC ACG CAG TCT CTG CAG TGC TGG AAG TAC TTC AGT
         P   W   K   N   C   T   Q   S   L   Q   C   W   K   Y   F   S

150          *        160          *        170          *        180          *        190          *
        GAC GGC CAC TGT GAC AGC CAG TGC AAC TCA GCC GGC CTC TTC GAC
         D   G   H   C   D   S   Q   C   N   S   A   G   L   F   D
```

FIG. 10A

```
          *         *         *         *         *
         200       210       220       230       240
GGC TTT GAC TGC CAG CGT GCG GAA GGC CAG TGC AAC CCC CTG TAC GAC
 G   F   D   C   Q   R   A   E   G   Q   C   N   P   L   Y   D >-|
          *         *         *         *         *
         250       260       270       280
CAG TAC TGC AAG GAC CAC TTC AGC GAC GGG CTG GAC TGC GAC CAG GGC TGC
 Q   Y   C   K   D   H   F   S   D   G   L   D   C   D   Q   G   C >
          *         *         *         *         *
         290       300       310       320       330
AAC AGC GCG GAG TGC GAG TGG GAC GAG TGC GAG CTG GAC TGT GCG GAG CAT GTA
 N   S   A   E   C   E   W   D   E   C   E   L   D   C   A   E   H   V >
          *         *         *         *         *
         340       350       360       370       380
CCC GAG AGG CTG GCG GCC ACG CTG GTG GTG GTG CTG ATG CCG
 P   E   R   L   A   A   T   L   V   V   V   L   M   P >
```

FIG. 10B

FIG. 10C

```
GGC CAG GTG AAG GCC TCG CTG CCT GGT GGC AGC GAG GGT GGG CGG
 G   Q   V   K   A   S   L   P   G   G   S   E   G   G   R

CGG AGG GAG CTG GAC CCC ATG GAC GTC CGC GGC TCC ATC GTC TAC
 R   R   E   L   D   P   M   D   V   R   G   S   I   V   Y

CTG GAG ATT GAC AAC CGG CAG TGT GTG CAG GCC TCC TCG CAG TGC TTC
 L   E   I   D   N   R   Q   C   V   Q   A   S   S   Q   C   F

CAG AGT GCC ACC GAC GTG GCC GCA TTC CTG GGA GCG CTC GCC TCG CTG
 Q   S   A   T   D   V   A   A   F   L   G   A   L   A   S   L
```

FIG. 10D

```
     770       780       790       800       810
      *         *         *         *         *
GGC AGC CTC AAC ATC CCC TAC AAG ATC GAG GCC GTG CAG AGT GAG ACC
 G   S   L   N   I   P   Y   K   I   E   A   V   Q   S   E   T>

820       830       840       850       860
      *         *         *         *         *
GTG GAG CCG CCC CCG CCG GCG CAG CTG CAC TTC ATG TAC GTG GCG GCG
 V   E   P   P   P   P   A   Q   L   H   F   M   Y   V   A   A>

870       880       890       900       910
      *         *         *         *         *
GCC GCC TTT GTG CTT CTG TTC TTC GTG GGC TGC GGG GTG CTG CTG TCC
 A   A   F   V   L   L   F   F   V   G   C   G   V   L   L   S>

920       930       940       950       960
      *         *         *         *         *
CGC AAG CGC CGG CAG CAT GGC CAG CTC TGG TTC CCT GAG GGC TTC
 R   K   R   R   Q   H   G   Q   L   W   F   P   E   G   F   E>
```

FIG.10E

```
        970             980             990             1000            1050
AAA GTG TCT GAG GCC AGC AAG AAG CGG CGG GAG CCC CTC GGC GAG
 K   V   S   E   A   S   K   K   R   R   E   P   L   G   E 1010            1020            1030            1040            1050
GAC TCC GTG GGC CTC AAG CCC CTG AAG AAC GCT TCA GAC GGT GCC CTC
 D   S   V   G   L   K   P   L   K   N   A   S   D   G   A   L 1060            1070            1080            1090            1100
ATG GAC GAC AAC CAG AAT GAG TGG GGG GAC GAG GAC CTG GAG ACC AAG
 M   D   D   N   Q   N   E   W   G   D   E   D   L   E   T   K 1110            1120            1130            1140            1150
AAG TTC CGG TTC GAG GAG CCC GTG CTT CTG CCT GAC CTG CCT GAC CAG
 K   F   R   F   E   E   P   V   V   L   P   D   L   P   D   Q
```

FIG.10F

```
           1160       1170       1180       1190       1200
            *          *          *          *          *
ACA GAC CAC CGG CAG TGG ACT CAG CAG CAC CTG GAT GCC GCT GAC CTG
 T   D   H   R   Q   W   T   Q   Q   H   L   D   A   A   D   L>

1210       1220       1230       1240
            *          *          *          *
CGC ATG TCT GCC ATG GCC CCC ACA CCG CCC CAG GGT GAG GTT GAC GCC
 R   M   S   A   M   A   P   T   P   P   Q   G   E   V   D   A>

1250       1260       1270       1280       1290
            *          *          *          *          *
GAC TGC ATG GAC GTC AAT GTC CGC GGG CCT GAT GGC TTC ACC CCG CTC
 D   C   M   D   V   N   V   R   G   P   D   G   F   T   P   L>

1300       1310       1320       1330       1340
            *          *          *          *          *
ATG ATC GCC TCC TGC AGC GGG GGC GGC CTG GAG ACG GGC AAC AGC GAG
 M   I   A   S   C   S   G   G   G   L   E   T   G   N   S   E>
```

FIG. 10G

```
                       1350                1360                1370                1380                1390
                        *                   *                   *                   *                   *
      GAA GAG GAC GCG CCG GCC GTC ATC TCC GAC TTC ATC TAC CAG GGC
       E   E   D   A   P   A   V   I   S   D   F   I   Y   Q   G>

1400                1410                1420                1430                1440
                        *                   *                   *                   *                   *
      GCC AGC CTG CAC AAC CAG ACA GAC CGC ACG GGC GAG ACC GCC TTG CAC
       A   S   L   H   N   Q   T   D   R   T   G   E   T   A   L   H>

1450                1460                1470                1480
                        *                   *                   *                   *
      CTG GCC GCC CGC TAC TCA CGC TCT GAT GCC GCC AAG CGC CTG CTG GAG
       L   A   A   R   Y   S   R   S   D   A   A   K   R   L   L   E>

1490                1500                1510                1520                1530
        *                   *                   *                   *                   *
      GCC AGC GCA GAT GCC AAC ATC CAG GAC AAC ATG GGC CGC ACC CCG CTG
       A   S   A   D   A   N   I   Q   D   N   M   G   R   T   P   L>
```

FIG. 10H

```
        1540                1550                1560                1570                1580
          *                   *                   *                   *                   *
CAT GCG GCT GTG TCT GCC GAC GCA CAA GGT GTC TTC CAG ATC CTG ATC
 H   A   A   V   S   A   D   A   Q   G   V   F   Q   I   L   I>

1590                1600                1610                1620                1630
          *                   *                   *                   *                   *
CGG AAC CGA GCC ACA GAC CTG GAT GCC CGC ATG CAT GAT GGC ACG ACG
 R   N   R   A   T   D   L   D   A   R   M   H   D   G   T   T>

1640                1650                1660                1670                1680
          *                   *                   *                   *                   *
CCA CTG ATC CTG GCT GCC CGC CTG GCC CGC CTG GTG GAG GGC ATG CTG GAG GAC
 P   L   I   L   A   A   R   L   A   R   L   V   E   G   M   L   E   D>

1690                1700                1710                1720                1770
          *                   *                   *                   *                   *
CTC ATC AAC TCA CAC GCC GAC GTC AAC GCC GTA GAT GAC CTG GGC AAG
 L   I   N   S   H   A   D   V   N   A   V   D   D   L   G   K>

1730                1740                1750                1760                1770
          *                   *                   *                   *                   *
TCC GCC CTG CAC TGG GCC GCC GTG AAC AAT GTG GAT GCC GCA GTT
 S   A   L   H   W   A   A   V   N   N   V   D   A   A   V>

FIG.10 I
```

```
        1780            1790            1800            1810            1820
         *               *               *               *               *
GTG CTC CTG AAG AAC GGG GCT AAC AAA GAT ATG CAG AAC AAC AGG GAG
 V   L   L   K   N   G   A   N   K   D   M   Q   N   N   R   E>

1830            1840            1850            1860            1870
         *               *               *               *               *
GAG ACA CCC CTG TTT CTG GCC GCC CGG GAG GGC AGC TAC GAG ACC GCC
 E   T   P   L   F   L   A   A   R   E   G   S   Y   E   T   A>

1880            1890            1900            1910            1920
         *               *               *               *               *
AAG GTG CTG CTG GAC CAC TTT GCC AAC CGG GAC ATC ACG GAT CAT ATG
 K   V   L   L   D   H   F   A   N   R   D   I   T   D   H   M>

1930            1940            1950            1960
         *               *               *               *
GAC CGC CTG CCG CGC GAC ATC GCA CAG GAG CGC ATG CAC CAC GAC ATC
 D   R   L   P   R   D   I   A   Q   E   R   M   H   H   D   I>
```

FIG.10J

```
1970         1980         1990         2000         2010
 *    *       *    *       *    *       *    *       *    *
GTG AGG GCC CTG CTG GAC GAG TAC AAC CTG GTG CGC AGC CCG CAG CTG CAC
 V   R   A   L   L   D   E   Y   N   L   V   R   S   P   Q   L   H 2020         2030         2040         2050         2060
 *    *       *    *       *    *       *    *       *    *
GGA GCC CCG CTG GGG GGC ACG CCC ACC CTG TCG CCC CTC TGC TCG
 G   A   P   L   G   G   T   P   T   L   S   P   L   C   S 2070         2080         2090         2100         2110
 *    *       *    *       *    *       *    *       *    *
CCC AAC GGC TAC CTG GGC AGC CTC AAG CCC GGC GTG CAG GGC AAG AAG
 P   N   G   Y   L   G   S   L   K   P   G   V   Q   G   K   K 2120         2130         2140         2150         2160
 *    *       *    *       *    *       *    *       *    *
GTC CGC AAG CCC AGC AGC AAA GGC CTG GCC TGT GGA AGC AAG GAG GCC
 V   R   K   P   S   S   K   G   L   A   C   G   S   K   E   A
```

FIG. 10K

```
        2170        2180        2190        2200
         *           *           *           *
AAG GAC CTC AAG GCA CGG AGG AAG TCC CAG GAT GGC AAG GGC TGC
 K   D   L   K   A   R   R   K   S   Q   D   G   K   G   C 2210        2220        2230        2240        2250
         *           *           *           *           *
CTG CTG GAC AGC TCC GGC ATG CTC TCG CCC GTG GAC TCC CTG GAG TCA
 L   L   D   S   S   G   M   L   S   P   V   D   S   L   E   S 2260        2270        2280        2290        2300
         *           *           *           *           *
CCC CAT GGC TAC CTG CTG TCA GAC GTG GCC TCG CCC CCA CTG CCC TCC
 P   H   G   Y   L   L   S   D   V   A   S   P   P   L   P   S 2310        2320        2330        2340        2350
         *           *           *           *           *
CCG TTC CAG CAG TCT CCG TCC GTG CCC CTC AAC CAC CTG CCT GGG ATG
 P   F   Q   Q   S   P   S   V   P   L   N   H   L   P   G   M
```

FIG.10L

```
        2360            2370            2380            2390            2400
     *       *       *       *       *       *       *       *       *
CCC GAC ACC CAC CTG GGC ATC GGG CAC CTG AAC GTG GCG GCC AAG CCC
 P   D   T   H   L   G   I   G   H   L   N   V   A   A   K   P>

2410            2420            2430            2440
     *       *       *       *       *       *       *       *
GAG ATG GCG GCG CTG GGT GGG CTG GGC CGG CTG GCC TTT GAG ACT GGC
 E   M   A   A   L   G   G   L   G   R   L   A   F   E   T   G>

2450            2460            2470            2480            2490
     *       *       *       *       *       *       *       *       *
CCA CCT CGT CTC TCC CAC CTG CCT GTG GCC TCT GGC ACC AGC ACC GTC
 P   P   R   L   S   H   L   P   V   A   S   G   T   S   T   V>

2500            2510            2520            2530            2540
     *       *       *       *       *       *       *       *       *
CTG GGC TCC AGC AGC GGA GGG GCC CTG AAT TTC ACT GTG GGC GGG TCC
 L   G   S   S   S   G   G   A   L   N   F   T   V   G   G   S>

FIG.10M
```

```
ACC AGT TTG AAT GGT CAA TGC GAG TGG CTG TCC CGG CTG CAG AGC GGC
 T   S   L   N   G   Q   C   E   W   L   S   R   L   Q   S   G>
    2550          2560          2570          2580          2590

ATG GTG CCG AAC TAC AAC CAA CCT CTG CGG GGG AGT GTG GCA CCA GGC
 M   V   P   N   Y   N   Q   P   L   R   G   S   V   A   P   G>
    2600          2610          2620          2630          2640

CCC CTG AGC ACA CAG GCC CCC TCC CTG CAG CAT GGC ATG GTA GGC CCG
 P   L   S   T   Q   A   P   S   L   Q   H   G   M   V   G   P>
    2650          2660          2670          2680

CTG CAC AGT AGC CTT GCT GCC AGC GCC CTG TCC CAG ATG AGC TAC
 L   H   S   S   L   A   A   S   A   L   S   Q   M   S   Y>
    2690          2700          2710          2720          2730
```

FIG. 10N

```
                                    2750          2760          2770          2780
CAG GGC CTG CCC AGC ACC CGG CTG GCC ACC CAG CCT CAC CTG GTG CAG
 Q   G   L   P   S   T   R   L   A   T   Q   P   H   L   V   Q>

2790          2800          2810          2820          2830
ACC CAG CAG GTG CAG CCA CAA AAC ATC CAG ATG CAG CAG AAC CTG
 T   Q   Q   V   Q   P   Q   N   I   Q   M   Q   Q   N   L>

2840          2850          2860          2870          2880
CAG CCA GCA AAC ATC CAG CAG CAA AGC CTG CAG CCG CCA CCA
 Q   P   A   N   I   Q   Q   Q   S   L   Q   P   P   P>

2890          2900          2910          2920
CCA CCA CAG CCG CAC CTT GGC GTG AGC TCA GCA GCC AGC GGC CAC CTG
 P   P   Q   P   H   L   G   V   S   S   A   A   S   G   H   L>

2930          2940          2950          2960          2970
GGC CGG AGC TTC CTG AGT GGA GAG CCG AGC CAG GCA GAC GTG CAG CCA
 G   R   S   F   L   S   G   E   P   S   Q   A   D   V   Q   P>
```

FIG. 10 O

```
     2980          2990          3000          3010          3020
      *    *    *    *    *    *    *    *    *    *    *
CTG  GGC  CCC  AGC  AGC  CTG  GCG  GTG  CAC  ACT  ATT  CTG  CCC  CAG  GAG  AGC
 L    G    P    S    S    L    A    V    H    T    I    L    P    Q    E    S>

3030          3040          3050          3060          3070
      *    *    *    *    *    *    *    *    *    *    *
CCC  GCC  CTG  CCC  ACG  TCG  CTG  CCA  TCC  TCG  CTG  GTC  CCA  CCC  GTG  ACC
 P    A    L    P    T    S    L    P    S    S    L    V    P    P    V    T>

3080          3090          3100          3110          3120
      *    *    *    *    *    *    *    *    *    *    *
GCA  GCC  CAG  TTC  CTG  ACG  CCC  CCC  TCG  CAG  CAC  AGC  TAC  TCC  TCG  CCT
 A    A    Q    F    L    T    P    P    S    Q    H    S    Y    S    S    P>
```

FIG. 10P

```
              3130        3140        3150         3160
                *           *           *            *
GTG GAC AAC ACC CCC AGC CAC CAG CTA CAG GTG CCT GTT CCT GTA ATG
 V   D   N   T   P   S   H   Q   L   Q   V   P   V   P   V   M>

3170        3180        3190         3200        3210
       *           *           *            *           *
GTA ATG ATC CGA TCT TCG GAT CCT TCT AAA GGC TCA TCA ATT TTG ATC
 V   M   I   R   S   S   D   P   S   K   G   S   S   I   L   I>

3220        3230
       *           *
GAA GCT CCC GAC TCA TGG
 E   A   P   D   S   W>
```

FIG.10Q

```
G GAG GTG GAT GTG TTA GAT GTG AAT GTC CGT GGC CCA GAT GGC TGC     46
  Glu Val Asp Val Leu Asp Val Asn Val Arg Gly Pro Asp Gly Cys
   1           5                  10                  15

ACC CCA TTG ATG TTG GCT TCT CTC CGA GGA GGC AGC TCA GAT TTG AGT   94
Thr Pro Leu Met Leu Ala Ser Leu Arg Gly Gly Ser Ser Asp Leu Ser
             20                  25                  30

GAT GAA GAT GAA GAT GCA GAG GAC TCT TCT GCT AAC ATC ATC ACA GAC  142
Asp Glu Asp Glu Asp Ala Glu Asp Ser Ser Ala Asn Ile Ile Thr Asp
             35                  40                  45

TTG GTC TAC CAG GGT GCC AGC CTC CAG GCC CAG ACA GAC CGG ACT GGT  190
Leu Val Tyr Gln Gly Ala Ser Leu Gln Ala Gln Thr Asp Arg Thr Gly
             50                  55                  60

GAG ATG GCC CTG CAC CTT GCA GCC CGC TAC TCA CGG GCT GAT GCT GCC  238
Glu Met Ala Leu His Leu Ala Ala Arg Tyr Ser Arg Ala Asp Ala Ala
             65                  70                  75

AAG CGT CTC CTG GAT GCA GGT GCA GAT GCC AAT GCC CAG GAC AAC ATG  286
Lys Arg Leu Leu Asp Ala Gly Ala Asp Ala Asn Ala Gln Asp Asn Met
 80              85                  90                  95

GGC CGC TGT CCA CTC CAT GCT GCA GTG GCA GCT GAT GCC CAA GGT GTC  334
Gly Arg Cys Pro Leu His Ala Ala Val Ala Ala Asp Ala Gln Gly Val
                100                 105                 110

TTC CAG ATT CTG ATT CGC AAC CGA GTA ACT GAT CTA GAT GCC AGG ATG  382
Phe Gln Ile Leu Ile Arg Asn Arg Val Thr Asp Leu Asp Ala Arg Met
             115                 120                 125

AAT GAT GGT ACT ACA CCC CTG ATC CTG GCT GCC CGC CTG GCT GTG GAG  430
Asn Asp Gly Thr Thr Pro Leu Ile Leu Ala Ala Arg Leu Ala Val Glu
             130                 135                 140
```

FIG.11A

```
GGA ATG GTG GCA GAA CTG ATC AAC TGC CAA GCG GAT GTG AAT GCA GTG      478
Gly Met Val Ala Glu Leu Ile Asn Cys Gln Ala Asp Val Asn Ala Val
        145                 150                 155

GAT GAC CAT GGA AAA TCT GCT CTT CAC TGG GCA GCT GCT GTC AAT AAT      526
Asp Asp His Gly Lys Ser Ala Leu His Trp Ala Ala Ala Val Asn Asn
    160                 165                 170                 175

GTG GAG GCA ACT CTT TTG TTG TTG AAA AAT GGG GCC AAC CGA GAC ATG      574
Val Glu Ala Thr Leu Leu Leu Leu Lys Asn Gly Ala Asn Arg Asp Met
                180                 185                 190

CAG GAC AAC AAG GAA GAG ACA CCT CTG TTT CTT GCT GCC CGG GAG GGG      622
Gln Asp Asn Lys Glu Glu Thr Pro Leu Phe Leu Ala Ala Arg Glu Gly
            195                 200                 205

AGC TAT GAA GCA GCC AAG ATC CTG TTA GAC CAT TTT GCC AAT CGA GAC      670
Ser Tyr Glu Ala Ala Lys Ile Leu Leu Asp His Phe Ala Asn Arg Asp
        210                 215                 220

ATC ACA GAC CAT ATG GAT CGT CTT CCC CGG GAT GTG GCT CGG GAT CGC      718
Ile Thr Asp His Met Asp Arg Leu Pro Arg Asp Val Ala Arg Asp Arg
    225                 230                 235

ATG CAC CAT GAC ATT GTG CGC CTT CTG GAT GAA TAC AAT GTG ACC CCA      766
Met His His Asp Ile Val Arg Leu Leu Asp Glu Tyr Asn Val Thr Pro
240                 245                 250                 255

AGC CCT CCA GGC ACC GTG TTG ACT TCT GCT CTC TCA CCT GTC ATC TGT      814
Ser Pro Pro Gly Thr Val Leu Thr Ser Ala Leu Ser Pro Val Ile Cys
            260                 265                 270

GGG CCC AAC AGA TCT TTC CTC AGC CTG AAG CAC ACC CCA ATG GGC AAG      862
Gly Pro Asn Arg Ser Phe Leu Ser Leu Lyn His Thr Pro Met Gly Lys
        275                 280                 285
```

FIG.11B

```
AAG TCT AGA CGG CCC AGT GCC AAG AGT ACC ATG CCT ACT AGC CTC CCT    910
Lys Ser Arg Arg Pro Ser Ala Lys Ser Thr Met Pro Thr Ser Leu Pro
        290             295             300

AAC CTT GCC AAG GAG GCA AAG GAT GCC AAG GGT AGT AGG AGG AAG AAG    958
Asn Leu Ala Lys Glu Ala Lys Asp Ala Lys Gly Ser Arg Arg Lys Lys
        305             310             315

TCT CTG AGT GAG AAG GTC CAA CTG TCT GAG AGT TCA GTA ACT TTA TCC   1006
Ser Leu Ser Glu Lys Val Gln Leu Ser Glu Ser Ser Val Thr Leu Ser
320             325             330             335

CCT GTT GAT TCC CTA GAA TCT CCT CAC ACG TAT GTT TCC GAC ACC ACA   1054
Pro Val Asp Ser Leu Glu Ser Pro His Thr Tyr Val Ser Asp Thr Thr
                340             345             350

TCC TCT CCA ATG ATT ACA TCC CCT GGG ATC TTA CAG GCC TCA CCC AAC   1102
Ser Ser Pro Met Ile Thr Ser Pro Gly Ile Leu Gln Ala Ser Pro Asn
            355             360             365

CCT ATG TTG GCC ACT GCC GCC CCT CCT GCC CCA GTC CAT GCC CAG CAT   1150
Pro Met Leu Ala Thr Ala Ala Pro Pro Ala Pro Val His Ala Gln His
        370             375             380

GCA CTA TCT TTT TCT AAC CTT CAT GAA ATG CAG CCT TTG GCA CAT GGG   1198
Ala Leu Ser Phe Ser Asn Leu His Glu Met Gln Pro Leu Ala His Gly
        385             390             395

GCC AGC ACT GTG CTT CCC TCA GTG AGC CAG TTG CTA TCC CAC CAC CAC   1246
Ala Ser Thr Val Leu Pro Ser Val Ser Gln Leu Leu Ser His His His
400             405             410             415

ATT GTG TCT CCA GGC AGT GGC AGT GCT GGA AGC TTG AGT AGG CTC CAT   1294
Ile Val Ser Pro Gly Ser Gly Ser Ala Gly Ser Leu Ser Arg Leu His
            420             425             430

CCA GTC CCA GTC CCA GCA GAT TGG ATG AAC CGC ATG GAG GTG AAT GAG   1342
Pro Val Pro Val Pro Ala Asp Trp Met Asn Arg Met Glu Val Asn Glu
            435             440             445
```

FIG.11C

```
ACC CAG TAC AAT GAG ATG TTT GGT ATG GTC CTG GCT CCA GCT GAG GGC    1390
Thr Gln Tyr Asn Glu Met Phe Gly Met Val Leu Ala Pro Ala Glu Gly
            450             455             460

ACC CAT CCT GGC ATA GCT CCC CAG AGC AGG CCA CCT GAA GGG AAG CAC    1438
Thr His Pro Gly Ile Ala Pro Gln Ser Arg Pro Pro Glu Gly Lys His
    465             470             475

ATA ACC ACC CCT CGG GAG CCC TTG CCC CCC ATT GTG ACT TTC CAG CTC    1486
Ile Thr Thr Pro Arg Glu Pro Leu Pro Pro Ile Val Thr Phe Gln Leu
480             485             490             495

ATC CCT AAA GGC AGT ATT GCC CAA CCA GCG GGG GCT CCC CAG CCT CAG    1534
Ile Pro Lys Gly Ser Ile Ala Gln Pro Ala Gly Ala Pro Gln Pro Gln
                500             505             510

TCC ACC TGC CCT CCA GCT GTT GCG GGC CCC CTG CCC ACC ATG TAC CAG    1582
Ser Thr Cys Pro Pro Ala Val Ala Gly Pro Leu Pro Thr Met Tyr Gln
            515             520             525

ATT CCA GAA ATG GCC CGT TTG CCC AGT GTG GCT TTC CCC ACT GCC ATG    1630
Ile Pro Glu Met Ala Arg Leu Pro Ser Val Ala Phe Pro Thr Ala Met
        530             535             540

ATG CCC CAG CAG GAC GGG CAG GTA GCT CAG ACC ATT CTC CCA GCC TAT    1678
Met Pro Gln Gln Asp Gly Gln Val Ala Gln Thr Ile Leu Pro Ala Tyr
    545             550             555

CAT CCT TTC CCA GCC TCT GTG GGC AAG TAC CCC ACA CCC CCT TCA CAG    1726
His Pro Phe Pro Ala Ser Val Gly Lys Tyr Pro Thr Pro Pro Ser Gln
560             565             570             575

CAC AGT TAT GCT TCC TCA AAT GCT GCT GAG CGA ACA CCC AGT CAC AGT    1774
His Ser Tyr Ala Ser Ser Asn Ala Ala Glu Arg Thr Pro Ser His Ser
                580             585             590

GGT CAC CTC CAG GGT GAG CAT CCC TAC CTG ACA CCA TCC CCA GAG TCT    1822
Gly His Leu Gln Gly Glu His Pro Tyr Leu Thr Pro Ser Pro Glu Ser
            595             600             605
```

FIG.11D

| | |
|---|---|
| CCT GAC CAG TGG TCA AGT TCA TCA CCC CAC TCT GCT TCT GAC TGG TCA<br>Pro Asp Gln Trp Ser Ser Ser Ser Pro His Ser Ala Ser Asp Trp Ser<br>          610                         615                    620 | 1870 |
| GAT GTG ACC ACC AGC CCT ACC CCT GGG GGT GCT GGA GGA GGT CAG CGG<br>Asp Val Thr Thr Ser Pro Thr Pro Gly Gly Ala Gly Gly Gly Gln Arg<br>625                      630                      635 | 1918 |
| GGA CCT GGG ACA CAC ATG TCT GAG CCA CCA CAC AAC AAC ATG CAG GTT<br>Gly Pro Gly Thr His Met Ser Glu Pro Pro His Asn Asn Met Gln Val<br>640                   645                   650               655 | 1966 |
| TAT GCG TGAGAGAGTC CACCTCCAGT GTAGAGACAT AACTGACTTT TGTAAATGCT<br>Tyr Ala | 2022 |
| GCTGAGGAAC AAATGAAGGT CATCCGGGAG AGAAATGAAG AAATCTCTGG AGCCAGCTTC | 2082 |
| TAGAGGTAGG AAAGAGAAGA TGTTCTTATT CAGATAATGC AAGAGAAGCA ATTCGTCAGT | 2142 |
| TTCACTGGGT ATCTGCAAGG CTTATTGATT ATTCTAATCT AATAAGACAA GTTTGTGGAA | 2202 |
| ATGCAAGATG AATACAAGCC TTGGGTCCAT GTTACTCTC TTCTATTTGG AGAATAAGAT | 2262 |
| GGATGCTTAT TGAAGCCCAG ACATTCTTGC AGCTTGGACT GCATTTTAAG CCCTGCAGGC | 2322 |
| TTCTGCCATA TCCATGAGAA GATTCTACAC TAGCGTCCTG TTGGGAATTA TGCCCTGGAA | 2382 |
| TTCTGCCTGA ATTGACCTAC GCATCTCCTC CTCCTTGGAC ATTCTTTTGT CTTCATTTGG | 2442 |
| TGCTTTTGGT TTGCACCTC TCCGTGATTG TAGCCCTACC AGCATGTTAT AGGGCAAGAC | 2502 |
| CTTTGTGCTT TTGATCATTC TGGCCCATGA AAGCAACTTT GGTCTCCTTT CCCCTCCTGT | 2562 |
| CTTCCCGGTA TCCCTTGGAG TCTCACAAGG TTTACTTTGG TATGGTTCTC AGCACAAACC | 2622 |
| TTTCAAGTAT GTTGTTTCTT TGGAAAATGG ACATACTGTA TTGTGTTCTC CTGCATATAT | 2682 |
| CATTCCTGGA GAGAGAAGGG GAGAAGAATA CTTTTCTTCA ACAAATTTTG GGGCAGGAG | 2742 |
| ATCCCTTCAA GAGGCTGCAC CTTAATTTTT CTTGTCTGTG TGCAGGTCTT CATATAAACT | 2802 |

FIG.11E

```
TTACCAGGAA GAAGGGTGTG AGTTTGTTGT TTTTCTGTGT ATGGGCCTGG TCAGTGTAAA    2862

GTTTTATCCT TGATAGTCTA GTTACTATGA CCCTCCCCAC TTTTTTAAAA CCAGAAAAAG    2922

GTTTGGAATG TTGGAATGAC CAAGAGACAA GTTAACTCGT GCAAGAGCCA GTTACCCACC    2982

CACAGGTCCC CCTACTTCCT GCCAAGCATT CCATTGACTG CCTGTATGGA ACACATTTGT    3042

CCCAGATCTG AGCATTCTAG GCCTGTTTCA CTCACTCACC CAGCATATGA AACTAGTCTT    3102

AACTGTTGAG CCTTTCCTTT CATATCCACA GAAGACACTG TCTCAAATGT TGTACCCTTG    3162

CCATTTAGGA CTGAACTTTC CTTAGCCCAA GGGACCCAGT GACAGTTGTC TTCCGTTTGT    3222

CAGATGATCA GTCTCTACTG ATTATCTTGC TGCTTAAAGG CCTGCTCACC AATCTTTCTT    3282

TCACACCGTG TGGTCCGTGT TACTGGTATA CCCAGTATGT TCTCACTGAA GACATGGACT    3342

TTATATGTTC AAGTGCAGGA ATTGGAAAGT TGGACTTGTT TTCTATGATC CAAAACAGCC    3402

CTATAAGAAG GTTGGAAAAG GAGGAACTAT ATAGCAGCCT TTGCTATTTT CTGCTACCAT    3462

TTCTTTTCCT CTGAAGCGGC CATGACATTC CCTTTGGCAA CTAACGTAGA AACTCAACAG    3522
```

FIG.11F

```
AACATTTTCC TTTCCTAGAG TCACCTTTTA GATGATAATG GACAACTATA GACTTGCTCA    3582

TTGTTCAGAC TGATTGCCCC TCACCTGAAT CCACTCTCTG TATTCATGCT CTTGGCAATT    3642

TCTTTGACTT TCTTTTAAGG GCAGAAGCAT TTTAGTTAAT TGTAGATAAA GAATAGTTTT    3702

CTTCCTCTTC TCCTTGGGCC AGTTAATAAT TGGTCCATGG CTACACTGCA ACTTCCGTCC    3762

AGTGCTGTGA TGCCCATGAC ACCTGCAAAA TAAGTTCTGC CTGGGCATTT TGTAGATATT    3822

AACAGGTGAA TTCCCGACTC TTTTGGTTTG AATGACAGTT CTCATTCCTT CTATGGCTGC    3882

AAGTATGCAT CAGTGCTTCC CACTTACCTG ATTTGTCTGT CGGTGGCCCC ATATGGAAAC    3942

CCTGCGTGTC TGTTGGCATA ATAGTTTACA AATGGTTTTT TCAGTCCTAT CCAAATTTAT    4002

TGAACCAACA AAAATAATTA CTTCTGCCCT GAGATAAGCA GATTAAGTTT GTTCATTCTC    4062

TGCTTTATTC TCTCCATGTG GCAACATTCT GTCAGCCTCT TTCATAGTGT GCAAACATTT    4122

TATCATTCTA AATGGTGACT CTCTGCCCTT GGACCCATTT ATTATTCACA GATGGGGAGA    4182

ACCTATCTGC ATGGACCCTC ACCATCCTCT GTGCAGCACA CACAGTGCAG GGAGCCAGTG    4242

GCGATGGCGA TGACTTTCTT CCCCTG                                         4268
```

FIG. 11G

```
hN5k                ----------------------------------------ITSPGIDQASPNPML--ATAAPPAPVHAQHALSF
TAN-1         2218  ----------------------------------------LRSPR--QQSPSVPLNHLPQMPDTHLGIGHLNVA
rat NOTCH     2209  ----------------------------------------LRSPR--QQSPSMPLSHLPGMPDTHLGISHLNVA
XENOPUS NOTCH 2214  ----------------------------------------MTSPR--QQSPSMPLNHLTSMPESQLGMNHINMA
DROSOPH NOTCH 2285  PVGVGMGGNLPSPYDTSSMYSNAMAAPLANGNPNTGAKQPRSYEDCIKNAQSMQSLQGNGLDMIKLDNYAYSMGSPR--QQELLNGQGLGMNGNGQRNGVGPGVLP
                                                                            CK-II hN5k                SNLHEMQ------------------------------------PLAHGASTVLPSVSQLLSHHHIVSPGS--GSAGSLSRLHPVPVPADV--MNRMEVNETQYNEMFGMVLAPAEG-THPGI
TAN-1         2250  A-KPEMAALGGGGRLAFETGPPRLSHLPVASGTSTVLGSSSGGALNFTVGGSTSLNGQCEWLSRLQSGMVPNQYNPLRGSYAPGPLSTQAPSLQHG-MVGPLHSSL
rat NOTCH     2242  A-KPEMAALAGGSRLAFEPPPPRLSHLPVASSASTVLSTNGTGAMNFTVGAPASLNGQCEWLPRLQNGMVPSQYNPLRPGVTPGTLSTQAAGLQHGMM-SPIHSSL
XENOPUS NOTCH 2247  T-KQEMAA--GSNRMAFDAMYPRLTHL-NASSPNTIMS----NGSMHFTVGGAPTMNSQCDWLARLQNGMVQNQYDPIRNGIQQGN-AQQAQALQHGLMTS-LHNGL
DROSOPH NOTCH 2390  GGLCGMGGLSGAGNGNGNSHEQGLSPPYS-NQSPPHSVQSSLALSPHAYLGSPSPAKSRPSLPTSPTHIQAMRHATQQKQFGGSNLNSLLGGANGGGVVGGGGGGGV
                                                          CK-II hN5k                APQSRPPEGK-----------HITTPREPLPP-IV-TFQLIPKGSIAQPAG----------------APQPQSTCPPAVAGPLPTMYQIP------EMARL-P
TAN-1         2354  AASALSQMMS-----------YQGLPSTRLATQPHLVQTQQVQPQNLQMQQQNLQPANIQQQQSLQPPPPPPQPHLGVSSAASGHLGRSFLSGEPSQADVQPLGP
rat NOTCH     2344  STNTLSPII------------YQGLPNTRLATQPHLVQTQQVQPQNLQTQQVQPQNLQ-IQPQN------------LQPPS---QPHLSVSSAANGHLGRSFLSGEPSQADVQPLGP
XENOPUS NOTCH 2343  PATTLSQMMT-----------YQAMPNTRLANQPHLMQAQQMQQQN------------------LQLHQSMQQQHHN-SSTSTHINSPFCSSDISQTDLQQM--
DROSOPH NOTCH 2495  VGQQPQNSPVSLGIISPTGSDMGIMLAPPQSSKNSAIMQTISPQQQQQQQQQQQQQQHQQQQQQQQQQQQQQQLGGLEFGSAGLDLNG-FCGSPDSFHSGQMNPP hN5k                SVAFPTAMMPQQDGQVAQTILPAYHPFPASVGKYHTPPSQHSYASSNAAERTPSHSGHLQGEHPYLTPSPESPDQWSSSSPHSA-SDWSDVTTSPTP
TAN-1         2448  SSLAVHTILPQ-ESPALPTSLPSSLVPPVTAAQFLTPPSQHSY-SS-PVENTPSHQLQVP-EHPFLTPSPESPDQWSSSSPHSNVSDWSEGVSSPPT
rat NOTCH     2423  SSLPVHTILPQ-ESQALPTSLPSSMVPPMTITQFLTPPSQHSY-SSSPVDNTPSHQLQVP-EHPFLTPSPESPDQWSSSSSRHSNISDWSEGISSPPT
XENOPUS NOTCH 2416  SSMNIHSVMPQ-DTQIFAASLPSNLTQSMTTAQFLTPPSQHSY-SS-PMDNTPSHQLQVP-DHPFLTPSPESPDQWSSSSPHSNMSDWSEGISSPPT
DROSOPH NOTCH 2599  S---IQSSMSG-SSPSTNMLSPSSQHNQQAFYQYLTPSSQHS-------GGHTPQHLVQTL-D-SYPTPSPGHWSSSPGHSPRSN-SDWSEGVQSPAA

PEST-CONTAINING REGION
```

FIG.12C

Potential signal cleavage site ↓

```
hum N    MP----------- ----------- ---ALRPAL LWALLALWLC CA------APA HA---------L
TAN-1    MP----------- ----------- ------PL LAPLLCLALL PA------LAA RG---------P
Xen N    MD----------- ----------- -------- RIGLAVLLCS LP------VLT QG---------L
Dros N   MQSQRSRRRS RAPNTWICFW INKMHAVASL PASLPLLLLT LAFANLPNIV RGTDTALVAA
```

```
hum N    MLGKATCRCA SGFTGEDCQY STSHPCFVSR PCLNGGTCHM LSRDT-YECT CQVGFTGKEC
Tan-1    GVADYACSCA LGFSGPLCLT PLDNAC-LTN PCRNGGTCDL LT-LTEYKCR CPPGWSGKSC
Xen N    NAIDFICHCP VGFTDKVCLT PVDNAC-VNN PCRNGGTCEL LNSVTEYKCR CPPGWTGDSC
Dros N   GRPGISCKCP LGFDESLCEI AVPNAC-DHV TCLNGGTCQL KT-LEEYTCA CANGYTGERC
```

```
hum N    NLPCSYQCQC PQGFTGQYCD SLYVPCAPSP CVNGGTCRQT GDFTFECNCL PGFEGSTCER
TAN-1    NEVGSYRCVC RATHTGPNCE RPYVPCSPSP CQNGGTCRPT GDVTHECACL PGFTGQNCEE
Xen N    NEFGSYRCTC QNRFTGRNCD EPYVPCNPSP CLNGGTCRQT DDTSYDCTCL PGFSGQNCEE
Dros N   NTHGSYQCMC PTGYTGKDCD TKYNPCSPSP CQNAGICRSN G-LSYECKCP KGFEGKNCEQ
```

EGF-like Repeats

```
QCRDGYEPCV NEGMCVTYHN GTGYCKCPEG FLGEYCQHRD PCE-KNRCQN GGTC--VAQA   83
RCSQPGETCL NGGKCEA-AN GTEACVCGGA FVGPRCQDPN PCL-STPCKN AGTCHVVDRR   80
RCTQTAEMCL NGGRCEMTPG GTGVCLCGNL YFGERCQFPN PCTIKNQCMN FGTCEPVLQG   90
SCTSVG--CQ NGGTCVTQLN GKTYCACDSH YVGDYCEHRN PCN-SMRCQN GGTCQVTFRN  117
```

```
QWTDACLSHP CANGSTCTTV —ANQFSCKC LTGFTGQKCE TDVNEC-DIP GHCQHGGTCL  199
QQADPCASNP CANGGQCLPF —EASYICHC PPSFHGPTCR QDVNECGQKP RLCRHGGTCH  196
QQADPCASNP CANGGKCLPF —EIQYICKC PPGFHGATCK QDINEC-S-Q NPCKNGGQCI  195
ETKNLCASSP CRNGATCTAL AGSSSFTCSC PPGFTGDTCS YDIEEC-Q-S NPCKYGGICV  233
```

```
NIDDCPNHRC QNGGVCVDGV NTYNCRCPPQ WTGQFCTEDV DECLLQPNA- CQNGGTCANR  318
NIDDCPGNNC KNGGACVDGV NTYNCPCPPE WTGQYCTEDV DECQLMPNA- CQNGGTCHNT  315
NIDDCPSNNC RNGGTCVDGV NTYNCQCPPD WTGQYCTEDV DECQLMPNA- CQNGGTCHNT  314
NYDDCLGHLC QNGGTCIDGI SDYTCRCPPN FTGRFCQDDV DECAQRDHPV CQNGATCTNT  352
```

FIG.13A

```
hum N    NGGYGCVCVN GWSGDDCSEN IDDCAFASCT PGSTCIDRVA SFSCMCPEGK AGLLCHLDDA
TAN-1    HGGYNCVCVN GWTGEDCSEN IDDCASAACF HGATCHDRVA SFYCECPHGR TGLLCHLNDA
Xen N    YGGYNCVCVN GWTGEDCSEN IDDCANAACH SGATCHDRVA SFYCECPHGR TGLLCHLDNA
Dros N   HGSYSCICVN GWAGLDCSNN TDDCKQAACF YGATCIDGVG SFYCQCTKGK TGLLCHLDDA hum N    AFHCECLKGY AGPRCEMDIN ECHSDPCQND ATCLDKIGGF TCLCMPGFKG VHCELEINEC
TAN-1    SFECQCLQGY TGPRCEIDVN ECVSNPCQND ATCLDQIGEF QCMCMPGYEG VHCEVNTDEC
Xen N    SFQCNCPQGY AGPRCEIDVN ECLSNPCQND STCLDQIGEF QCICMPGYEG LYCETNIDEC
Dros N   SYRCNCSQGF TGPRCETNIN ECESHPCQNE GSCLDDPGTF RCVCMPGFTG TQCEIDIDEC hum N    ATGFTGVLCE ENIDNCDPDP CHHGQCQDGI DSYTCICNPG YMGAICSDQI DECYSSPCLN
TAN-1    TEGYTGTHCE VDIDECDPDP CHYGSCKDGV ATFTCLCRPG YTGHHCETNI NECSSQPCRL
Xen N    TEGFTGRHCE QDINECIPDP CHYGTCKDGI ATFTCLCRPG YTGRLCDNDI NECLSKPCLN
Dros N   PPCYTGTSCE ININDCDSNP CHRGKCIDDV NSFKCLCDPG YTGYICQKQI NECESNPCQF CISNPCHKGA LCDTNPLNGQ YICTCPQGYK GADCTEDVDE CAMANSNPCE HAGKCVNTDG   438
CISNPCNEGS NCDTNPVNGK AICTCPSGYT GPACSQDVDE CSLG-ANPCE HAGKCINTLG   434
CISNPCNEGS NCDTNPVNGK AICTCPPGYT GPACNNDVDE CSLG-ANPCE HGGRCTNTLG   433
CTSNPCHADA ICDTSPINGS YACSCATGYK GVDCSEDIDE CDQG—SPCE HNGICVNTPG    470

QSNPCVNNGQ CVDKVNRFQC LCPPGFTGPV CQIDIDDCSS TPCLNGAKCI DHPNGYECQC   558
ASSPCLHNGR CLDKINEFQC ECPTGFTGHL CQYDVDECAS TPCKNGAKCL DGPNTYTCVC   554
ASNPCLHNGK CIDKINEFRC DCPTGFSGNL CQHDFDECTS TPCKNGAKCL DGPNSYTCQC   553
QSNPCLNDGT CHDKINGFKC SCALGFTGAR CQINIDDCQS QPCRNRGICH DSIAGYSCEC   590

DGRCIDLVNG YQCNCQPGTS GVNCEINFDD CASNPCIHG- ICMDGINRYS CVCSPGFTGQ   677
RGTCQDPDNA YLCFCLKGTT GPNCEINLDD CASSPCDSG- TCLDKIDGYE CACEPGYTGS   673
GGQCTDRENG YICTCPKGTT GVNCETKIDD CASNLCDNG- KCIDKIDGYE CTCEPGYTGK   672
DGHCQDRVGS YYCQCQAGTS GKNCEVNVNE CHSNPCNNGA TCIDGINSYK CQCVPGFTGQ   710
```

FIG.13B

```
hum N    RCNIDIDECA SNPCRKGATC INGVNGFRCI CPEGPHHPSC YSQVNECLSN PCI-HGNCTG
TAN-1    MCNSNIDECA GNPCHNGGTC EDGINGFTCR CPEGYHDPTC LSEVNECNSN PCV-HGACRD
Xen N    LCNININECD SNPCRNGGTC KDQINGFTCV CPDGYHDHMC LSEVNECNSN PCI-HGACHD
Dros N   HCEKNVDECI SSPCANNGVC IDQVNGYKCE CPRGFYDAHC LSDVDECASN PCVNEGRCED hum N    DECASNPCLN QGTCFDDISG YTCHCVLPYT GKNCQTVLAP CSPNPCENAA VCKESPNFES
TAN-1    NECASNPCLN KGTCIDDVAG YKCNCLLPYT GATCEVVLAP CAPSPCRNGG ECRQSEDYES
Xen N    NECSSNPCLN HGTCIDDVAG YKCNCMLPYT GAICEAVLAP CAGSPCKNGG RCKESEDFET
Dros N   DDCVTNPCGN GGTCIDKVNG YKCVCKVPFT GRDCESKMDP CASNRCKNEA KCTPSSNFLD hum N    CLANPCQNGG SCMDGVNTFS CLCLPGFTGD KCQTDNMECL SEPCKNGGTC SDYVNSYTCK
TAN-1    CRPNPCHNGG SCTDGINTAF CDCLPGFRGT FCEEDINECA SDPCRNGANC TDCVDSYTCT
Xen N    CQPNPCHNGG SCSDGINMFF CNCPAGFRGP KCEEDINECA SNPCKNGANC TDCVNSYTCT
Dros N   CASFPCQNGG TCLDGIGDYS CLCVDGFDGK HCETDINECL SQPCQNGATC SQYVNSYTCT
```

```
GLSGYKCLCD AGWVGINCEV DKNECLSNPC QNGGTCDNLV NCYRCTCKKG FKGYNCQVNI   796
SLNGYKCDCD PGWSGTNCDI NNNECESNPC VNGGTCKDMT SGIVCTCREG FSGPNCQTNI   792
GVNGYKCDCE AGWSGSNCDI NNNECESNPC MNGGTCKDMT GAYICTCKAG FSGPNCQTNI   791
GINEFICHCP PGYTGKRCEL DIDECSSNPC QHGGTCYDKL NAFSCQCMPG YTGQKCETNI   830

YTCLCA-PGW QGQRCTIDID EC-ISKPCMN HGLCHNTQGS YMCECPPGFS GMDCEEDIDD   914
FSCVCPTAGA KGQTCEVDIN EC-VLSPCRH GASCQNTHGG YRCHCQAGYS GRNCETDIDD   911
FSCECP-PGW QGQTCEIDMN EC-VNRPCRN GATCQNTNGS YKCNCKPGYT GRNCEMDIDD   909
FSCTCK-LGY TGRYCDEDID ECSLSSPCRN GASCLNVPGS YRCLCTKGYE GRDCAINTDD   949

CQAGFDGVHC ENNINECTES SCFNGGTCVD GINSFSCLCP VGFTGSFCLH EINECSSHPC  1034
CPAGFSGIHC ENNTPDCTES SCFNGGTCVD GINSFTCLCP PGFTGSYCQH VVNECDSRPC  1031
CQPGFSGIHC ESNTPDCTES SCFNGGTCID GINTFTCQCP PGFTGSYCQH DINECDSKPC  1029
CPLGFSGINC QTNDEDCTES SCLNGGSCID GINGYNCSCL AGYSGANCQY KLNKCDSNPC  1069
```

FIG.13C

```
hum N    LNEGTCVDGL GTYRCSCPLG YTGKNCQTLV NLCSRSPCKN KGTCVQKKAE SQCLCPSGWA
TAN-1    LLGGTCQDGR GLHRCTCPQG YTGPNCQNLV HWCDSSPCKN GGKCWQTHTQ YRCECPSGWT
Xen N    LNGGTCQDSY GTYKCTCPQG YTGLNCQNLV RWCDSSPCKN GGKCWQTNNF YRCECKSGWT
Dros N   LNGATCHEQN NEYTCHCPSG FTGKQCSEYV DWCGQSPCEN GATCSQMKHQ FSCKCSAGWT hum N    SNPCQHGATC SDFIGGYRCE CVPGYQGVNC EYEVDECQNQ PCQNGGTCID LVNHFKCSCP
TAN-1    PSPCQNGATC TDYLGGYSCK CVAGYHGVNC SEEIDECLSH PCQNGGTCLD LPNTYKCSCP
Xen N    PNPCQNGATC TDYLGGYSCE CVAGYHGVNC SEEINECLSH PCQNGGTCID LINTYKCSCP
Dros N   SQPCQNGGTC RDLIGAYECQ CRQGFQGQNC ELNIDDCAPN PCQNGGTCHD RVMNFSCSCP hum N    CLSNPCSSEG SLDCIQLTND YLCVCRSAFT GRHCETFVDV CPQMPCLNGG TCAVASNMPD
TAN-1    CLSNPCDARG TQNCVQRVND FHCECRAGHT GRRCESVING CKGKPCKNGG TCAVASNTAR
Xen N    CLSNPCDSRG TQNCIQLVND YRCECRQGFT GRRCESVVDG CKGMPCRNGG TCAVASNTER
Dros N   CLSNPCSNAG TLDCVQLVNN YHCNCRPGHM GRHCEHKVDF CAQSPCQNGG NCNI----RQS
```

```
GAYCDVPNVS CDIAASRRGV LVEHLCQHSG VCINAGNTHY CQCPLGYTGS YCEEQLDECA  1154
GLYCDVPSVS CEVAAQRQGV DVARLCQHGG LCVDAGNTHH CRCQAGYTGS YCEDLVDECS  1151
GVYCDVPSVS CEVAAKQQGV DIVHLCRNSG MCVDTGNTHF CRCQAGYTGS YCEEQVDECS  1149
GKLCDVQTIS CQDAADRKGL SLRQLC-NNG TCKDYGNSHV CYCSQGYAGS YCQKEIDECQ  1188

PGTRGLLCEE NIDDCAR--- ---GPHCLN GGQCMDRIGG YSCRCLPGFA GERCEGDINE  1267
RGTQGVHCEI NVDDCNPPVD PVSRSPKCFN NGTCVDQVGG YSCTCPPGFV GERCEGDVNE  1271
RGTQGVHCEI NVDDCTPFYD SFTLEPKCFN NGKCIDRVGG YNCICPPGFV GERCEGDVNE  1269
PGTMGIICEI NKDDCKP--- ---GACHN NGSCIDRVGG FECVCQPGFV GARCEGDINE  1300

GFICRCPPGF SGARCQS--- SCGQVKCRKG EQCVHTAS-- GPRCFCPSP- --RDCES--  1376
GFICKCPAGF EGATCENDAR TCGSLRCLNG GTCISGPR-- SPTCLCLGPF TGPECQFPAS  1389
GFICKCPPGF DGATCEYDSR TCSNLRCQNG GTCISVLT-- SSKCVCSEGY TGATCQYPVI  1387
GHHCICNNGF YGKNCELSGQ DCDSNPCRVG -NCVVADEGF GYRCECPRGT LGEHCEIDTL  1415
```

FIG. 13D

```
hum N   -GC-ASSPCQ HGGSCHPQRQ PPYYSCQCAP PFSGSRCEL- -YTAPP---- -S----TPP
TAN-1   SPCLGGNPCY NQGTCEPTSE SPFYRCLCPA KFNGLLCHIL DYSFGG---- -GAGRDIPPP
Xen N   SPC-ASHPCY NGGTCQFFAE EPFFQCFCPK NFNGLFCHIL DYEFPG---- -GLGKNITPP
Dros N  DEC-SPNPCA QGAACEDLLG D--YECLCPS KWKGKRCDIY DANYPGWNGG SGSGNDRYAA hum N   NN-QCDELCN TVECLFDNFE CQGNSKTCK- -YDKYCADHF KDNHCNQGCN SEECGWDGLD
TAN-1   SDGHCDSQCN SAGCLFDGFD CQRAEGQCNP LYDQYCKDHF SDGHCDQGCN SAECEWDGLD
Xen N   NDGKCDSQCN NTGCLYDGFD CQKVEVQCNP LYDQYCKDHF QDGHCDQGCN NAECEWDGLD
Dros N  KNGKCNEECN NAACHYDGHD CERKLKSCDS LFDAYCQKHY GDGFCDYGCN NAECSWDGLD hum N   YYGEKSAAMK KQ--R----- ---------- ---MTRRSL PGEQ----E QEVAGSKVFL
TAN-1   YYGREEELRK HPIKRAAEGW AAPDALLGQV KASLLPGGSE GGRRRRELDP MDVRGSIVYL
Xen N   YYGNEEELKK HHIKRSTDYW SDAPSAI--- -FSTMKESIL LGRHRRELDE MEVRGSIVYL
Dros N  WKDNVRVPEI EDTDFARKNK ILYTQQVHQ- ---------- ---------- ---TGIQIYL
```

LNR (Notch/Lin-12 Repeats)

```
---A---TCL SQYCADKARD GVCDEACNSH ACQWDGGDCS LTMENPWANC SSPLPCWDYI  1476
LIEE---ACE LPECQEDAGN KVCSLQCNNH ACGWDGGDCS LNFNDPWKNC TQSLQCWKYF  1501
DNDD---ICE NEQCSELADN KVCNANCNNH ACGWDGGDCS LNFNDPWKNC TQSLQCWKYF  1498
DLEQQRAMCD KRGCTEKQGN GICDSDCNTY ACNFDGNDCS LGI-NPWANC TAN-EXWNKF  1531

CAADQPEN-L AEGTLVIVVL MPPEQLLQDA R-SFLRALGT LLHTNLRIKR DSQGELMVYP  1591
CAEHVPER-L AAGTL-VVVV LMPPEQLRNS SFHFLRELSR VLHTNVVFKR DAHGQQMIFP  1619
C-ANMPEN-L AEGTLVLVVL MPPERLKNNS V-NFLRELSR VLHTNVVFKK DSKGEYKIYP  1615
CENKTQSPVL AEGAMSVVML MNVEAFREIQ A-QFLRNMSH MLRTTVRLKK DALGHDIIIN  1650

TM
EIDNRQCVQD SDHCFKNTDA AAALLASHAI QG--TLSYP LVSVVSESLT PERT-Q-LLY  1680
EIDNRQCVQA SSQCFQSATD VAAFLGALAS LCSL-NIPYK IEAVQSETVE PPPPAQ-LHF  1737
EIDNRQCYKS SSQCFNSATD VAAFLGALAS LCSLDTLSYK IEAVKSENME TPKPST-LYP  1730
EIDNRKCTEC FTHAVEAAEF LAATAAKHQL RNDFQ-IHSV RGIKNPGDED NGEPPANVKY  1745
```

FIG.13E

| | | | | | | |
|---|---|---|---|---|---|---|
| hum N | LLAVAVVIIL | FIILLGVIMA | KRKRK—HGS | LWLPEGFTLR | RDASNHKRRE | PVGQDAVGLK |
| TAN-1 | MYVAAAAFVL | LFFVGCGVLL | SRKRRRQHGQ | LWFPEGFKV- | SEASKKKRRE | ELGEDSVGLK |
| Xen N | MLSMLVIPLL | IIFVFMMVIV | NKKRRREHDS | FGSPTALFQK | NPA-KRNGET | PW-EDSVGLK |
| Dros N | VITGIILVII | ALAFFGMVL- | STQRKRAHGV | TWFPEGFRAP | AAVMSRRRRD | PHGQEMRNLN |

CDC-10/Ankyrin Repeats

| | | | | | | |
|---|---|---|---|---|---|---|
| hum N | PIDRRPWTQQ | HLEAADIRRT | PSLALTPPQA | EQEVDVLDVN | VRGPDGCTPL | MLASLRGGSS |
| TAN-1 | QTDHRQWTQQ | HLDAADL-RM | SAMAPTPPQG | EVDADCMDVN | VRGPDGFTPL | MIASCSGGGL |
| Xen N | KTDPRQWTRQ | HLDAADL-RI | SSMAPTPPQG | EIEADCMDVN | VRGPDGFTPL | MIASCSGGGL |
| Dros N | EADQRVWSQA | HLDVVDV-R- | AIM---TPP-A | HQDGGKHDVD | ARGPCGLTPL | MIAAVRGGGL |

| | | | | | | |
|---|---|---|---|---|---|---|
| hum N | ANAQDNMGRC | PLHAAVAADA | QGVFQILIRN | RVTDLDARMN | DGTTPLILAA | RLAVEGMVAE |
| TAN-1 | ANIQDNMGRT | PLHAAVSADA | QGVFQILIRN | RATDLDARMH | DGTTPLILAA | RLAVEGMLED |
| Xen N | ANVQDNMGRT | PLHAAVAADA | QGVFQILIRN | RATDLDARMF | DGTTPLILAA | RLAVEGMVEE |
| Dros N | ANCQDNTGRT | PLHAAVAADA | MGVFQILLRN | RATNLNARMH | DGTTPLILAA | RLAIEGMVED |

| | | | | | | |
|---|---|---|---|---|---|---|
| NLSVQVSEAN | LIGTGTSEHW | VDDE—— | ————G | PQPKKVKAED | EALLSE-EDD | 1782 |
| PLK-NASDGA | LMDDNQNE-W | GDED—— | ———— | LETKKFRFEE | PVVLPD-LDD | 1837 |
| PIK-NMTDGS | FMDDNQNE-W | GDEET—— | ———— | LENKRFRFEE | QVILPELVDD | 1831 |
| KQVAMQSQGV | GQPGAH—-W | SDDESDMPLP | KRQRSDPVSG | VGLGNNGGYA | SDHTMVSEYE | 1861 |

| | | | | | | |
|---|---|---|---|---|---|---|
| DLSDEDEDAE | DSSANIITDL | VYQGASLQAQ | TDRTGEMALH | LAARYSRADA | AKRLLDAGAD | 1902 |
| ETGNSEEE-E | DAPA-VISDF | IYQGASLHNQ | TDRTGETALH | LAARYSRSDA | AKRLLEASAD | 1954 |
| ETGNSEEE-E | DASANMISDF | IGQGAQLHNQ | TDRTGETALH | LAARYARADA | AKRLLESSAD | 1949 |
| DTGEDIENNE | DSTAQVISDL | LAQGAELNAT | MDKTGETSLH | LAARFARADA | AKRLLDAGAD | 1976 |

| | | | | | | |
|---|---|---|---|---|---|---|
| LINCQADVNA | VDDHGKSALH | WAAAVNNVEA | TLLLLKNGAN | RDMQDNKEET | PLFLAAREGS | 2022 |
| LINSHADVNA | VDDLGKSALH | WAAAVNNVDA | AVVLLKNGAN | KDMQNNREET | PLFLAAREGS | 2074 |
| LINAHADVNA | VDEFGKSALH | WAAAVNNVDA | AAVLLKNSAN | KDMQNNKEET | SLFLAAREGS | 2069 |
| LITADADINA | ADNSGKTALH | WAAAVNNTEA | VNILLMHHAN | RDAQDDKDET | PLFLAAREGS | 2096 |

FIG.13F

```
hum N    YEAAKILLDH FANRDITDHM DRLPRDVARD RMHHDIVRLL DEYNVTPSPP ---GTVL---TS
TAN-1    YETAKVLLDH FANRDITDHM DRLPRDIAQE RMHHDIVRLL DEYNLVRSPQ LHGAPLGGTP
Xen N    YETAKVLLDH YANRDITDHM DRLPRDIAQE RMHHDIVHLL DEYNLVKSPT LHNGPLGAT-
Dros N   YEACKALLDN FANREITDHM DRLPRDVASE RLHHDIVRLL DE-HVPRSPQ MLSMTPQAMI NLS                        CK II       cdc2        cdc2
hum N    GSRRKKSLSE KVQLSE--SS VTLSPVDSLE SPHTYVSDTT SSPM----
TAN-1    A-RRKKSQDG KGCLLD--SS GMLSPVDSLE SPHGYLSDVA SPPL----
Xen N    A-RRKKSQDG KTTLLDSGSS GVLSPVDSLE STHGYLSDVS SPPL----
Dros N   GS-PDNGLDA TGSLRRKASS KKTSAASKKA ANLNGLNPGQ LTGGVSGVPG VPPTNSAAQA
         BNTS hum N    ---------- ---------- ---------- ITSPGILQAS PNPML--ATA APPAPVHAQH
TAN-1    ---------- ---------- ---------- LPSPF--QQS PSVPLNHLPG MPDTHLGIGH
Xen N    ---------- ---------- ---------- MTSPF--QQS PSMPLNHLTS MPESQLGMNH
Dros N   YEDCIKNAQS MQSLQGNGLD MIKLDNYAYS MGSPF--QQE LLNGQGLGMN GNGQRNGVGP
         CK II                             cdc2

ALSPV----- -----ICGP NRSFLSLKHT PMGKKSRRPS AKSTMPTSLP NLAKEAKDAK   2127
TLSPP----- -----LCSP NGYLGSLKPG VQGKKVRKPS SKGLACGS-- --KEAKDLK    2178
TLSPP----- -----ICSP NGYMGNMKPS VQSKKARKPS IKGNCC---- ---KEAKELK   2170
GSPPPGQQQP QLITQPTVIS AGNGGNNGNG NASGKQSNQT AKQKAA---- ---KKAKLIE  2208

---------- ---------- ---------- ---------- ---------- ---------- 2169
---------- ---------- ---------- ---------- ---------- ---------- 2219
---------- ---------- ---------- ---------- ---------- ---------- 2213
AAAAAAAVAA MSHELEGSPV GVGMGGNLPS PYDTSSMYSN AMAAPLANGN PNTGAKQPPS   2327

ALSFSNLHEM Q--------- ---------- -PLAHGASTV LPSVSQLLSH HHIVSPCS--  2235
LNVAA-KPEM AALGGGGRLA FETGPPRLSH LPVASGTSTV LGSSSGGALN FTVGGSTSLN  2306
INMAT-KQEM AA--GSNRMA FDAMVPRLTH L-NASSPNTI MS---NGSMH FTVGGAPTMN  2294
GVLPGGLCGM GGLSGAGNCN SHEQGLSPPY SNQSPPHSVQ SSLALSPHAY LGSPSPAKSR  2445
```

FIG. 13G

```
hum N    GSAGSLSRLH PVPVPADW-- MNRMEVNETQ YNEMFGMVLA PAEG-THPGI APQSRPPEGK
TAN-1    GQCEWLSRLQ SGMVPNQYNP LRGSVAPGPL STQAPSLQHG -MVGPLHSSL AASALSQMMS
Xen N    SQCDWLARLQ NGMVQNQYDP IRNGIQQGN- AQQAQALQHG LMTS-LHNGL PATTLSQMMT
Dros N   PSLPTSPTHI QAMRHATQQK QFGGSNLNSL LGGANGGGVV GGGGGGGGGV GQGPQNSPVS hum N    APQPQSTCPP AVAGPLPTMY QIP------EM ARL-PSVAFP TAMMPQQDGQ VAQTILPAYH
TAN-1    PPQPHLGVSS AASGHLGRSF LSGEPSQADV QPLGPSSLAV HTILPQ-ESP ALPTSLPSSL
Xen N    MQQQHHN-SS TTSTHINSPF CSSDISQTDL QQM--SSNNI HSVMPQ-DTQ IFAASLPSNL
Dros N   QQQLGGLEFG SAGLDLNG-F CGSPDSFHSG QMNPPS---I QSSMSG-SSP STNMLSPSSQ hum N    SDWSDVTTSP TPGGAGGGQR GPGTHMSEPPHNN MQVYA
TAN-1    SDWSEGVSSP PT------SMQ SQIARIPEAFK
Xen N    SDWSEGISSP PT------SMQ PQRTHIPEAFK
Dros N   SDWSEGVQSP AANNLYISGG HQANKGSEAIYI ---------- ---HITTPRE PLPP-IV-TF QLIPKGSIAQ PAG------- ---------- 2320
         ---------- -YQGLPSTRL ATQPHLVQTQ QVQPQNLQMQ QQNLQPANIQ QQQSLQPPPP 2414
         ---------- -YQAMPNTRL ANQPHLMQAQ QMQQQQN--- ---------- ----LQLHQS 2384
         LGIISPTGSD MGIMLAPPQS SKNSAIMQTI SPQQQQQQQQ QQQQHQQQQ  QQQQQQQQQQ 2565

PEST-containing Region
         PFPASVGKYP TPPSQHSYAS SNAAERTPSH SGHLQGEHPY LTPSPESPDQ WSSSSPHSA- 2433
         VPPVTAAQFL TPPSQHSY-S S-PVENTPSH QLQVP-EGPF LTPSPESPDQ WSSSSPHSNV 2530
         TQSMTTAQFL TPPSQHSY-S S-PMDNTPSH QLQVP-DHPF LTPSPESPDQ WSSSSPHSNM 2497
         HNQQAFYQYL TPSSQHS--- ---GGHTPQH LVQTL-D-SY PTPSPESPGH WSSSSPRSN- 2671
                                                                          2471
                                                                          2556
                                                                          2523
                                                                          2703
```

FIG.13H

```
           10         20         30         40         50         60         70         80         90
            •          •          •          •          •          •          •          •          •
   GGAATTCCGC CCGCCCTGCG CCCCGCTCTG CTGTGGGCGC TGCTGGCCCT CTGGCTGTGC TGCGCGGCCC CCGCGCATGC ATTGCAGTGT
      P  A  L  R    P  A  L    L  W  A    L  L  A  L    W  L  C    C  A  A    P  A  H    A  L  Q  C>

100        110        120        130        140        150        160        170        180
            •          •          •          •          •          •          •          •          •
   CGAGATGGCT ATGAACCCTG TGTAAATGAA GGAATGTGTG TTACCTACCA CAATGGCACA GGATACTGCA AATGTCCAGA AGGCTTCTTG
      R  D  G    Y  E  P    C  V  N    E  G  M  C    V  T  Y    H  N  G    T  G  Y  C    K  C  P  E    G  F  L>

190        200        210        220        230        240        250        260        270
            •          •          •          •          •          •          •          •          •
   GGGGAATATT GTCAACATCG AGACCCTGT GAGAAGAACC GCTGCCAGAA TGGTGGGACT TGTGTGGCCC AGGCCATGCT GGGGAAAGCC
      G  E  Y    C  Q  H  R    D  P  C    E  K  N    R  C  Q  N    G  G  T    C  V  A    Q  A  M  L    G  K  A>

280        290        300        310        320        330        340        350        360
            •          •          •          •          •          •          •          •          •
   ACGTGCCGAT GTGCCTCAGG CGTTTACAGGA GAGGACTGCC AGTACTCAAC ATCTCATCCA TGCTTTGTGT CTCGACCCTG CCTGAATGGC
      T  C  R    C  A  S  G    F  T  G    E  D  C    Q  Y  S  T    S  H  P    C  F  V    S  R  P  C    L  N  G>

370        380        390        400        410        420        430        440        450
            •          •          •          •          •          •          •          •          •
   GGCACATGCC ATATGCTCAG CCGGGATACC TATGAGTGCA CCTGTCAAGT CGGGTTTACA GGTAAGGAGT GCCAATGGAC GGATGCCTGC
      G  T  C    H  M  L  S    R  D  T    Y  E  C    T  C  Q  V    G  F  T    G  K  E    C  Q  W  T    D  A  C>

460        470        480        490        500        510        520        530        540
            •          •          •          •          •          •          •          •          •
   CTGTCTCATC CCTGTGCAAA TGGAAGTACC TGTACCACTG TGGCCAACCA GTTCTCCTGC AAATGCCTCA CAGGCTTCAC AGGGCAGAAA
      L  S  H    P  C  A  N    G  S  T    C  T  T    V  A  N  Q    F  S  C    K  C  L    T  G  F  T    G  Q  K>

550        560        570        580        590        600        610        620        630
            •          •          •          •          •          •          •          •          •
   TGTGAGACTG ATGTCAATGA GTGTGACATT CCAGGACACT GCCAGCATGG TGGCACCTGC CTCAACCTGC CTGGTTCCTA CCAGTGCCAG
      C  E  T    D  V  N  E    C  D  I    P  G  H    C  Q  H  G    G  T  C    L  N  L    P  G  S  Y    Q  C  Q>

640        650        660        670        680        690        700        710        720
            •          •          •          •          •          •          •          •          •
   TGCCCTCAGG GCTTCACAGG CCAGTACTGT GACAGCCTGT ATGTGCCCTG TGCACCCTCA CCTTGTGTCA ATGGAGGCAC CTGTCGGCAG
      C  P  Q    G  F  T  G    Q  Y  C    D  S  L    Y  V  P  C    A  P  S    P  C  V    N  G  G  T    C  R  Q>

730        740        750        760        770        780        790        800        810
            •          •          •          •          •          •          •          •          •
   ACTGGTGACT TCACTTTTGA GTGCAACTGC CTTCCAGGTT TTGAAGGCAG CACCTGTGAG AGGAATATTG ATGACTGCCC TAACCACAGG
      T  G  D    F  T  F  E    C  N  C    L  P  G    F  E  G  S    T  C  E    R  N  I    D  D  C  P    N  H  R>
```

FIG.17A

```
        820         830        840         850        860        870        880        890        900
          •           •          •           •          •          •          •          •          •
TGTCAGAATC GAGGGGTTTG TGTGGATGCG GTCAACACTT ACAACTGCCG CTGTCCCCCA CAATGGACAG GACACTTCTG CACAGAGGAT
 C Q N      G G V      C V D G    V N T      Y N C R    C P P      Q W T      G Q F C    T E D>

910         920        930         940        950        960        970        980        990
          •           •          •           •          •          •          •          •          •
GTGGATGAAT GCCTGCTGCA GCCCAATGCC TGTCAAAATG GGGGCACCTG TGCCAACCGC AATGGAGGCT ATGGCTGTGT ATGTGTCAAC
 V D E      C L L Q    P N A      C Q N      G G T      C A N R    N G G      Y G C V    C V N>

1000        1010       1020        1030       1040       1050       1060       1070       1080
          •           •          •           •          •          •          •          •          •
GGCTGGAGTG GAGATGACTG CAGTGAGAAC ATTGATGATT GTGCCTTCGC CTCCTGTACT CCAGGCTCCA CCTGCATCGA CCGTGTGGCC
 G W S      G D D C    S E N      I D D      C A F A    S C T      P G S      T C I D    R V A>

1090        1100       1110        1120       1130       1140       1150       1160       1170
          •           •          •           •          •          •          •          •          •
TCCTTCTCTT GCATGTGCCC AGAGGGGAAG GCAGGTCTCC TGTGTCATCT GGATGATGCA TGCATCAGCA ATCCTTGCCA CAAGGGGGCA
 S F S      C M C P    E G K      A G L      L C H L    D D A      C I S      N P C H    K G A>

1180        1190       1200        1210       1220       1230       1240       1250       1260
          •           •          •           •          •          •          •          •          •
CTGTGTGACA CCAACCCCCT AAATGGGCAA TATATTTGCA CCTGCCCACA AGGCTACAAA GGGGCTGACT GCACAGAAGA TGTGGATGAA
 L C D      T N P L    N G Q      Y I C      T C P Q    G Y K      G A D      C T E D    V D E>

1270        1280       1290        1300       1310       1320       1330       1340       1350
          •           •          •           •          •          •          •          •          •
TGTGCCATGG CCAATAGCAA TCCTTGTGAG CATGCAGGAA AATGTGTGAA CACGGATGGC GCCTTCCACT GTGAGTGTCT GAAGGGTTAT
 C A M      A N S N    P C E      H A G      K C V N    T D G      A F H      C E C L    K G Y>

1360        1370       1380        1390       1400       1410       1420       1430       1440
          •           •          •           •          •          •          •          •          •
GCAGGACCTC GTTGTGAGAT GGACATCAAT GAGTGCCATT CAGACCCCTG CCAGAATGAT GCTACCTGTC TGGATAAGAT TGGAGGCTTC
 A G P      R C E M    D I N      E C H      S D P C    Q N D      A T C      L D K I    G G F>

1450        1460       1470        1480       1490       1500       1510       1520       1530
          •           •          •           •          •          •          •          •          •
ACATGTCTGT GCATGCCAGG TTTCAAAGGT GTGCATTGTG AATTAGAAAT AAATGAATGT CAGAGCAACC CTTGTGTGAA CAATGGGCAG
 T C L      C M P G    F K G      V H C      E L E I    N E C      Q S N      P C V N    N G Q>

1540        1550       1560        1570       1580       1590       1600       1610       1620
          •           •          •           •          •          •          •          •          •
TGTGTGGATA AACTCAATCG TTTCCAGTGC CTGTGTCCTC CTGGTTTCAC TGGGCCAGTT TGCCAGATTG ATATTGATGA CTGTTCCAGT
 C V D      K V N R    F Q C      L C P      P G F T    G P V      C Q I      D I D D    C S S>
```

FIG.17B

```
      1630        1640        1650        1660        1670        1680        1690        1700        1710
       *           *           *           *           *           *           *           *           *
ACTCCGTGTC TGAATGGGGC AAAGTGTATC GATCACCCGA ATGGCTATGA ATGCCAGTGT GCCACAGGTT TCACTGGTGT GTTGTGTGAG
 T  P  C    L  N  G    K  C  I    D  H  P    N  G  Y  E   C  Q  C    A  T  G    F  T  G  V    L  C  E>

1720        1730        1740        1750        1760        1770        1780        1790        1800
       *           *           *           *           *           *           *           *           *
GAGAACATTG ACAACTGTGA CCCCGATCCT TGCCACCATG GTCAGTGTCA GGATGGTATT GATTCCTACA CCTGCATCTG CAATCCCGGC
 E  N  I    D  N  C  D   P  D  P    C  H  H    G  Q  C  Q   D  G  I    D  S  Y    T  C  I  C    N  P  G>

1810        1820        1830        1840        1850        1860        1870        1880        1890
       *           *           *           *           *           *           *           *           *
TACATGGGCC CCATCTGCAG TGACCAGATT GATGAATGTT ACAGCAGCCC TTGCCTGAAC GATGGTCGCT GCATTGACCT GGTCAATGGC
 Y  M  G    A  I  C  S   D  Q  I    D  E  C    Y  S  S  P   C  L  N    D  G  R    C  I  D  L    V  N  G>

1900        1910        1920        1930        1940        1950        1960        1970        1980
       *           *           *           *           *           *           *           *           *
TACCAGTGCA ACTGCCAGCC AGGCACCTCA GGGGTTAATT GTGAAATTAA TTTTGATGAC TGTGCAAGTA ACCCTTGTAT CCATGGAATC
 Y  Q  C    N  C  Q  P   G  T  S    G  V  N    C  E  I  N   F  D  D    C  A  S    N  P  C  I    H  G  I>

1990        2000        2010        2020        2030        2040        2050        2060        2070
       *           *           *           *           *           *           *           *           *
TGTATGGATG GCATTAATCG CTACAGTTGT GTCTGCTCAC CAGGATTCAC AGGGCAGAGA TGTAACATTG ACATTGATGA GTGTGCCTCC
 C  M  D    G  I  N  R   Y  S  C    V  C  S    P  G  F  T   G  Q  R    C  N  I    D  I  D  E    C  A  S>

2080        2090        2100        2110        2120        2130        2140        2150        2160
       *           *           *           *           *           *           *           *           *
AATCCCTGTC GCAAGGGTGC AACATGTATC AACGGTGTGA ATGGTTTCCG CTGTATATGC CCCGAGGGAC CCCATCACCC CAGCTGCTAC
 N  P  C    R  K  G  A   T  C  I    N  G  V    N  G  F  R   C  I  C    P  E  G    P  H  H  P    S  C  Y>

2170        2180        2190        2200        2210        2220        2230        2240        2250
       *           *           *           *           *           *           *           *           *
TCACAGGTGA ACGAATGCCT GAGCAATCCC TGCATCCATG GAAACTGTAC TGGAGGTCTC AGTGGATATA AGTGTCTCTG TGATGCAGGC
 S  Q  V    N  E  C  L   S  N  P    C  I  H    G  N  C  T   G  G  L    S  G  Y    K  C  L  C    D  A  G>

2260        2270        2280        2290        2300        2310        2320        2330        2340
       *           *           *           *           *           *           *           *           *
TGGGTTGGCA TCAACTGTGA AGTGGACAAA AATGAATGCC TTTCGAATCC ATGCCAGAAT GGAGGAACTT GTGACAATCT GGTGAATGGA
 W  V  G    I  N  C  E   V  D  K    N  E  C    L  S  N  P   C  Q  N    G  G  T    C  D  N  L    V  N  G>

2350        2360        2370        2380        2390        2400        2410        2420        2430
       *           *           *           *           *           *           *           *           *
TACAGGTGTA CTTGCAAGAA GGGCTTTAAA GGCTATAACT GCCAGGTGAA TATTGATGAA TGTGCCTCAA ATCCATGCCT GAACCAAGGA
 Y  R  C    T  C  K  F   G  F  K    G  Y  N    C  Q  V  N   I  D  E    C  A  S    N  P  C  L    N  Q  G>
```

FIG.17C

```
         2440       2450       2460       2470       2480       2490       2500       2510       2520
           •          •          •          •          •          •          •          •          •
      ACCTGCTTTG ATGACATAAG TGGCTACACT TGCCACTGTG TGCTGCCATA CACAGGCAAG AATTGTCAGA CAGTATTGGC TCCCTGTTCC
       T C F     D D I S    G Y T      C H C      V L P Y    T G K      N C Q      T V L A    P C S>

2530       2540       2550       2560       2570       2580       2590       2600       2610
           •          •          •          •          •          •          •          •          •
      CCAAACCCTT GTGAGAATGC TGCTGTTTGC AAAGAGTCAC CAAATTTTGA GACTTATACT TGCTTGTGTC CTCCTGGCTG GCAAGGTCAG
       P N P     C E N A    A V C      K E S      P N F E    S Y T      C L C      A P G W    Q G Q>

2620       2630       2640       2650       2660       2670       2680       2690       2700
           •          •          •          •          •          •          •          •          •
      CGGTGTACCA TTGACATTGA CGAGTGTATC TCCAAGCCCT GCATGAACCA TGGTCTCTGC CATAACACCC AGGGCAGCTA CATGTGTGAA
       R C T     I D I D    E C I      S K P      C M N H    G L C      H N T      Q G S Y    M C E>

2710       2720       2730       2740       2750       2760       2770       2780       2790
           •          •          •          •          •          •          •          •          •
      TGTCCACCAG GCTTCAGTGG TATGGACTGT GAGGAGGACA TTGATGACTG CCTTGCCAAT CCTTGCCAGA ATGGAGGTTC CTGTATGGAT
       C P P     G F S G    M D C      E E D      I D D C    L A N      P C Q      N G G S    C M D>

2800       2810       2820       2830       2840       2850       2860       2870       2880
           •          •          •          •          •          •          •          •          •
      GGAGTGAATA CTTTCTCCTG CCTCTGCCTT CCGGGTTTCA CTGGGGATAA GTGCCAGACA GACATGAATG AGTGTCTGAG TGAACCCTGT
       G V N     T F S C    L C L      P G F      T G D K    C Q T      D M N      E C L S    E P C>

2890       2900       2910       2920       2930       2940       2950       2960       2970
           •          •          •          •          •          •          •          •          •
      AAGAATGGAG GGACCTGCTC TGACTACGTC AACAGTTACA CTTGCAAGTG CCAGGCAGGA TTTGATGGAG TCCATTGTGA GAACAACATC
       K N G     G T C S    D Y V      N S Y      T C K C    Q A G      F D G      V H C E    N N I>

2980       2990       3000       3010       3020       3030       3040       3050       3060
           •          •          •          •          •          •          •          •          •
      AATGAGTGCA CTGAGAGCTC CTGTTTCAAT GGTGGCACAT GTGTTGATGG GATTAACTCC TTCTCTTGCT TGTGCCCTGT GGGTTTCACT
       N E C     T E S S    C F N      G G T      C V D G    I N S      F S C      L C P V    G F T>

3070       3080       3090       3100       3110       3120       3130       3140       3150
           •          •          •          •          •          •          •          •          •
      GGATCCTTCT GCCTCCATGA GATCAATGAA TGCAGCTCTC ATCCATGCCT GAATGAGGGA ACGTGTGTTG ATGGCCTGGG TACCTACCGC
       G S F     C L H E    I N E      C S S      H P C L    N E G      T C V      D G L G    T Y R>

3160       3170       3180       3190       3200       3210       3220       3230       3240
           •          •          •          •          •          •          •          •          •
      TGCAGCTGCC CCCTGGGCTA CACTGGGAAA AACTGTCAGA CCCTGGTGAA TCTCTGCAGT CGGTCTCCAT GTAAAAACAA AGGTACTTGT
       C S C     P L G Y    T G K      N C Q      T L V N    L C S      R S P      C K N K    G T C>
```

FIG.17D

```
     3250       3260       3270       3280       3290       3300       3310       3320       3330
      *          *          *          *          *          *          *          *          *
GTTCAGAAAA AAGCAGAGTC CCAGTGCCTA TGTCCATCTG GATGGGCTGG TGCCTATTGT GACGTGCCCA ATGTCTCTTG TGACATAGCA
 V Q K K    K A E S Q    C L C P S    G W A G    A Y C D    V P N V S    C D I A>

3340       3350       3360       3370       3380       3390       3400       3410       3420
      *          *          *          *          *          *          *          *          *
GCCTCCAGGA GAGGTGTGCT TGTTGAACAC TTGTGCCACC ACTCAGGTGT CTGCATCAAT GCTGGCAACA CGCCATTACTG TCAGTGCCCC
 A S R R    G V L V E    H L C Q    H S G V C    I N A G N    T H Y C Q    C P>

3430       3440       3450       3460       3470       3480       3490       3500       3510
      *          *          *          *          *          *          *          *          *
CTGGGCTATA CTGGGAGCTA CTGTGAGGAG CAACTCGATG AGTGTGCGTC CAACCCCTGC CAGCACGGGG CAACATGCAG TGACTTCATT
 L G Y T    G S Y C E    E Q L D E    C A S N P    C Q H G    A T C S    D F I>

3520       3530       3540       3550       3560       3570       3580       3590       3600
      *          *          *          *          *          *          *          *          *
GGTGGATACA GATGCGAGTG TGTCCCAGGC TATCAGGGTG TCAACTGTGA GTATGAAGTG GATGAGTGCC AGAATCAGCC CTGCCAGAAT
 G G Y R    C E C V P    G Y Q G V    N C E Y E V    D E C Q N Q    P C Q N>

3610       3620       3630       3640       3650       3660       3670       3680       3690
      *          *          *          *          *          *          *          *          *
GGAGGCACCT GTATTGACCT TGTGAACCAT TTCAAGTGCT CTTGCCCACC AGGCACTCGG GGCCTACTCT GTGAAGAGAA CATTGATGAC
 G G T C    I D L V N    H F K C S    C P P G T    R G L L    C E E N I D D>

3700       3710       3720       3730       3740       3750       3760       3770       3780
      *          *          *          *          *          *          *          *          *
TGTGCCCCGG GTCCCCATTG CCTTAATGGT GGTCAGTGCA TGGATAGGAT TGGAGGCTAC AGTTGTCGCT GCTTGCCTGG CTTTGCTGGG
 C A R G    P H C L N    G G Q C M    D R I G    G Y S C R    C L P G F A G>

3790       3800       3810       3820       3830       3840       3850       3860       3870
      *          *          *          *          *          *          *          *          *
GAGCGTTGTG AGGGAGACAT CAACGAGTGC CTCTCCAACC CCTGCAGCTC TGAGGGCAGC CTGGACTGTA TACAGCTCAC CAATGACTAC
 E R C E    G D I N E    C L S N P    C S S E G S    L D C I Q L T    N D Y>

3880       3890       3900       3910       3920       3930       3940       3950       3960
      *          *          *          *          *          *          *          *          *
CTGTGTGTTT GCCGTAGTGC CTTTACTGGC CGGCACTGTG AAACCTTCGT CGATGTGTGT CCCCAGATGC CCTGCCTGAA TGGAGGGACT
 L C V C    R S A F T G    R H C E T F V    D V C P Q M    P C L N G G T>

3970       3980       3990       4000       4010       4020       4030       4040       4050
      *          *          *          *          *          *          *          *          *
TGTGCTGTGG CCAGTAACAT GCCTGATGGT TTCATTTGCC GTTGTCCCCC GGGATTTTCC GGGGCAAGGT GCCAGAGCAG CTGTGGACAA
 C A V A    S N M P D G    F I C R C P P    G F S G A R    C Q S S C G Q>
```

FIG.17E

```
      4060       4070       4080       4090       4100       4110       4120       4130       4140
        *          *          *          *          *          *          *          *          *
GTGAAATGTA GGAAGGGGGA GCAGTGTGTG CACACCGCCT CTGGACCCCG CTGCTTCTGC CCCAGTCCCC GGGACTGCCA GTCAGGCTGT
 V  K  C    R  K  G  E   Q  C  V   H  T  A   S  G  P    C  F  C   P  S  P    R  D  C   S  G  C>

4150       4160       4170       4180       4190       4200       4210       4220       4230
        *          *          *          *          *          *          *          *          *
GCCAGTAGCC CCTGCCAGCA CGGGGGCAGC TGCCACCCTC AGCCCAGCC  TCCTTATTAC TCCTGCCAGT GTGCCCCACC ATTCTCGGGT
 A  S  S    P  C  Q  H   G  G  S   C  H  P   Q  R  Q  P   P  Y  Y   S  C  Q   C  A  P  P   F  S  G>

4240       4250       4260       4270       4280       4290       4300       4310       4320
        *          *          *          *          *          *          *          *          *
AGCCGCTGTG AACTCTACAC GGCACCCCCC AGCACCCCTC CTGCCACCTG TCTGAGCCAG TATTGTGCCG ACAAAGCTCG GGATGGCGTC
 S  R  C    E  L  Y  T   A  P  P   S  T  P   P  A  T  C   L  S  Q   Y  C  A   D  K  A  R   D  G  V>

4330       4340       4350       4360       4370       4380       4390       4400       4410
        *          *          *          *          *          *          *          *          *
TGTGATGAGG CCTGCAACAG CCATGCCTGC CAGTGGGATG GGGGTGACTG TTCTCTCACC ATGGAGAACC CCTGGGCCAA CTGCTCCTCC
 C  D  E    A  C  N  S   H  A  C   Q  W  D   G  G  D  C   S  L  T   M  E  N   P  W  A  N   C  S  S>

4420       4430       4440       4450       4460       4470       4480       4490       4500
        *          *          *          *          *          *          *          *          *
CCACTTCCCT GCTGGGATTA TATCAACAAC CAGTGTGATG AGCTGTGCAA CACGGTCGAG TGCCTGTTTG ACAACTTTGA ATGCCAGGGG
 P  L  P    C  W  D  Y   I  N  N   Q  C  D   E  L  C  N   T  V  E   C  L  F   D  N  F  E   C  Q  G>

4510       4520       4530       4540       4550       4560       4570       4580       4590
        *          *          *          *          *          *          *          *          *
AACAGCAAGA CATGCAAGTA TGACAAATAC TGTGCAGACC ACTTCAAAGA CAACCACTGT AACCAGGGGT GCAACAGTGA GGAGTGTGGT
 N  S  K    T  C  K  Y   D  K  Y   C  A  D   H  F  K  D   N  H  C   N  Q  G   C  N  S  E   E  C  G>

4600       4610       4620       4630       4640       4650       4660       4670       4680
        *          *          *          *          *          *          *          *          *
TGGGATGGGC TGGACTGTGC TGCTGACCAA CCTGAGAACC TGGCAGAAGG TACCCTGGTT ATTGTGGTAT TGATGCCACC TGAACAACTG
 W  D  G    L  D  C  A   A  D  Q   P  E  N   L  A  E  G   T  L  V   I  V  V   L  M  P  P   E  Q  L>

4690       4700       4710       4720       4730       4740       4750       4760       4770
        *          *          *          *          *          *          *          *          *
CTCCAGGATG CTGGCAGCTT CTTGCGGGCA CTGGGTACCC TGCTCCACAC CAACCTGCGC ATTAAGCGGG ACTCCCAGGG GGAACTCATG
 L  Q  D    A  R  S  F   L  R  A   L  G  T   L  L  H  T   N  L  R   I  K  R   D  S  Q  G   E  L  M>

4780       4790       4800       4810       4820       4830       4840       4850       4860
        *          *          *          *          *          *          *          *          *
GTGTACCCCT ATTATGGTGA GAAGTCAGCT GCTATGAAGA AACAGAGGAT GACACGCAGA TCCCTTCCTG GTGAACAAGA ACAGGAGGTG
 V  Y  P    Y  Y  G  E   K  S  A   A  M  K   K  Q  R  M   T  R  R   S  L  P   G  E  Q  E   Q  E  V>
```

FIG.17F

```
         4870        4880       4890       4900       4910       4920       4930       4940       4950
          *           *          *          *          *          *          *          *          *
    GCTGGCTCTA AAGTCTTTCT CGAAATTGAC AACCGCCAGT GTGTTCAAGA CTCAGACCAC TGCTTCAAGA ACACGGATGC AGCAGCAGCT
     A G S  K V F L  E I D  N R Q  C V Q D  S D H  C F K  N T D A  A A A>

4960        4970       4980       4990       5000       5010       5020       5030       5040
          *           *          *          *          *          *          *          *          *
    CTCCTGGCCT CTCACGCCAT ACAGGGGACC CTGTCATACC CTCTTGTGTC TGTCGTCAGT GAATCCCTGA CTCCAGAACC CACTCAGCTC
     L L A  S H A I  Q G T  L S Y  P L V S  V V S  E S L  T P E R  T Q L>

5050        5060       5070       5080       5090       5100       5110       5120       5130
          *           *          *          *          *          *          *          *          *
    CTCTATCTCC TTGCTGTTGC TGTTGTCATC ATTCTGTTTA TTATTCTGCT GGGGGTAATC ATGGCAAAAC GAAAGCGTAA GCATGGCTCT
     L Y L  L A V A  V V I  I L F  I I L L  G V I  M A K R  K R K  H G S>

5140        5150       5160       5170       5180       5190       5200       5210       5220
          *           *          *          *          *          *          *          *          *
    CTCTGGCTGC CTGAAGGTTT CACTCTTCGC CGAGATGCAA GCAATCACAA GCGTCGTGAG CCAGTGGGAC AGGATGCTGT GGGGCTGAAA
     L W L  P E G F  T L R  R D A  S N H K  R R E  P V G  Q D A V  G L K>

5230        5240       5250       5260       5270       5280       5290       5300       5310
          *           *          *          *          *          *          *          *          *
    AATCTCTCAG TGCAAGTCTC AGAAGCTAAC CTAATTGGTA CTGGAACAAG TGAACACTGG GTCGATGATG AAGGCCCCCA GCCAAAGAAA
     N L S  V Q V S  E A N  L I G  T G T S  E H W  V D D  E G P Q  P K K>

5320        5330       5340       5350       5360       5370       5380       5390       5400
          *           *          *          *          *          *          *          *          *
    GTAAAGGCTG AAGATGAGGC CTTACTCTCA GAAGAAGATG ACCCCATTGA TCGACGGCCA TGGACACAGC AGCACCTTGA AGCTGCAGAC
     V K A  E D E A  L L S  E E D  D P I D  R R P  W T Q  Q H L E  A A D>

5410        5420       5430       5440       5450       5460       5470       5480       5490
          *           *          *          *          *          *          *          *          *
    ATCCGTAGGA CACCATCGCT GGCTCTCACC CCTCCTCAGG CAGAGCAGGA GGTGGATGTG TTAGATGTGA ATGTCCGTGG CCCAGATGGC
     I R R  T P S L  A L T  P P Q  A E Q E  V D V  L D V  N V R G  P D G>

5500        5510       5520       5530       5540       5550       5560       5570       5580
          *           *          *          *          *          *          *          *          *
    TGCACCCCAT TGATGTTGGC TTCTCTCCGA GGAGGCAGCT CAGATTTGAG TGATGAAGAT GAAGATGCAG AGGACTCTTC TGCTAACATC
     C T P  L M L A  S L R  G G S  S D L S  D E D  E D A  E D S S  A N I>

5590        5600       5610       5620       5630       5640       5650       5660       5670
          *           *          *          *          *          *          *          *          *
    ATCACAGACT TGGTCTACCA GGGTGCCAGC CTCCAGGCCC AGACAGACCG GACTGGTGAG ATGGCCCTGC ACCTTGCAGC CCGCTACTCA
     I T D  L V Y Q  G A S  L Q A  Q T D R  T G E  M A L  H L A A  R Y S>
```

FIG.17G

```
        5680       5690       5700       5710       5720       5730       5740       5750       5760
          *          *          *          *          *          *          *          *          *
    CGGGCTGATG CTGCCAAGCG TCTCCTGGAT GCAGGTGCAG ATGCCAATGC CCAGGACAAC ATGGGCCGCT GTCCACTCCA TGCTGCAGTG
     R  A  D   A  A  K  R   L  L  D   A  G  A   D  A  N  A   Q  D  N   M  G  R   C  P  L  H   A  A  V>

5770       5780       5790       5800       5810       5820       5830       5840       5850
          *          *          *          *          *          *          *          *          *
    GCAGCTGATG CCCAACGTGT CTTCCAGATT CTGATTCGCA ACCGAGTAAC TGATCTAGAT GCCAGGATGA ATGATGGTAC TACACCCCTG
     A  A  D   A  Q  G  V   F  Q  I   L  I  R   N  R  V  T   D  L  D   A  R  M   N  D  G  T   T  P  L>

5860       5870       5880       5890       5900       5910       5920       5930       5940
          *          *          *          *          *          *          *          *          *
    ATCCTGGCTG CCCGCCTGGC TGTGGAGGGA ATGGTGGCAG AACTGATCAA CTGCCAAGCC GATGTGAATG CAGTGGATGA CCATGGAAAA
     I  L  A   A  R  L  A   V  E  G   M  V  A   E  L  I  N   C  Q  A   D  V  N   A  V  D  D   H  G  K>

5950       5960       5970       5980       5990       6000       6010       6020       6030
          *          *          *          *          *          *          *          *          *
    TCTGCTCTTC ACTGGGCAGC TGCTGTCAAT AATGTGGAGG CAACTCTTTT GTTGTTGAAA AATGGGGCCA ACCGAGACAT GCAGGACAAC
     S  A  L   H  W  A  A   A  V  N   N  V  E   A  T  L  L   L  L  K   N  G  A   N  R  D  M   Q  D  N>

6040       6050       6060       6070       6080       6090       6100       6110       6120
          *          *          *          *          *          *          *          *          *
    AAGGAAGAGA CACCTCTGTT TCTTGCTGCC CGGGAGGGGA GCTATGAAGC AGCCAAGATC CTGTTAGACC ATTTTGCCAA TCGAGACATC
     K  E  E   T  P  L  F   L  A  A   R  E  G   S  Y  E  A   A  K  I   L  L  D   H  F  A  N   R  D  I>

6130       6140       6150       6160       6170       6180       6190       6200       6210
          *          *          *          *          *          *          *          *          *
    ACAGACCATA TGGATCGTCT TCCCCGGGAT GTGGCTCGGG ATCGCATGCA CCATGACATT GTGCGCCTTC TGGATGAATA CAATGTGACC
     T  D  H   M  D  R  L   P  R  D   V  A  R   D  R  M  H   H  D  I   V  R  L   L  D  E  Y   N  V  T>

6220       6230       6240       6250       6260       6270       6280       6290       6300
          *          *          *          *          *          *          *          *          *
    CCAAGCCCTC CAGGCACCGT GTTGACTTCT GCTCTCTCAC CTGTCATCTG TGGGCCCAAC AGATCTTTCC TCAGCCTGAA GCACACCCCA
     P  S  P   P  G  T  V   L  T  S   A  L  S   P  V  I  C   G  P  N   R  S  F   L  S  L  K   H  T  P>

6310       6320       6340       6350       6360       6370       6380       6390       6400
          *          *          *          *          *          *          *          *          *
    ATGGGCAAGA AGTCTAGACG GCCCAGTGCC AAGAGTACCA TGCCTACTAG CCTCCCTAAC CTTGCCAAGG AGGCAAAGGA TGCCAAGGGT
     M  G  K   K  S  R  R   P  S  A   K  S  T   M  P  T  S   L  P  N   L  A  K   E  A  K  D   A  K  G>

6400       6410       6420       6430       6440       6450       6460       6470       6480
          *          *          *          *          *          *          *          *          *
    AGTAGGAGGA AGAAGTCTCT GAGTGAGAAG GTCCAACTGT CTGAGAGTTC AGTAACTTTA TCCCCTGTTG ATTCCCTAGA ATCTCCTCAC
     S  R  R   K  K  S  L   S  E  K   V  Q  L   S  E  S  S   V  T  L   S  P  V   D  S  L  E   S  P  H>
```

FIG.17H

```
      6490       6500       6510       6520       6530       6540       6550       6560       6570
        •          •          •          •          •          •          •          •          •
ACGTATGTTT CCGACACCAC ATCCTCTCCA ATGATTACAT CCCCTGGGAT CTTACAGGCC TCACCCAACC CTATGTTGGC CACTGCCGCC
 T Y V   S D T T   S S P   M I T   S P G I   L Q A   S P N   P M L A   T A A>

6580       6590       6600       6610       6620       6630       6640       6650       6660
        •          •          •          •          •          •          •          •          •
CCTCCTGCCC CAGTCCATGC CCAGCATGCA CTATCTTTTT CTAACCTTCA TGAAATGCAG CCTTTGGCAC ATGGGGCCAG CACTGTGCTT
 P P A   P V H A   Q H A   L S F   S N L H   E M Q   P L A   H G A S   T V L>

6670       6680       6690       6700       6710       6720       6730       6740       6750
        •          •          •          •          •          •          •          •          •
CCCTCAGTGA GCCAGTTGCT ATCCCACCAC CACATTGTGT CTCCAGGCAG TGGCAGTGCT GGAAGCTTGA GTAGGCTCCA TCCAGTCCCA
 P S V   S Q L L   S H H   H I V   S P G S   G S A   G S L   S R L H   P V P>

6760       6770       6780       6790       6800       6810       6820       6830       6840
        •          •          •          •          •          •          •          •          •
GTCCCACCAG ATTGGATGAA CCGCATGGAG GTGAATGAGA CCCAGTACAA TGAGATGTTT GGTATGGTCC TGGCTCCAGC TGAGGGCACC
 V P A   D W M N   R M E   V N E   T Q Y N   E M F   G M V   L A P A   E G T>

6850       6860       6870       6880       6890       6900       6910       6920       6930
        •          •          •          •          •          •          •          •          •
CATCCTGGCA TAGCTCCCCA GAGCAGGCCA CCTGAAGGGA AGCACATAAC CACCCCTCGG GAGCCCTTGC CCCCCATTGT GACTTTCCAG
 H P G   I A P Q   S R P   P E G   K H I T   T P R   E P L   P P I V   T F Q>

6940       6950       6960       6970       6980       6990       7000       7010       7020
        •          •          •          •          •          •          •          •          •
CTCATCCCTA AAGGCAGTAT TGCCCAACCA GCGGGGGCTC CCCAGCCTCA GTCCACCTGC CCTCCAGCTG TTGCGGGCCC CCTGCCCACC
 L I P   K G S I   A Q P   A G A   P Q P Q   S T C   P P A   V A G P   L P T>

7030       7040       7050       7060       7070       7080       7090       7100       7110
        •          •          •          •          •          •          •          •          •
ATGTACCAGA TTCCAGAAAT GGCCCGTTTG CCCAGTGTGG CTTTCCCCAC TGCCATGATG CCCCAGCAGG ACGGGCAGGT AGCTCAGACC
 M Y Q   I P E M   A R L   P S V   A F P T   A M M   P Q Q   D G Q V   A Q T>

7120       7130       7140       7150       7160       7170       7180       7190       7200
        •          •          •          •          •          •          •          •          •
ATTCTCCCAG CCTATCATCC TTTCCCAGCC TCTGTGGGCA AGTACCCCAC ACCCCCTTCA CAGCACAGTT ATGCTTCCTC AAATGCTGCT
 I L P   A Y H P   F P A   S V G   K Y P T   P P S   Q H S   Y A S S   N A A>

7210       7220       7230       7240       7250       7260       7270       7280       7290
        •          •          •          •          •          •          •          •          •
GAGCGAACAC CCAGTCACAG TGGTCACCTC CAGGGTGAGC ATCCCTACCT GACACCATCC CCAGAGTCTC CTGACCAGTG GTCAAGTTCA
 E R T   P S H S   G H L   Q G E   H P Y L   T P S   P E S   P D Q W   S S S>
```

FIG.171

```
            7300       7310       7320       7330       7340       7350       7360       7370       7380
              *          *          *          *          *          *          *          *          *
        TCACCCCACT CTGCTTCTGA CTGGTCAGAT GTGACCACCA GCCCTACCCC TGGGGGTGCT GGAGGACGTC AGCGGGGACC TGGGACACAC
         S  P  H  S  A  S  D  W  S  D  V  T  T  S  P  T  P  G  G  A  G  G  Q  R  G  P  G  T  H>

7390       7400       7410       7420       7430       7440       7450       7460       7470
              *          *          *          *          *          *          *          *          *
        ATGTCTGAGC CACCACACAA CAACATGCAG GTTTATGCGT GAGAGAGTCC ACCTCCACTG TAGACACATA ACTGACTTTT GTAAATGCTG
         M  S  E  P  P  H  N  N  M  Q  V  Y  A>

7480       7490       7500       7510       7520       7530       7540       7550       7560
              *          *          *          *          *          *          *          *          *
        CTGAGGAACA AATGAAGGTC ATCCGGCAGA GAAATGAAGA AATCTCTGGA GCCAGCTTCT AGAGGTAGGA AAGAGAAGAT GTTCTTATTC 7570       7580       7590       7600       7610       7620       7630       7640       7650
              *          *          *          *          *          *          *          *          *
        AGATAATGCA AGAGAAGCAA TTCGTCAGTT TCACTGGGTA TCTGCAAGGC TTATTGATTA TTCTAATCTA ATAAGACAAG TTTGTGGAAA 7660       7670       7680       7690       7700       7710       7720       7730       7740
              *          *          *          *          *          *          *          *          *
        TGCAAGATGA ATACAAGCCT TGGGTCCATG TTTACTCTCT TCTATTTGGA GAATAAGATG GATGCTTATT GAAGCCCAGA CATTCTTGCA 7750       7760       7770       7780       7790       7800       7810       7820       7830
              *          *          *          *          *          *          *          *          *
        GCTTGGACTG CATTTTAAGC CCTGCAGGCT TCTGCCATAT CCATGAGAAG ATTCTACACT AGCCTCCTGT TGGGAATTAT GCCCTGGAAT 7840       7850       7860       7870       7880       7890       7900       7910       7920
              *          *          *          *          *          *          *          *          *
        TCTGCCTGAA TTGACCTACG CATCTCCTCC TCCTTGGACA TTCTTTTGTC TTCATTTGGT GCTTTTGGTT TTGCACCTCT CCGTGATTGT 7930       7940       7950       7960       7970       7980       7990       8000       8010
              *          *          *          *          *          *          *          *          *
        AGCCCTACCA GCATGTTATA GGGCAAGACC TTTGTGCTTT TGATCATTCT GGCCCATGAA AGCAACTTTG GTCTCCTTTC CCTCCTGTC 8020       8030       8040       8050       8060       8070       8080       8090       8100
              *          *          *          *          *          *          *          *          *
        TTCCCGGTAT CCCTTGGAGT CTCACAAGGT TTACTTTGGT ATGGTTCTCA GCACAAACCT TTCAAGTATG TTGTTTCTTT GGAAAATGGA 8110       8120       8130       8140       8150       8160       8170       8180       8190
              *          *          *          *          *          *          *          *          *
        CATACTGTAT TGTGTTCTCC TGCATATATC ATTCCTGGAG AGAGAAGGGG AGAAGAATAC TTTTCTTCAA CAAATTTTGG GGGCAGGAGA 8200       8210       8220       8230       8240       8250       8260       8270       8280
              *          *          *          *          *          *          *          *          *
        TCCCTTCAAG AGGCTGCACC TTAATTTTTC TTGTCTGTGT GCAGGTCTTC ATATAAACTT TACCAGGAAG AAGGGTGTGA GTTTGTTGTT
```

FIG.17J

```
8290       8300       8310       8320       8330       8340       8350       8360       8370
  *          *          *          *          *          *          *          *          *
TTTCTGTGTA TGGGCCTGGT CAGTGTAAAG TTTTATCCTT GATAGTCTAG TTACTATGAC CCTCCCCACT TTTTTAAAAC CACAAAAAGG 8380       8390       8400       8410       8420       8430       8440       8450       8460
  *          *          *          *          *          *          *          *          *
TTTGGAATGT TGGAATGACC AAGAGACAAC TTAACTCGTG CAAGAGCCAG TTACCCACCC ACAGGTCCCC CTACTTCCTG CCAAGCATTC 8470       8480       8490       8500       8510       8520       8530       8540       8550
  *          *          *          *          *          *          *          *          *
CATTGACTGC CTGTATGGAA CACATTTGTC CCAGATCTGA GCATTCTAGG CCTGTTTCAC TCACTCACCC AGCATATGAA ACTAGTCTTA 8560       8570       8580       8590       8600       8610       8620       8630       8640
  *          *          *          *          *          *          *          *          *
ACTGTTGAGC CTTTCCTTTC ATATCCACAG AAGACACTGT CTCAAATGTT GTACCCTTGC CATTTAGGAC TGAACTTTCC TTAGCCCAAG 8650       8660       8670       8680       8690       8700       8710       8720       8730
  *          *          *          *          *          *          *          *          *
GGACCCAGTG ACAGTTGTCT TCCGTTTGTC AGATGATCAG TCTCTACTGA TTATCTTGCT GCTTAAAGGC CTGCTCACCA ATCTTTCTTT 8740       8750       8760       8770       8780       8790       8800       8810       8820
  *          *          *          *          *          *          *          *          *
CACACCGTGT GGTCCGTGTT ACTGGTATAC CCAGTATGTT CTCACTGAAG ACATGGACTT TATATGTTCA AGTGCAGGAA TTGGAAAGTT 8830       8840       8850       8860       8870       8880       8890       8900       8910
  *          *          *          *          *          *          *          *          *
GGACTTGTTT TCTATGATCC AAAACAGCCC TATAAGAAGG TTGGAAAAGG AGGAACTATA TAGCAGCCTT TGCTATTTTC TGCTACCATT 8920       8930       8940       8950       8960       8970       8980       8990       9000
  *          *          *          *          *          *          *          *          *
TCTTTTCCTC TGAAGCGGCC ATGACATTCC CTTTGGCAAC TAACGTAGAA ACTCAACAGA ACATTTTCCT TTCCTAGAGT CACCTTTTAG 9010       9020       9030       9040       9050       9060       9070       9080       9090
  *          *          *          *          *          *          *          *          *
ATGATAATGG ACAACTATAG ACTTGCTCAT TGTTCAGACT GATTGCCCCT CACCTGAATC CACTCTCTGT ATTCATGCTC TTGGCAATTT 9100       9110       9120       9130       9140       9150       9160       9170       9180
  *          *          *          *          *          *          *          *          *
CTTTGACTTT CTTTTAAGGG CAGAAGCATT TTAGTTAATT GTAGATAAAG AATAGTTTTC TTCCTCTTCT CCTTGGGCCA GTTAATAATT 9190       9200       9210       9220       9230       9240       9250       9260       9270
  *          *          *          *          *          *          *          *          *
GGTCCATGGC TACACTGCAA CTTCCGTCCA GTGCTGTGAT GCCCATGACA CCTGCAAAAT AAGTTCTGCC TGGGCATTTT GTAGATATTA
```

FIG.17K

```
      9280       9290       9300       9310       9320       9330       9340       9350       9360
        *          *          *          *          *          *          *          *          *
ACAGGTGAAT TCCCGACTCT TTTGGTTTGA ATGACAGTTC TCATTCCTTC TATGCCTGCA AGTATGCATC AGTGCTTCCC ACTTACCTGA 9370       9380       9390       9400       9410       9420       9430       9440       9450
        *          *          *          *          *          *          *          *          *
TTTGTCTGTC GGTGGCCCCA TATGGAAACC CTGCGTGTCT GTTGGCATAA TAGTTTACAA ATGGTTTTTT CAGTCCTATC CAAATTTATT 9460       9470       9480       9490       9500       9510       9520       9530       9540
        *          *          *          *          *          *          *          *          *
GAACCAACAA AAATAATTAC TTCTGCCCTG AGATAAGCAG ATTAAGTTTG TTCATTCTCT GCTTTATTCT CTCCATGTGG CAACATTCTG 9550       9560       9570       9580       9590       9600       9610       9620       9630
        *          *          *          *          *          *          *          *          *
TCAGCCTCTT TCATAGTGTG CAAACATTTT ATCATTCTAA ATGGTGACTC TCTGCCCTTG GACCCATTTA TTATTCACAG ATGGGAGAA 9640       9650       9660       9670       9680       9690       9700       9710       9720
        *          *          *          *          *          *          *          *          *
CCTATCTGCA TGGACCCTCA CCATCCTCTG TGCAGCACAC ACAGTGCAGG GAGCCAGTGG CGATGGCGAT GACTTTCTTC CCCTGGGAAT

TCC
```

FIG.17L

12
THERAPEUTIC AND DIAGNOSTIC METHODS AND COMPOSITIONS BASED ON NOTCH PROTEINS AND NUCLEIC ACIDS

This application is a continuation-in-part of both application Ser. No. 07/955,012 filed Sep. 30, 1992, now abandoned, and application Ser. No. 07/879,038 filed Apr. 30, 1992, now abandoned, each of which is incorporated by reference herein in its entirety.

This invention was made in part with government support under grant numbers GM 29093 and NS 26084 awarded by the National Institutes of Health. The government has certain rights in the invention.

TABLE OF CONTENTS

1. INTRODUCTION
2. BACKGROUND OF THE INVENTION
   2.1. The Notch Gene and Protein
   2.2. Cancer
3. SUMMARY OF THE INVENTION
   3.1. Definitions
4. DESCRIPTION OF THE FIGURES
5. DETAILED DESCRIPTION OF THE INVENTION
   5.1. Therapeutic Uses
      5.1.1. Malignancies
      5.1.2. Nervous System Disorders
      5.1.3. Tissue Repair and Regeneration
   5.2. Prophylactic Uses
      5.2.1. Malignancies
      5.2.2. Other Disorders
   5.3. Demonstration of Therapeutic or Prophylactic Utility
   5.4. Therapeutic/Prophylactic Administration and Composition
   5.5. Antisense Regulation of Notch Expression
      5.5.1. Notch Antisense Nucleic Acids
      5.5.2. Therapeutic Utility of Notch Antisense Nucleic Acids
   5.6. Diagnostic Utility
   5.7. Notch Nucleic Acids
   5.8. Recombinant Production of Protein Therapeutics
      5.8.1. Identification and Purification of the Expressed Gene Product
   5.9. Derivatives and Analogs of Notch and Other Toporythmic Proteins
      5.9.1. Derivatives of Notch Containing One or More Domains of the Protein
      5.9.2. Derivatives of Notch or Other Toporythmic Proteins that Mediate Binding to Toporythmic Protein Domains, and Inhibitors Thereof
   5.10. Assays of Notch Proteins, Derivatives and Analogs
   5.11. Antibodies to Notch Proteins, Derivatives and Analogs
6. DOMAINS OF NOTCH MEDIATE BINDING WITH DELTA
   6.1. Experimental Procedures
      6.1.1. Expression Constructs
      6.1.2. Antibody Preparation
      6.1.3. Cell Culture and Transfection
      6.1.4. Aggregation Assays
      6.1.5. Immunofluorescence
      6.1.6. Cell Lysates, Immunoprecipitations, and Western Blots
   6.2. Results
      6.2.1. The Expression of Notch and Delta in Cultured Cells
      6.2.2. Cells that Express Notch and Delta Aggregate
      6.2.3. Notch-Delta-Mediated Aggregation is Calcium Dependent
      6.2.4. Notch and Delta Interact within a Single Cell
      6.2.5. Interactions with Delta Do Not Require the Intracellular Domain of Notch
      6.2.6. Notch and Delta Form Detergent-Soluble Intermolecular Complexes
   6.3. Discussion
7. EGF REPEATS 11 AND 12 OF NOTCH ARE REQUIRED AND SUFFICIENT FOR NOTCH-DELTA-MEDIATED AGGREGATION
   7.1. Experimental Procedures
      7.1.1. Expression Constructs
      7.1.2. Cell Culture and Transfection
      7.1.3. Aggregation Assays and Immunofluorescence
   7.2. Results
      7.2.1. EGF Repeats 11 and 12 of Notch are Required for Notch-Delta Mediated Aggregation
      7.2.2. EGF Repeats 11 and 12 of Notch are Sufficient for Notch-Delta Mediated Aggregation
      7.2.3. EGF Repeats 11 and 12 of Notch Maintain the Calcium Dependence of Notch-Delta Mediated Aggregation
      7.2.4. The Delta Binding Function of EGF Repeats 11 and 12 of Notch is Conserved in the Xenopus Homolog of Notch
   7.3. Discussion
8. SEQUENCES WHICH MEDIATE NOTCH-SERRATE INTERACTIONS
9. THE CLONING, SEQUENCING, AND EXPRESSION OF HUMAN NOTCH
   9.1. Isolation and Sequencing of Human Notch
   9.2. Expression of Human Notch
10. NOTCH EXPRESSION IN NORMAL AND MALIGNANT CELLS
    10.1. Expression of Human Notch Protein is Increased in Various Malignancies
11. DEPOSIT OF MICROORGANISMS

1. INTRODUCTION

The present invention relates to therapeutic compositions comprising Notch proteins, analogs and derivatives thereof, antibodies thereto, nucleic acids encoding the Notch proteins, derivatives or analogs, Notch antisense nucleic acids, and toporythmic proteins which bind to Notch and their nucleic acids and antibodies. Therapeutic and diagnostic methods are also provided.

2. BACKGROUND OF THE INVENTION

2.1. The Notch Gene and Protein

Null mutations in any one of the zygotic neurogenic loci—Notch (N), Delta (Dl), mastermind (mam), Enhancer of Split (E(spl), neuralized (neu), and big brain (bib)—result in hypertrophy of the nervous system at the expense of ventral and lateral epidermal structures. This effect is due to the misrouting of epidermal precursor cells into a neuronal pathway, and implies that neurogenic gene function is necessary to divert cells within the neurogenic region from a neuronal fate to an epithelial fate. Studies that assessed the effects of laser ablation of specific embryonic neuroblasts in grasshoppers (Doe and Goodman 1985, Dev. Biol. 111, 206–219) have shown that cellular interactions between neuroblasts and the surrounding accessory cells serve to inhibit these accessory cells from adopting a neuroblast fate. Together, these genetic and developmental observations have led to the hypothesis that the protein products of the neurogenic loci function as components of a cellular interaction mechanism necessary for proper epidermal development (Artavanis-Tsakonas, 1988. Trends Genet. 4, 95–100).

Sequence analyses (Wharton et al., 1985, Cell 43, 567–581; Kidd et al., 1986, Mol. Cell. Biol. 6, 3094–3108; Vassin et al., 1987, EMBO J. 6, 3431–3440; Kopczynski et al., 1988, Genes Dev. 2, 1723–1735) have shown that two of the neurogenic loci, Notch and Delta, appear to encode transmembrane proteins that span the membrane a single time. The Drosophila Notch gene encodes a ~300 kd protein (we use "Notch" to denote this protein) with a large N-terminal extracellular domain that includes 36 epidermal growth factor (EGF)-like tandem repeats followed by three other cysteine-rich repeats, designated Notch/lin-12 repeats (Wharton et al., 1985, Cell 43, 567–581; Kidd et al., 1986, Mol. Cell Biol. 6, 3094–3108; Yochem et al., 1988, Nature 335, 547–550). The sequences of Xenopus (Coffman et al., 1990, Science 249:1438–1441) and a human Notch homolog termed TAN-1 (Ellisen et al., 1991, Cell 66:649–661) have also been reported. Delta encodes a ~100 kd protein (we use "Delta" to denote DLZM, the protein product of the predominant zygotic and maternal transcripts; Kopczynski et al., 1988, Genes Dev. 2, 1723–1735) that has nine EGF-like repeats within its extracellular domain (Vassin et al., 1987, EMBO J. 6, 3431–3440; Kopczynski et al., 1988, Genes Dev. 2, 1723–1735). Although little is known about the functional significance of these repeats, the EGF-like motif has been found in a variety of proteins, including those involved in the blood clotting cascade (Furie and Furie, 1988, Cell 53, 505–518). In particular, this motif has been found in extracellular proteins such as the blood clotting factors IX and X (Rees et al., 1988, EMBO J. 7, 2053–2061; Furie and Furie, 1988, Cell 53, 505–518), in other Drosophila genes (Knust et al., 1987, EMBO J. 761–766; Rothberg et al., 1988, Cell 55, 1047–1059), and in some cell-surface receptor proteins, such as thrombomodulin (Suzuki et al., 1987, EMBO J. 6, 1891–1897) and LDL receptor (Sudhof et al., 1985, Science 228, 815–822). A protein binding site has been mapped to the EGF repeat domain in thrombomodulin and urokinase Kurosawa et al., 1988, J. Biol. Chem 263, 5993–5996; Appella et al., 1987, J. Biol. Chem. 262, 4437–4440).

An intriguing array of interactions between Notch and Delta mutations has been described (Vassin, et al., 1985, J. Neurogenet. 2, 291–308; Shepard et al., 1989, Genetics 122, 429–438; Xu et al., 1990, Genes Dev., 4, 464–475). A number of genetic studies (summarized in Alton et al., 1989, Dev. Genet. 10, 261–272) has indicated that the gene dosages of Notch and Delta in relation to one another are crucial for normal development. A 50% reduction in the dose of Delta in a wild-type Notch background causes a broadening of the wing veins creating a "delta" at the base (Lindsley and Grell, 1968, Publication Number 627, Washington, D.C., Carnegie Institute of Washington). A similar phenotype is caused by a 50% increase in the dose of Notch in a wild-type Delta background (a "Confluens" phenotype; Welshons, 1965, Science 150, 1122–1129). This Delta phenotype is partially suppressed by a reduction in the Notch dosage. Work has shown that lethal interactions between alleles that correlate with alterations in the EGF-like repeats in Notch can be rescued by reducing the dose of Delta (Xu et al., 1990, Genes Dev. 4, 464–475). Xu et al. (1990, Genes Dev. 4, 464–475) found that null mutations at either Delta or mam suppress lethal interactions between heterozygous combinations of certain Notch alleles, known as the Abruptex (Ax) mutations. Ax alleles are associated with missense mutations within the EGF-like repeats of the Notch extracellular domain (Kelley et al., 1987, Cell 51, 539–548; Hartley et al., 1987, EMBO J. 6, 3407–3417).

Recent studies have shown that Notch and Delta, and Notch and Serrate, directly interact on the molecular level (Fehon et al., 1990, Cell 61:523–534; Rebay et al., 1991, Cell 67:687–699).

Notch is expressed on axonal processes during the outgrowth of embryonic neurons (Johansen et al., 1989, J. Cell Biol. 109:2427–2440; Kidd et al., 1989, Genes Dev. 3:1113–1129; Fehon et al., 1991, J. Cell Biol. 113:657–669).

A study has shown that certain Ax alleles of Notch can severely alter axon pathfinding during sensory neural outgrowth in the imaginal discs, although it is not yet known whether aberrant Notch expression in the axon itself or the epithelium along which it grows is responsible for this defect (Palka et al., 1990, Development 109, 167–175).

2.2. Cancer

A neoplasm, or tumor, is a neoplastic mass resulting from abnormal uncontrolled cell growth, which may cause swelling on the body surface, and which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68–122).

Effective treatment and prevention of cancer remains a long-felt need, and a major goal of biomedical research.

3. SUMMARY OF THE INVENTION

The present invention relates to therapeutic and diagnostic methods and compositions based on Notch proteins and nucleic acids. The invention provides for treatment of disorders of cell fate or differentiation by administration of a therapeutic compound of the invention. Such therapeutic compounds (termed herein "Therapeutics") include: Notch proteins and analogs and derivatives (including fragments) thereof; antibodies thereto; nucleic acids encoding the Notch proteins, analogs, or derivatives; Notch antisense nucleic acids; as well as toporythmic proteins and derivatives which bind to or otherwise interact with Notch proteins, and their encoding nucleic acids and antibodies. In a preferred embodiment, a Therapeutic of the invention is administered to treat a cancerous condition, or to prevent progression from a pre-neoplastic or non-malignant state into a neoplastic or a malignant state. In other specific embodiments, a Therapeutic of the invention is administered to treat a nervous system disorder or to promote tissue regeneration and repair.

In one embodiment, Therapeutics which antagonize, or inhibit, Notch function (hereinafter "Antagonist Therapeutics") are administered for therapeutic effect; disorders which can be thus treated can be identified by in vitro assays such as described in Section 5.1, infra. Such Antagonist Therapeutics include but are not limited to Notch antisense nucleic acids, anti-Notch neutralizing antibodies, and competitive inhibitors of Notch protein-protein interactions (e.g., a protein comprising Notch ELR-11 and ELR-12 and derivatives thereof), all as detailed infra.

In another embodiment, Therapeutics which promote Notch function (hereinafter "Agonist Therapeutics") are administered for therapeutic effect; disorders which can thus be treated can be identified by in vitro assays such as described in Section 5.1, infra. Such Agonist Therapeutics include but are not limited to Notch proteins and derivatives thereof comprising the intracellular domain, and proteins that interact with Notch (e.g., a protein comprising a Delta sequence homologous to Drosophila Delta amino acids 1–230 (see FIGS. 1A–1F and SEQ ID NO:2), or comprising a Serrate sequence homologous to Drosophila Serrate amino acids 79–282 (see FIGS. 5A–5B and SEQ ID NO:4)).

Disorders of cell fate, in particular hyperproliferative (e.g., cancer) or hypoproliferative disorders, involving aberrant or undesirable levels of expression or activity of Notch protein can be diagnosed by detecting such levels, as described more fully infra.

In a preferred aspect, a Therapeutic of the invention is a protein consisting of at least a fragment (termed herein "adhesive fragment") of the proteins encoded by toporythmic genes which mediates binding to Notch proteins or adhesive fragments thereof. Toporythmic genes, as used herein, shall mean the genes Notch, Delta, and Serrate, as well as other members of the Delta/Serrate family which may be identified by virtue of sequence homology or genetic interaction, and in general, members of the "Notch cascade" or the "Notch group" of genes, which are identified by molecular interactions (e.g., binding in vitro) or genetic interactions (as detected phenotypically, e.g., in Drosophila).

In another aspect, the invention is directed to human Notch proteins; in particular, that encoded by the hN homolog, and proteins comprising the extracellular domain of the protein and subsequences thereof. Nucleic acids encoding the foregoing, and recombinant cells are also provided.

3.1. Definitions

As used herein, the following terms shall have the meanings indicated:

AA=amino acid

EGF=epidermal growth factor

ELR=EGF-like (homologous) repeat

IC=intracellular

PCR=polymerase chain reaction

As used herein, underscoring the name of a gene shall indicate the gene, in contrast to its encoded protein product which is indicated by the name of the gene in the absence of any underscoring. For example, "Notch" shall mean the Notch gene, whereas "Notch" shall indicate the protein product of the Notch gene.

4. DESCRIPTION OF THE FIGURES

FIGS. 1A–1F Primary Nucleotide Sequence of the Delta cDNA Dl1 (SEQ ID NO:1), and Delta amino acid sequence (SEQ ID NO:2). The DNA sequence of the 5'-3' strand of the Dl1 cDNA is shown, which contains a number of corrections in comparison to that presented in Kopczynkski et al. (1988, Genes Dev. 2:1723–1735).

FIGS. 2A–2B. Notch Expression Constructs and the Deletion Mapping of the Delta/Serrate Binding Domain. S2 cells in log phase growth were transiently transfected with the series of expression constructs shown; the drawings represent the predicted protein products of the various Notch deletion mutants created. All expression constructs were derived from construct #1 pMtNMg. Transiently transfected cells were mixed with Delta expressing cells from the stably transformed line L49-6-7 or with transiently transfected Serrate expressing cells, induced with $CuSO_4$, incubated under aggregation conditions and then scored for their ability to aggregate using specific antisera and immunofluorescence microscopy. Aggregates were defined as clusters of four or more cells containing both Notch and Delta/Serrate expressing cells. The values given for % Aggregation refer to the percentage of all Notch expressing cells found in such clusters either with Delta (Dl) (left column) or with Serrate (Ser) (right column). The various Notch deletion constructs are represented diagrammatically with splice lines indicating the ligation junctions. Each EGF repeat is denoted as a stippled rectangular box and numbers of the EGF repeats on either side of a ligation junction are noted. At the ligation junctions, partial EGF repeats produced by the various deletions are denoted by open boxes and closed brackets (for example see #23 ΔCla+EGF(10–12)). Constructs #3–13 represent the ClaI deletion series. As diagrammed, four of the ClaI sites, in repeats 7, 9, 17 and 26, break the repeat in the middle, immediately after the third cysteine (denoted by open box repeats; see FIG. 3 for further clarification), while the fifth and most 3' site breaks neatly between EGF repeats 30 and 31 (denoted by closed box repeat 31; again see FIG. 3). In construct #15 split, EGF repeat 14 which carries the split point mutation, is drawn as a striped box. In construct #33 ΔCla+XEGF(10–13), the Xenopus Notch derived EGF repeats are distinguished from Drosophila repeats by a different pattern of shading. SP, signal peptide; EGF, epidermal growth factor repeat; N, Notch/lin-12 repeat; TM, transmembrane domain; cdc10, cdc10/ankyrin repeats; PA, putative nucleotide binding consensus sequence; opa, polyglutamine stretch termed opa; Dl, Delta; Ser, Serrate.

Figure 3:
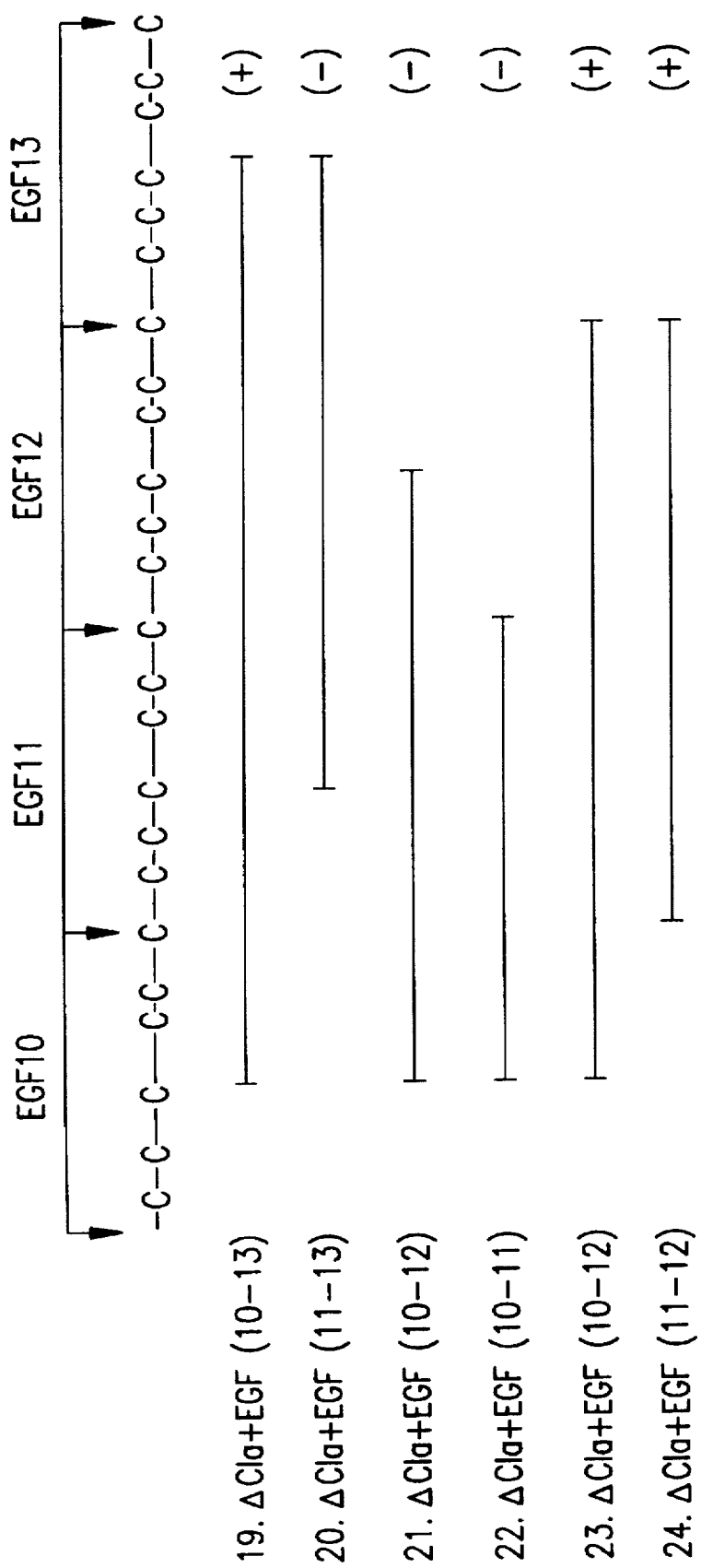

FIG. 3. Detailed Structure of Notch Deletion Constructs #19–24: Both EGF Repeats 11 and 12 are Required for Notch-Delta Aggregation. EGF repeats 10–13 are diagrammed at the top showing the regular spacing of the six cysteine residues (C). PCR products generated for these constructs (names and numbers as given in FIG. 2) are represented by the heavy black lines and the exact endpoints are noted relative to the various EGF repeats. Ability to aggregate with Delta is recorded as (+) or (−) for each construct. The PCR fragments either break the EGF repeats in the middle, just after the third cysteine in the same place as four out of the five ClaI sites, or exactly in between two repeats in the same place as the most C-terminal ClaI site.

Figure 4:
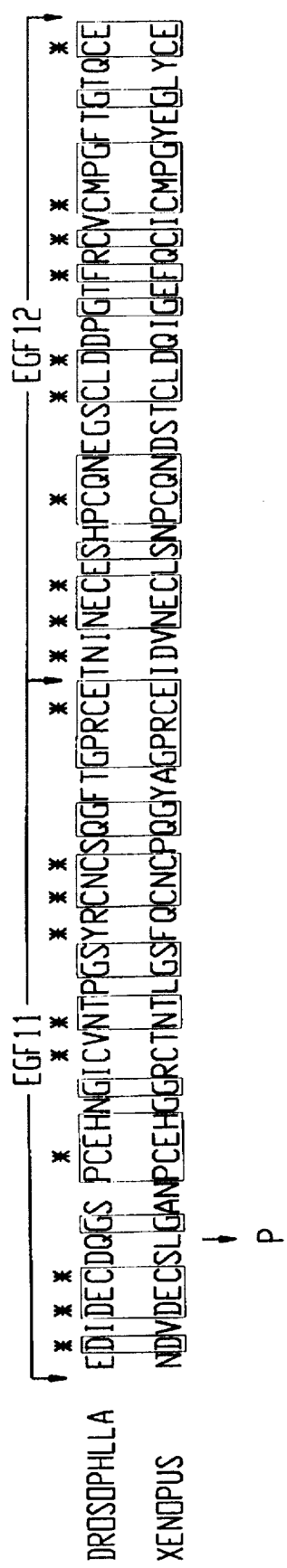

FIG. 4. Comparison of Amino Acid Sequence of EGF Repeats 11 and 12 from Drosophila and Xenopus Notch. The amino acid sequence of EGF repeats 11 and 12 of Drosophila Notch (SEQ ID NO:14) (Wharton et al., 1985, Cell 43:567–581; Kidd et al., 1986, Mol. Cell Biol. 6:3094–3108) is aligned with that of the same two EGF repeats from Xenopus Notch (SEQ ID NO:15) (Coffman et al., 1990, Science 249:1438–1441). Identical amino acids are boxed. The six conserved cysteine residues of each EGF repeat and the $Ca^{++}$ binding consensus residues (Rees et al., 1988, EMBO J. 7:2053–2061) are marked with an asterisk (*). The leucine to proline change found in the Xenopus PCR clone that failed to aggregate is noted underneath.

FIGS. 5A–5B. Nucleic Acid Sequence Homologies Between Serrate and Delta. A portion of the Drosophila Serrate nucleotide sequence (SEQ ID NO:3), with the encoded Serrate protein sequence (SEQ ID NO:4) written below (Fleming et al., 1990, Genes & Dev. 4:2188–2201 at 2193–94) is shown. The four regions showing high sequence homology with the Drosophila Delta sequence are numbered above the line and indicated by brackets. The total region of homology spans nucleotide numbers 627 through 1290 of the Serrate nucleotide sequence (numbering as in FIG. 4 of Fleming et al., 1990, Genes & Dev. 4:2188–2201).

Figure 6:
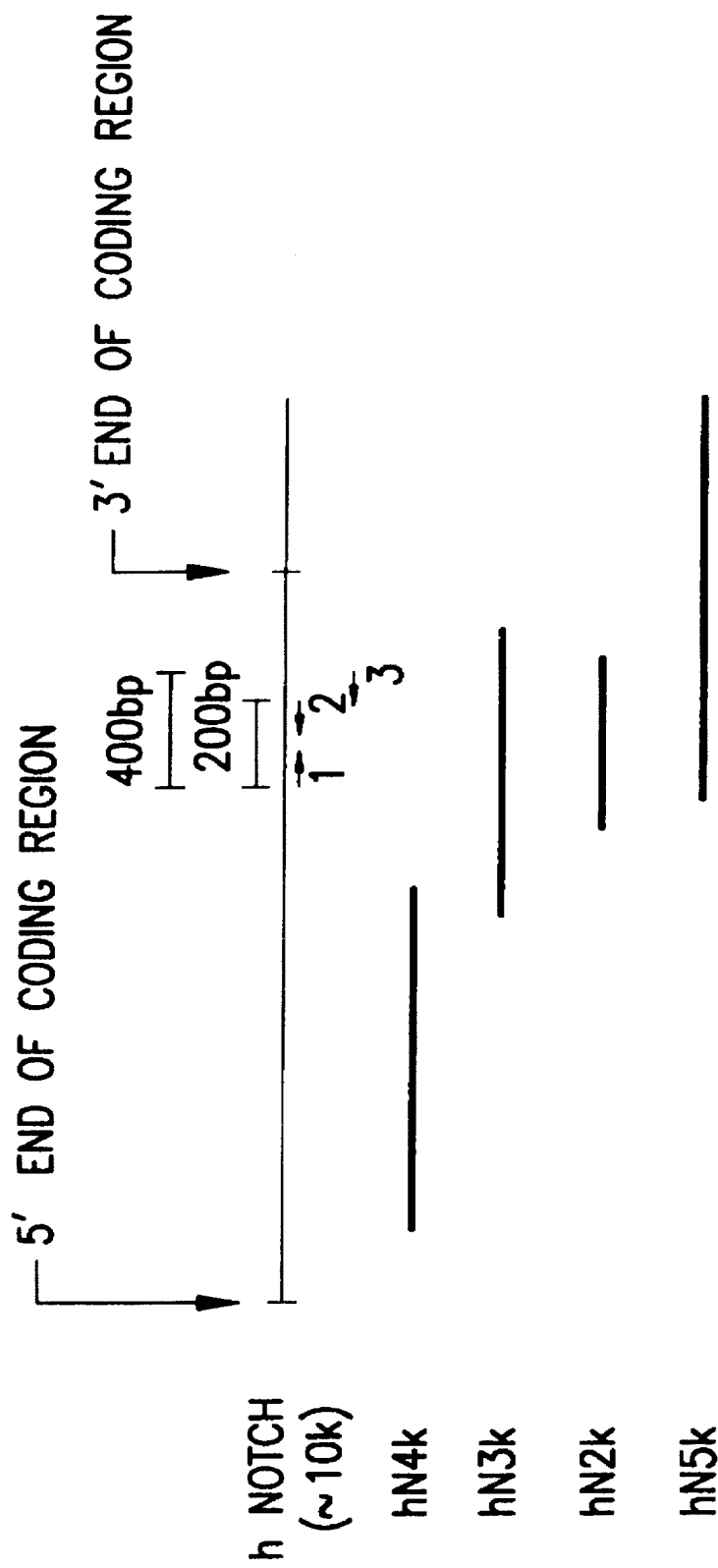

FIG. 6. Schematic Diagram of Human Notch Clones. A schematic diagram of human Notch is shown. Heavy boldface lines below the diagram show that portion of the Notch sequence contained in each of the four cDNA clones. The location of the primers used in PCR, and their orientation, are indicated by arrows.

Figure 7:
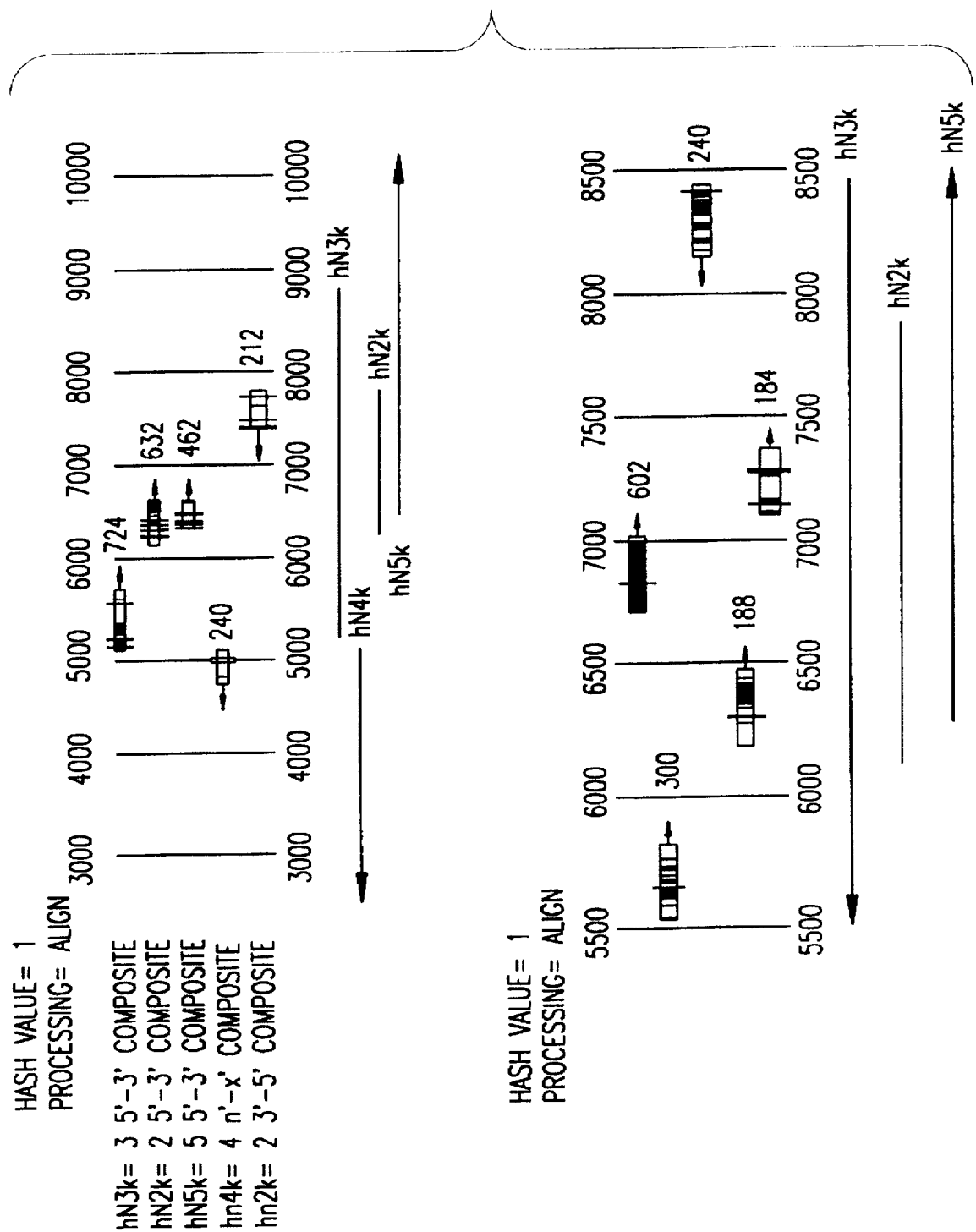

FIG. 7. Human Notch Sequences Aligned with Drosophila Notch Sequence. Numbered vertical lines correspond to Drosophila Notch coordinates. Horizontal lines below each map show where clones lie relative to stretches of sequence (thick horizontal lines).

FIGS. 8A–8C. Nucleotide Sequences of Human Notch Contained in Plasmid cDNA Clone hN2k. FIG. 8A: The DNA sequence (SEQ ID NO:5) of a portion of the human Notch insert is shown, starting at the EcoRI site at the 3' end, and proceeding in the 3' to 5' direction. FIG. 8B: The DNA sequence (SEQ ID NO:6) of a portion of the human Notch insert is shown, starting at the EcoRI site at the 5' end, and proceeding in the 5' to 3' direction. FIG. 8C: The DNA sequence (SEQ ID NO:7) of a portion of the human Notch insert is shown, starting 3' of the sequence shown in FIG. 8B, and proceeding in the 5' to 3' direction. The sequences shown are tentative, subject to confirmation by determination of overlapping sequences.

FIGS. 9A–9B. Nucleotide Sequences of Human Notch Contained in Plasmid cDNA clone hN4k. FIG. 9A: The DNA sequence (SEQ ID NO:8) of a portion of the human Notch insert is shown, starting at the EcoRI site at the 5' end, and proceeding in the 5' to 3' direction. FIG. 9B: The DNA sequence (SEQ ID NO:9) of a portion of the human Notch insert is shown, starting near the 3' end, and proceeding in the 3' to 5' direction. The sequences shown are tentative, subject to confirmation by determination of overlapping sequences.

Figure 10C:
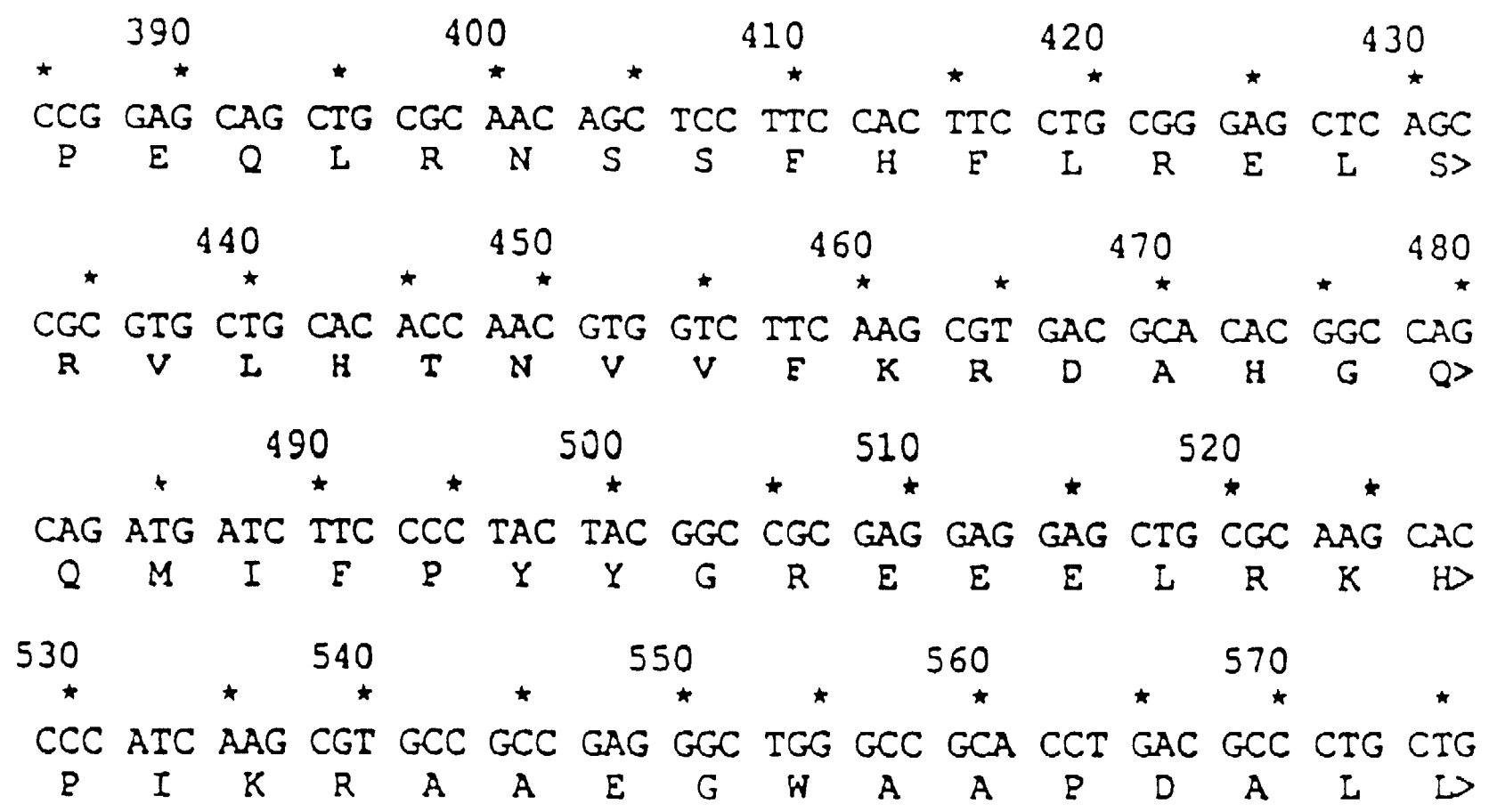

FIGS. 10A–10Q. DNA (SEQ ID NO:10) and Amino Acid (SEQ ID NO:11) Sequences of Human Notch Contained in Plasmid cDNA Clone hN3k.

FIGS. 11A–11G. DNA (SEQ ID NO:12) and Amino Acid (SEQ ID NO:13) Sequences of Human Notch Contained in Plasmid cDNA Clone hN5k.

Figure 12A:
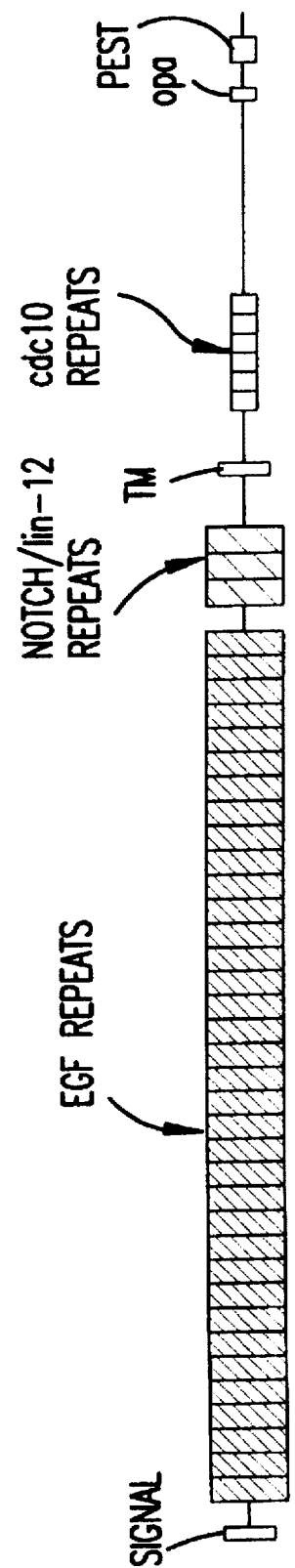
Figure 12B:
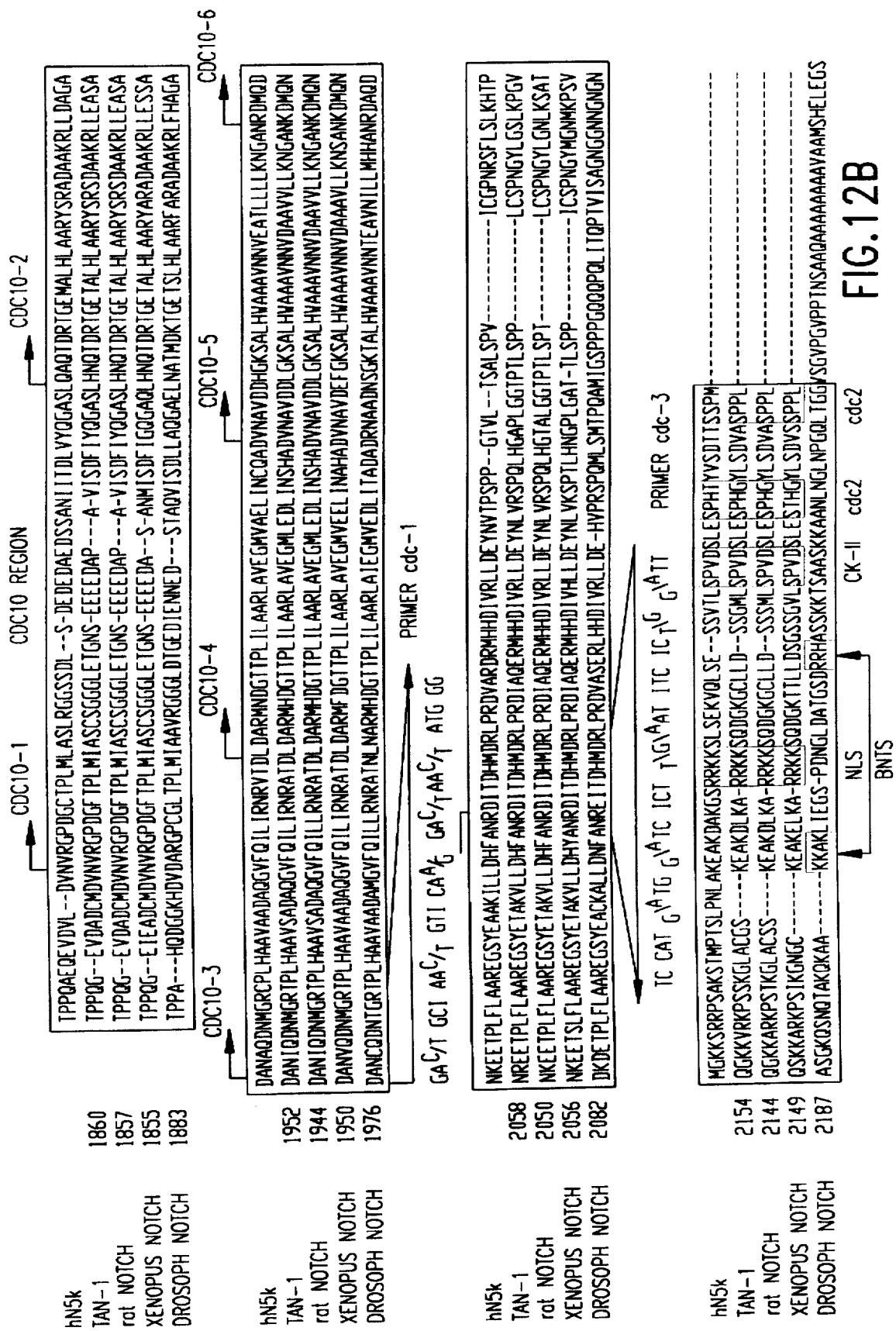

FIGS. 12A–12C. Comparison of hN5k With Other Notch Homologs. FIG. 12A. Schematic representation of Drosophila Notch. Indicated are the signal sequence (signal), the 36 EGF-like repeats, the three Notch/lin-12 repeats, the transmembrane domain (TM), the six CDC10 repeats, the OPA repeat, and the PEST (proline, glutamic acid, serine, threonine)-rich region. FIGS. 12B–12C. Alignment of the deduced amino acid sequence of hN5k with sequences of other Notch homologs. Amino acids are numbered on the left side. The cdc10 and PEST-rich regions are both boxed, and individual cdc10 repeats are marked. Amino acids which are identical in three or more sequences are highlighted. The primers used to clone hN5k are indicated below the sequences from which they were designed. The nuclear localization sequence (NLS), casein kinase II (CKII), and cdc2 kinase (cdc2) sites of the putative CcN motif of the vertebrate Notch homologs are boxed. The possible bipartite nuclear targeting sequence (BNTS) and proximal phosphorylation sites of Drosophila Notch are also boxed.

FIGS. 13A–13H. Aligned amino acid sequences of Notch proteins of various species. humN: the human Notch protein encoded by the hN homolog (contained in part in plasmid hN5k) (SEQ ID NO:19). TAN-1: the human Notch protein encoded by the TAN-1 homolog (SEQ ID NO:20) (the sequence shown is derived partly from our own work and partly from the TAN-1 sequence as published by Ellisen et al., 1991, Cell 66:649–661); Xen N: Xenopus Notch protein (Coffman et al., 1990, Science 249:1438–1441). Dros N: Drosophila Notch protein (Wharton et al., 1985, Cell 43:567–581). Structural domains are indicated.

Figure 14:
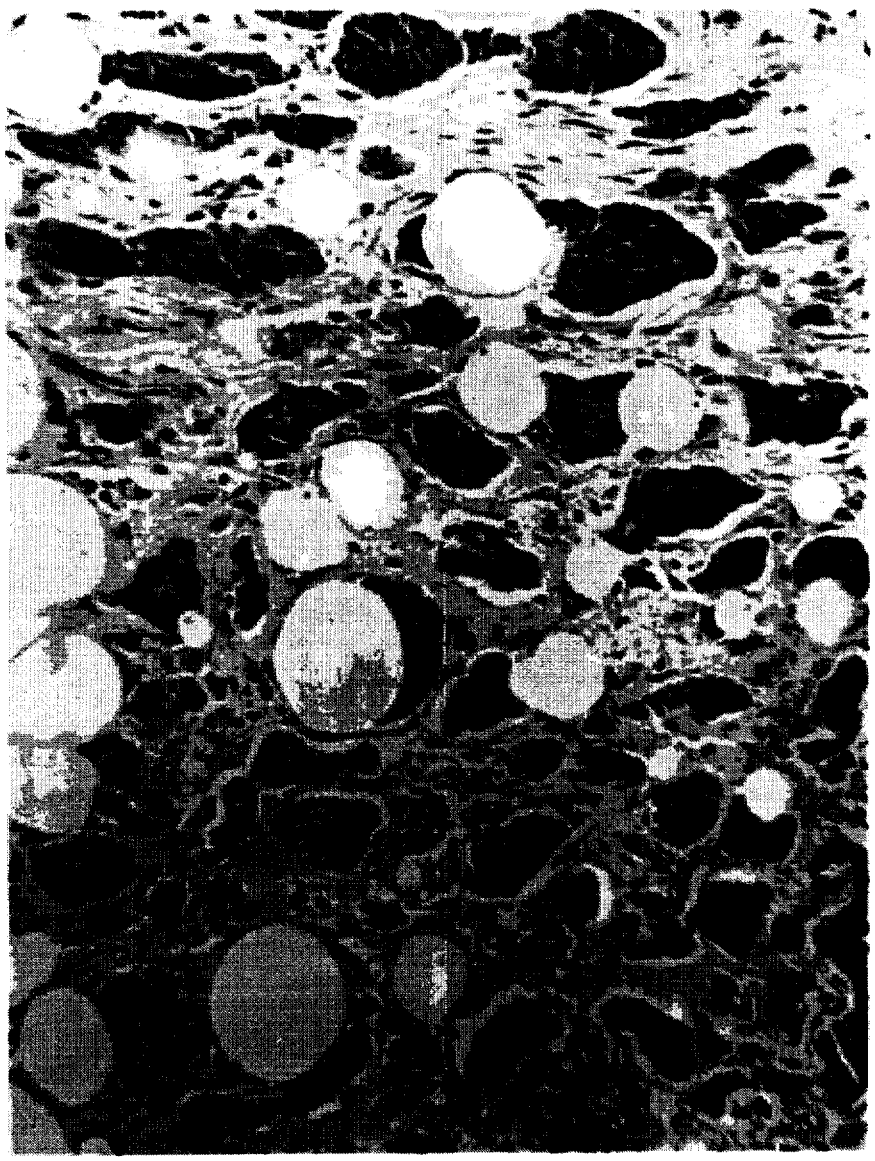

FIG. 14. Immunocytochemical staining of breast cancer tissue from a human patient. Malignant breast tissue in a sample obtained from a human patient was embedded in a paraffin section, and subjected to immunocytochemical staining with anti-human Notch monoclonal antibody P4, directed against the TAN-1 protein. Non-malignant breast tissue exhibited much less staining (not shown).

Figure 15A:
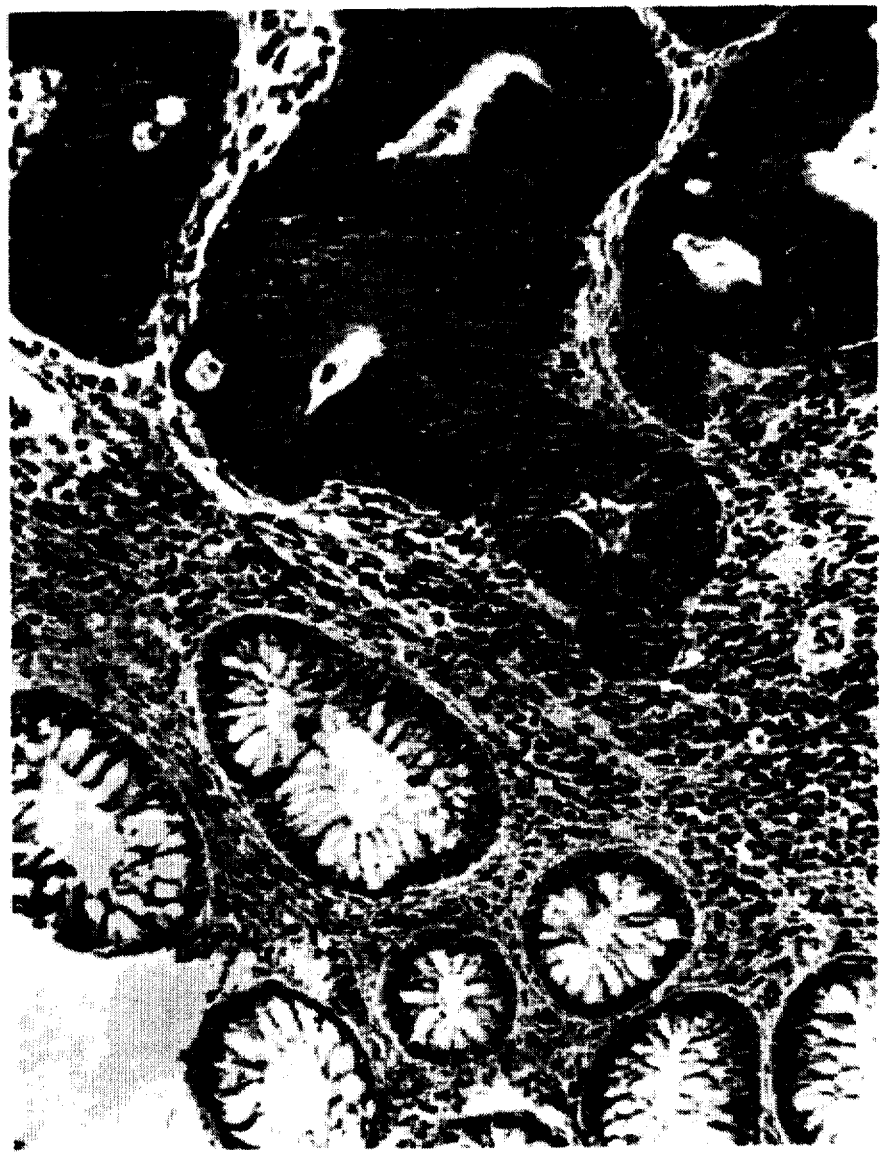
Figure 15B:

FIGS. 15A–15B. Immunocytochemical staining of colon tissue from a human patient with colon cancer. A colon tissue sample obtained from a patient with colon cancer was embedded in a paraffin section, and subjected to immunocytochemical staining with anti-human Notch monoclonal antibody P1, directed against the hN-encoded protein. Areas of increased staining are those areas in which malignant cells are present, as determined by cell morphology.

Figure 16A:
Figure 16B:

FIGS. 16A–16B. Immunocytochemical staining of cervical tissue. Human tissue samples were obtained, containing cancer of the cervix (FIG. 16A) or normal cervical epithelium (FIG. 16B) from the same patient, embedded in a paraffin section, and subjected to immunocytochemical staining with anti-human Notch monoclonal antibody directed against the TAN-1 protein. Areas containing malignant cells (as determined by morphology) exhibited increasing staining relative to non-malignant cells. Among non-malignant cells, connective tissue and the basal layer of the epithelium (containing stem cells) stained with the anti-Notch antibody.

FIGS. 17A–17L. DNA (SEQ ID NO:21) and encoded amino acid sequence (contained in SEQ ID NO:19) of human Notch homolog hN. The entire DNA coding sequence is presented (as well as noncoding sequence), with the exclusion of that encoding the initiator Met.

5. DETAILED DESCRIPTION OF THE INVENTION

The present invention relates to therapeutic and diagnostic methods and compositions based on Notch proteins and nucleic acids. The invention provides for treatment of disorders of cell fate or differentiation by administration of a therapeutic compound of the invention. Such therapeutic compounds (termed herein "Therapeutics") include: Notch proteins and analogs and derivatives (including fragments) thereof; antibodies thereto; nucleic acids encoding the Notch proteins, analogs, or derivatives; Notch antisense nucleic acids; as well as toporythmic proteins and derivatives and analogs thereof which bind to or otherwise interact with Notch proteins, and their encoding nucleic acids and antibodies. Also included are proteins and derivatives and analogs thereof which are capable of inhibiting the interactions of a Notch protein with another toporythmic protein (e.g. Delta, Serrate). In a preferred embodiment, a Therapeutic of the invention is administered to treat a cancerous condition, or to prevent progression from a pre-neoplastic or non-malignant state (e.g., metaplastic condition) into a neoplastic or a malignant state. In another specific embodiment, a Therapeutic of the invention is administered to treat a nervous system disorder, such as nerve injury or a degenerative disease. In yet another specific embodiment, a Therapeutic of the invention is administered to promote tissue regeneration and repair for treatment of various conditions.

In one embodiment, Therapeutics which antagonize, or inhibit, Notch function (hereinafter "Antagonist Therapeutics") are administered for therapeutic effect; disorders which can be thus treated can be identified by in vitro assays such as described in Section 5.1, infra. Such Antagonist Therapeutics include but are not limited to Notch antisense nucleic acids, anti-Notch neutralizing antibodies, competitive inhibitors of Notch protein-protein interactions (e.g., a protein comprising Notch ELR-11 and ELR-12), and molecules which interfere with notch intracellular function such as that mediated by the cdc10 repeats, as detailed infra.

In another embodiment, Therapeutics which promote Notch function (hereinafter "Agonist Therapeutics") are administered for therapeutic effect; disorders which can thus be treated can be identified by in vitro assays such as described in Section 5.1, infra. Such Agonist Therapeutics include but are not limited to Notch proteins and derivatives thereof comprising the intracellular domain, Notch nucleic acids encoding the foregoing, and proteins comprising toporythmic protein domains that interact with Notch (e.g., a protein comprising an extracellular domain of a Delta protein or a Delta sequence homologous to Drosophila Delta amino acids 1-230 (see FIGS. 1A-1F and SEQ ID NO:2), or comprising a Serrate sequence homologous to Drosophila Serrate amino acids 79-282 (see FIGS. 5A-5B and SEQ ID NO:4)).

Disorders of cell fate, in particular precancerous conditions such as metaplasia and dysplasia, and hyperproliferative (e.g., cancer) or hypoproliferative disorders, involving aberrant or undesirable levels of expression or activity of Notch protein can be diagnosed by detecting such levels, as described more fully infra.

In a preferred aspect, a Therapeutic of the invention is a protein consisting of at least a fragment (termed herein "adhesive fragment") of the proteins encoded by toporythmic genes which mediates binding to Notch proteins or adhesive fragments thereof. Toporythmic genes, as used herein, shall mean the genes Notch, Delta, and Serrate, as well as other members of the Delta/Serrate family which may be identified by virtue of sequence homology or genetic interaction, and, more generally, members of the "Notch cascade" or the "Notch group" of genes, which are identified by molecular interactions (e.g., binding in vitro) or genetic interactions (as detected phenotypically, e.g., in Drosophila).

For clarity of disclosure, and not by way of limitation, the detailed description of the invention is divided into the following subsections:

(i) Therapeutic Uses;
(ii) Prophylactic Uses;
(iii) Demonstration of Therapeutic or Prophylactic Utility;
(iv) Therapeutic/Prophylactic Administration and Compositions;
(v) Antisense Regulation of Notch Expression;
(vi) Diagnostic Utility;
(vii) Notch Nucleic Acids;
(viii) Recombinant Production of Protein Therapeutics;
(ix) Derivatives and Analogs of Notch and Other Toporythmic Proteins;
(x) Assays of Notch Proteins, Derivatives and Analogs; and
(xi) Antibodies to Notch Proteins, Derivatives and Analogs.

5.1. Therapeutic Uses

As stated supra, the Antagonist Therapeutics of the invention are those Therapeutics which antagonize, or inhibit, a Notch function. Such Antagonist Therapeutics are most preferably identified by use of known convenient in vitro assays, e.g., based on their ability to inhibit binding of Notch to other proteins (see Sections 6-8 herein), or inhibit any known Notch function as assayed in vitro, although genetic assays (e.g., in Drosophila) may also be employed. In a preferred embodiment, the Antagonist Therapeutic is a protein or derivative thereof comprising a functionally active fragment such as an adhesive fragment of Notch. In specific embodiments, such an Antagonist Therapeutic may be those adhesive proteins encoded by the appropriate constructs described in Sections 6 and 7 infra, or proteins comprising the Notch extracellular region, in particular ELR-11 and ELR-12, or an antibody thereto, or an analog/competitive inhibitor of a Notch intracellular signal-transducing region, a nucleic acid capable of expressing a Notch adhesive fragment, or a Notch antisense nucleic acid (see Section 5.5 herein). It should be noted that in certain instances, a Notch adhesive fragment (or possibly other presumed Antagonist Therapeutics) may alternatively act as an Agonist Therapeutic, depending on the developmental history of the tissue being exposed to the Therapeutic; preferably, suitable in vitro or in vivo assays, as described infra, should be utilized to determine the effect of a specific Therapeutic and whether its administration is indicated for treatment of the affected tissue.

In another embodiment of the invention, a nucleic acid containing a portion of a Notch gene is used, as an Antagonist Therapeutic, to promote Notch inactivation by homologous recombination (Koller and Smithies, 1989, Proc. Natl. Acad. Sci. USA 86:8932-8935; Zijlstra et al., 1989, Nature 342:435-438).

The Agonist Therapeutics of the invention, as described supra, promote Notch function. Such Agonist Therapeutics include but are not limited to proteins and derivatives comprising the portions of toporythmic proteins such as Delta or Serrate that mediate binding to Notch, and nucleic acids encoding the foregoing (which can be administered to express their encoded products in vivo). In a specific embodiment, such a portion of Delta is D. melanogaster Delta amino acids 1-230 (SEQ ID NO:1) or a portion of a human Delta most homologous thereto. In another specific embodiment, such a portion of Serrate is D. melanogaster Serrate amino acids 79-282 (SEQ ID NO:5), or a portion of a human Serrate most homologous thereto. In other specific embodiments, such a portion of Delta or Serrate is the extracellular portion of such protein.

Further descriptions and sources of Therapeutics of the inventions are found in Sections 5.4 through 5.8 herein.

The Agonist and Antagonist Therapeutics of the invention have therapeutic utility for disorders of cell fate. The Agonist Therapeutics are administered therapeutically (including prophylactically): (1) in diseases or disorders involving an absence or decreased (relative to normal, or desired) levels of Notch function, for example, in patients where Notch protein is lacking, genetically defective, biologically inactive or underactive, or underexpressed; and (2) in diseases or disorders wherein in vitro (or in vivo) assays (see infra) indicate the utility of Notch agonist administration. The absence or decreased levels in Notch function can be readily detected, e.g., by obtaining a patient tissue sample (e.g., from biopsy tissue) and assaying it in vitro for protein levels, structure and/or activity of the expressed Notch protein. Many methods standard in the art can be thus employed, including but not limited to immunoassays to detect and/or visualize Notch protein (e.g., Western blot, immunoprecipitation followed by sodium dodecyl sulfate polyacrylamide gel electrophoresis, immunocytochemistry, etc.; see also those assays listed in Section 5.6, infra), and/or hybridization assays to detect Notch expression by detecting and/or visualizing Notch MRNA (e.g., Northern assays, dot blots, in situ hybridization, etc.)

In vitro assays which can be used to determine whether administration of a specific Agonist Therapeutic or Antagonist Therapeutic is indicated, include in vitro cell culture assays in which a patient tissue sample is grown in culture, and exposed to or otherwise administered a Therapeutic, and the effect of such Therapeutic upon the tissue sample is observed. In one embodiment, where the patient has a malignancy, a sample of cells from such malignancy is plated out or grown in culture, and the cells are then exposed to a Therapeutic. A Therapeutic which inhibits survival or growth of the malignant cells (e.g., by promoting terminal differentiation) is selected for therapeutic use in vivo. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, etc. In a specific aspect, the malignant cell cultures are separately exposed to (1) an Agonist Therapeutic, and (2) an Antagonist Therapeutic; the result of the assay can indicate which type of Therapeutic has therapeutic efficacy.

In another embodiment, a Therapeutic is indicated for use which exhibits the desired effect, inhibition or promotion of cell growth, upon a patient cell sample from tissue having or suspected of having a hyper- or hypoproliferative disorder, respectively. Such hyper- or hypoproliferative disorders include but are not limited to those described in Sections 5.1.1 through 5.1.3 infra.

In another specific embodiment, a Therapeutic is indicated for use in treating nerve injury or a nervous system degenerative disorder (see Section 5.1.2) which exhibits in vitro promotion of nerve regeneration/neurite extension from nerve cells of the affected patient type.

In addition, administration of an Antagonist Therapeutic of the invention is also indicated in diseases or disorders determined or known to involve a Notch dominant activated phenotype ("gain of function" mutations.) Administration of an Agonist Therapeutic is indicated in diseases or disorders determined or known to involve a Notch dominant negative phenotype ("loss of function" mutations). We have investigated the functions of various structural domains of the Notch protein in vivo, by ectopically expressing a series of Drosophila Notch deletion mutants under the hsp70 heat-shock promoter, as well as eye-specific promoters. Two classes of dominant phenotypes were observed, one suggestive of Notch loss-of function mutations and the other of Notch gain-of-function mutations. Dominant "activated" phenotypes resulted from overexpression of a protein lacking most extracellular sequences, while dominant "negative" phenotypes resulted from overexpression of a protein lacking most intracellular sequences. Our results indicate that Notch functions as a receptor whose extracellular domain mediates ligand-binding, resulting in the transmission of developmental signals by the cytoplasmic domain. The phenotypes observed also suggested that the cdc10/ankyrin repeat region within the intracellular domain plays an essential role in Notch mediated signal transduction events (intracellular function).

In various specific embodiments, in vitro assays can be carried out with representative cells of cell types involved in a patient's disorder, to determine if a Therapeutic has a desired effect upon such cell types.

In another embodiment, cells of a patient tissue sample suspected of being pre-neoplastic are similarly plated out or grown in vitro, and exposed to a Therapeutic. The Therapeutic which results in a cell phenotype that is more normal (i.e., less representative of a pre-neoplastic state, neoplastic state, malignant state, or transformed phenotype) is selected for therapeutic use. Many assays standard in the art can be used to assess whether a pre-neoplastic state, neoplastic state, or a transformed or malignant phenotype, is present (see Section 5.2.1). For example, characteristics associated with a transformed phenotype (a set of in vitro characteristics associated with a tumorigenic ability in vivo) include a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250,000 dalton surface protein, etc. (see Luria et al., 1978, General Virology, 3d Ed., John Wiley & Sons, New York pp. 436–446).

In other specific embodiments, the in vitro assays described supra can be carried out using a cell line, rather than a cell sample derived from the specific patient to be treated, in which the cell line is derived from or displays characteristic(s) associated with the malignant, neoplastic or pre-neoplastic disorder desired to be treated or prevented, or is derived from the neural or other cell type upon which an effect is desired, according to the present invention.

The Antagonist Therapeutics are administered therapeutically (including prophylactically): (1) in diseases or disorders involving increased (relative to normal, or desired) levels of Notch function, for example, where the Notch protein is overexpressed or overactive; and (2) in diseases or disorders wherein in vitro (or in vivo) assays indicate the utility of Notch antagonist administration. The increased levels of Notch function can be readily detected by methods such as those described above, by quantifying protein and/or RNA. In vitro assays with cells of patient tissue sample or the appropriate cell line or cell type, to determine therapeutic utility, can be carried out as described above.

5.1.1. Malignancies

Malignant and pre-neoplastic conditions which can be tested as described supra for efficacy of intervention with Antagonist or Agonist Therapeutics, and which can be treated upon thus observing an indication of therapeutic utility, include but are not limited to those described below in Sections 5.1.1 and 5.2.1.

Malignancies and related disorders, cells of which type can be tested in vitro (and/or in vivo), and upon observing the appropriate assay result, treated according to the present invention, include but are not limited to those listed in Table 1 (for a review of such disorders, see Fishman et al., 1985, Medicine, 2d Ed., J.B. Lippincott Co., Philadelphia):

TABLE 1

MALIGNANCIES AND RELATED DISORDERS

Leukemia
    acute leukemia
        acute lymphocytic leukemia
        acute myelocytic leukemia
            myeloblastic
            promyelocytic
            myelomonocytic
            monocytic

TABLE 1-continued

MALIGNANCIES AND RELATED DISORDERS erythroleukemia
  chronic leukemia
    chronic myelocytic (granulocytic) leukemia
    chronic lymphocytic leukemia
Polycythemia vera
Lymphoma
  Hodgkin's disease
  non-Hodgkin's disease
Multiple myeloma
Waldenström's macroglobulinemia
Heavy chain disease
Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    testicular tumor
    lung carcinoma
    small cell lung carcinoma
    bladder carcinoma
    epithelial carcinoma
    glioma
    astrocytoma
    medulloblastoma
    craniopharyngioma
    ependymoma
    pinealoma
    hemangioblastoma
    acoustic neuroma
    oligodendroglioma
    menangioma
    melanoma
    neuroblastoma
    retinoblastoma In specific embodiments, malignancy or dysproliferative changes (such as metaplasias and dysplasias) are treated or prevented in epithelial tissues such as those in the cervix, esophagus, and lung.

As detailed in the examples section 10.1 infra, malignancies of the breast, colon, and cervix exhibit increased expression of human Notch relative to such non-malignant tissue. Thus, in specific embodiments, malignancies of the breast, colon, or cervix are treated or prevented by administering an effective amount of an Antagonist Therapeutic of the invention. The presence of increased Notch expression in breast, colon, and cervical cancer suggests that many more cancerous conditions exhibit upregulated Notch. Thus, we envision that many more cancers, e.g., seminoma, melanoma, and lung cancer, can be treated or prevented by administration of an Antagonist Therapeutic.

5.1.2. Nervous System Disorders

Nervous system disorders, involving cell types which can be tested as described supra for efficacy of intervention with Antagonist or Agonist Therapeutics, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons (see also Section 5.1). For example, and not by way of limitation, Therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

5.1.3. Tissue Repair and Regeneration

In another embodiment of the invention, a Therapeutic of the invention is used for promotion of tissue regeneration and repair, including but not limited to treatment of benign dysproliferative disorders. Specific embodiments are directed to treatment of cirrhosis of the liver (a condition in which scarring has overtaken normal liver regeneration processes), treatment of keloid (hypertrophic scar) formation (disfiguring of the skin in which the scarring process interferes with normal renewal), psoriasis (a common skin condition characterized by excessive proliferation of the skin and delay in proper cell fate determination), and baldness (a condition in which terminally differentiated hair follicles (a tissue rich in Notch) fail to function properly).

5.2. Prophylactic Uses 5.2.1. Malignancies

The Therapeutics of the invention can be administered to prevent progression to a neoplastic or malignant state, including but not limited to those disorders listed in Table 1. Such administration is indicated where the Therapeutic is shown in assays, as described supra, to have utility for treatment or prevention of such disorder. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of a Therapeutic of the invention. As mentioned supra, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84–90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

In other embodiments, a patient which exhibits one or more of the following predisposing factors for malignancy is treated by administration of an effective amount of a Therapeutic: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112–113) etc.)

In another specific embodiment, an Antagonist Therapeutic of the invention is administered to a human patient to prevent progression to breast, colon, or cervical cancer.

5.2.2. Other Disorders

In other embodiments, a Therapeutic of the invention can be administered to prevent a nervous system disorder described in Section 5.1.2, or other disorder (e.g., liver cirrhosis, psoriasis, keloids, baldness) described in Section 5.1.3.

5.3. Demonstration of Therapeutic or Prophylactic Utility

The Therapeutics of the invention can be tested in vivo for the desired therapeutic or prophylactic activity. For example, such compounds can be tested in suitable animal model systems prior to testing in humans, including but not limited to rats, mice, chicken, cows, monkeys, rabbits, etc. For in vivo testing, prior to administration to humans, any animal model system known in the art may be used.

5.4. Therapeutic/Prophylactic Administration and Compositions

The invention provides methods of treatment (and prophylaxis) by administration to a subject of an effective amount of a Therapeutic of the invention. In a preferred aspect, the Therapeutic is substantially purified. The subject is preferably an animal, including but not limited to animals such as cows, pigs, chickens, etc., and is preferably a mammal, and most preferably human.

Various delivery systems are known and can be used to administer a Therapeutic of the invention, e.g., encapsulation in liposomes, microparticles, microcapsules, expression by recombinant cells, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In a specific embodiment, administration of a Therapeutic into a Notch-expressing cell is accomplished by linkage of the Therapeutic to a Delta (or other toporythmic) protein or portion thereof capable of mediating binding to Notch. Contact of a Notch-expressing cell with the linked Therapeutic results in binding of the linked Therapeutic via its Delta portion to Notch on the surface of the cell, followed by uptake of the linked Therapeutic into the Notch-expressing cell.

In a specific embodiment wherein an analog of a Notch intracellular signal-transducing domain is employed as a Therapeutic, such that it can inhibit Notch signal transduction, the analog is preferably delivered intracellularly (e.g., by expression from a nucleic acid vector, or by linkage to a Delta protein capable of binding to Notch followed by binding and internalization, or by receptor-mediated mechanisms).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid Therapeutic can be introduced intracellularly and incorporated within host cell DNA for expression, by homologous recombination.

In specific embodiments directed to treatment or prevention of particular disorders, preferably the following forms of administration are used:

| Disorder | Preferred Forms of Administration |
| --- | --- |
| Cervical cancer | Topical |
| Gastrointestinal cancer | Oral; intravenous |
| Lung cancer | Inhaled; intravenous |
| Leukemia | Intravenous; extracorporeal |
| Metastatic carcinomas | Intravenous; oral |
| Brain cancer | Targeted; intravenous; intrathecal |
| Liver cirrhosis | Oral; intravenous |
| Psoriasis | Topical |
| Keloids | Topical |
| Baldness | Topical |
| Spinal cord injury | Targeted; intravenous; intrathecal |
| Parkinson's disease | Targeted; intravenous; intrathecal |
| Motor neuron disease | Targeted; intravenous; intrathecal |
| Alzheimer's disease | Targeted; intravenous; intrathecal |

The present invention also provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.5. Antisense Regulation of Notch Expression

The present invention provides the therapeutic or prophylactic use of nucleic acids of at least six nucleotides that are antisense to a gene or cDNA encoding Notch or a portion thereof. "Antisense" as used herein refers to a nucleic acid capable of hybridizing to a portion of a Notch RNA (preferably mRNA) by virtue of some sequence complementarity. Such antisense nucleic acids have utility as Antagonist Therapeutics of the invention, and can be used in the treatment or prevention of disorders as described supra in Section 5.1 and its subsections.

The antisense nucleic acids of the invention can be oligonucleotides that are double-stranded or single-stranded, RNA or DNA or a modification or derivative thereof, which can be directly administered to a cell, or which can be produced intracellularly by transcription of exogenous, introduced sequences.

In a specific embodiment, the Notch antisense nucleic acids provided by the instant invention can be used for the treatment of tumors or other disorders, the cells of which tumor type or disorder can be demonstrated (in vitro or in vivo) to express the Notch gene. Such demonstration can be by detection of Notch RNA or of Notch protein.

The invention further provides pharmaceutical compositions comprising an effective amount of the Notch antisense nucleic acids of the invention in a pharmaceutically acceptable carrier, as described supra in Section 5.4. Methods for treatment and prevention of disorders (such as those described in Sections 5.1 and 5.2) comprising administering the pharmaceutical compositions of the invention are also provided.

In another embodiment, the invention is directed to methods for inhibiting the expression of a Notch nucleic acid sequence in a prokaryotic or eukaryotic cell comprising providing the cell with an effective amount of a composition comprising an antisense Notch nucleic acid of the invention.

In another embodiment, the identification of cells expressing functional Notch receptors can be carried out by observing the ability of Notch to "rescue" such cells from the cytotoxic effects of a Notch antisense nucleic acid.

In an alternative embodiment of the invention, nucleic acids antisense to a nucleic acid encoding a ("adhesive") toporythmic protein or fragment that binds to Notch, are envisioned as Therapeutics.

Notch antisense nucleic acids and their uses are described in detail below.

5.5.1. Notch Antisense Nucleic Acids

The Notch antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549).

In a preferred aspect of the invention, a Notch antisense oligonucleotide is provided, preferably of single-stranded DNA. In a most preferred aspect, such an oligonucleotide comprises a sequence antisense to the sequence encoding ELR 11 and ELR 12 of Notch, most preferably, of human Notch. The oligonucleotide may be modified at any position on its structure with substituents generally known in the art.

The Notch antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. U.S.A. 85:7448–7451), etc.

In a specific embodiment, the Notch antisense oligonucleotide comprises catalytic RNA, or a ribozyme (see, e.g., PCT International Publication WO 90/11364, published Oct. 4, 1990; Sarver et al., 1990, Science 247:1222–1225). In another embodiment, the oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

In an alternative embodiment, the Notch antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the Notch antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the Notch antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of a Notch gene, preferably a human Notch gene. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded Notch antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a Notch RNA it may contain and still form a stable duplex (or triplex, as the case may be). One skilled in the art can ascertain a tolerable degree of mismatch by use of standard procedures to determine the melting point of the hybridized complex.

5.5.2. Therapeutic Utility of Notch Antisense Nucleic Acids

The Notch antisense nucleic acids can be used to treat (or prevent) malignancies, of a cell type which has been shown to express Notch RNA. Malignant, neoplastic, and pre-neoplastic cells which can be tested for such expression include but are not limited to those described supra in Sections 5.1.1 and 5.2.1. In a preferred embodiment, a single-stranded DNA antisense Notch oligonucleotide is used.

Malignant (particularly, tumor) cell types which express Notch RNA can be identified by various methods known in the art. Such methods include but are not limited to hybridization with a Notch-specific nucleic acid (e.g. by Northern hybridization, dot blot hybridization, in situ hybridization), observing the ability of RNA from the cell type to be translated in vitro into Notch, etc. In a preferred aspect, primary tumor tissue from a patient can be assayed for Notch expression prior to treatment.

Pharmaceutical compositions of the invention (see Section 5.1.4), comprising an effective amount of a Notch antisense nucleic acid in a pharmaceutically acceptable carrier, can be administered to a patient having a malignancy which is of a type that expresses Notch RNA.

The amount of Notch antisense nucleic acid which will be effective in the treatment of a particular disorder or condition will depend on the nature of the disorder or condition, and can be determined by standard clinical techniques. Where possible, it is desirable to determine the antisense cytotoxicity of the tumor type to be treated in vitro, and then in useful animal model systems prior to testing and use in humans.

In a specific embodiment, pharmaceutical compositions comprising Notch antisense nucleic acids are administered via liposomes, microparticles, or microcapsules. In various embodiments of the invention, it may be useful to use such compositions to achieve sustained release of the Notch antisense nucleic acids. In a specific embodiment, it may be desirable to utilize liposomes targeted via antibodies to specific identifiable tumor antigens (Leonetti et al., 1990, Proc. Natl. Acad. Sci. U.S.A. 87:2448–2451; Renneisen et al., 1990, J. Biol. Chem. 265:16337–16342).

5.6. Diagnostic Utility

Notch proteins, analogues, derivatives, and subsequences thereof, Notch nucleic acids (and sequences complementary thereto), anti-Notch antibodies, and other toporythmic proteins and derivatives and analogs thereof which interact with Notch proteins, and inhibitors of North-toporythmic protein interactions, have uses in diagnostics. Such molecules can be used in assays, such as immunoassays, to detect, prognose, diagnose, or monitor various conditions, diseases, and disorders affecting Notch expression, or monitor the treatment thereof. In particular, such an immunoassay is carried out by a method comprising contacting a sample derived from a patient with an anti-Notch antibody under conditions such that immunospecific binding can occur, and detecting or measuring the amount of any immunospecific binding by the antibody. In a specific embodiment, antibody to Notch can be used to assay in a patient tissue or serum sample for the presence of Notch where an aberrant level of Notch is an indication of a diseased condition.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffuision assays, agglutination assays, complement-fixation assays, immunoradiometric assays, fluorescent immunoassays, protein A immunoassays, to name but a few.

Notch genes and related nucleic acid sequences and subsequences, including complementary sequences, and other toporythmic gene sequences, can also be used in hybridization assays. Notch nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in Notch expression and/or activity as described supra. In particular, such a hybridization assay is carried out by a method comprising contacting a sample containing nucleic acid with a nucleic acid probe capable of hybridizing to Notch DNA or RNA, under conditions such that hybridization can occur, and detecting or measuring any resulting hybridization.

As detailed in examples section 10.1 infra, increased Notch expression occurs in human breast, colon, and cervical cancer. Accordingly, in specific embodiments, human breast, colon, or cervical cancer or premalignant changes in such tissues is diagnosed by detecting increased Notch expression in patient samples relative to the level of Notch expression in an analogous non-malignant sample (from the patient or another person, as determined experimentally or as is known as a standard level in such samples).

In one embodiment, the Notch protein (or derivative having Notch antigenicity) that is detected or measured is on the cell surface. In another embodiment, the Notch protein (or derivative) is a cell free soluble molecule (e.g., as measured in a blood or serum sample) or is intracellular. Without intending to be bound mechanistically, Applicants believe that cell free Notch may result from secretion or shedding from the cell surface. In yet another embodiment, soluble, cell-surface, and intracellular amounts of Notch protein or derivative are detected or measured.

5.7. Notch Nucleic Acids

Therapeutics of the invention which are Notch nucleic acids or Notch antisense nucleic acids, as well as nucleic acids encoding protein Therapeutics, include those described below, which can be obtained by methods known in the art, and in particular, as described below.

In particular aspects, the invention provides amino acid sequences of Notch, preferably human Notch, and fragments and derivatives thereof which comprise an antigenic determinant (i.e., can be recognized by an antibody) or which are functionally active, as well as nucleic acid sequences encoding the foregoing. "Functionally active" material as used herein refers to that material displaying one or more known functional activities associated with the full-length (wild-type) Notch protein product, e.g., binding to Delta, binding to Serrate, binding to any other Notch ligand, antigenicity (binding to an anti-Notch antibody), etc.

In specific embodiments, the invention provides fragments of a Notch protein consisting of at least 40 amino acids, or of at least 75 amino acids. In other embodiments, the proteins comprise or consist essentially of the intracellular domain, transmembrane region, extracellular domain, cdc10 region, Notch/lin-12 repeats, or the EGF-homologous repeats, or any combination of the foregoing, of a Notch protein. Fragments, or proteins comprising fragments, lacking some or all of the EGF-homologous repeats of Notch are also provided. Nucleic acids encoding the foregoing are provided.

In other specific embodiments, the invention provides nucleotide sequences and subsequences of Notch, preferably human Notch, consisting of at least 25 nucleotides, at least 50 nucleotides, or at least 150 nucleotides. Nucleic acids encoding the proteins and protein fragments described above are provided, as well as nucleic acids complementary to and capable of hybridizing to such nucleic acids. In one embodiment, such a complementary sequence may be complementary to a Notch cDNA sequence of at least 25 nucleotides, or of at least 100 nucleotides. In a preferred aspect, the invention utilizes cDNA sequences encoding human Notch or a portion thereof. In a specific embodiment, such sequences of the human Notch gene or cDNA are as contained in plasmids hN3k, hN4k, or hN5k (see Section 9, infra) or in the gene corresponding thereto; such a human Notch protein sequence can be as shown in FIGS. 10A–10Q (SEQ ID NO:11) or 11A–11G (SEQ ID NO:13). In other embodiments, the Notch nucleic acid and/or its encoded protein has at least a portion of the sequence shown in one of the following publications: Wharton et al., 1985, Cell 43:567–581 (Drosophila Notch); Kidd et al., 1986, Mol. Cell. Biol. 6:3094–3108 (Drosophila Notch); Coffman et al., 1990, Science 249:1438–1441 (Xenopus Notch); Ellisen et al., 1991, Cell 66:649–661 (a human Notch). In another aspect, the sequences of human Notch are those encoding the human Notch amino acid sequences or a portion thereof as shown in FIGS. 13A–13H. In a particular aspect, the human Notch sequences are those of the hN homolog (represented in part by plasmid hN5k) or the TAN-1 homolog.

In one embodiment of the invention, the invention is directed to the full-length human Notch protein encoded by the hN homolog as depicted in FIGS. 13A–13H, both containing the signal sequence (i.e., the precursor protein; amino acids 1–2169) and lacking the signal sequence (i.e., the mature protein; amino acids ~26–2169), as well as portions of the foregoing (e.g., the extracellular domain, EGF homologous repeat region, EGF-like repeats 11 and 12, cdc-10/ankyrin repeats, etc.) and proteins comprising the foregoing, as well as nucleic acids encoding the foregoing.

As is readily apparent, as used herein, a "nucleic acid encoding a fragment or portion of a Notch protein" shall be construed as referring to a nucleic acid encoding only the recited fragment or portion of the Notch protein and not other portions of the Notch protein.

In a preferred, but not limiting, aspect of the invention, a human Notch DNA sequence can be cloned and sequenced by the method described in Section 9, infra.

In another preferred aspect, PCR is used to amplify the desired sequence in the library, prior to selection. For example, oligonucleotide primers representing part of the adhesive domains encoded by a homologue of the desired gene can be used as primers in PCR.

The above-methods are not meant to limit the following general description of methods by which clones of Notch may be obtained.

Any eukaryotic cell can potentially serve as the nucleic acid source for the molecular cloning of the Notch gene. The DNA may be obtained by standard procedures known in the art from cloned DNA (e.g., a DNA "library"), by chemical synthesis, by cDNA cloning, or by the cloning of genomic DNA, or fragments thereof, purified from the desired human cell (see, for example Sambrook et al., 1989, Molecular Cloning, A Laboratory Manual, Cold Spring Harbor Laboratory, 2d. Ed., Cold Spring Harbor, N.Y.; Glover, D. M. (ed.), 1985, DNA Cloning: A Practical Approach, MRL Press, Ltd., Oxford, U.K. Vol. I, II.) Clones derived from genomic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a Notch (of any species) gene or its specific RNA, or a fragment thereof e.g., the adhesive domain, is available and can be purified and labeled, the generated DNA fragments may be screened by nucleic acid hybridization to the labeled probe (Benton, W. and Davis, R., 1977, Science 196, 180; Grunstein, M. And Hogness, D., 1975, Proc. Natl. Acad. Sci. U.S.A. 72, 3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isolectric focusing behavior, proteolytic digestion maps, in vitro aggregation activity ("adhesiveness") or antigenic properties as known for Notch. If an antibody to Notch is available, the Notch protein may be identified by binding of labeled antibody to the putatively Notch synthesizing clones, in an ELISA (enzyme-linked immunosorbent assay)-type procedure.

The Notch gene can also be identified by niRNA selection by nucleic acid hybridization followed by in vitro translation. In this procedure, fragments are used to isolate complementary mRNAs by hybridization. Such DNA fragments may represent available, purified Notch DNA of another species (e.g., Drosophila). Immunoprecipitation analysis or functional assays (e.g., aggregation ability in vitro; see examples infra) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against Notch or Delta protein. A radiolabelled Notch cDNA can be synthesized using the selected mRNA (from the adsorbed polysomes) as a template. The radiolabelled mRNA or cDNA may then be used as a probe to identify the Notch DNA fragments from among other genomic DNA fragments.

Alternatives to isolating the Notch genomic DNA include, but are not limited to, chemically synthesizing the gene sequence itself from a known sequence or making cDNA to the mRNA which encodes the Notch gene. For example, RNA for cDNA cloning of the Notch gene can be isolated from cells which express Notch. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and Notch or Delta gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate the isolated Notch gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The Notch sequences provided by the instant invention include those nucleotide sequences encoding substantially the same amino acid sequences as found in native Notch protein, and those encoded amino acid sequences with functionally equivalent amino acids, all as described in Section 5.6 infra for Notch derivatives.

Similar methods to those described supra can be used to obtain a nucleic acid encoding Delta, Serrate, or adhesive portions thereof, or other toporythmic gene of interest. In a specific embodiment, the Delta nucleic acid has at least a portion of the sequence shown in FIGS. 1A–1F (SEQ ID NO:1). In another specific embodiment, the Serrate nucleic acid has at least a portion of the sequence shown in FIGS. 5A–5B (SEQ ID NO:3). The nucleic acid sequences encoding toporythmic proteins can be isolated from porcine, bovine, feline, avian, equine, or canine, as well as primate sources and any other species in which homologs of known toporythmic genes [including but not limited to the following genes (with the publication of sequences in parentheses): Delta (Vassin et al., 1987, EMBO J. 6, 3431–3440; Kopczynski et al., 1988, Genes Dev. 2, 1723–1735; note corrections to the Kopczynski et al. sequence found in FIG. 1 hereof (SEQ ID NO:1 and SEQ ID NO:2)) and Serrate (Fleming et al., 1990, Genes & Dev. 4, 2188–2201)] can be identified. Such sequences can be altered by substitutions, additions or deletions that provide for functionally equivalent molecules, as described supra.

5.8. Recombinant Production of Protein Therapeutics

The nucleic acid coding for a protein Therapeutic of the invention can be inserted into an appropriate expression vector, i.e., a vector which contains the necessary elements for the transcription and translation of the inserted protein-coding sequence. The necessary transcriptional and translational signals can also be supplied by the native toporythmic gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. In a specific embodiment, the adhesive portion of the Notch gene, e.g., that encoding EGF-like repeats (ELR) 11 and 12, is expressed. In other specific embodiments, the human Notch gene is expressed, or a sequence encoding a functionally active portion of human Notch.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Notch protein or peptide fragment may be regulated by a second nucleic acid sequence so that the Notch protein or peptide is expressed in a host transformed with the recombinant DNA molecule. For example, expression of a Notch protein may be controlled by any promoter/enhancer element known in the art. Promoters which may be used to control toporythmic gene expression include, but are not limited to, the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner et al., 1981, Proc. Natl. Acad. Sci. U.S.A. 78, 1441-1445), the regulatory sequences of the metallothionein gene (Brinster et al., 1982, Nature 296, 39–42); prokaryotic expression vectors such as the β-lactamase promoter (Villa-Kamaroff, et al., 1978, Proc. Natl. Acad. Sci. U.S.A. 75, 3727–3731), or the tac promoter (DeBoer, et al., 1983, Proc. Natl. Acad. Sci. U.S.A. 80, 21–25); see also "Useful proteins from recombinant bacteria" in Scientific American, 1980, 242, 74–94; plant expression vectors comprising the nopaline synthetase promoter region (Herrera-Estrella et al., Nature 303, 209–213) or the cauliflower mosaic virus 35S RNA promoter (Gardner, et al., 1981, Nucl. Acids Res. 9, 2871), and the promoter of the photosynthetic enzyme ribulose biphosphate carboxylase (Herrera-Estrella et al., 1984, Nature 310, 115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38, 639–646; Ornitz et al., 1986, Cold Spring Harbor Symp. Quant. Biol. 50, 399–409; MacDonald, 1987, Hepatology 7, 425–515); insulin gene control region which is active in pancreatic beta cells (Hanahan, 1985, Nature 315, 115–122), immunoglobulin gene control region which is active in lymphoid cells (Grosschedl et al., 1984, Cell 38, 647–658; Adames et al., 1985, Nature 318, 533–538; Alexander et al., 1987,Mol. Cell. Biol. 7, 1436–1444), mouse mammary tumor virus control region which is active in testicular, breast, lymphoid and mast cells (Leder et al., 1986, Cell 45, 485–495), albumin gene control region which is active in liver (Pinkert et al., 1987, Genes and Devel. 1, 268–276), alpha-fetoprotein gene control region which is active in liver (Krumlauf et al., 1985, Mol. Cell. Biol. 5, 1639–1648; Hammer et al., 1987, Science 235, 53–58; alpha 1-antitrypsin gene control region which is active in the liver (Kelsey et al., 1987, Genes and Devel. 1, 161–171), beta-globin gene control region which is active in myeloid cells (Mogram et al., 1985, Nature 315, 338–340; Kollias et al., 1986, Cell 46, 89–94; myelin basic protein gene control region which is active in oligodendrocyte cells in the brain (Readhead et al., 1987, Cell 48, 703–712); myosin light chain-2 gene control region which is active in skeletal muscle (Sani, 1985, Nature 314, 283–286), and gonadotropic releasing hormone gene control region which is active in the hypothalamus (Mason et al., 1986, Science 234, 1372–1378).

Expression vectors containing Notch gene inserts can be identified by three general approaches: (a) nucleic acid hybridization, (b) presence or absence of "marker" gene functions, and (c) expression of inserted sequences. In the first approach, the presence of a foreign gene inserted in an expression vector can be detected by nucleic acid hybridization using probes comprising sequences that are homologous to an inserted toporythmic gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the Notch gene is inserted within the marker gene sequence of the vector, recombinants containing the Notch insert can be identified by the absence of the marker gene function. In the third approach, recombinant expression vectors can be identified by assaying the foreign gene product expressed by the recombinant. Such assays can be based, for example, on the physical or functional properties of the Notch gene product in vitro assay systems, e.g., aggregation (adhesive) ability (see Sections 6–7, infra).

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Notch protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian toporythmic protein. Furthermore, different vector/host expression systems may effect processing reactions such as proteolytic cleavages to different extents.

In other specific embodiments, the Notch protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

In other embodiments, a Notch cDNA sequence may be chromosomally integrated and expressed. Homologous recombination procedures known in the art may be used.

5.8.1. Identification and Purification of the Expressed Gene Product

Once a recombinant which expresses the Notch gene sequence is identified, the gene product may be analyzed. This can be achieved by assays based on the physical or functional properties of the product, including radioactive labelling of the product followed by analysis by gel electrophoresis.

Once the Notch protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay, including, but not limited to, aggregation assays (see Sections 6–7).

5.9. Derivatives and Analogs of Notch and Other Toporythmic Proteins

The invention further provides, as Therapeutics, derivatives (including but not limited to fragments) and analogs of Notch proteins. Also provided as Therapeutics are other toporythmic proteins and derivatives and analogs thereof, or Notch ligands, in particular, which promote or, alternatively, inhibit the interactions of such other toporythmic proteins with Notch.

The production and use of derivatives and analogs related to Notch are within the scope of the present invention. In a specific embodiment, the derivative or analog is functionally active, i.e., capable of exhibiting one or more functional activities associated with a full-length, wild-type Notch protein. As one example, such derivatives or analogs which have the desired antigenicity can be used, for example, in diagnostic immunoassays as described in Section 5.3. Molecules which retain, or alternatively inhibit, a desired Notch property, e.g., binding to Delta or other toporythmic proteins, binding to a intracellular ligand, can be used therapeutically as inducers, or inhibitors, respectively, of such property and its physiological correlates. Derivatives or analogs of Notch can be tested for the desired activity by procedures known in the art, including but not limited to the assays described infra. In one specific embodiment, peptide libraries can be screened to select a peptide with the desired activity; such screening can be carried out by assaying, e.g., for binding to Notch or a Notch binding partner such as Delta.

In particular, Notch derivatives can be made by altering Notch sequences by substitutions, additions or deletions that provide for functionally equivalent molecules. Due to the degeneracy of nucleotide coding sequences, other DNA sequences which encode substantially the same amino acid sequence as a Notch gene may be used in the practice of the present invention. These include but are not limited to nucleotide sequences comprising all or portions of Notch genes which are altered by the substitution of different codons that encode a functionally equivalent amino acid residue within the sequence, thus producing a silent change. Likewise, the Notch derivatives of the invention include, but are not limited to, those containing, as a primary amino acid sequence, all or part of the amino acid sequence of a Notch protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of Notch include but are not limited to those peptides which are substantially homologous to Notch or fragments thereof, or whose encoding nucleic acid is capable of hybridizing to a Notch nucleic acid sequence.

The Notch derivatives and analogs of the invention can be produced by various methods known in the art. The manipulations which result in their production can occur at the gene or protein level. For example, the cloned Notch gene sequence can be modified by any of numerous strategies known in the art (Maniatis, T., 1989, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of Notch, care should be taken to ensure that the modified gene remains within the same translational reading frame as Notch, uninterrupted by translational stop signals, in the gene region where the desired Notch activity is encoded.

Additionally, the Notch-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem 253:6551), use of TABS linkers (Pharmacia), etc.

Manipulations of the Notch sequence may also be made at the protein level. Included within the scope of the invention are Notch protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of Notch can be chemically synthesized. For example, a peptide corresponding to a portion of a Notch protein which comprises the desired domain, or which mediates the desired aggregation activity in vitro, or binding to a receptor, can be synthesized by use of a peptide synthesizer. Furthermore, if desired, nonclassical amino acids or chemical amino acid analogs can be introduced as a substitution or addition into the Notch sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the Notch derivative is a chimeric, or fusion, protein comprising a Notch protein or fragment thereof fused via a peptide bond at its amino- and/or carboxy-terminus to a non-Notch amino acid sequence. In one embodiment, such a chimeric protein is produced by recombinant expression of a nucleic acid encoding the protein (comprising a Notch-coding sequence joined in-frame to a non-Notch coding sequence). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a mature Notch protein with a heterologous signal sequence is expressed such that the chimeric protein is expressed and processed by the cell to the mature Notch protein. As another example, and not by way of limitation, a recombinant molecule can be constructed according to the invention, comprising coding portions of both Notch and another toporythmic gene, e.g., Delta. The encoded protein of such a recombinant molecule could exhibit properties associated with both Notch and Delta and portray a novel profile of biological activities, including agonists as well as antagonists. The primary sequence of Notch and Delta may also be used to predict tertiary structure of the molecules using computer simulation (Hopp and Woods, 1981, Proc. Natl. Acad. Sci. U.S.A. 78:3824-3828); Notch/Delta chimeric recombinant genes could be designed in light of correlations between tertiary structure and biological function. Likewise, chimeric genes comprising portions of Notch fused to any heterologous (non-Notch) protein-encoding sequences may be constructed. A specific embodiment relates to a chimeric protein comprising a fragment of Notch of at least six amino acids.

In another specific embodiment, the Notch derivative is a fragment of Notch comprising a region of homology with another toporythmic protein. As used herein, a region of a first protein shall be considered "homologous" to a second protein when the amino acid sequence of the region is at least 30% identical or at least 75% either identical or involving conservative changes, when compared to any sequence in the second protein of an equal number of amino acids as the number contained in the region.

Derivatives of Serrate, Delta, other toporythmic proteins, and the adhesive portions thereof, can be made by methods similar to those described supra.

5.9.1. Derivatives of Notch Containing One or More Domains of the Protein

In a specific embodiment, the invention provides Therapeutics that are Notch derivatives and analogs, in particular Notch fragments and derivatives of such fragments, that comprise one or more domains of the Notch protein, including but not limited to the extracellular domain, transmembrane domain, intracellular domain, membrane-associated region, one or more of the EGF-like repeats (ELR) of the Notch protein, the cdc10 repeats, and the Notch/lin-12 repeats. In specific embodiments, the Notch derivative may lack all or a portion of the ELRs, or one or more other regions of the protein.

In a specific embodiment, relating to a Notch protein of a species other than *D. melanogaster*, preferably human, the fragments comprising specific portions of Notch are those comprising portions in the respective Notch protein most homologous to specific fragments of the Drosophila Notch protein (e.g., ELR 11 and ELR 12).

5.9.2. Derivatives of Notch or Other Toporythmic Proteins that Mediate Binding to Toporythmic Protein Domains, and Inhibitors Thereof The invention also provides Notch fragments, and analogs or derivatives of such fragments, which mediate binding to toporythmic proteins (and thus are termed herein "adhesive"), and nucleic acid sequences encoding the foregoing.

Also included as Therapeutics of the invention are toporythmic (e.g., Delta, Serrate) protein fragments, and analogs or derivatives thereof, which mediate heterotypic binding to Notch (and thus are termed herein "adhesive"), and nucleic acid sequences relating to the foregoing.

Also included as Therapeutics of the invention are inhibitors (e.g., peptide inhibitors) of the foregoing toporythmic protein interactions with Notch.

The ability to bind to a toporythmic protein can be demonstrated by in vitro aggregation assays with cells expressing such a toporythmic protein as well as cells expressing Notch or a Notch derivative (See Section 6). That is, the ability of a protein fragment to bind to a Notch protein can be demonstrated by detecting the ability of the fragment, when expressed on the surface of a first cell, to bind to a Notch protein expressed on the surface of a second cell. Inhibitors of the foregoing interactions can be detected by their ability to inhibit such aggregation in vitro.

The nucleic acid sequences encoding toporythmic proteins or adhesive domains thereof, for use in such assays, can be isolated from human, porcine, bovine, feline, avian, equine, canine, or insect, as well as primate sources and any other species in which homologs of known toporythmic genes can be identified.

In a specific embodiment, the adhesive fragment of Notch is that comprising the portion of Notch most homologous to ELR 11 and 12, i.e., amino acid numbers 447 through 527 (SEQ ID NO:14) of the Drosophila Notch sequence (see FIG. 4). In yet another specific embodiment, the adhesive fragment of Delta mediating binding to Notch is that comprising the portion of Delta most homologous to about amino acid numbers 1–230 of the Drosophila Delta sequence (SEQ ID NO:2). In a specific embodiment relating to an adhesive fragment of Serrate, such fragment is that comprising the portion of Serrate most homologous to about amino acid numbers 85–283 or 79–282 of the Drosophila Serrate sequence (see FIGS. 5A–5B (SEQ ID NO:4)).

Due to the degeneracy of nucleotide coding sequences, other DNA sequences which encode substantially the same amino acid sequence as the adhesive sequences may be used in the practice of the present invention. These include but are not limited to nucleotide sequences comprising all or portions of the Notch, Delta, or Serrate genes which are altered by the substitution of different codons that encode a functionally equivalent amino acid residue within the sequence, thus producing a silent change. Likewise, the adhesive protein fragments or derivatives thereof, of the invention include, but are not limited to, those containing, as a primary amino acid sequence, all or part of the amino acid sequence of the adhesive domains including altered sequences in which functionally equivalent amino acid residues are substituted for residues within the sequence resulting in a silent change.

Adhesive fragments of toporythmic proteins and potential derivatives, analogs or peptides related to adhesive toporythmic protein sequences, can be tested for the desired binding activity e.g., by the in vitro aggregation assays described in the examples herein. Adhesive derivatives or adhesive analogs of adhesive fragments of toporythmic proteins include but are not limited to those peptides which are substantially homologous to the adhesive fragments, or whose encoding nucleic acid is capable of hybridizing to the nucleic acid sequence encoding the adhesive fragments, and which peptides and peptide analogs have positive binding activity e.g., as tested in vitro by an aggregation assay such as described in the examples sections infra. Such derivatives and analogs are envisioned as Therapeutics and are within the scope of the present invention.

The adhesive-protein related derivatives, analogs, and peptides of the invention can be produced by various methods known in the art. The manipulations which result in their production can occur at the gene or protein level (see Section 5.6).

Additionally, the adhesive-encoding nucleic acid sequence can be mutated in vitro or in vivo; and manipulations of the adhesive sequence may also be made at the protein level (see Section 5.6).

In addition, analogs and peptides related to adhesive fragments can be chemically synthesized.

5.10. Assays of Notch Proteins, Derivatives and Analogs

The in vitro activity of Notch proteins, derivatives and analogs, and other toporythmic proteins which bind to Notch, can be assayed by various methods.

For example, in one embodiment, where one is assaying for the ability to bind or compete with wild-type Notch for binding to anti-Notch antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

In another embodiment, where one is assaying for the ability to mediate binding to Notch, one can carry out an in vitro aggregation assay such as described infra in Section 6 or 7 (see also Fehon et al., 1990, Cell 61:523–534; Rebay et al., 1991, Cell 67:687–699).

In another embodiment, where another ligand for Notch is identified, ligand binding can be assayed, e.g., by binding assays well known in the art. In another embodiment, physiological correlates of ligand binding to cells expressing a Notch receptor (signal transduction) can be assayed.

In another embodiment, in insect or other model systems, genetic studies can be done to study the phenotypic effect of a Notch mutant that is a derivative or analog of wild-type Notch.

Other methods will be known to the skilled artisan and are within the scope of the invention.

5.11. Antibodies to Notch Proteins, Derivatives and Analogs

According to one embodiment of the invention, antibodies and fragments containing the binding domain thereof, directed against Notch are Therapeutics. Accordingly, Notch proteins, fragments or analogs or derivatives thereof, in particular, human Notch proteins or fragments thereof, may be used as immunogens to generate anti-Notch protein antibodies. Such antibodies can be polyclonal, monoclonal, chimeric, single chain, Fab fragments, or from an Fab expression library. In a specific embodiment, antibodies specific to EGF-like repeats 11 and 12 of Notch may be prepared. In other embodiments, antibodies reactive with the extracellular domain of Notch can be generated. One example of such antibodies may prevent aggregation in an in vitro assay. In another embodiment, antibodies specific to human Notch are produced.

Various procedures known in the art may be used for the production of polyclonal antibodies to a Notch protein or peptide. In a particular embodiment, rabbit polyclonal antibodies to an epitope of the human Notch protein encoded by a sequence depicted in FIGS. 10A-10Q or 11A-11G, or a subsequence thereof, can be obtained. For the production of antibody, various host animals can be immunized by injection with the native Notch protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies directed toward a Notch protein sequence, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize the adhesive domain of a Notch protein, one may assay generated hybridomas for a product which binds to a protein fragment containing such domain. For selection of an antibody specific to human Notch, one can select on the basis of positive binding to human Notch and a lack of binding to Drosophila Notch.

In addition to therapeutic utility, the foregoing antibodies have utility in diagnostic immunoassays as described in Section 5.6 supra.

Similar procedures to those described supra can be used to make Therapeutics which are antibodies to domains of other proteins (particularly toporythmic proteins) that bind or otherwise interact with Notch (e.g., adhesive fragments of Delta or Serrate).

6. DOMAINS OF NOTCH MEDIATE BINDING WITH DELTA

Intermolecular association between the products of the Notch and Delta genes was detected by studying the effects of their expression on aggregation in Drosophila Schneider's 2 (S2) cells (Fehon et al., 1990, Cell 61, 523–534). Direct evidence of intermolecular interactions between Notch and Delta is described herein, as well as an assay system that can be used in dissecting the components of this interaction. Normally nonadhesive Drosophila S2 cultured cells that express Notch bind specifically in a calcium-dependent manner to cells that express Delta. Furthermore, while cells that express Notch do not bind to one another, cells that express Delta do bind to one another, suggesting that Notch and Delta can compete for binding to Delta at the cell surface. Notch and Delta form detergent-soluble complexes both in cultured cells and embryonic cells, suggesting that Notch and Delta interact directly at the molecular level in vitro and in vivo. The analyses suggest that Notch and Delta proteins interact at the cell surface via their extracellular domains.

6.1. Experimental Procedures

6.1.1. Expression Constructs

Expression constructs are described in Fehon et al., 1990, Cell 61:523-534. Briefly, Notch encoded by the MgIIa minigene a cDNA/genomic chimeric construct (Ramos et al., 1989, Genetics 123, 337-348) was expressed following insertion into pRmHa-3 (Bunch, et al., 1988, Nucl. Acids Res. 16, 1043-1061). In the resulting construct, designated pMtNMg, the metallothionein promoter in pRmHa-3 is fused to Notch sequences starting 20 nucleotides upstream of the translation start site.

The extracellular Notch construct (ECN1), was derived from a Notch cosmid (Ramos et al., 1989, Genetics 123, 337–348), and has an internal deletion of the Notch coding sequences from amino acids 1790 to 2625 inclusive (Wharton et al., 1985, Cell 43, 567–581), and a predicted frameshift that produces a novel 59 amino acid carboxyl terminus.

For the Delta expression construct, the Dl1 cDNA (Kopczynski et al., 1988, Genes Dev. 2, 1723-1735; FIGS. 1A-1F; SEQ ID NO:1), which includes the complete coding capacity for Delta, was inserted into the EcoRI site of pRmHa-3. This construct was called pMTDl1.

6.1.2. Antibody Preparation

Hybridoma cell line C17.9C6 was obtained from a mouse immunized with a fusion protein based on a 2.1 kb SalI-HindIII fragment that includes coding sequences for most of the intracellular domain of Notch (amino acids 1791–2504; Wharton et al., 1985, Cell 43, 567–581). The fragment was subcloned into pUR289 (Ruther and Muller-Hill, 1983, EMBO J. 2, 1791–1794), and then transferred into the pATH 1 expression vector (Dieckmann and Tzagoloff, 1985, J. Biol. Chem. 260, 1513–1520) as a BglII-HindIII fragment. Soluble fusion protein was expressed, precipitated by 25% $(NH_4)_2SO_4$, resuspended in 6M urea, and purified by preparative isoelectric focusing using a Rotofor (Bio-Rad) (for details, see Fehon, 1989, Rotofor Review No. 7, Bulletin 1518, Richmond, Calif.: Bio-Rad Laboratories).

Mouse polyclonal antisera were raised against the extracellular domain of Notch using four BstYl fragments of 0.8 kb (amino acids 237–501: Wharton et al., 1985, Cell 43, 567–581), 1.1 kb (amino acids 501–868), 0.99 kb (amino acids 868–1200), and 1.4 kb (amino acids 1465–1935) length, which spanned from the fifth EGF-like repeat across the transmembrane domain, singly inserted in-frame into the appropriate pGEX expression vector (Smith and Johnson, 1988, Gene 67, 31–40). Fusion proteins were purified on glutathione-agarose beads (SIGMA). Mouse and rat antisera were precipitated with 50% $(NH_4)_2SO_4$ and resuspended in PBS (150 mM NaCl, 14 mM $Na_2HPO_4$, 6 mM $NaH_2PO_4$) with 0.02% $NaN_3$.

Hybridoma cell line 201 was obtained from a mouse immunized with a fusion protein that includes coding sequences from the extracellular domain of Delta (Kopczynski et al., 1988, Genes Dev. 2, 1723–1735), including sequences extending from the fourth through the ninth EGF-like repeats in Delta (amino acids 350–529).

Rat polyclonal antisera were obtained following immunization with antigen derived from the same fusion protein construct. In this case, fusion protein was prepared by lysis of IPTG-induced cells in SDS-Laemmli buffer (Carroll and Laughon, 1987, in DNA Cloning, Volume III, D. M. Glover, ed. (Oxford: IRL Press), pp. 89–111), separation of proteins by SDS-PAGE, excision of the appropriate band from the gel, and electroelution of antigen from the gel slice for use in immunization (Harlow and Lane, 1988, Antibodies: A Laboratory Manual (Cold Spring Harbor, N.Y.: Cold Spring Harbor Laboratory)).

6.1.3. Cell Culture and Transfection

The S2 cell line (Schneider, 1972, J. Embryol. Exp. Morph. 27, 353–365) was grown in M3 medium (prepared by Hazleton Co.) supplemented with 2.5 mg/ml Bacto-Peptone (Difco), 1 mg/ml TC Yeastolate (Difco), 11% heat-inactivated fetal calf serum (FCS) (Hyclone), and 100 U/ml penicillin-100 µg/ml streptomycin-0.25 µg/ml fungizone (Hazleton). Cells growing in log phase at $\sim 2 \times 10^6$ cells/ml were transfected with 20 µg of DNA-calcium phosphate coprecipitate in 1 ml per 5 ml of culture as previously described (Wigler et al., 1979, Proc. Natl. Acad. Sci. USA 78, 1373–1376), with the exception that BES buffer (SIGMA) was used in place of HEPES buffer (Chen and Okayama, 1987, Mol. Cell. Biol. 7, 2745–2752). After 16–18 hr, cells were transferred to conical centrifuge tubes, pelleted in a clinical centrifuge at full speed for 30 seconds, rinsed once with ¼ volume of fresh complete medium, resuspended in their original volume of complete medium, and returned to the original flask. Transfected cells were then allowed to recover for 24 hr before induction.

6.1.4. Aggregation Assays

Expression of the Notch and Delta metallothionein constructs was induced by the addition of $CuSO_4$ to 0.7 mM. Cells transfected with the ECN1 construct were treated similarly. Cells were then mixed, incubated under aggregation conditions, and scored for their ability to aggregate using specific antisera and immunofluorescence microscopy to visualize expressing cells.

Two types of aggregation assays were used. In the first assay, a total of 3 ml of cells ($5-10 \times 10^6$ cells/ml) was placed in a 25 ml Erlenmeyer flask and rotated at 40–50 rpm on a rotary shaker for 24–48 hr at room temperature. For these experiments, cells were mixed 1–4 hr after induction began and induction was continued throughout the aggregation period. In the second assay, ~0.6 ml of cells were placed in a 0.6 ml Eppendorf tube (leaving a small bubble) after an overnight induction (12–16 hr) at room temperature and rocked gently for 1–2 hr at 4° C. The antibody inhibition and $Ca^{2+}$ dependence experiments were performed using the latter assay. For $Ca^{2+}$ dependence experiments, cells were first collected and rinsed in balanced saline solution (BSS) with 11% FCS (BSS-FCS; FCS was dialyzed against 0.9% NaCl, 5 mM Tris [pH 7.5]) or in $Ca^{2+}$ free BSS-FCS containing 10 mM EGTA (Snow et al., 1989, Cell 59, 313–323) and then resuspended in the same medium at the original volume. For the antibody inhibition experiments, Notch-transfected cells were collected and rinsed in M3 medium and then treated before aggregation in M3 medium for 1 hr at 4° C. with a 1:250 dilution of immune or preimmune sera from each of the four mice immunized with fusion proteins containing segments from the extracellular domain of Notch (see Antibody Preparation above).

6.1.5. Immunofluorescence

Cells were collected by centrifugation (3000 rpm for 20 seconds in an Eppendorf microcentrifuge) and fixed in 0.6 ml Eppendorf tubes with 0.5 ml of freshly made 2% paraformaldehyde in PBS for 10 min at room temperature. After fixing, cells were collected by centrifugation, rinsed twice in PBS, and stained for 1 hr in primary antibody in PBS with 0.1% saponin (SIGMA) and 1% normal goat serum (Pocono Rabbit Farm, Canadensis, Pa.). Monoclonal antibody supernatants were diluted 1:10 and mouse or rat sera were diluted 1:1000 for this step. Cells were then rinsed once in PBS and stained for 1 hr in specific secondary antibodies (double-labeling grade goat anti-mouse and goat anti-rat, Jackson Immunoresearch) in PBS-saponin-normal goat serum. After this incubation, cells were rinsed twice in PBS and mounted on slides in 90% glycerol, 10% 1M Tris (pH 8.0), and 0.5% n-propyl gallate. Cells were viewed under epifluorescence on a Leitz Orthoplan 2 microscope.

Confocal micrographs were taken using the Bio-Rad MRC 500 system connected to a Zeiss Axiovert compound microscope. Images were collected using the BHS and GHS filter sets, aligned using the ALIGN program, and merged using MERGE. Fluorescent bleed-through from the green into the red channel was reduced using the BLEED program (all software provided by Bio-Rad). Photographs were obtained directly from the computer monitor using Kodak Ektar 125 film.

6.1.6. Cell Lysates, Immunoprecipitations, and Western Blots

Nondenaturing detergent lysates of tissue culture and wild-type Canton-S embryos were prepared on ice in ~10 cell vol of lysis buffer (300 mM NaCl, 50 mM Tris [pH8.0], 0.5% NP-40, 0.5% deoxycholate, 1 mM $CaCl_2$, 1 mM $MgCl_2$) with 1 mM phenylmethysulfonyl fluoride (PMSF) and diisopropyl fluorophosphate diluted 1:2500 as protease inhibitors. Lysates were sequentially triturated using 18G, 21G, and 25G needles attached to 1 cc tuberculin syringes and then centrifuged at full speed in a microfuge 10 min at 4° C. to remove insoluble material. Immunoprecipitation was performed by adding ~1 µg of antibody (1–2 µl of polyclonal antiserum) to 250–500 µl of cell lysate and incubating for 1 hr at 4° C. with agitation. To this mixture, 15 µg of goat anti-mouse antibodies (Jackson Immunoresearch; these antibodies recognize both mouse and rat IgG) were added and allowed to incubate for 1 hr at 4° C. with agitation. This was followed by the addition of 100 µl of fixed *Staphylococcus aureus* (Staph A) bacteria (Zysorbin, Zymed; resuspended according to manufacturer's instructions), which had been collected, washed five times in lysis buffer, and incubated for another hour. Staph A-antibody complexes were then pelleted by centrifugation and washed three times in lysis buffer followed by two 15 min washes in lysis buffer. After being transferred to a new tube, precipitated material was suspended in 50 µl of SDS-PAGE sample buffer, boiled immediately for 10 min, run on 3%–15% gradient gels, blotted to nitrocellulose, and detected using monoclonal antibodies and HRP-conjugated goat anti-mouse secondary antibodies as previously described (Johansen et al., 1989, J. Cell Biol. 109, 2427–2440). For total cellular protein samples used on Western blots, cells were collected by centrifugation, lysed in 10 cell vol of sample buffer that contained 1 mM PMSF, and boiled immediately.

6.2. Results

6.2.1. The Expression of Notch and Delta in Cultured Cells

To detect interactions between Notch and Delta, we examined the behavior of cells expressing these proteins on their surfaces using an aggregation assay. We chose the S2 cell line (Schneider, 1972, J. Embryol. Exp. Morph. 27, 353–365) for these studies. S2 cells express an aberrant Notch message and no detectable Notch due to a rearrangement of the 5' end of the Notch coding sequence. These cells also express no detectable Delta.

Results of Western blot and immunofluorescent analysis clearly showed that the Notch and Delta constructs support expression of proteins of the expected sizes and subcellular localization.

6.2.2. Cells that Express Notch and Delta Aggregate

A simple aggregation assay was used to detect interactions between Notch and Delta expressed on the surface of S2 cells.

S2 cells in log phase growth were separately transfected with either the Notch or Delta metallothionein promoter construct. After induction with $CuSO_4$, transfected cells were mixed in equal numbers and allowed to aggregate overnight at room temperature (for details, see Experimental Procedures, Section 6.1). Alternatively, in some experiments intended to reduce metabolic activity, cells were mixed gently at 4° C. for 1–2 hr. To determine whether aggregates had formed, cells were processed for immunofluorescence microscopy using antibodies specific for each gene product and differently labeled fluorescent secondary antibodies. Expressing cells usually constituted less than 5% of the total cell population because transient rather than stable transformants were used. The remaining cells either did not express a given protein or expressed at levels too low for detection by immunofluorescence microscopy. As controls, we performed aggregations with only a single type of transfected cell.

The results (Fehon et al., 1990, Cell 61:523–534) showed that while Notch-expressing (Notch$^+$) cells alone did not form aggregates in the assay, Delta-expressing (Delta$^+$) cells did. The tendency for Delta$^+$ cells to aggregate was apparent even in nonaggregated control samples, where cell clusters of 4–8 cells that probably arose from adherence between mitotic sister cells commonly occurred. However, clusters were more common after incubation under aggregation conditions (e.g., 19% of Delta$^+$ cells in aggregates before incubation vs. 37% of Delta$^+$ cells in aggregates after incubation), indicating that Delta$^+$ cells are able to form stable contacts with one another in this assay.

In remarkable contrast to control experiments with Notch$^+$ cells alone, aggregation of mixtures of Notch$^+$ and Delta$^+$ cells resulted in the formation of clusters of up to 20 or more cells. The fraction of expressing cells found in clusters of four or more stained cells after 24 hr of aggregation ranged from 32%–54% in mixtures of Notch$^+$ and Delta$^+$ cells. This range was similar to that seen for Delta$^+$ cells alone (37%–40%) but very different from that for Notch$^+$ cells alone (only 0%–5%). Although a few clusters that consisted only of Delta$^+$ cells were found, Notch$^+$ cells were never found in clusters of greater than four to five cells unless Delta$^+$ cells were also present. Again, all cells within these clusters expressed either Notch or Delta, even though transfected cells composed only a small fraction of the total cell population. At 48 hr, the degree of aggregation appeared higher (63%–71%), suggesting that aggregation had not yet reached a maximum after 24 hr under these conditions. Also, cells cotransfected with Notch and Delta constructs (so that all transfected cells express both proteins) aggregated in a similar fashion under the same experimental conditions.

Notch involvement in the aggregation process was directly tested by examining the effect of a mixture of polyclonal antisera directed against fusion proteins that spanned almost the entire extracellular domain of Notch on aggregation (see Experimental Procedures, Section 6.1). To minimize artifacts that might arise due to a metabolic response to patching of surface antigens, antibody treatment and the aggregation assay were performed at 4° C. in these experiments. Notch$^+$ cells were incubated with either preimmune or immune mouse sera for 1 hr, Delta$^+$ cells were added, and aggregation was performed for 1–2 hr. While Notch$^+$ cells pretreated with preimmune sera aggregated with Delta$^+$ cells (in one of three experiments, 23% of the Notch$^+$ cells were in Notch$^+$–Delta$^+$ cell aggregates), those treated with immune sera did not (only 2% of Notch$^+$ cells were in aggregates). This result suggested that the extracellular domain of Notch was required for Notch$^+$–Delta$^+$ cell aggregation.

6.2.3. Notch-Delta-Mediated Aggregation Is Calcium Dependent

The ability of expressing cells to aggregate in the presence or absence of $Ca^{2+}$ ions was tested to determine whether there is a $Ca^{2+}$ ion requirement for Notch-Delta aggregation. To minimize possible nonspecific effects due to metabolic responses to the removal of $Ca^{2+}$, these experiments were performed at 4° C. The results clearly demonstrated a dependence of Notch-Delta-mediated aggregation on exogenous $Ca^{2+}$.

6.2.4. Notch and Delta Interact Within a Single Cell

The question whether Notch and Delta are associated within the membrane of one cell that expresses both proteins was posed by examining the distributions of Notch and Delta in cotransfected cells. To test whether the observed colocalization was coincidental or represented a stable interaction between Notch and Delta, live cells were treated with an excess of polyclonal anti-Notch antiserum. This treatment resulted in "patching" of Notch on the surface of expressing cells into discrete patches as detected by immunofluorescence. There was a distinct correlation between the distributions of Notch and Delta on the surfaces of these cells after this treatment, indicating that these proteins are associated within the membrane.

6.2.5. Interactions With Delta Do Not Require the Intracellular Domain of Notch In addition to a large extracellular domain that contains EGF-like repeats, Notch has a sizeable intracellular (IC) domain of ~940 amino acids. The IC domain includes a phosphorylation site (Kidd et al., 1989, Genes Dev. 3, 1113–1129), a putative nucleotide binding domain, a polyglutamine stretch (Wharton et al., 1985, Cell 43, 567–581; Kidd, et al., 1986, Mol. Cell. Biol. 6, 3094–3108), and sequences homologous to the yeast cdc10 gene, which is involved in cell cycle control in yeast (Breeden and Nasmyth, 1987, Nature 329, 651–654). A variant Notch construct was used from which coding sequences for ~835 amino acids of the IC domain, including all of the structural features noted above, had been deleted (leaving 25 membrane-proximal amino acids and a novel 59 amino acid carboxyl terminus; see Experimental Procedures).

In aggregation assays, cells that expressed the ECN1 construct consistently formed aggregates with Delta$^+$ cells, but not with themselves, just as was observed for cells that expressed intact Notch. Sharp bands of ECN1 staining were observed within regions of contact with Delta$^+$ cells, again indicating a localization of ECN1 within regions of contact between cells. To test for interactions within the membrane, surface antigen co-patching experiments were conducted using cells cotransfected with the ECN1 and Delta constructs. As observed for intact Notch, when ECN1 was patched using polyclonal antisera against the extracellular domain of Notch, ECN1 and Delta colocalized at the cell surface. These results demonstrate that the observed interactions between Notch and Delta within the membrane do not require the deleted portion of the IC domain of Notch and are therefore probably mediated by the extracellular domain.

6.2.6. Notch and Delta Form Detergent-Soluble Intermoleular Complexes

The preceding results indicated molecular interactions between Notch and Delta present within the same membrane and between these proteins expressed on different cells. A further test for such interactions is whether these proteins would coprecipitate from nondenaturing detergent extracts of cells that express Notch and Delta. If Notch and Delta form a stable intermolecular complex either between or within cells, then it should be possible to precipitate both proteins from cell extracts using specific antisera directed against one of these proteins. This analysis was performed by immunoprecipitating Delta with polyclonal antisera from NP-40/deoxycholate lysates (see Experimental Procedures) of cells cotransfected with the Notch and Delta constructs that had been allowed to aggregate overnight or of 0–24 hr wild-type embryos.

Coprecipitation of Notch was detected in Delta immunoprecipitates from cotransfected cells and embryos. However, coprecipitating Notch appeared to be present in much smaller quantities than Delta and was therefore difficult to detect. The fact that immunoprecipitation of Delta results in the coprecipitation of Notch constitutes direct evidence that these two proteins form stable intermolecular complexes in transfected S2 cells and in embryonic cells.

6.3. Discussion

Use of an in vitro aggregation assay that employs normally nonadhesive S2 cells showed that cells that express Notch and Delta adhere specifically to one another.

7. EGF REPEATS 11 AND 12 OF NOTCH ARE REQUIRED AND SUFFICIENT FOR NOTCH-DELTA-MEDIATED AGGREGATION

The same aggregation assay was used as described in Section 6, together with deletion mutants of Notch to identify regions within the extracellular domain of Notch necessary for interactions with Delta. The evidence shows that the EGF repeats of Notch are directly involved in this interaction and that only two (ELR 11 and 12) of the 36 EGF repeats appear necessary. These two EGF repeats are sufficient for binding to Delta and that the calcium dependence of Notch-Delta mediated aggregation also associates with these two repeats. Finally, the two corresponding EGF repeats from the Xenopus homolog of Notch also mediate aggregation with Delta, implying that not only has the structure of Notch been evolutionarily conserved, but also its function. These results suggest that the extracellular domain of Notch is surprisingly modular, and could potentially bind a variety of proteins in addition to Delta. (See Rebay et al., 1991, Cell 67:687–699.)

7.1. Experimental Procedures

7.1.1. Expression Constructs

The constructs described are all derivatives of the full length Notch expression construct #1 pMtNMg (see Section 6, supra), and were made as described (Rebay et al., 1991, Cell 67:687–699).

7.1.2. Cell Culture and Transfection

The Drosophila S2 cell line was grown and transfected as described in Section 6, supra. The Delta-expressing stably transformed S2 cell line L-49-6-7 (kindly established by L. Cherbas) was grown in M3 medium (prepared by Hazleton Co.) supplemented with 11% heat inactivated fetal calf serum (FCS) (Hyclone), 100 U/ml penicillin-100 µg/ml streptomycin-0.25 µg/ml fungizone (Hazleton), $2 \times 10^{-7}$M methotrexate, 0.1 mM hypoxanthine, and 0.016 mM thymidine.

7.1.3. Aggregation Assays and Immunofluorescence

Aggregation assays and $Ca^{++}$ dependence experiments were as described supra, Section 6. Cells were stained with the anti-Notch monoclonal antibody 9C6.C17 and anti-Delta rat polyclonal antisera (details described in Section 6, supra). Surface expression of Notch constructs in unpermeabilized cells was assayed using rat polyclonal antisera raised against the 0.8 kb (amino acids 237–501; Wharton et al., 1985, Cell 43, 567–581) BstYI fragment from the extracellular domain of Notch. Cells were viewed under epifluorescence on a Leitz Orthoplan 2 microscope.

7.2. Results

7.2.1. EGF Repeats 11 and 12 of Notch are Required for Notch-Delta Mediated Aggregation An extensive deletion analysis was undertaken of the extracellular domain of the Notch protein, which was shown (supra, Section 6; Fehon et al., 1990, Cell 61:523–534) to be involved in Notch-Delta interactions, to identify the precise domain of Notch mediating these interactions. The ability of cells transfected with the various deletion constructs to interact with Delta was tested using the aggregation assay described in Section 6. Briefly, Notch deletion constructs were transiently transfected into Drosophila S2 cells, induced with $CuSO_4$, and then aggregated overnight at room temperature with a small amount of cells from the stably transformed Delta expressing cell line L49-6-7(Cherbas), yielding a population typically composed of ~1% Notch expressing cells and ~5% Delta expressing cells, with the remaining cells expressing neither protein.

Schematic drawings of the constructs tested and results of the aggregation experiments are shown in FIGS. 2A–2B. To assay the degree of aggregation, cells were stained with antisera specific to each gene product and examined with immunofluorescent microscopy. Aggregates were defined as clusters of four or more cells containing both Notch and Delta expressing cells, and the values shown in FIG. 2 represent the percentage of all Notch expressing cells found in such clusters. All numbers reflect the average result from at least two separate transfection experiments in which at least 100 Notch expressing cell units (either single cells or clusters) were scored.

The initial constructs (#2 DSph and #3 ΔCla) deleted large portions of the EGF repeats. Their inability to promote Notch-Delta aggregation suggested that the EGF repeats of Notch were involved in the interaction with Delta. A series of six in-frame ClaI restriction sites was used to further dissect the region between EGF repeats 7 and 30. Due to sequence homology between repeats, five of the ClaI sites occur in the same relative place within the EGF repeat, just after the third cysteine, while the sixth site occurs just before the first cysteine of EGF repeat 31 (FIG. 3). Thus, by performing a partial ClaI digestion and then religating, deletions were obtained that not only preserved the open reading frame of the Notch protein but in addition frequently maintained the structural integrity and conserved spacing, at least theoretically, of the three disulfide bonds in the chimeric EGF repeats produced by the religation (FIGS.

2A–2B, constructs #4–14). Unfortunately, the most 3' ClaI site was resistant to digestion while the next most 3' ClaI site broke between EGF repeats 30 and 31. Therefore, when various ClaI digestion fragments were reinserted into the framework of the complete ClaI digest (construct #3 ΔCla), the overall structure of the EGF repeats was apparently interrupted at the 3' junction.

Several points about this series of constructs are worth noting. First, removal of the ClaI restriction fragment breaking in EGF repeats 9 and 17 (construct #8 ΔEGF9–17) abolished aggregation with Delta, while reinsertion of this piece into construct #3 ΔCla, which lacks EGF repeats 7–30, restored aggregation to roughly wild type levels (construct #13 ΔCla+EGF9–17), suggesting that EGF repeats 9 through 17 contain sequences important for binding to Delta. Second, all constructs in this series (#4–14) were consistent with the binding site mapping to EGF repeats 9 through 17. Expression constructs containing these repeats (#6, 7, 9, 10, 13) promoted Notch-Delta interactions while constructs lacking these repeats (#4, 5, 8, 11, 12, 14) did not. To confirm that inability to aggregate with Delta cells was not simply due to failure of the mutagenized Notch protein to reach the cell surface, but actually reflected the deletion of the necessary binding site, cell surface expression of all constructs was tested by immunofluorescently staining live transfected cells with antibodies specific to the extracellular domain of Notch. All constructs failing to mediate Notch-Delta interactions produced a protein that appeared to be expressed normally at the cell surface. Third, although the aggregation assay is not quantitative, two constructs which contained EGF repeats 9–17, #9ΔEGF17–26 or most noticeably #10ΔEGF26–30, aggregated at a seemingly lower level. Cells transfected with constructs #9ΔEGF17–26 and 10ΔEGF26–30 showed considerably less surface staining than normal, although fixed and permeabilized cells reacted with the same antibody stained normally, indicating the epitopes recognized by the antisera had not been simply deleted. By comparing the percentage of transfected cells in either permeabilized or live cell populations, it was found that roughly 50% of transfected cells for construct #9ΔEGF17–26 and 10% for construct #10ΔEGF26–30 produced detectable protein at the cell surface. Thus these two constructs produced proteins which often failed to reach the cell surface, perhaps because of misfolding, thereby reducing, but not abolishing, the ability of transfected cells to aggregate with Delta-expressing cells.

Having mapped the binding site to EGF repeats 9 through 17, further experiments (Rebay et al., 1991, Cell 67:687–699) revealed that EGF repeat 14 of Notch was not involved in the interactions with Delta modelled by the tissue culture assay.

To further map the Delta binding domain within EGF repeats 9–17, specific oligonucleotide primers and the PCR technique were used to generate several subfragments of this region. Three overlapping constructs, #16, 17 and 18 were produced, only one of which, #16ΔCla+EGF9–13, when transfected into S2 cells, allowed aggregation with Delta cells. Construct #19ΔCla+EGF(10–13), which lacks EGF repeat 9, further defined EGF repeats 10–13 as the region necessary for Notch-Delta interactions.

Constructs #20–24 represented attempts to break this domain down even further using the same PCR strategy (see FIG. 3). Constructs #20ΔCla+EGF(11–13), in which EGF repeat 12 is the only entire repeat added, and #21ΔCla+EGF(10–12), in which EGF repeat 11 is the only entire repeat added, failed to mediate aggregation, suggesting that the presence of either EGF repeat 11 or 12 alone was not sufficient for Notch-Delta interactions. However, since the 3' ligation juncture of these constructs interrupted the overall structure of the EGF repeats, it was possible that a short "buffer" zone was needed to allow the crucial repeat to function normally. Thus for example in construct #19ΔCla+EGF(10–13), EGF repeat 12 might not be directly involved in binding to Delta but instead might contribute the minimum amount of buffer sequence needed to protect the structure of EGF repeat 11, thereby allowing interactions with Delta. Constructs #22–24 addressed this issue. Constructs #22ΔCla+EGF(10–11), which did not mediate aggregation, and #23ΔCla+EGF(10–12), which did, again suggested that both repeats 11 and 12 are required while the flanking sequence from repeat 13 clearly is not. Finally, construct #24ΔCla+EGF(11–12), although now potentially structurally disrupted at the 5' junction, convincingly demonstrated that the sequences from EGF repeat 10 are not crucial. Thus based on entirely consistent data from 24 constructs, EGF repeats 11 and 12 of Notch together define the smallest functional unit obtainable from this analysis that contains the necessary sites for binding to Delta in transfected S2 cells.

7.2.2. EGF Repeats 11 and 12 of Notch Are Sufficient for Notch-Delta Mediated Aggregation The large ClaI deletion into which PCR fragments were inserted (#3ΔCla) retains roughly ⅓ of the original 36 EGF repeats as well as the three Notch/lin-12 repeats. While these are clearly not sufficient to promote aggregation, it is possible that they form a necessary framework within which specific EGF repeats can interact with Delta. To test whether only a few EGF repeats were in fact sufficient to promote aggregation, two constructs were designed, #25ΔEGF which deleted all 36 EGF repeats except for the first two-thirds of repeat 1, and #30ΔECN which deleted the entire extracellular portion of Notch except for the first third of EGF repeat 1 and ~35 amino acids just before the transmembrane domain. Fragments which had mediated Notch-Delta aggregation in the background of construct #3ΔCla, when inserted into construct #25ΔEGF, were again able to promote interactions with Delta (constructs #26–30). Analogous constructs (#31,32) in which the Notch/lin-12 repeats were also absent, again successfully mediated Notch-Delta aggregation. Thus EGF repeats 11 and 12 appear to function as independent modular units which are sufficient to mediate Notch-Delta interactions in S2 cells, even in the absence of most of the extracellular domain of Notch.

7.2.3. EGF Repeats 11 and 12 of Notch Maintain the Calcium Dependence of Notch-Delta Mediated Aggregation The ability of cells expressing certain deletion constructs to aggregate with Delta expressing cells was examined in the presence or absence of $Ca^{++}$ ions. The calcium dependence of the interaction was preserved in even the smallest construct, consistent with the notion that the minimal constructs containing EGF repeats 11 and 12 bind to Delta in a manner similar to that of full length Notch.

7.2.4. The Delta Binding Function of EGF Repeats 11 and 12 of Notch is Conserved in the Xenopus Homolog of Notch PCR primers based on the Xenopus Notch sequence (Coffman et al., 1990, Science 249, 1438–1441) were used to obtain an ~350 bp fragment from a Xenopus Stage 17 cDNA library that includes EGF repeats 11 and 12 flanked by half of repeats 10 and 13 on either side. This fragment was cloned into construct #3ΔCla, and three independent clones were tested for ability to interact with Delta in the cell culture aggregation assay. Two of the clones, #33a&bΔCla+

XEGF(10–13), when transfected into S2 cells were able to mediate Notch-Delta interactions at a level roughly equivalent to the analogous Drosophila Notch construct #19ΔCla+EGF(10–13), and again in a calcium dependent manner (Table III). However, the third clone #33cΔCla+XEGF (10–13) failed to mediate Notch-Delta interactions although the protein was expressed normally at the cell surface as judged by staining live unpermeabilized cells. Sequence comparison of the Xenopus PCR product in constructs #33a and 33c revealed a missense mutation resulting in a leucine to proline change (amino acid #453, Coffman, et al., 1990, Science 249, 1438–1441) in EGF repeat 11 of construct #33c. Although this residue is not conserved between Drosophila and Xenopus Notch (FIGS. 8A–8C), the introduction of a proline residue might easily disrupt the structure of the EGF repeat, and thus prevent it from interacting properly with Delta.

Comparison of the amino acid sequence of EGF repeats 11 and 12 of Drosophila and Xenopus Notch reveals a high degree of amino acid identity, including the calcium binding consensus sequence (FIG. 4, SEQ ID NO:1 and NO:2). However the level of homology is not strikingly different from that shared between most of the other EGF repeats, which overall exhibit about 50% identity at the amino acid level. This one to one correspondence between the individual EGF repeats of Drosophila and Xenopus Notch, together with the functional conservation of ELR 11 and 12, suggests that the 36 EGF repeats of Notch comprise a tandem area of conserved functional units.

7.3. Discussion

An extensive deletion analysis of the extracellular domain of Notch was used to show that the regions of Notch containing EGF-homologous repeats 11 and 12 are both necessary and sufficient for Notch-Delta-mediated aggregation, and that this Delta binding capability has been conserved in the same two EGF repeats of Xenopus Notch. The finding that the aggregation mapped to EGF repeats 11 and 12 of Notch demonstrates that the EGF repeats of Notch also function as specific protein binding domains. EGF repeats 11 and 12 alone (#32ΔECN+EGF(11–12)) were sufficient to maintain the $Ca^{++}$ dependence of Notch-Delta interactions.

The various deletion constructs suggest that ELR 11 and ELR 12 function as a modular unit, independent of the immediate context into which they are placed. Thus, neither the remaining 34 EGF repeats nor the three Notch/lin-12 repeats appear necessary to establish a structural framework required for EGF repeats 11 and 12 to function. Interestingly, almost the opposite effect was observed: although the aggregation assay does not measure the strength of the interaction, as the binding site was narrowed down to smaller and smaller fragments, an increase was observed in the ability of the transfected cells to aggregate with Delta expressing cells, suggesting that the normal flanking EGF sequences actually impede association between the proteins. The remaining 34 EGF repeats may also form modular binding domains for other proteins interacting with Notch at various times during development.

The finding that EGF repeats 11 and 12 of Notch form a discrete Delta binding unit represents the first concrete evidence supporting the idea that each EGF repeat or small subset of repeats may play a unique role during development, possibly through direct interactions with other proteins. The homologies seen between the adhesive domain of Delta and Serrate (FIGS. 5A–5B) suggest that the homologous portion of Serrate is "adhesive" in that it mediates binding to other toporythmic proteins (see Section 8, infra). In addition, the gene scabrous, which encodes a secreted protein with similarity to fibrinogen, may interact with Notch.

In addition to the EGF repeat, multiple copies of other structural motifs commonly occur in a variety of proteins. One relevant example is the cdc10/ankyrin motif, six copies of which are found in the intracellular domain of Notch. Ankyrin contains 22 of these repeats. Perhaps repeated arrays of structural motifs may in general represent a linear assembly of a series of modular protein binding units. Given these results together with the known structural, genetic and developmental complexity of Notch, Notch may interact with a number of different ligands in a precisely regulated temporal and spacial pattern throughout development. Such context specific interactions with extracellular proteins could be mediated by the EGF and Notch/lin-12 repeats, while interactions with cytoskeletal and cytoplasmic proteins could be mediated by the intracellular cdc10/ankyrin motifs.

8. SEQUENCES WHICH MEDIATE NOTCH-SERRATE INTERACTIONS

As described herein, the two EGF repeats of Notch which mediate interactions with Delta, namely EGF repeats 11 and 12, also constitute a Serrate binding domain (see Rebay et al., 1991, Cell 67:687–699).

To test whether Notch and Serrate directly interact, S2 cells were transfected with a Serrate expression construct and mixed with Notch expressing cells in an aggregation assay. For the Serrate expression construct, a synthetic primer containing an artificial BamHI site immediately 5' to the initiator AUG at position 442 (all sequence numbers are according to Fleming et al., 1990, Genes & Dev. 4:2188–2201) and homologous through position 464, was used in conjunction with a second primer from position 681–698 to generate a DNA fragment of ~260 base pairs. This fragment was cut with BamHI and KpnI (position 571) and ligated into Bluescript KS+(Stratagene). This construct, BTSer5'PCR, was checked by sequencing, then cut with KpnI. The Serrate KpnI fragment (571–2981) was inserted and the proper orientation selected, to generate BTSer5'PCR-Kpn. The 5' SacII fragment of BTSer5'PCR-Kpn (SacII sites in Bluescript polylinker and in Serrate (1199)) was isolated and used to replace the 5' SacII fragment of cDNA C1 (Fleming et al., 1990, Genes & Dev. 4:2188–2201), thus regenerating the full length Serrate cDNA minus the 5' untranslated regions. This insert was isolated by a SalI and partial BamHI digestion and shuttled into the BamHI and SalI sites of pRmHa-3 to generate the final expression construct, Ser-mtn.

Serrate expressing cells adhered to Notch expressing cells in a calcium dependent manner (FIGS. 2A–2B and Rebay et al., 1991, supra). However, unlike Delta, under the experimental conditions tested, Serrate did not appear to interact homotypically. In addition, no interactions were detected between Serrate and Delta.

A subset of Notch deletion constructs were tested, and showed that EGF repeats 11 and 12, in addition to binding to Delta, also mediate interactions with Serrate (FIGS. 2A–2B; Constructs #1, 7–10, 13, 16, 17, 19, 28, and 32). In addition, the Serrate-binding function of these repeats also appears to have been conserved in the corresponding two EGF repeats of Xenopus Notch (#33ΔCla+XEGF(10–13)). These results unambiguously show that Notch interacts with both Delta and Serrate, and that the same two EGF repeats of Notch mediate both interactions. The Serrate region which is essential for the Notch/Serrate aggregation was also defined. Deleting nucleotides 676–1287 (i.e. amino acids 79–282) (See FIGS. 5A–5B; SEQ ID NO:3 and NO:4) eliminates the ability of the Serrate protein to aggregate with Notch.

Notch and Serrate appear to aggregate less efficiently than Notch and Delta, perhaps because the Notch-Serrate interaction is weaker. One trivial explanation for this reduced amount of aggregation could be that the Serrate construct simply did not express as much protein at the cell surface as the Delta construct, thereby diminishing the strength of the interaction. Alternatively, the difference in strength of interaction may indicate a fundamental functional difference between Notch-Delta and Notch-Serrate interactions that may be significant in vivo.

9. THE CLONING, SEQUENCING, AND EXPRESSION OF HUMAN NOTCH

9.1. Isolation and Sequencing of Human Notch

Clones for the human Notch sequence were originally obtained using the polymerase chain reaction (PCR) to amplify DNA from a 17–18 week human fetal brain cDNA library in the Lambda Zap II vector (Stratagene).

The 400 bp fragment obtained in this manner was then used as a probe with which to screen the same library for human Notch clones. The original screen yielded three unique clones, hN3k, hN2K, and hN5k, all of which were shown by subsequent sequence analysis to fall in the 3' end of human Notch (FIG. 6). A second screen using the 5' end of hN3k as probe was undertaken to search for clones encompassing the 5' end of human Notch. One unique clone, hN4k, was obtained from this screen, and preliminary sequencing data indicate that it contains most of the 5' end of the gene (FIG. 6). Together, clones hN4k, hN3k and hN5k encompass about 10 kb of the human Notch homolog(s), beginning early in the EGF-repeats and extending into the 3' untranslated region of the gene. All three clones are cDNA inserts in the EcoRI site of pBluescript SK⁻(Stratagene). The host E. coli strain is XL1-Blue (see Maniatis, T., 1990, Molecular Cloning, A Laboratory Manual, 2d ed., Cold Spring Harbor Laboratory, Cold Spring Harbor, N.Y., p. A12). An alignment of the human Notch sequences with Drosophila Notch is shown in FIG. 7.

The sequence of various portions of Notch contained in the cDNA clones was determined (by use of Sequenase®, U.S. Biochemical Corp.) and is shown for hN2k and hN4k in FIGS. 8A–8C (SEQ ID NO:5–7) and 9A–9B (SEQ ID NO:8, 9), respectively. Further sequence analysis of hN2k revealed that it encodes a human Notch sequence overlapping that contained in hN5k.

The complete nucleotide sequences of the human Notch cDNA contained in hN3k and hN5k was determined by the dideoxy chain termination method using the Sequenase® kit (U.S. Biochemical Corp.). Those nucleotide sequences encoding human Notch, in the appropriate reading frame, were readily identified since there are no introns and translation in only one out of the three possible reading frames yields a sequence which, upon comparison with the published Drosophila Notch deduced amino acid sequence, yields a sequence with a substantial degree of homology to the Drosophila Notch sequence. The DNA and deduced protein sequences of the human Notch cDNA in hN3k and hN5k are presented in FIGS. 10A–10Q (SEQ ID NO:10, 11) and 11A–11G (SEQ ID NO:12, 13), respectively. Clone hN3k encodes a portion of a Notch polypeptide starting at approximately the third Notch/lin-12 repeat to several amino acids short of the carboxy-terminal amino acid. Clone hN5k encodes a portion of a Notch polypeptide starting approximately before the cdc10 region through the end of the polypeptide, and also contains a 3' untranslated region.

Comparing the DNA and protein sequences presented in FIGS. 10A–10Q (SEQ ID NO:10, 11) with those in FIGS. 11A–11G (SEQ ID NO:12, 13) reveals significant differences between the sequences, suggesting that hN3k and hN5k represent part of two distinct Notch-homologous genes. The data thus suggest that the human genome harbors more than one Notch-homologous gene. This is unlike Drosophila, where Notch appears to be a single-copy gene.

Comparison of the DNA and amino acid sequences of the human Notch homologs contained in hN3k and hN5k with the corresponding Drosophila Notch sequences (as published in Wharton et al., 1985, Cell 43:567–581) and with the corresponding Xenopus Notch sequences (as published in Coffman et al., 1990, Science 249:1438–1441 or available from Genbank® (accession number M33874)) also revealed differences.

The amino acid sequence shown in FIGS. 10A–10Q (hN3k) was compared with the predicted sequence of the TAN-1 polypeptide shown in FIG. 2 of Ellisen et al., August 1991, Cell 66:649–661. Some differences were found between the deduced amino acid sequences; however, overall the hN3k Notch polypeptide sequence is 99% identical to the corresponding TAN-1 region (TAN-1 amino acids 1455 to 2506). Four differences were noted: in the region between the third Notch/lin-12 repeat and the first cdc10 motif, there is an arginine (hN3k) instead of an X (TAN-1 amino acid 1763); (2) there is a proline (hN3k) instead of an X (TAN-1, amino acid 1787); (3) there is a conservative change of an aspartic acid residue (hN3k) instead of a glutamic acid residue (TAN-1, amino acid 2495); and (4) the carboxyl-terminal region differs substantially between TAN-1 amino acids 2507 and 2535.

The amino acid sequence shown in FIGS. 11A–11G (hN5k) was compared with the predicted sequence of the TAN-1 polypeptide shown in FIG. 2 of Ellisen et al., August 1991, Cell 66:649–661. Differences were found between the deduced amino acid sequences. The deduced Notch polypeptide of hN5k is 79% identical to the TAN-1 polypeptide (64% identical to Drosophila Notch) in the cdc10 region that encompasses both the cc10 motif (TAN-1 amino acids 1860 to 2217) and the well-conserved flanking regions (FIGS. 12A–12C). The cdc10 region covers amino acids 1860 through 2217 of the TAN-1 sequence. In addition, the hN5k encoded polypeptide is 65% identical to the TAN-1 polypeptide (44% identical to Drosophila Notch) at the carboxy-terminal end of the molecule containing a PEST (proline, glutamic acid, serine, threonine)-rich region (TAN-1 amino acids 2482 to 2551) (FIGS. 12B–12C). The stretch of 215 amino acids lying between the aforementioned regions is not well conserved among any of the Notch-homologous clones represented by hN3k, hN5k, and TAN-1. Neither the hN5k polypeptide nor Drosophila Notch shows significant levels of amino acid identity to the other proteins in this region (e.g., hN5k/TAN-1=24% identity; hN5k/Drosophila Notch=11% identity; TAN-1/Drosophila Notch=17% identity). In contrast, Xenopus Notch (Xotch) (SEQ ID NO:16), rat Notch (SEQ ID NO:17), and TAN-1 (SEQ ID NO:18) continue to share significant levels of sequence identity with one another (e.g., TAN-1/rat Notch= 75% identity, TAN-1/Xenopus Notch=45% identity, rat Notch/Xenopus Notch=50% identity).

Examination of the sequence of the intracellular domains of the vertebrate Notch homologs shown in FIGS. 12B–12C revealed an unexpected finding: all of these proteins, including hN5k, contain a putative CcN motif, associated with nuclear targeting function, in the conserved region following the last of the six cdc10 repeats (FIGS. 12B–12C). Although Drosophila Notch lacks such a defined motif, closer inspection of its sequence revealed the presence of a possible bipartite nuclear localization sequence (Robbins et al., 1991, Cell 64:615–623), as well as of possible CK II and cdc2 phosphorylation sites, all in relative proximity to one another, thus possibly defining an alternative type of CcN motif (FIG. 12B).

To isolate clones covering the 5' end of hN (the human Notch homolog contained in part in hN5k), clone hN2k was used as a probe to screen 260,000 plaques of human fetal brain phage library, commercially available from Stratagene, for crosshybridizing clones. Four clones were identified and isolated using standard procedures (Maniatis et al., 1982, *Molecular Cloning: A Laboratory Manual*, Cold Spring Harbor Laboratory, Cold Spring Harbor, N.Y.). Four clones were also isolated by hybridization to the Notch-homologous sequence of Adams et al., 1992, Nature 355:632–655, which was obtained from the ATCC.

To isolate clones covering the 5' end of TAN-1, the human fetal brain library that is commercially available from Stratagene was screened for clones which would extend the sequence to the 5' end. 880,000 plaques were screened and four clones were identified which crosshybridized with the hN3k sequences. Sequencing confirmed the relative position of these sequences within the Notch protein encoded by TAN-1.

The 5' sequence of our isolated TAN-1 homolog has been determined through nucleotide number 972 (nucleotide number 1 being the A in the ATG initiation codon), and compared to the sequence as published by Ellisen et al (1991, Cell 66:649–661). At nucleotide 559, our TAN-1 homolog has a G, whereas Ellisen et al. disclose an A, which change results in a different encoded amino acid. Thus, within the first 324 amino acids, our TAN-1-encoded protein differs from that taught by Ellisen et al., since our protein has a Gly at position 187, whereas Ellisen et al. disclose an Arg at that position (as presented in FIGS. 13A–13H.)

The full-length amino acid sequences of both the hN (SEQ ID NO:19) and TAN-1-encoded (SEQ ID NO:20) proteins, as well as Xenopus and Drosophila Notch proteins, are shown in FIGS. 13A–13H. The full-length DNA coding sequence (except for that encoding the initiator Met) (contained in SEQ ID NO:21) and encoded amino acid sequence (except that the initiator Met is not shown) (contained in SEQ ID NO:19) of hN are shown in FIGS. 17A–17L.

9.2. Expression of Human Notch

Expression constructs were made using the human Notch cDNA clones discussed in Section 9.1 above. In the cases of hN3k and hN2k, the entire clone was excised from its vector as an EcoRI restriction fragment and subcloned into the EcoRI restriction site of each of the three pGEX vectors (Glutathione S-Transferase expression vectors; Smith and Johnson, 1988, Gene 7, 31–40). This allows for the expression of the Notch protein product from the subclone in the correct reading frame. In the case of hN5k, the clone contains two internal EcoRI restriction sites, producing 2.6, 1.5 and 0.6 kb fragments. Both the 2.6 and the 1.5 kb fragments have also been subcloned into each of the pGEX vectors.

The pGEX vector system was used to obtain expression of human Notch fusion (chimeric) proteins from the constructs described below. The cloned Notch DNA in each case was inserted, in phase, into the appropriate pGEX vector. Each construct was then electroporated into bacteria (*E. coli*), and was expressed as a fusion protein containing the Notch protein sequences fused to the carboxyl terminus of glutathione S-transferase protein. Expression of the fusion proteins was confirmed by analysis of bacterial protein extracts by polyacrylamide gel electrophoresis, comparing protein extracts obtained from bacteria containing the pGEX plasmids with and without the inserted Notch DNA. The fusion proteins were soluble in aqueous solution, and were purified from bacterial lysates by affinity chromatography using glutathione-coated agarose (since the carboxyl terminus of glutathione S-transferase binds to glutathionine). The expressed fusion proteins were bound by an antibody to Drosophila Notch, as assayed by Western blotting.

The constructs used to make human Notch-glutathione S-transferase fusion proteins were as follows:

hNFP#2—PCR was used to obtain a fragment starting just before the cdc10 repeats at nucleotide 192 of the hN5k insert to just before the PEST-rich region at nucleotide 1694. The DNA was then digested with BamHI and SmaI and the resulting fragment was ligated into pGEX-3. After expression, the fusion protein was purified by binding to glutathione agarose. The purified polypeptide was quantitated on a 4–15% gradient polyacrylamide gel. The resulting fusion protein had an approximate molecular weight of 83 kD.

hN3FP#1—The entire hN3k DNA insert (nucleotide 1 to 3235) was excised from the Bluescript (SK) vector by digesting with EcoRI. The DNA was ligated into pGEX-3.

hN3FP#2—A 3' segment of hN3k DNA (nucleotide 1847 to 3235) plus some of the polylinker was cut out of the Bluescript (SK) vector by digesting with XmaI. The fragment was ligated into pGEX-1.

Following purification, these fusion proteins are used to make either polyclonal and/or monoclonal antibodies to human Notch.

10. NOTCH EXPRESSION IN NORMAL AND MALIGNANT CELLS

Various human patient tissue samples and cell lines, representing both normal and a wide variety of malignant cells are assayed to detect and/or quantitate expression of Notch. Patient tissue samples are obtained from the pathology department at the Yale University School of Medicine.

The following assays are used to measure Notch expression in patient tissue samples: (a) Northern hybridization; (b) Western blots; (c) in situ hybridization; and (d) immunocytochemistry. Assays are carried out using standard techniques. Northern hybridization and in situ hybridization are carried out (i) using a DNA probe specific to the Notch sequence of clone hN3k; and (ii) using a DNA probe specific to the Notch sequence of clone hN5k. Western blots and immunocytochemistry are carried out using an antibody to Drosophila Notch protein (which also recognizes human Notch proteins).

Northern hybridization and Western blots, as described above, are also used to analyze numerous human cell lines, representing various normal or cancerous tissues. The cell lines tested are listed in Table 2.

TABLE 2

HUMAN CELL LINES

| Tissue/Tumor | Cell line |
|---|---|
| Bone marrow | IM-9 |
| | KG-1 |
| Brain | A-172 |
| | HS 683 |
| | U-87MG |
| | TE 671 |
| Breast | BT-20 |
| | Hs 578Bs |
| | MDA-MB-330 |
| Colon | Caco-2 |
| | SW48 |
| | T84 |
| | WiDr |
| Embryo | FHs 173We |
| Kidney | A-498 |
| | A-704 |
| | Caki-2 |
| Leukemia | ARH-77 |
| | KG-1 |
| Liver | Hep G2 |
| | WRL 68 |
| Lung | Calu-1 |
| | HLF-a |
| | SK-Lu-1 |
| Lymphoblasts | CCRF-CEM |
| | HuT 78 |
| Lymphoma | Hs 445 |
| | MS116 |
| | U-937 |
| Melanoma | A-375 |
| | G-361 |
| | Hs 294T |
| | SK-MEL-1 |
| Myeloma | IM-9 |
| | RPMI 8226 |
| Neuroblastoma | IMR-32 |
| | SK-N-SH |
| | SK-N-MC |
| Ovary | Caov-3 |
| | Caov-4 |
| | PA-1 |
| Plasma Cells | ARH-77 |
| Sarcoma | A-204 |
| | A673 |
| | HOS |
| Skin | Amdur II |
| | BUD-8 |
| Testis | Tera-1 |
| | Tera-2 |
| Thymus | Hs67 |
| Uterus | AN3 Ca |
| | HEC-1-A |

Malignancies of malignant cell tissue types which are thus shown to specifically express Notch can be treated as described in Section 5.1 et seq.

10.1. Expression of Human Notch Protein Is Increased In Various Malignancies

As described below, we have found that human Notch protein expression is increased in at least three human cancers, namely cervical, breast, and colon cancer. Immunocytochemical staining of tissue samples from cervical, breast, and colon cancers of human patients showed clearly that the malignant tissue expresses high levels of Notch, at increased levels relative to non-malignant tissue sections. This broad spectrum of different neoplasias in which there is elevated Notch expression suggests that many more cancerous conditions will be seen to upregulate Notch.

Slides of human tumor samples (for breast, colon, and cervical tumors) were obtained from the tissue bank of the Pathology Department, Yale Medical School. The stainings were done using monoclonal antibodies raised against the P1 and P4 fusion proteins which were generated from sequences of hN and TAN-1, respectively.

The P1 and P4 fusion proteins were obtained by insertion of the desired human Notch sequence into the appropriate pGEX expression vector (Smith and Johnson, 1988, Gene 7:31–40; AMRAD Corp., Melbourne, Australia) and were affinity-purified according to the instructions of the manufacturer (AMRAD Corp.). For production of the P1 fusion protein, pGEX-2 was cut with BamHI and ligated to a concatamer which consists of three copies of a 518 bp BamHI-BglII fragment of hN. Rats were immunized with the expressed protein and monoclonal antibodies were produced by standard procedures. For production of the P4 fusion protein, pGEX-2 was cut with BamHI and ligated to a concatamer which consists of three copies of a 473 bp BamHI-BglII fragment of TAN-1. Rats were immunized with the expressed protein, and monoclonal antibodies were produced by standard procedures.

In all tumors examined, the Notch proteins encoded by both human Notch homologs TAN-1 and hN were present at increased levels in the malignant part of the tissue compared to the normal part. Representative stainings are shown in the pictures provided (FIGS. 14–16B).

The staining procedure was as follows: The tissues were fixed in paraformaldehyde, embedded in paraffin, cut in 5 micrometer thick sections and placed on glass slides. Then the following steps were carried out:

1. Deparafinization through 4 changes of xylene, 4 minutes each.
2. Removal of xylene through 3 changes in absolute ethanol, 4 minutes each.
3. Gradual rehydration of the tissues by immersing the slides into 95%, 90%, 80%, 60% and 30% ethanol, 4 minutes each. At the end the slides were rinsed in distilled water for 5 minutes.
4. Quenching of endogenous, peroxidase by incubating for 30 minutes in 0.3% hydrogen peroxide in methanol.
5. Washing in PBS (10 mM sodium phosphate pH 7.5, 0.9% NaCl) for 20 minutes.
6. Incubation for 1 hour in blocking solution. (Blocking solution: PBS containing 4% normal rabbit serum and 0.1 Triton X-100.)
7. Incubation overnight at 4° C. with primary antibody diluted in blocking solution. Final concentration of primary antibody 20–50 µg/ml.
8. Washing for 20 minutes with PBS+0.1% Triton X-100 (3 changes).
9. Incubation for 30 minutes with biotinylated rabbit anti-rat antibody: 50 µl of biotinylated antibody (VECTOR) in 10 ml of blocking solution.
10. Washing for 20 minutes with PBS+0.1% Triton X-100 (3 changes).
11. Incubation with ABC reagent (VECTOR) for 30 minutes (the reagent is made in PBS+0.1% Triton X-100).
12. Washing for 20 minutes in PBS+0.1% Triton X-100. Followed by incubation for 2 minutes in PBS+0.5% Triton X-100.
13. Incubation for 2–5 minutes in peroxidase substrate solution. Peroxidase substrate solution: Equal volumes of 0.02% hydrogen peroxide in distilled water and 0.1% diaminobenzidine tetrahydrochloride (DAB) in 0.1M Tris buffer pH 7.5 are mixed just before the incubation with the tissues. Triton X-100 is added to the final solution at a concentration of 0.5%.

14. Washing for 15 minutes in tap water.
15. Counterstaining for 10 minutes with Mayer's hematoxylin.
16. Washing for 15 minutes in tap water.
17. Dehydration through changes in 30%, 60%, 80%, 90%, 95% and absolute ethanol (4 minutes each).
18. Immersion into xylene (2 changes, 4 minutes each).
19. Mounting, light microscopy.

11. DEPOSIT OF MICROORGANISMS

The following recombinant bacteria, each carrying a plasmid encoding a portion of human Notch, were deposited on May 2, 1991 with the American Type Culture Collection, 1201 Parklawn Drive, Rockville, Md. 20852, under the provisions of the Budapest Treaty on the International Recognition of the Deposit of Microorganisms for the Purposes of Patent Procedures.

| Bacteria | carrying | Plasmid | ATCC Accession No. |
|---|---|---|---|
| E. coli XL1-Blue | | hN4k | 68610 |
| E. coli XL1-Blue | | hN3k | 68609 |
| E. coli XL1-Blue | | hN5k | 68611 |

The present invention is not to be limited in scope by the microorganisms deposited or the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 2892 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 142..2640

( x i ) SEQUENCE DESCRIPTION: SEQ ID NO:1:

```
GAATTCGGAG  GAATTATTCA  AAACATAAAC  ACAATAAACA  ATTTGAGTAG  TTGCCGCACA        60

CACACACACA  CACAGCCCGT  GGATTATTAC  ACTAAAAGCG  ACACTCAATC  CAAAAAATCA       120

GCAACAAAAA  CATCAATAAA  C  ATG  CAT  TGG  ATT  AAA  TGT  TTA  TTA  ACA  GCA   171
                          Met  His  Trp  Ile  Lys  Cys  Leu  Leu  Thr  Ala
                           1                 5                         10

TTC  ATT  TGC  TTC  ACA  GTC  ATC  GTG  CAG  GTT  CAC  AGT  TCC  GGC  AGC  TTT   219
Phe  Ile  Cys  Phe  Thr  Val  Ile  Val  Gln  Val  His  Ser  Ser  Gly  Ser  Phe
               15                      20                      25

GAG  TTG  CGC  CTG  AAG  TAC  TTC  AGC  AAC  GAT  CAC  GGG  CGG  GAC  AAC  GAG   267
Glu  Leu  Arg  Leu  Lys  Tyr  Phe  Ser  Asn  Asp  His  Gly  Arg  Asp  Asn  Glu
               30                      35                      40

GGT  CGC  TGC  TGC  AGC  GGG  GAG  TCG  GAC  GGA  GCG  ACG  GGC  AAG  TGC  CTG   315
Gly  Arg  Cys  Cys  Ser  Gly  Glu  Ser  Asp  Gly  Ala  Thr  Gly  Lys  Cys  Leu
               45                      50                      55

GGC  AGC  TGC  AAG  ACG  CGG  TTT  CGC  GTC  TGC  CTA  AAG  CAC  TAC  CAG  GCC   363
Gly  Ser  Cys  Lys  Thr  Arg  Phe  Arg  Val  Cys  Leu  Lys  His  Tyr  Gln  Ala
               60                      65                      70

ACC  ATC  GAC  ACC  ACC  TCC  CAG  TGC  ACC  TAC  GGG  GAC  GTG  ATC  ACG  CCC   411
Thr  Ile  Asp  Thr  Thr  Ser  Gln  Cys  Thr  Tyr  Gly  Asp  Val  Ile  Thr  Pro
 75                      80                      85                      90

ATT  CTC  GGC  GAG  AAC  TCG  GTC  AAT  CTG  ACC  GAC  GCC  CAG  CGC  TTC  CAG   459
Ile  Leu  Gly  Glu  Asn  Ser  Val  Asn  Leu  Thr  Asp  Ala  Gln  Arg  Phe  Gln
               95                      100                     105
```

-continued

| | | | | | | | | | | | | | | | | |
|---|---|---|---|---|---|---|---|---|---|---|---|---|---|---|---|---|
| AAC | AAG | GGC | TTC | ACG | AAT | CCC | ATC | CAG | TTC | CCC | TTC | TCG | TTC | TCA | TGG | 507 |
| Asn | Lys | Gly | Phe | Thr | Asn | Pro | Ile | Gln | Phe | Pro | Phe | Ser | Phe | Ser | Trp | |
| | | 110 | | | | | 115 | | | | | 120 | | | | |
| CCG | GGT | ACC | TTC | TCG | CTG | ATC | GTC | GAG | GCC | TGG | CAT | GAT | ACG | AAC | AAT | 555 |
| Pro | Gly | Thr | Phe | Ser | Leu | Ile | Val | Glu | Ala | Trp | His | Asp | Thr | Asn | Asn | |
| | | 125 | | | | | 130 | | | | | 135 | | | | |
| AGC | GGC | AAT | GCG | CGA | ACC | AAC | AAG | CTC | CTC | ATC | CAG | CGA | CTC | TTG | GTG | 603 |
| Ser | Gly | Asn | Ala | Arg | Thr | Asn | Lys | Leu | Leu | Ile | Gln | Arg | Leu | Leu | Val | |
| | | 140 | | | | | 145 | | | | | 150 | | | | |
| CAG | CAG | GTA | CTG | GAG | GTG | TCC | TCC | GAA | TGG | AAG | ACG | AAC | AAG | TCG | GAA | 651 |
| Gln | Gln | Val | Leu | Glu | Val | Ser | Ser | Glu | Trp | Lys | Thr | Asn | Lys | Ser | Glu | |
| 155 | | | | | 160 | | | | | 165 | | | | | 170 | |
| TCG | CAG | TAC | ACG | TCG | CTG | GAG | TAC | GAT | TTC | CGT | GTC | ACC | TGC | GAT | CTC | 699 |
| Ser | Gln | Tyr | Thr | Ser | Leu | Glu | Tyr | Asp | Phe | Arg | Val | Thr | Cys | Asp | Leu | |
| | | | | 175 | | | | | 180 | | | | | 185 | | |
| AAC | TAC | TAC | GGA | TCC | GGC | TGT | GCC | AAG | TTC | TGC | CGG | CCC | CGC | GAC | GAT | 747 |
| Asn | Tyr | Tyr | Gly | Ser | Gly | Cys | Ala | Lys | Phe | Cys | Arg | Pro | Arg | Asp | Asp | |
| | | | 190 | | | | | 195 | | | | | 200 | | | |
| TCA | TTT | GGA | CAC | TCG | ACT | TGC | TCG | GAG | ACG | GGC | GAA | ATT | ATC | TGT | TTG | 795 |
| Ser | Phe | Gly | His | Ser | Thr | Cys | Ser | Glu | Thr | Gly | Glu | Ile | Ile | Cys | Leu | |
| | | | | 205 | | | | | 210 | | | | | 215 | | |
| ACC | GGA | TGG | CAG | GGC | GAT | TAC | TGT | CAC | ATA | CCC | AAA | TGC | GCC | AAA | GGC | 843 |
| Thr | Gly | Trp | Gln | Gly | Asp | Tyr | Cys | His | Ile | Pro | Lys | Cys | Ala | Lys | Gly | |
| | | | 220 | | | | | 225 | | | | | 230 | | | |
| TGT | GAA | CAT | GGA | CAT | TGC | GAC | AAA | CCC | AAT | CAA | TGC | GTT | TGC | CAA | CTG | 891 |
| Cys | Glu | His | Gly | His | Cys | Asp | Lys | Pro | Asn | Gln | Cys | Val | Cys | Gln | Leu | |
| 235 | | | | | 240 | | | | | 245 | | | | | 250 | |
| GGC | TGG | AAG | GGA | GCC | TTG | TGC | AAC | GAG | TGC | GTT | CTG | GAA | CCG | AAC | TGC | 939 |
| Gly | Trp | Lys | Gly | Ala | Leu | Cys | Asn | Glu | Cys | Val | Leu | Glu | Pro | Asn | Cys | |
| | | | | 255 | | | | | 260 | | | | | 265 | | |
| ATC | CAT | GGC | ACC | TGC | AAC | AAA | CCC | TGG | ACT | TGC | ATC | TGC | AAC | GAG | GGT | 987 |
| Ile | His | Gly | Thr | Cys | Asn | Lys | Pro | Trp | Thr | Cys | Ile | Cys | Asn | Glu | Gly | |
| | | | 270 | | | | | 275 | | | | | 280 | | | |
| TGG | GGA | GGC | TTG | TAC | TGC | AAC | CAG | GAT | CTG | AAC | TAC | TGC | ACC | AAC | CAC | 1035 |
| Trp | Gly | Gly | Leu | Tyr | Cys | Asn | Gln | Asp | Leu | Asn | Tyr | Cys | Thr | Asn | His | |
| | | 285 | | | | | 290 | | | | | 295 | | | | |
| AGA | CCC | TGC | AAG | AAT | GGC | GGA | ACC | TGC | TTC | AAC | ACC | GGC | GAG | GGA | TTG | 1083 |
| Arg | Pro | Cys | Lys | Asn | Gly | Gly | Thr | Cys | Phe | Asn | Thr | Gly | Glu | Gly | Leu | |
| | 300 | | | | | 305 | | | | | 310 | | | | | |
| TAC | ACA | TGC | AAA | TGC | GCT | CCA | GGA | TAC | AGT | GGT | GAT | GAT | TGC | GAA | AAT | 1131 |
| Tyr | Thr | Cys | Lys | Cys | Ala | Pro | Gly | Tyr | Ser | Gly | Asp | Asp | Cys | Glu | Asn | |
| 315 | | | | | 320 | | | | | 325 | | | | | 330 | |
| GAG | ATC | TAC | TCC | TGC | GAT | GCC | GAT | GTC | AAT | CCC | TGC | CAG | AAT | GGT | GGT | 1179 |
| Glu | Ile | Tyr | Ser | Cys | Asp | Ala | Asp | Val | Asn | Pro | Cys | Gln | Asn | Gly | Gly | |
| | | | | 335 | | | | | 340 | | | | | 345 | | |
| ACC | TGC | ATC | GAT | GAG | CCG | CAC | ACA | AAA | ACC | GGC | TAC | AAG | TGT | CAT | TGC | 1227 |
| Thr | Cys | Ile | Asp | Glu | Pro | His | Thr | Lys | Thr | Gly | Tyr | Lys | Cys | His | Cys | |
| | | | 350 | | | | | 355 | | | | | 360 | | | |
| GCC | AAC | GGC | TGG | AGC | GGA | AAG | ATG | TGC | GAG | GAG | AAA | GTG | CTC | ACG | TGT | 1275 |
| Ala | Asn | Gly | Trp | Ser | Gly | Lys | Met | Cys | Glu | Glu | Lys | Val | Leu | Thr | Cys | |
| | | 365 | | | | | 370 | | | | | 375 | | | | |
| TCG | GAC | AAA | CCC | TGT | CAT | CAG | GGA | ATC | TGC | CGC | AAC | GTT | CGT | CCT | GGC | 1323 |
| Ser | Asp | Lys | Pro | Cys | His | Gln | Gly | Ile | Cys | Arg | Asn | Val | Arg | Pro | Gly | |
| | 380 | | | | | 385 | | | | | 390 | | | | | |
| TTG | GGA | AGC | AAG | GGT | CAG | GGC | TAC | CAG | TGC | GAA | TGT | CCC | ATT | GGC | TAC | 1371 |
| Leu | Gly | Ser | Lys | Gly | Gln | Gly | Tyr | Gln | Cys | Glu | Cys | Pro | Ile | Gly | Tyr | |
| 395 | | | | | 400 | | | | | 405 | | | | | 410 | |
| AGC | GGA | CCC | AAC | TGC | GAT | CTC | CAG | CTG | GAC | AAC | TGC | AGT | CCG | AAT | CCA | 1419 |
| Ser | Gly | Pro | Asn | Cys | Asp | Leu | Gln | Leu | Asp | Asn | Cys | Ser | Pro | Asn | Pro | |
| | | | | 415 | | | | | 420 | | | | | 425 | | |

| | | | | | | | | | | | | | | | | |
|---|---|---|---|---|---|---|---|---|---|---|---|---|---|---|---|---|
| TGC | ATA | AAC | GGT | GGA | AGC | TGT | CAG | CCG | AGC | GGA | AAG | TGT | ATT | TGC | CCA | 1467 |
| Cys | Ile | Asn | Gly | Gly | Ser | Cys | Gln | Pro | Ser | Gly | Lys | Cys | Ile | Cys | Pro | |
| | | | 430 | | | | | 435 | | | | | 440 | | | |
| GCG | GGA | TTT | TCG | GGA | ACG | AGA | TGC | GAG | ACC | AAC | ATT | GAC | GAT | TGT | CTT | 1515 |
| Ala | Gly | Phe | Ser | Gly | Thr | Arg | Cys | Glu | Thr | Asn | Ile | Asp | Asp | Cys | Leu | |
| | | | | 445 | | | | | 450 | | | | | 455 | | |
| GGC | CAC | CAG | TGC | GAG | AAC | GGA | GGC | ACC | TGC | ATA | GAT | ATG | GTC | AAC | CAA | 1563 |
| Gly | His | Gln | Cys | Glu | Asn | Gly | Gly | Thr | Cys | Ile | Asp | Met | Val | Asn | Gln | |
| | 460 | | | | | 465 | | | | | 470 | | | | | |
| TAT | CGC | TGC | CAA | TGC | GTT | CCC | GGT | TTC | CAT | GGC | ACC | CAC | TGT | AGT | AGC | 1611 |
| Tyr | Arg | Cys | Gln | Cys | Val | Pro | Gly | Phe | His | Gly | Thr | His | Cys | Ser | Ser | |
| 475 | | | | 480 | | | | | 485 | | | | | | 490 | |
| AAA | GTT | GAC | TTG | TGC | CTC | ATC | AGA | CCG | TGT | GCC | AAT | GGA | GGA | ACC | TGC | 1659 |
| Lys | Val | Asp | Leu | Cys | Leu | Ile | Arg | Pro | Cys | Ala | Asn | Gly | Gly | Thr | Cys | |
| | | | | 495 | | | | | 500 | | | | | 505 | | |
| TTG | AAT | CTC | AAC | AAC | GAT | TAC | CAG | TGC | ACC | TGT | CGT | GCG | GGA | TTT | ACT | 1707 |
| Leu | Asn | Leu | Asn | Asn | Asp | Tyr | Gln | Cys | Thr | Cys | Arg | Ala | Gly | Phe | Thr | |
| | | 510 | | | | | 515 | | | | | 520 | | | | |
| GGC | AAG | GAT | TGC | TCT | GTG | GAC | ATC | GAT | GAG | TGC | AGC | AGT | GGA | CCC | TGT | 1755 |
| Gly | Lys | Asp | Cys | Ser | Val | Asp | Ile | Asp | Glu | Cys | Ser | Ser | Gly | Pro | Cys | |
| | | 525 | | | | | 530 | | | | | 535 | | | | |
| CAT | AAC | GGC | GGC | ACT | TGC | ATG | AAC | CGC | GTC | AAT | TCG | TTC | GAA | TGC | GTG | 1803 |
| His | Asn | Gly | Gly | Thr | Cys | Met | Asn | Arg | Val | Asn | Ser | Phe | Glu | Cys | Val | |
| | 540 | | | | | 545 | | | | | 550 | | | | | |
| TGT | GCC | AAT | GGT | TTC | AGG | GGC | AAG | CAG | TGC | GAT | GAG | GAG | TCC | TAC | GAT | 1851 |
| Cys | Ala | Asn | Gly | Phe | Arg | Gly | Lys | Gln | Cys | Asp | Glu | Glu | Ser | Tyr | Asp | |
| 555 | | | | | 560 | | | | | 565 | | | | | 570 | |
| TCG | GTG | ACC | TTC | GAT | GCC | CAC | CAA | TAT | GGA | GCG | ACC | ACA | CAA | GCG | AGA | 1899 |
| Ser | Val | Thr | Phe | Asp | Ala | His | Gln | Tyr | Gly | Ala | Thr | Thr | Gln | Ala | Arg | |
| | | | | 575 | | | | | 580 | | | | | 585 | | |
| GCC | GAT | GGT | TTG | ACC | AAT | GCC | CAG | GTA | GTC | CTA | ATT | GCT | GTT | TTC | TCC | 1947 |
| Ala | Asp | Gly | Leu | Thr | Asn | Ala | Gln | Val | Val | Leu | Ile | Ala | Val | Phe | Ser | |
| | | | 590 | | | | | 595 | | | | | 600 | | | |
| GTT | GCG | ATG | CCT | TTG | GTG | GCG | GTT | ATT | GCG | GCG | TGC | GTG | GTC | TTC | TGC | 1995 |
| Val | Ala | Met | Pro | Leu | Val | Ala | Val | Ile | Ala | Ala | Cys | Val | Val | Phe | Cys | |
| | | 605 | | | | | 610 | | | | | 615 | | | | |
| ATG | AAG | CGC | AAG | CGT | AAG | CGT | GCT | CAG | GAA | AAG | GAC | GAC | GCG | GAG | GCC | 2043 |
| Met | Lys | Arg | Lys | Arg | Lys | Arg | Ala | Gln | Glu | Lys | Asp | Asp | Ala | Glu | Ala | |
| | 620 | | | | | 625 | | | | | 630 | | | | | |
| AGG | AAG | CAG | AAC | GAA | CAG | AAT | GCG | GTG | GCC | ACA | ATG | CAT | CAC | AAT | GGC | 2091 |
| Arg | Lys | Gln | Asn | Glu | Gln | Asn | Ala | Val | Ala | Thr | Met | His | His | Asn | Gly | |
| 635 | | | | 640 | | | | | 645 | | | | | | 650 | |
| AGT | GGG | GTG | GGT | GTA | GCT | TTG | GCT | TCA | GCC | TCT | CTG | GGC | GGC | AAA | ACT | 2139 |
| Ser | Gly | Val | Gly | Val | Ala | Leu | Ala | Ser | Ala | Ser | Leu | Gly | Gly | Lys | Thr | |
| | | | | 655 | | | | | 660 | | | | | 665 | | |
| GGC | AGC | AAC | AGC | GGT | CTC | ACC | TTC | GAT | GGC | GGC | AAC | CCG | AAT | ATC | ATC | 2187 |
| Gly | Ser | Asn | Ser | Gly | Leu | Thr | Phe | Asp | Gly | Gly | Asn | Pro | Asn | Ile | Ile | |
| | | | 670 | | | | | 675 | | | | | 680 | | | |
| AAA | AAC | ACC | TGG | GAC | AAG | TCG | GTC | AAC | AAC | ATT | TGT | GCC | TCA | GCA | GCA | 2235 |
| Lys | Asn | Thr | Trp | Asp | Lys | Ser | Val | Asn | Asn | Ile | Cys | Ala | Ser | Ala | Ala | |
| | | 685 | | | | | 690 | | | | | 695 | | | | |
| GCA | GCG | GCG | GCG | GCG | GCA | GCA | GCG | GCG | GAC | GAG | TGT | CTC | ATG | TAC | GGC | 2283 |
| Ala | Ala | Ala | Ala | Ala | Ala | Ala | Ala | Ala | Asp | Glu | Cys | Leu | Met | Tyr | Gly | |
| | 700 | | | | | 705 | | | | | 710 | | | | | |
| GGA | TAT | GTG | GCC | TCG | GTG | GCG | GAT | AAC | AAC | AAT | GCC | AAC | TCA | GAC | TTT | 2331 |
| Gly | Tyr | Val | Ala | Ser | Val | Ala | Asp | Asn | Asn | Asn | Ala | Asn | Ser | Asp | Phe | |
| 715 | | | | 720 | | | | | 725 | | | | | | 730 | |
| TGT | GTG | GCT | CCG | CTA | CAA | AGA | GCC | AAG | TCG | CAA | AAG | CAA | CTC | AAC | ACC | 2379 |
| Cys | Val | Ala | Pro | Leu | Gln | Arg | Ala | Lys | Ser | Gln | Lys | Gln | Leu | Asn | Thr | |
| | | | | 735 | | | | | 740 | | | | | 745 | | |

| | | | | | | | | | | | | | | | | |
|---|---|---|---|---|---|---|---|---|---|---|---|---|---|---|---|---|
| GAT | CCC | ACG | CTC | ATG | CAC | CGC | GGT | TCG | CCG | GCA | GGC | AGC | TCA | GCC | AAG | 2427 |
| Asp | Pro | Thr | Leu | Met | His | Arg | Gly | Ser | Pro | Ala | Gly | Ser | Ser | Ala | Lys | |
| | | | 750 | | | | | 755 | | | | 760 | | | | |
| GGA | GCG | TCT | GGC | GGA | GGA | CCG | GGA | GCG | GCG | GAG | GGC | AAG | AGG | ATC | TCT | 2475 |
| Gly | Ala | Ser | Gly | Gly | Gly | Pro | Gly | Ala | Ala | Glu | Gly | Lys | Arg | Ile | Ser | |
| | | 765 | | | | | 770 | | | | | 775 | | | | |
| GTT | TTA | GGC | GAG | GGT | TCC | TAC | TGT | AGC | CAG | CGT | TGG | CCC | TCG | TTG | GCG | 2523 |
| Val | Leu | Gly | Glu | Gly | Ser | Tyr | Cys | Ser | Gln | Arg | Trp | Pro | Ser | Leu | Ala | |
| | | 780 | | | | 785 | | | | | 790 | | | | | |
| GCG | GCG | GGA | GTG | GCC | GGA | GCC | TGT | TCA | TCC | CAG | CTA | ATG | GCT | GCA | GCT | 2571 |
| Ala | Ala | Gly | Val | Ala | Gly | Ala | Cys | Ser | Ser | Gln | Leu | Met | Ala | Ala | Ala | |
| 795 | | | | 800 | | | | | 805 | | | | | | 810 | |
| TCG | GCA | GCG | GGC | AGC | GGA | GCG | GGG | ACG | GCG | CAA | CAG | CAG | CGA | TCC | GTG | 2619 |
| Ser | Ala | Ala | Gly | Ser | Gly | Ala | Gly | Thr | Ala | Gln | Gln | Gln | Arg | Ser | Val | |
| | | | | 815 | | | | 820 | | | | | 825 | | | |
| GTC | TGC | GGC | ACT | CCG | CAT | ATG | TAACTCCAAA | AATCCGGAAG | GGCTCCTGGT | | | | | | | 2670 |
| Val | Cys | Gly | Thr | Pro | His | Met | | | | | | | | | | |
| | | | 830 | | | | | | | | | | | | | |

```
AAATCCGGAG  AAATCCGCAT  GGAGGAGCTG  ACAGCACATA  CACAAAGAAA  AGACTGGGTT     2730

GGGTTCAAAA  TGTGAGAGAG  ACGCCAAAAT  GTTGTTGTTG  ATTGAAGCAG  TTTAGTCGTC     2790

ACGAAAAATG  AAAAATCTGT  AACAGGCATA  ACTCGTAAAC  TCCCTAAAAA  ATTTGTATAG     2850

TAATTAGCAA  AGCTGTGACC  CAGCCGTTTC  GATCCCGAAT  TC                         2892
```

( 2 ) INFORMATION FOR SEQ ID NO:2:

( i ) SEQUENCE CHARACTERISTICS:
        ( A ) LENGTH: 833 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

```
Met  His  Trp  Ile  Lys  Cys  Leu  Leu  Thr  Ala  Phe  Ile  Cys  Phe  Thr  Val
 1              5                   10                  15

Ile  Val  Gln  Val  His  Ser  Ser  Gly  Ser  Phe  Glu  Leu  Arg  Leu  Lys  Tyr
              20                  25                  30

Phe  Ser  Asn  Asp  His  Gly  Arg  Asp  Asn  Glu  Gly  Arg  Cys  Cys  Ser  Gly
              35                  40                  45

Glu  Ser  Asp  Gly  Ala  Thr  Gly  Lys  Cys  Leu  Gly  Ser  Cys  Lys  Thr  Arg
         50                  55                  60

Phe  Arg  Val  Cys  Leu  Lys  His  Tyr  Gln  Ala  Thr  Ile  Asp  Thr  Thr  Ser
 65                  70                  75                       80

Gln  Cys  Thr  Tyr  Gly  Asp  Val  Ile  Thr  Pro  Ile  Leu  Gly  Glu  Asn  Ser
              85                  90                  95

Val  Asn  Leu  Thr  Asp  Ala  Gln  Arg  Phe  Gln  Asn  Lys  Gly  Phe  Thr  Asn
              100                 105                 110

Pro  Ile  Gln  Phe  Pro  Phe  Ser  Phe  Ser  Trp  Pro  Gly  Thr  Phe  Ser  Leu
              115                 120                 125

Ile  Val  Glu  Ala  Trp  His  Asp  Thr  Asn  Asn  Ser  Gly  Asn  Ala  Arg  Thr
              130                 135                 140

Asn  Lys  Leu  Leu  Ile  Gln  Arg  Leu  Leu  Val  Gln  Gln  Val  Leu  Glu  Val
145                 150                 155                      160

Ser  Ser  Glu  Trp  Lys  Thr  Asn  Lys  Ser  Glu  Ser  Gln  Tyr  Thr  Ser  Leu
              165                 170                 175

Glu  Tyr  Asp  Phe  Arg  Val  Thr  Cys  Asp  Leu  Asn  Tyr  Tyr  Gly  Ser  Gly
              180                 185                 190
```

```
Cys Ala Lys Phe Cys Arg Pro Arg Asp Asp Ser Phe Gly His Ser Thr
        195                 200                 205
Cys Ser Glu Thr Gly Glu Ile Ile Cys Leu Thr Gly Trp Gln Gly Asp
        210                 215                 220
Tyr Cys His Ile Pro Lys Cys Ala Lys Gly Cys Glu His Gly His Cys
225                     230                 235                 240
Asp Lys Pro Asn Gln Cys Val Cys Gln Leu Gly Trp Lys Gly Ala Leu
                245                 250                 255
Cys Asn Glu Cys Val Leu Glu Pro Asn Cys Ile His Gly Thr Cys Asn
            260                 265                 270
Lys Pro Trp Thr Cys Ile Cys Asn Glu Gly Trp Gly Gly Leu Tyr Cys
        275                 280                 285
Asn Gln Asp Leu Asn Tyr Cys Thr Asn His Arg Pro Cys Lys Asn Gly
    290                 295                 300
Gly Thr Cys Phe Asn Thr Gly Glu Gly Leu Tyr Thr Cys Lys Cys Ala
305                 310                 315                 320
Pro Gly Tyr Ser Gly Asp Asp Cys Glu Asn Glu Ile Tyr Ser Cys Asp
                325                 330                 335
Ala Asp Val Asn Pro Cys Gln Asn Gly Gly Thr Cys Ile Asp Glu Pro
            340                 345                 350
His Thr Lys Thr Gly Tyr Lys Cys His Cys Ala Asn Gly Trp Ser Gly
        355                 360                 365
Lys Met Cys Glu Glu Lys Val Leu Thr Cys Ser Asp Lys Pro Cys His
    370                 375                 380
Gln Gly Ile Cys Arg Asn Val Arg Pro Gly Leu Gly Ser Lys Gly Gln
385                 390                 395                 400
Gly Tyr Gln Cys Glu Cys Pro Ile Gly Tyr Ser Gly Pro Asn Cys Asp
                405                 410                 415
Leu Gln Leu Asp Asn Cys Ser Pro Asn Pro Cys Ile Asn Gly Gly Ser
            420                 425                 430
Cys Gln Pro Ser Gly Lys Cys Ile Cys Pro Ala Gly Phe Ser Gly Thr
        435                 440                 445
Arg Cys Glu Thr Asn Ile Asp Asp Cys Leu Gly His Gln Cys Glu Asn
    450                 455                 460
Gly Gly Thr Cys Ile Asp Met Val Asn Gln Tyr Arg Cys Gln Cys Val
465                 470                 475                 480
Pro Gly Phe His Gly Thr His Cys Ser Ser Lys Val Asp Leu Cys Leu
                485                 490                 495
Ile Arg Pro Cys Ala Asn Gly Gly Thr Cys Leu Asn Leu Asn Asn Asp
            500                 505                 510
Tyr Gln Cys Thr Cys Arg Ala Gly Phe Thr Gly Lys Asp Cys Ser Val
        515                 520                 525
Asp Ile Asp Glu Cys Ser Ser Gly Pro Cys His Asn Gly Gly Thr Cys
530                 535                 540
Met Asn Arg Val Asn Ser Phe Glu Cys Val Cys Ala Asn Gly Phe Arg
545                 550                 555                 560
Gly Lys Gln Cys Asp Glu Glu Ser Tyr Asp Ser Val Thr Phe Asp Ala
                565                 570                 575
His Gln Tyr Gly Ala Thr Thr Gln Ala Arg Ala Asp Gly Leu Thr Asn
            580                 585                 590
Ala Gln Val Val Leu Ile Ala Val Phe Ser Val Ala Met Pro Leu Val
        595                 600                 605
Ala Val Ile Ala Ala Cys Val Val Phe Cys Met Lys Arg Lys Arg Lys
610                 615                 620
```

| Arg<br>625 | Ala | Gln | Glu | Lys | Asp<br>630 | Asp | Ala | Glu | Ala<br>635 | Arg | Lys | Gln | Asn | Glu<br>640 | Gln |
| --- | --- | --- | --- | --- | --- | --- | --- | --- | --- | --- | --- | --- | --- | --- | --- |
| Asn | Ala | Val | Ala | Thr<br>645 | Met | His | His | Asn | Gly<br>650 | Ser | Gly | Val | Gly | Val<br>655 | Ala |
| Leu | Ala | Ser | Ala<br>660 | Ser | Leu | Gly | Gly | Lys<br>665 | Thr | Gly | Ser | Asn | Ser<br>670 | Gly | Leu |
| Thr | Phe | Asp<br>675 | Gly | Gly | Asn | Pro | Asn<br>680 | Ile | Ile | Lys | Asn | Thr<br>685 | Trp | Asp | Lys |
| Ser | Val<br>690 | Asn | Asn | Ile | Cys | Ala<br>695 | Ser | Ala | Ala | Ala | Ala<br>700 | Ala | Ala | Ala | Ala |
| Ala<br>705 | Ala | Ala | Asp | Glu | Cys<br>710 | Leu | Met | Tyr | Gly | Gly<br>715 | Tyr | Val | Ala | Ser | Val<br>720 |
| Ala | Asp | Asn | Asn | Asn<br>725 | Ala | Asn | Ser | Asp | Phe<br>730 | Cys | Val | Ala | Pro | Leu<br>735 | Gln |
| Arg | Ala | Lys | Ser<br>740 | Gln | Lys | Gln | Leu | Asn<br>745 | Thr | Asp | Pro | Thr | Leu<br>750 | Met | His |
| Arg | Gly | Ser<br>755 | Pro | Ala | Gly | Ser | Ser<br>760 | Ala | Lys | Gly | Ala | Ser<br>765 | Gly | Gly | Gly |
| Pro | Gly<br>770 | Ala | Ala | Glu | Gly | Lys<br>775 | Arg | Ile | Ser | Val | Leu<br>780 | Gly | Glu | Gly | Ser |
| Tyr<br>785 | Cys | Ser | Gln | Arg | Trp<br>790 | Pro | Ser | Leu | Ala | Ala<br>795 | Ala | Gly | Val | Ala | Gly<br>800 |
| Ala | Cys | Ser | Ser | Gln<br>805 | Leu | Met | Ala | Ala | Ala<br>810 | Ser | Ala | Ala | Gly | Ser<br>815 | Gly |
| Ala | Gly | Thr | Ala<br>820 | Gln | Gln | Gln | Arg | Ser<br>825 | Val | Val | Cys | Gly | Thr<br>830 | Pro | His |
| Met | | | | | | | | | | | | | | | |

( 2 ) INFORMATION FOR SEQ ID NO:3:

( i ) SEQUENCE CHARACTERISTICS:
        ( A ) LENGTH: 1320 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 442..1320

( x i ) SEQUENCE DESCRIPTION: SEQ ID NO:3:

```
CCGAGTCGAG CGCCGTGCTT CGAGCGGTGA TGAGCCCCTT TTCTGTCAAC GCTAAAGATC      60

TACAAAACAT CAGCGCCTAT CAAGTGGAAG TGTCAAGTGT GAACAAAACA AAAACGAGAG     120

AAGCACATAC TAAGGTCCAT ATAAATAATA AATAATAATT GTGTGTGATA ACAACATTAT     180

CCAAACAAAA CCAAACAAAA CGAAGGCAAA GTGGAGAAAA TGATACAGCA TCCAGAGTAC     240

GGCCGTTATT CAGCTATCCA GAGCAAGTGT AGTGTGGCAA AATAGAAACA AACAAAGGCA     300

CCAAAATCTG CATACATGGG CTAATTAAGG CTGCCCAGCG AATTTACATT TGTGTGGTGC     360

CAATCCAGAG TGAATCCGAA ACAAACTCCA TCTAGATCGC CAACCAGCAT CACGCTCGCA     420

AACGCCCCCA GAATGTACAA A ATG TTT AGG AAA CAT TTT CGG CGA AAA CCA      471
                        Met Phe Arg Lys His Phe Arg Arg Lys Pro
                         1               5                      10

GCT ACG TCG TCG TCG TTG GAG TCA ACA ATA GAA TCA GCA GAC AGC CTG      519
Ala Thr Ser Ser Ser Leu Glu Ser Thr Ile Glu Ser Ala Asp Ser Leu
         15                  20                  25
```

```
GGA ATG TCC AAG AAG ACG GCG ACA AAA AGG CAG CGT CCG AGG CAT CGG      567
Gly Met Ser Lys Lys Thr Ala Thr Lys Arg Gln Arg Pro Arg His Arg
             30                  35                  40

GTA CCC AAA ATC GCG ACC CTG CCA TCG ACG ATC CGC GAT TGT CGA TCA      615
Val Pro Lys Ile Ala Thr Leu Pro Ser Thr Ile Arg Asp Cys Arg Ser
         45                  50                  55

TTA AAG TCT GCC TGC AAC TTA ATT GCT TTA ATT TTA ATA CTG TTA GTC      663
Leu Lys Ser Ala Cys Asn Leu Ile Ala Leu Ile Leu Ile Leu Leu Val
         60                  65                  70

CAT AAG ATA TCC GCA GCT GGT AAC TTC GAG CTG GAA ATA TTA GAA ATC      711
His Lys Ile Ser Ala Ala Gly Asn Phe Glu Leu Glu Ile Leu Glu Ile
 75              80                  85                  90

TCA AAT ACC AAC AGC CAT CTA CTC AAC GGC TAT TGC TGC GGC ATG CCA      759
Ser Asn Thr Asn Ser His Leu Leu Asn Gly Tyr Cys Cys Gly Met Pro
                 95                 100                 105

GCG GAA CTT AGG GCC ACC AAG ACG ATA GGC TGC TCG CCA TGC ACG ACG      807
Ala Glu Leu Arg Ala Thr Lys Thr Ile Gly Cys Ser Pro Cys Thr Thr
             110                 115                 120

GCA TTC CGG CTG TGC CTG AAG GAG TAC CAG ACC ACG GAG CAG GGT GCC      855
Ala Phe Arg Leu Cys Leu Lys Glu Tyr Gln Thr Thr Glu Gln Gly Ala
         125                 130                 135

AGC ATA TCC ACG GGC TGT TCG TTT GGC AAC GCC ACC ACC AAG ATA CTG      903
Ser Ile Ser Thr Gly Cys Ser Phe Gly Asn Ala Thr Thr Lys Ile Leu
 140                 145                 150

GGT GGC TCC AGC TTT GTG CTC AGC GAT CCG GGT GTG GGA GCC ATT GTG      951
Gly Gly Ser Ser Phe Val Leu Ser Asp Pro Gly Val Gly Ala Ile Val
155                 160                 165                 170

CTG CCC TTT ACG TTT CGT TGG ACG AAG TCG TTT ACG CTG ATA CTG CAG      999
Leu Pro Phe Thr Phe Arg Trp Thr Lys Ser Phe Thr Leu Ile Leu Gln
             175                 180                 185

GCG TTG GAT ATG TAC AAC ACA TCC TAT CCA GAT GCG GAG AGG TTA ATT     1047
Ala Leu Asp Met Tyr Asn Thr Ser Tyr Pro Asp Ala Glu Arg Leu Ile
         190                 195                 200

GAG GAA ACA TCA TAC TCG GGC GTG ATA CTG CCG TCG CCG GAG TGG AAG     1095
Glu Glu Thr Ser Tyr Ser Gly Val Ile Leu Pro Ser Pro Glu Trp Lys
     205                 210                 215

ACG CTG GAC CAC ATC GGG CGG AAC GCG CGG ATC ACC TAC CGT GTC CGG     1143
Thr Leu Asp His Ile Gly Arg Asn Ala Arg Ile Thr Tyr Arg Val Arg
 220                 225                 230

GTG CAA TGC GCC GTT ACC TAC TAC AAC ACG ACC TGC ACG ACC TTC TGC     1191
Val Gln Cys Ala Val Thr Tyr Tyr Asn Thr Thr Cys Thr Thr Phe Cys
235                 240                 245                 250

CGT CCG CGG GAC GAT CAG TTC GGT CAC TAC GCC TGC GGC TCC GAG GGT     1239
Arg Pro Arg Asp Asp Gln Phe Gly His Tyr Ala Cys Gly Ser Glu Gly
             255                 260                 265

CAG AAG CTC TGC CTG AAT GGC TGG CAG GGC GTC AAC TGC GAG GAG GCC     1287
Gln Lys Leu Cys Leu Asn Gly Trp Gln Gly Val Asn Cys Glu Glu Ala
         270                 275                 280

ATA TGC AAG GCG GGC TGC GAC CCC GTC CAC GGC                         1320
Ile Cys Lys Ala Gly Cys Asp Pro Val His Gly
         285                 290
```

( 2 ) INFORMATION FOR SEQ ID NO:4:

( i ) SEQUENCE CHARACTERISTICS:
        ( A ) LENGTH: 293 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
|Met<br>1|Phe|Arg|Lys|His<br>5|Phe|Arg|Arg|Lys|Pro<br>10|Ala|Thr|Ser|Ser|Ser<br>15|Leu|
|Glu|Ser|Thr|Ile<br>20|Glu|Ser|Ala|Asp|Ser<br>25|Leu|Gly|Met|Ser|Lys<br>30|Lys|Thr|
|Ala|Thr|Lys<br>35|Arg|Gln|Arg|Pro|Arg<br>40|His|Arg|Val|Pro|Lys<br>45|Ile|Ala|Thr|
|Leu|Pro<br>50|Ser|Thr|Ile|Arg|Asp<br>55|Cys|Arg|Ser|Leu|Lys<br>60|Ser|Ala|Cys|Asn|
|Leu<br>65|Ile|Ala|Leu|Ile|Leu<br>70|Ile|Leu|Leu|Val|His<br>75|Lys|Ile|Ser|Ala|Ala<br>80|
|Gly|Asn|Phe|Glu|Leu<br>85|Glu|Ile|Leu|Glu|Ile<br>90|Ser|Asn|Thr|Asn|Ser<br>95|His|
|Leu|Leu|Asn|Gly<br>100|Tyr|Cys|Cys|Gly|Met<br>105|Pro|Ala|Glu|Leu|Arg<br>110|Ala|Thr|
|Lys|Thr|Ile<br>115|Gly|Cys|Ser|Pro|Cys<br>120|Thr|Thr|Ala|Phe|Arg<br>125|Leu|Cys|Leu|
|Lys|Glu<br>130|Tyr|Gln|Thr|Thr|Glu<br>135|Gln|Gly|Ala|Ser|Ile<br>140|Ser|Thr|Gly|Cys|
|Ser<br>145|Phe|Gly|Asn|Ala|Thr<br>150|Thr|Lys|Ile|Leu|Gly<br>155|Gly|Ser|Ser|Phe|Val<br>160|
|Leu|Ser|Asp|Pro|Gly<br>165|Val|Gly|Ala|Ile|Val<br>170|Leu|Pro|Phe|Thr|Phe<br>175|Arg|
|Trp|Thr|Lys|Ser<br>180|Phe|Thr|Leu|Ile|Leu<br>185|Gln|Ala|Leu|Asp|Met<br>190|Tyr|Asn|
|Thr|Ser|Tyr<br>195|Pro|Asp|Ala|Glu|Arg<br>200|Leu|Ile|Glu|Glu|Thr<br>205|Ser|Tyr|Ser|
|Gly|Val<br>210|Ile|Leu|Pro|Ser|Pro<br>215|Glu|Trp|Lys|Thr|Leu<br>220|Asp|His|Ile|Gly|
|Arg<br>225|Asn|Ala|Arg|Ile|Thr<br>230|Tyr|Arg|Val|Arg|Val<br>235|Gln|Cys|Ala|Val|Thr<br>240|
|Tyr|Tyr|Asn|Thr|Thr<br>245|Cys|Thr|Thr|Phe|Cys<br>250|Arg|Pro|Arg|Asp|Asp<br>255|Gln|
|Phe|Gly|His|Tyr<br>260|Ala|Cys|Gly|Ser|Glu<br>265|Gly|Gln|Lys|Leu|Cys<br>270|Leu|Asn|
|Gly|Trp|Gln<br>275|Gly|Val|Asn|Cys|Glu<br>280|Glu|Ala|Ile|Cys|Lys<br>285|Ala|Gly|Cys|
|Asp|Pro|Val|His|Gly<br>290| | | | | | | | | | | |

( 2 ) INFORMATION FOR SEQ ID NO:5:

( i ) SEQUENCE CHARACTERISTICS:
      ( A ) LENGTH: 267 base pairs
      ( B ) TYPE: nucleic acid
      ( C ) STRANDEDNESS: double
      ( D ) TOPOLOGY: unknown ( i i ) MOLECULE TYPE: cDNA ( x i ) SEQUENCE DESCRIPTION: SEQ ID NO:5:

```
CGGTGGACTT CCTTCGTGTA TTGGTGGGAG CCCTCGGGAA CGGGGGGTAA CACTGAAAGG        60

TCGAGTACCC ATTTCCGTCA TAACGGGTTG GTCGCCCCCT AGGGGTCGGA GTCAGGTGGA       120

CGGGAGGTCG ACAACGCCCG GGGGACGGGT GGTACATGGT GTAAGGTCTT TACCGGACCG       180

GGCAAACGGG TCACACCGAA AGGGGTGAAC GGTAACTACG GGTCGTCCT GCCCGTCCAT        240

CGAGTCTGGT AAGAGGGTCG CCTTAAG                                          267
```

( 2 ) INFORMATION FOR SEQ ID NO:6:

( i ) SEQUENCE CHARACTERISTICS:
        ( A ) LENGTH: 574 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:6:

```
GAATTCCTTC  CATTATACGT  GACTTTTCTG  AAACTGTAGC  CACCCTAGTG  TCTCTAACTC      60
CCTCTGGAGT  TTGTCAGCTT  TGGTCTTTTC  AAAGAGCAGG  CTCTCTTCAA  GCTCCTTAAT     120
GCGGGCATGC  TCCAGTTTGG  TCTGCGTCTC  AAGATCACCT  TTGGTAATTG  ATTCTTCTTC     180
AACCCGGAAC  TGAAGGCTGG  CTCTCACCCT  CTAGGCAGAG  CAGGAATTCC  GAGGTGGATG     240
TGTTAGATGT  GAATGTCCGT  GGCCCAGATG  GCTGCACCCC  ATTGATGTTG  GCTTCTCTCC     300
GAGGAGGCAG  CTCAGATTTG  AGTGATGAAG  ATGAAGATGC  AGAGGACTGT  TCTGCTAACA     360
TCATCACAGA  CTTGGTCTAC  CAGGGTGCCA  GCCTCCAGNC  CAGACAGACC  GGACTGGTGA     420
GATGGCCCTG  CACCTTGCAG  CCCGCTACTC  ACGGCTGAT   GCTGCCAAGC  GTCTCCTGGA     480
TGCAGGTGCA  GATGCCAATG  CCCAGGACAA  CATGGGCCGC  TGTCCACTCC  ATGCTGCAGT     540
GGCACGTGAT  GCCAAGGTGT  ATTCAGATCT  GTTA                                   574
```

( 2 ) INFORMATION FOR SEQ ID NO:7:

( i ) SEQUENCE CHARACTERISTICS:
        ( A ) LENGTH: 295 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:7:

```
TCCAGATTCT  GATTCGCAAC  CGAGTAACTG  ATCTAGATGC  CAGGATGAAT  GATGGTACTA      60
CACCCCTGAT  CCTGGCTGCC  CGCCTGGCTG  TGGAGGGAAT  GGTGGCAGAA  CTGATCAACT     120
GCCAAGCGGA  TGTGAATGCA  GTGGATGACC  ATGGAAAATC  TGCTCTTCAC  TGGGCAGCTG     180
CTGTCAATAA  TGTGGAGGCA  ACTCTTTTGT  TGTTGAAAAA  TGGGCCAAC   CGAGACATGC     240
AGGACAACAA  GGAAGAGACA  CCTCTGTTTC  TTGCTGCCCG  GGAGGAGCTA  TAAGC          295
```

( 2 ) INFORMATION FOR SEQ ID NO:8:

( i ) SEQUENCE CHARACTERISTICS:
        ( A ) LENGTH: 248 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:8:

```
GAATTCCATT  CAGGAGGAAA  GGGTGGGGAG  AGAAGCAGGC  ACCCACTTTC  CCGTGGCTGG      60
ACTCGTTCCC  AGGTGGCTCC  ACCGGCAGCT  GTGACCGCCG  CAGGTGGGGG  CGGAGTGCCA     120
TTCAGAAAAT  TCCAGAAAAG  CCCTACCCCA  ACTCGGACGG  CAACGTCACA  CCCGTGGGTA     180
GCAACTGGCA  CACAAACAGC  CAGCGTGTCT  GGGGCACGGG  GGATGGCAC   CCCCTGCAGG     240
CAGAGCTG                                                                   248
```

5,786,158

-continued ( 2 ) INFORMATION FOR SEQ ID NO:9:

( i ) SEQUENCE CHARACTERISTICS:
        ( A ) LENGTH: 323 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:9:

```
TACGTATCTC  GAGCACAGAC  AGCTGACGTA  CACTTTTNNA  GTGCGAGGGA  CATTCGTCCG    60

ACCAGTACGA  ACATTTAGGC  TCAGTACGGT  AGGTCCATGG  CCAAGACTAG  GAGACGTAGG   120

GAGCTACAGG  TCCCGCTCGC  TAAACTCGGA  CCACTGAAAC  CTCCGGTCGA  CAGTCGGTAA   180

GCGAACAAGA  GGGCCAGATC  TTAGAGAAGG  TGTCGCGGCG  AGACTCGGGC  TCGGGTCAGG   240

CGGCCTTAAG  GACGTCGGGC  CCNNNAGGTG  ATCAAGATCT  CGNCNGGCG   GGCGCCACCT   300

CGAGGNCGAA  AACAAGGGAA  ATC                                             323
```

( 2 ) INFORMATION FOR SEQ ID NO:10:

( i ) SEQUENCE CHARACTERISTICS:
        ( A ) LENGTH: 3234 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..3234

( x i ) SEQUENCE DESCRIPTION: SEQ ID NO:10:

```
TGC  CAG  GAG  GAC  GCG  GGC  AAC  AAG  GTC  TGC  AGC  CTG  CAG  TGC  AAC  AAC    48
Cys  Gln  Glu  Asp  Ala  Gly  Asn  Lys  Val  Cys  Ser  Leu  Gln  Cys  Asn  Asn
 1                    5                        10                      15

CAC  GCG  TGC  GGC  TGG  GAC  GGC  GGT  GAC  TGC  TCC  CTC  AAC  TTC  AAT  GAC    96
His  Ala  Cys  Gly  Trp  Asp  Gly  Gly  Asp  Cys  Ser  Leu  Asn  Phe  Asn  Asp
                 20                      25                      30

CCC  TGG  AAG  AAC  TGC  ACG  CAG  TCT  CTG  CAG  TGC  TGG  AAG  TAC  TTC  AGT   144
Pro  Trp  Lys  Asn  Cys  Thr  Gln  Ser  Leu  Gln  Cys  Trp  Lys  Tyr  Phe  Ser
            35                      40                      45

GAC  GGC  CAC  TGT  GAC  AGC  CAG  TGC  AAC  TCA  GCC  GGC  TGC  CTC  TTC  GAC   192
Asp  Gly  His  Cys  Asp  Ser  Gln  Cys  Asn  Ser  Ala  Gly  Cys  Leu  Phe  Asp
       50                      55                      60

GGC  TTT  GAC  TGC  CAG  CGT  GCG  GAA  GGC  CAG  TGC  AAC  CCC  CTG  TAC  GAC   240
Gly  Phe  Asp  Cys  Gln  Arg  Ala  Glu  Gly  Gln  Cys  Asn  Pro  Leu  Tyr  Asp
 65                      70                      75                      80

CAG  TAC  TGC  AAG  GAC  CAC  TTC  AGC  GAC  GGG  CAC  TGC  GAC  CAG  GGC  TGC   288
Gln  Tyr  Cys  Lys  Asp  His  Phe  Ser  Asp  Gly  His  Cys  Asp  Gln  Gly  Cys
                 85                      90                      95

AAC  AGC  GCG  GAG  TGC  GAG  TGG  GAC  GGG  CTG  GAC  TGT  GCG  GAG  CAT  GTA   336
Asn  Ser  Ala  Glu  Cys  Glu  Trp  Asp  Gly  Leu  Asp  Cys  Ala  Glu  His  Val
            100                     105                     110

CCC  GAG  AGG  CTG  GCG  GCC  GGC  ACG  CTG  GTG  GTG  GTG  GTG  CTG  ATG  CCG   384
Pro  Glu  Arg  Leu  Ala  Ala  Gly  Thr  Leu  Val  Val  Val  Val  Leu  Met  Pro
       115                     120                     125

CCG  GAG  CAG  CTG  CGC  AAC  AGC  TCC  TTC  CAC  TTC  CTG  CGG  GAG  CTC  AGC   432
Pro  Glu  Gln  Leu  Arg  Asn  Ser  Ser  Phe  His  Phe  Leu  Arg  Glu  Leu  Ser
130                     135                     140

CGC  GTG  CTG  CAC  ACC  AAC  GTG  GTC  TTC  AAG  CGT  GAC  GCA  CAC  GGC  CAG   480
Arg  Val  Leu  His  Thr  Asn  Val  Val  Phe  Lys  Arg  Asp  Ala  His  Gly  Gln
```

-continued

| | | | | | | | | | | | | | | | | |
|---|---|---|---|---|---|---|---|---|---|---|---|---|---|---|---|---|
| 145 | | | | | 150 | | | | | 155 | | | | | 160 | |
| CAG | ATG | ATC | TTC | CCC | TAC | TAC | GGC | CGC | GAG | GAG | GAG | CTG | CGC | AAG | CAC | 528 |
| Gln | Met | Ile | Phe | Pro | Tyr | Tyr | Gly | Arg | Glu | Glu | Glu | Leu | Arg | Lys | His | |
| | | | | 165 | | | | | 170 | | | | | 175 | | |
| CCC | ATC | AAG | CGT | GCC | GCC | GAG | GGC | TGG | GCC | GCA | CCT | GAC | GCC | CTG | CTG | 576 |
| Pro | Ile | Lys | Arg | Ala | Ala | Glu | Gly | Trp | Ala | Ala | Pro | Asp | Ala | Leu | Leu | |
| | | | 180 | | | | | 185 | | | | | 190 | | | |
| GGC | CAG | GTG | AAG | GCC | TCG | CTG | CTC | CCT | GGT | GGC | AGC | GAG | GGT | GGG | CGG | 624 |
| Gly | Gln | Val | Lys | Ala | Ser | Leu | Leu | Pro | Gly | Gly | Ser | Glu | Gly | Gly | Arg | |
| | | 195 | | | | | 200 | | | | | 205 | | | | |
| CGG | CGG | AGG | GAG | CTG | GAC | CCC | ATG | GAC | GTC | CGC | GGC | TCC | ATC | GTC | TAC | 672 |
| Arg | Arg | Arg | Glu | Leu | Asp | Pro | Met | Asp | Val | Arg | Gly | Ser | Ile | Val | Tyr | |
| | 210 | | | | | 215 | | | | | 220 | | | | | |
| CTG | GAG | ATT | GAC | AAC | CGG | CAG | TGT | GTG | CAG | GCC | TCC | TCG | CAG | TGC | TTC | 720 |
| Leu | Glu | Ile | Asp | Asn | Arg | Gln | Cys | Val | Gln | Ala | Ser | Ser | Gln | Cys | Phe | |
| 225 | | | | | 230 | | | | | 235 | | | | | 240 | |
| CAG | AGT | GCC | ACC | GAC | GTG | GCC | GCA | TTC | CTG | GGA | GCG | CTC | GCC | TCG | CTG | 768 |
| Gln | Ser | Ala | Thr | Asp | Val | Ala | Ala | Phe | Leu | Gly | Ala | Leu | Ala | Ser | Leu | |
| | | | 245 | | | | | 250 | | | | | 255 | | | |
| GGC | AGC | CTC | AAC | ATC | CCC | TAC | AAG | ATC | GAG | GCC | GTG | CAG | AGT | GAG | ACC | 816 |
| Gly | Ser | Leu | Asn | Ile | Pro | Tyr | Lys | Ile | Glu | Ala | Val | Gln | Ser | Glu | Thr | |
| | | | 260 | | | | | 265 | | | | | 270 | | | |
| GTG | GAG | CCG | CCC | CCG | CCG | GCG | CAG | CTG | CAC | TTC | ATG | TAC | GTG | GCG | GCG | 864 |
| Val | Glu | Pro | Pro | Pro | Pro | Ala | Gln | Leu | His | Phe | Met | Tyr | Val | Ala | Ala | |
| | | 275 | | | | | 280 | | | | | 285 | | | | |
| GCC | GCC | TTT | GTG | CTT | CTG | TTC | GTG | GGC | TGC | GGG | GTG | CTG | CTG | TCC | | 912 |
| Ala | Ala | Phe | Val | Leu | Leu | Phe | Val | Gly | Cys | Gly | Val | Leu | Leu | Ser | | |
| | | 290 | | | | | 295 | | | | | 300 | | | | |
| CGC | AAG | CGC | CGG | CGG | CAG | CAT | GGC | CAG | CTC | TGG | TTC | CCT | GAG | GGC | TTC | 960 |
| Arg | Lys | Arg | Arg | Arg | Gln | His | Gly | Gln | Leu | Trp | Phe | Pro | Glu | Gly | Phe | |
| 305 | | | | | 310 | | | | | 315 | | | | | 320 | |
| AAA | GTG | TCT | GAG | GCC | AGC | AAG | AAG | AAG | CGG | CGG | GAG | CCC | CTC | GGC | GAG | 1008 |
| Lys | Val | Ser | Glu | Ala | Ser | Lys | Lys | Lys | Arg | Arg | Glu | Pro | Leu | Gly | Glu | |
| | | | 325 | | | | | 330 | | | | | 335 | | | |
| GAC | TCC | GTG | GGC | CTC | AAG | CCC | CTG | AAG | AAC | GCT | TCA | GAC | GGT | GCC | CTC | 1056 |
| Asp | Ser | Val | Gly | Leu | Lys | Pro | Leu | Lys | Asn | Ala | Ser | Asp | Gly | Ala | Leu | |
| | | | 340 | | | | | 345 | | | | | 350 | | | |
| ATG | GAC | GAC | AAC | CAG | AAT | GAG | TGG | GGG | GAC | GAG | GAC | CTG | GAG | ACC | AAG | 1104 |
| Met | Asp | Asp | Asn | Gln | Asn | Glu | Trp | Gly | Asp | Glu | Asp | Leu | Glu | Thr | Lys | |
| | | | 355 | | | | | 360 | | | | | 365 | | | |
| AAG | TTC | CGG | TTC | GAG | GAG | CCC | GTG | GTT | CTG | CCT | GAC | CTG | GAC | GAC | CAG | 1152 |
| Lys | Phe | Arg | Phe | Glu | Glu | Pro | Val | Val | Leu | Pro | Asp | Leu | Asp | Asp | Gln | |
| | 370 | | | | | 375 | | | | | 380 | | | | | |
| ACA | GAC | CAC | CGG | CAG | TGG | ACT | CAG | CAG | CAC | CTG | GAT | GCC | GCT | GAC | CTG | 1200 |
| Thr | Asp | His | Arg | Gln | Trp | Thr | Gln | Gln | His | Leu | Asp | Ala | Ala | Asp | Leu | |
| 385 | | | | | 390 | | | | | 395 | | | | | 400 | |
| CGC | ATG | TCT | GCC | ATG | GCC | CCC | ACA | CCG | CCC | CAG | GGT | GAG | GTT | GAC | GCC | 1248 |
| Arg | Met | Ser | Ala | Met | Ala | Pro | Thr | Pro | Pro | Gln | Gly | Glu | Val | Asp | Ala | |
| | | | | 405 | | | | | 410 | | | | | 415 | | |
| GAC | TGC | ATG | GAC | GTC | AAT | GTC | CGC | GGG | CCT | GAT | GGC | TTC | ACC | CCG | CTC | 1296 |
| Asp | Cys | Met | Asp | Val | Asn | Val | Arg | Gly | Pro | Asp | Gly | Phe | Thr | Pro | Leu | |
| | | | 420 | | | | | 425 | | | | | 430 | | | |
| ATG | ATC | GCC | TCC | TGC | AGC | GGG | GGC | GGC | CTG | GAG | ACG | GGC | AAC | AGC | GAG | 1344 |
| Met | Ile | Ala | Ser | Cys | Ser | Gly | Gly | Gly | Leu | Glu | Thr | Gly | Asn | Ser | Glu | |
| | | | 435 | | | | | 440 | | | | | 445 | | | |
| GAA | GAG | GAG | GAC | GCG | CCG | GCC | GTC | ATC | TCC | GAC | TTC | ATC | TAC | CAG | GGC | 1392 |
| Glu | Glu | Glu | Asp | Ala | Pro | Ala | Val | Ile | Ser | Asp | Phe | Ile | Tyr | Gln | Gly | |
| | 450 | | | | | 455 | | | | | 460 | | | | | |
| GCC | AGC | CTG | CAC | AAC | CAG | ACA | GAC | CGC | ACG | GGC | GAG | ACC | GCC | TTG | CAC | 1440 |
| Ala | Ser | Leu | His | Asn | Gln | Thr | Asp | Arg | Thr | Gly | Glu | Thr | Ala | Leu | His | |

| | | | | | | | | | | | | | | | | |
|---|---|---|---|---|---|---|---|---|---|---|---|---|---|---|---|---|
| | | | 465 | | | | 470 | | | | 475 | | | | 480 | |
| CTG | GCC | GCC | CGC | TAC | TCA | CGC | TCT | GAT | GCC | GCC | AAG | CGC | CTG | CTG | GAG | 1488 |
| Leu | Ala | Ala | Arg | Tyr 485 | Ser | Arg | Ser | Asp | Ala 490 | Ala | Lys | Arg | Leu | Leu 495 | Glu | |
| GCC | AGC | GCA | GAT | GCC | AAC | ATC | CAG | GAC | AAC | ATG | GGC | CGC | ACC | CCG | CTG | 1536 |
| Ala | Ser | Ala | Asp 500 | Ala | Asn | Ile | Gln | Asp 505 | Asn | Met | Gly | Arg | Thr 510 | Pro | Leu | |
| CAT | GCG | GCT | GTG | TCT | GCC | GAC | GCA | CAA | GGT | GTC | TTC | CAG | ATC | CTG | ATC | 1584 |
| His | Ala | Ala 515 | Val | Ser | Ala | Asp | Ala 520 | Gln | Gly | Val | Phe | Gln 525 | Ile | Leu | Ile | |
| CGG | AAC | CGA | GCC | ACA | GAC | CTG | GAT | GCC | CGC | ATG | CAT | GAT | GGC | ACG | ACG | 1632 |
| Arg | Asn 530 | Arg | Ala | Thr | Asp | Leu 535 | Asp | Ala | Arg | Met | His 540 | Asp | Gly | Thr | Thr | |
| CCA | CTG | ATC | CTG | GCT | GCC | CGC | CTG | GCC | GTG | GAG | GGC | ATG | CTG | GAG | GAC | 1680 |
| Pro 545 | Leu | Ile | Leu | Ala | Ala 550 | Arg | Leu | Ala | Val | Glu 555 | Gly | Met | Leu | Glu | Asp 560 | |
| CTC | ATC | AAC | TCA | CAC | GCC | GAC | GTC | AAC | GCC | GTA | GAT | GAC | CTG | GGC | AAG | 1728 |
| Leu | Ile | Asn | Ser | His 565 | Ala | Asp | Val | Asn | Ala 570 | Val | Asp | Asp | Leu | Gly 575 | Lys | |
| TCC | GCC | CTG | CAC | TGG | GCC | GCC | GCC | GTG | AAC | AAT | GTG | GAT | GCC | GCA | GTT | 1776 |
| Ser | Ala | Leu | His 580 | Trp | Ala | Ala | Ala | Val 585 | Asn | Asn | Val | Asp | Ala 590 | Ala | Val | |
| GTG | CTC | CTG | AAG | AAC | GGG | GCT | AAC | AAA | GAT | ATG | CAG | AAC | AAC | AGG | GAG | 1824 |
| Val | Leu | Leu 595 | Lys | Asn | Gly | Ala | Asn 600 | Lys | Asp | Met | Gln | Asn 605 | Asn | Arg | Glu | |
| GAG | ACA | CCC | CTG | TTT | CTG | GCC | GCC | CGG | GAG | GGC | AGC | TAC | GAG | ACC | GCC | 1872 |
| Glu | Thr 610 | Pro | Leu | Phe | Leu | Ala 615 | Ala | Arg | Glu | Gly | Ser 620 | Tyr | Glu | Thr | Ala | |
| AAG | GTG | CTG | CTG | GAC | CAC | TTT | GCC | AAC | CGG | GAC | ATC | ACG | GAT | CAT | ATG | 1920 |
| Lys 625 | Val | Leu | Leu | Asp | His 630 | Phe | Ala | Asn | Arg | Asp 635 | Ile | Thr | Asp | His | Met 640 | |
| GAC | CGC | CTG | CCG | CGC | GAC | ATC | GCA | CAG | GAG | CGC | ATG | CAT | CAC | GAC | ATC | 1968 |
| Asp | Arg | Leu | Pro | Arg 645 | Asp | Ile | Ala | Gln | Glu 650 | Arg | Met | His | His | Asp 655 | Ile | |
| GTG | AGG | CTG | CTG | GAC | GAG | TAC | AAC | CTG | GTG | CGC | AGC | CCG | CAG | CTG | CAC | 2016 |
| Val | Arg | Leu | Leu 660 | Asp | Glu | Tyr | Asn | Leu 665 | Val | Arg | Ser | Pro | Gln 670 | Leu | His | |
| GGA | GCC | CCG | CTG | GGG | GGC | ACG | CCC | ACC | CTG | TCG | CCC | CCG | CTC | TGC | TCG | 2064 |
| Gly | Ala | Pro 675 | Leu | Gly | Gly | Thr | Pro 680 | Thr | Leu | Ser | Pro | Pro 685 | Leu | Cys | Ser | |
| CCC | AAC | GGC | TAC | CTG | GGC | AGC | CTC | AAG | CCC | GGC | GTG | CAG | GGC | AAG | AAG | 2112 |
| Pro | Asn | Gly 690 | Tyr | Leu | Gly | Ser | Leu 695 | Lys | Pro | Gly | Val | Gln 700 | Gly | Lys | Lys | |
| GTC | CGC | AAG | CCC | AGC | AGC | AAA | GGC | CTG | GCC | TGT | GGA | AGC | AAG | GAG | GCC | 2160 |
| Val | Arg | Lys | Pro 705 | Ser | Ser | Lys | Gly | Leu 710 | Ala | Cys | Gly | Ser | Lys 715 | Glu | Ala 720 | |
| AAG | GAC | CTC | AAG | GCA | CGG | AGG | AAG | AAG | TCC | CAG | GAT | GGC | AAG | GGC | TGC | 2208 |
| Lys | Asp | Leu | Lys | Ala 725 | Arg | Arg | Lys | Lys | Ser 730 | Gln | Asp | Gly | Lys | Gly 735 | Cys | |
| CTG | CTG | GAC | AGC | TCC | GGC | ATG | CTC | TCG | CCC | GTG | GAC | TCC | CTG | GAG | TCA | 2256 |
| Leu | Leu | Asp | Ser 740 | Gly | Met | Leu | Ser | Pro 745 | Val | Asp | Ser | Leu | Glu 750 | Ser | |
| CCC | CAT | GGC | TAC | CTG | TCA | GAC | GTG | GCC | TCG | CCG | CCA | CTG | CTG | CCC | TCC | 2304 |
| Pro | His | Gly 755 | Tyr | Leu | Ser | Asp | Val 760 | Ala | Ser | Pro | Pro | Leu 765 | Leu | Pro | Ser | |
| CCG | TTC | CAG | CAG | TCT | CCG | TCC | GTG | CCC | CTC | AAC | CAC | CTG | CCT | GGG | ATG | 2352 |
| Pro | Phe 770 | Gln | Gln | Ser | Pro | Ser 775 | Val | Pro | Leu | Asn | His 780 | Leu | Pro | Gly | Met | |
| CCC | GAC | ACC | CAC | CTG | GGC | ATC | GGG | CAC | CTG | AAC | GTG | GCG | GCC | AAG | CCC | 2400 |
| Pro | Asp | Thr | His | Leu | Gly | Ile | Gly | His | Leu | Asn | Val | Ala | Ala | Lys | Pro | |

| | | | | | | | | | | | | | | | | |
|---|---|---|---|---|---|---|---|---|---|---|---|---|---|---|---|---|
| 785 | | | | | 790 | | | | | 795 | | | | | 800 | |
| GAG | ATG | GCG | GCG | CTG | GGT | GGG | GGC | GGC | CGG | CTG | GCC | TTT | GAG | ACT | GGC | 2448 |
| Glu | Met | Ala | Ala | Leu | Gly | Gly | Gly | Gly | Arg | Leu | Ala | Phe | Glu | Thr | Gly | |
| | | | | 805 | | | | | 810 | | | | | 815 | | |
| CCA | CCT | CGT | CTC | TCC | CAC | CTG | CCT | GTG | GCC | TCT | GGC | ACC | AGC | ACC | GTC | 2496 |
| Pro | Pro | Arg | Leu | Ser | His | Leu | Pro | Val | Ala | Ser | Gly | Thr | Ser | Thr | Val | |
| | | | 820 | | | | | 825 | | | | | 830 | | | |
| CTG | GGC | TCC | AGC | AGC | GGA | GGG | GCC | CTG | AAT | TTC | ACT | GTG | GGC | GGG | TCC | 2544 |
| Leu | Gly | Ser | Ser | Ser | Gly | Gly | Ala | Leu | Asn | Phe | Thr | Val | Gly | Gly | Ser | |
| | | 835 | | | | | 840 | | | | | 845 | | | | |
| ACC | AGT | TTG | AAT | GGT | CAA | TGC | GAG | TGG | CTG | TCC | CGG | CTG | CAG | AGC | GGC | 2592 |
| Thr | Ser | Leu | Asn | Gly | Gln | Cys | Glu | Trp | Leu | Ser | Arg | Leu | Gln | Ser | Gly | |
| | 850 | | | | | 855 | | | | | 860 | | | | | |
| ATG | GTG | CCG | AAC | CAA | TAC | AAC | CCT | CTG | CGG | GGG | AGT | GTG | GCA | CCA | GGC | 2640 |
| Met | Val | Pro | Asn | Gln | Tyr | Asn | Pro | Leu | Arg | Gly | Ser | Val | Ala | Pro | Gly | |
| 865 | | | | | 870 | | | | | 875 | | | | | 880 | |
| CCC | CTG | AGC | ACA | CAG | GCC | CCC | TCC | CTG | CAG | CAT | GGC | ATG | GTA | GGC | CCG | 2688 |
| Pro | Leu | Ser | Thr | Gln | Ala | Pro | Ser | Leu | Gln | His | Gly | Met | Val | Gly | Pro | |
| | | | | 885 | | | | | 890 | | | | | 895 | | |
| CTG | CAC | AGT | AGC | CTT | GCT | GCC | AGC | GCC | CTG | TCC | CAG | ATG | ATG | AGC | TAC | 2736 |
| Leu | His | Ser | Ser | Leu | Ala | Ala | Ser | Ala | Leu | Ser | Gln | Met | Met | Ser | Tyr | |
| | | | 900 | | | | | 905 | | | | | 910 | | | |
| CAG | GGC | CTG | CCC | AGC | ACC | CGG | CTG | GCC | ACC | CAG | CCT | CAC | CTG | GTG | CAG | 2784 |
| Gln | Gly | Leu | Pro | Ser | Thr | Arg | Leu | Ala | Thr | Gln | Pro | His | Leu | Val | Gln | |
| | | 915 | | | | | 920 | | | | | 925 | | | | |
| ACC | CAG | CAG | GTG | CAG | CCA | CAA | AAC | TTA | CAG | ATG | CAG | CAG | CAG | AAC | CTG | 2832 |
| Thr | Gln | Gln | Val | Gln | Pro | Gln | Asn | Leu | Gln | Met | Gln | Gln | Gln | Asn | Leu | |
| | 930 | | | | | 935 | | | | | 940 | | | | | |
| CAG | CCA | GCA | AAC | ATC | CAG | CAG | CAG | CAA | AGC | CTG | CAG | CCG | CCA | CCA | CCA | 2880 |
| Gln | Pro | Ala | Asn | Ile | Gln | Gln | Gln | Gln | Ser | Leu | Gln | Pro | Pro | Pro | Pro | |
| 945 | | | | | 950 | | | | | 955 | | | | | 960 | |
| CCA | CCA | CAG | CCG | CAC | CTT | GGC | GTG | AGC | TCA | GCA | GCC | AGC | GGC | CAC | CTG | 2928 |
| Pro | Pro | Gln | Pro | His | Leu | Gly | Val | Ser | Ser | Ala | Ala | Ser | Gly | His | Leu | |
| | | | | 965 | | | | | 970 | | | | | 975 | | |
| GGC | CGG | AGC | TTC | CTG | AGT | GGA | GAG | CCG | AGC | CAG | GCA | GAC | GTG | CAG | CCA | 2976 |
| Gly | Arg | Ser | Phe | Leu | Ser | Gly | Glu | Pro | Ser | Gln | Ala | Asp | Val | Gln | Pro | |
| | | | 980 | | | | | 985 | | | | | 990 | | | |
| CTG | GGC | CCC | AGC | AGC | CTG | GCG | GTG | CAC | ACT | ATT | CTG | CCC | CAG | GAG | AGC | 3024 |
| Leu | Gly | Pro | Ser | Ser | Leu | Ala | Val | His | Thr | Ile | Leu | Pro | Gln | Glu | Ser | |
| | | 995 | | | | | 1000 | | | | | 1005 | | | | |
| CCC | GCC | CTG | CCC | ACG | TCG | CTG | CCA | TCC | TCG | CTG | GTC | CCA | CCC | GTG | ACC | 3072 |
| Pro | Ala | Leu | Pro | Thr | Ser | Leu | Pro | Ser | Ser | Leu | Val | Pro | Pro | Val | Thr | |
| | 1010 | | | | | 1015 | | | | | 1020 | | | | | |
| GCA | GCC | CAG | TTC | CTG | ACG | CCC | CCC | TCG | CAG | CAC | AGC | TAC | TCC | TCG | CCT | 3120 |
| Ala | Ala | Gln | Phe | Leu | Thr | Pro | Pro | Ser | Gln | His | Ser | Tyr | Ser | Ser | Pro | |
| 1025 | | | | | 1030 | | | | | 1035 | | | | | 1040 | |
| GTG | GAC | AAC | ACC | CCC | AGC | CAC | CAG | CTA | CAG | GTG | CCT | GTT | CCT | GTA | ATG | 3168 |
| Val | Asp | Asn | Thr | Pro | Ser | His | Gln | Leu | Gln | Val | Pro | Val | Pro | Val | Met | |
| | | | | 1045 | | | | | 1050 | | | | | 1055 | | |
| GTA | ATG | ATC | CGA | TCT | TCG | GAT | CCT | TCT | AAA | GGC | TCA | TCA | ATT | TTG | ATC | 3216 |
| Val | Met | Ile | Arg | Ser | Ser | Asp | Pro | Ser | Lys | Gly | Ser | Ser | Ile | Leu | Ile | |
| | | | 1060 | | | | | 1065 | | | | | 1070 | | | |
| GAA | GCT | CCC | GAC | TCA | TGG | | | | | | | | | | | 3234 |
| Glu | Ala | Pro | Asp | Ser | Trp | | | | | | | | | | | |
| | | | | 1075 | | | | | | | | | | | | |

( 2 ) INFORMATION FOR SEQ ID NO:11:

( i ) SEQUENCE CHARACTERISTICS:
        ( A ) LENGTH: 1078 amino acids
        ( B ) TYPE: amino acid (D) TOPOLOGY: unknown (ii) MOLECULE TYPE: protein (xi) SEQUENCE DESCRIPTION: SEQ ID NO:11:

| Cys | Gln | Glu | Asp | Ala | Gly | Asn | Lys | Val | Cys | Ser | Leu | Gln | Cys | Asn | Asn |
|---|---|---|---|---|---|---|---|---|---|---|---|---|---|---|---|
| 1 | | | | 5 | | | | | 10 | | | | | 15 | |
| His | Ala | Cys | Gly | Trp | Asp | Gly | Gly | Asp | Cys | Ser | Leu | Asn | Phe | Asn | Asp |
| | | | 20 | | | | 25 | | | | | | 30 | | |
| Pro | Trp | Lys | Asn | Cys | Thr | Gln | Ser | Leu | Gln | Cys | Trp | Lys | Tyr | Phe | Ser |
| | | 35 | | | | | 40 | | | | | 45 | | | |
| Asp | Gly | His | Cys | Asp | Ser | Gln | Cys | Asn | Ser | Ala | Gly | Cys | Leu | Phe | Asp |
| | 50 | | | | | 55 | | | | | 60 | | | | |
| Gly | Phe | Asp | Cys | Gln | Arg | Ala | Glu | Gly | Gln | Cys | Asn | Pro | Leu | Tyr | Asp |
| 65 | | | | | 70 | | | | | 75 | | | | | 80 |
| Gln | Tyr | Cys | Lys | Asp | His | Phe | Ser | Asp | Gly | His | Cys | Asp | Gln | Gly | Cys |
| | | | | 85 | | | | | 90 | | | | | 95 | |
| Asn | Ser | Ala | Glu | Cys | Glu | Trp | Asp | Gly | Leu | Asp | Cys | Ala | Glu | His | Val |
| | | | 100 | | | | | 105 | | | | | 110 | | |
| Pro | Glu | Arg | Leu | Ala | Ala | Gly | Thr | Leu | Val | Val | Val | Val | Leu | Met | Pro |
| | | 115 | | | | | 120 | | | | | 125 | | | |
| Pro | Glu | Gln | Leu | Arg | Asn | Ser | Ser | Phe | His | Phe | Leu | Arg | Glu | Leu | Ser |
| | | 130 | | | | | 135 | | | | | 140 | | | |
| Arg | Val | Leu | His | Thr | Asn | Val | Val | Phe | Lys | Arg | Asp | Ala | His | Gly | Gln |
| 145 | | | | | 150 | | | | | 155 | | | | | 160 |
| Gln | Met | Ile | Phe | Pro | Tyr | Tyr | Gly | Arg | Glu | Glu | Leu | Arg | Lys | His | |
| | | | | 165 | | | | | 170 | | | | | 175 | |
| Pro | Ile | Lys | Arg | Ala | Ala | Glu | Gly | Trp | Ala | Ala | Pro | Asp | Ala | Leu | Leu |
| | | | 180 | | | | | 185 | | | | | 190 | | |
| Gly | Gln | Val | Lys | Ala | Ser | Leu | Leu | Pro | Gly | Gly | Ser | Glu | Gly | Gly | Arg |
| | | 195 | | | | | 200 | | | | | 205 | | | |
| Arg | Arg | Arg | Glu | Leu | Asp | Pro | Met | Asp | Val | Arg | Gly | Ser | Ile | Val | Tyr |
| 210 | | | | | 215 | | | | | 220 | | | | | |
| Leu | Glu | Ile | Asp | Asn | Arg | Gln | Cys | Val | Gln | Ala | Ser | Ser | Gln | Cys | Phe |
| 225 | | | | | 230 | | | | | 235 | | | | | 240 |
| Gln | Ser | Ala | Thr | Asp | Val | Ala | Ala | Phe | Leu | Gly | Ala | Leu | Ala | Ser | Leu |
| | | | | 245 | | | | | 250 | | | | | 255 | |
| Gly | Ser | Leu | Asn | Ile | Pro | Tyr | Lys | Ile | Glu | Ala | Val | Gln | Ser | Glu | Thr |
| | | | 260 | | | | | 265 | | | | | 270 | | |
| Val | Glu | Pro | Pro | Pro | Ala | Gln | Leu | His | Phe | Met | Tyr | Val | Ala | Ala |
| | | 275 | | | | | 280 | | | | | 285 | | | |
| Ala | Ala | Phe | Val | Leu | Leu | Phe | Phe | Val | Gly | Cys | Gly | Val | Leu | Leu | Ser |
| | 290 | | | | | 295 | | | | | 300 | | | | |
| Arg | Lys | Arg | Arg | Arg | Gln | His | Gly | Gln | Leu | Trp | Phe | Pro | Glu | Gly | Phe |
| 305 | | | | | 310 | | | | | 315 | | | | | 320 |
| Lys | Val | Ser | Glu | Ala | Ser | Lys | Lys | Lys | Arg | Arg | Glu | Pro | Leu | Gly | Glu |
| | | | | 325 | | | | | 330 | | | | | 335 | |
| Asp | Ser | Val | Gly | Leu | Lys | Pro | Leu | Lys | Asn | Ala | Ser | Asp | Gly | Ala | Leu |
| | | | 340 | | | | | 345 | | | | | 350 | | |
| Met | Asp | Asp | Asn | Gln | Asn | Glu | Trp | Gly | Asp | Glu | Asp | Leu | Glu | Thr | Lys |
| | | 355 | | | | | 360 | | | | | 365 | | | |
| Lys | Phe | Arg | Phe | Glu | Glu | Pro | Val | Val | Leu | Pro | Asp | Leu | Asp | Asp | Gln |
| | | 370 | | | | | 375 | | | | | 380 | | | |
| Thr | Asp | His | Arg | Gln | Trp | Thr | Gln | Gln | His | Leu | Asp | Ala | Ala | Asp | Leu |
| 385 | | | | | 390 | | | | | 395 | | | | | 400 |

```
Arg Met Ser Ala Met Ala Pro Thr Pro Pro Gln Gly Glu Val Asp Ala
            405             410             415
Asp Cys Met Asp Val Asn Val Arg Gly Pro Asp Gly Phe Thr Pro Leu
        420             425             430
Met Ile Ala Ser Cys Ser Gly Gly Leu Glu Thr Gly Asn Ser Glu
    435             440             445
Glu Glu Glu Asp Ala Pro Ala Val Ile Ser Asp Phe Ile Tyr Gln Gly
450             455             460
Ala Ser Leu His Asn Gln Thr Asp Arg Thr Gly Glu Thr Ala Leu His
465             470             475             480
Leu Ala Ala Arg Tyr Ser Arg Ser Asp Ala Ala Lys Arg Leu Leu Glu
            485             490             495
Ala Ser Ala Asp Ala Asn Ile Gln Asp Asn Met Gly Arg Thr Pro Leu
        500             505             510
His Ala Ala Val Ser Ala Asp Ala Gln Gly Val Phe Gln Ile Leu Ile
        515             520             525
Arg Asn Arg Ala Thr Asp Leu Asp Ala Arg Met His Asp Gly Thr Thr
    530             535             540
Pro Leu Ile Leu Ala Ala Arg Leu Ala Val Glu Gly Met Leu Glu Asp
545             550             555             560
Leu Ile Asn Ser His Ala Asp Val Asn Ala Val Asp Asp Leu Gly Lys
            565             570             575
Ser Ala Leu His Trp Ala Ala Ala Val Asn Asn Val Asp Ala Ala Val
        580             585             590
Val Leu Leu Lys Asn Gly Ala Asn Lys Asp Met Gln Asn Asn Arg Glu
    595             600             605
Glu Thr Pro Leu Phe Leu Ala Ala Arg Glu Gly Ser Tyr Glu Thr Ala
610             615             620
Lys Val Leu Leu Asp His Phe Ala Asn Arg Asp Ile Thr Asp His Met
625             630             635             640
Asp Arg Leu Pro Arg Asp Ile Ala Gln Glu Arg Met His His Asp Ile
            645             650             655
Val Arg Leu Leu Asp Glu Tyr Asn Leu Val Arg Ser Pro Gln Leu His
        660             665             670
Gly Ala Pro Leu Gly Gly Thr Pro Thr Leu Ser Pro Pro Leu Cys Ser
        675             680             685
Pro Asn Gly Tyr Leu Gly Ser Leu Lys Pro Gly Val Gln Gly Lys Lys
    690             695             700
Val Arg Lys Pro Ser Ser Lys Gly Leu Ala Cys Gly Ser Lys Glu Ala
705             710             715             720
Lys Asp Leu Lys Ala Arg Arg Lys Lys Ser Gln Asp Gly Lys Gly Cys
            725             730             735
Leu Leu Asp Ser Ser Gly Met Leu Ser Pro Val Asp Ser Leu Glu Ser
        740             745             750
Pro His Gly Tyr Leu Ser Asp Val Ala Ser Pro Pro Leu Leu Pro Ser
        755             760             765
Pro Phe Gln Gln Ser Pro Ser Val Pro Leu Asn His Leu Pro Gly Met
770             775             780
Pro Asp Thr His Leu Gly Ile Gly His Leu Asn Val Ala Ala Lys Pro
785             790             795             800
Glu Met Ala Ala Leu Gly Gly Gly Gly Arg Leu Ala Phe Glu Thr Gly
            805             810             815
Pro Pro Arg Leu Ser His Leu Pro Val Ala Ser Gly Thr Ser Thr Val
```

|           |           |           |           | 820       |           |           |           |           | 825       |           |           |           |           | 830       |           |           |
|-----------|-----------|-----------|-----------|-----------|-----------|-----------|-----------|-----------|-----------|-----------|-----------|-----------|-----------|-----------|-----------|-----------|

Leu Gly Ser Ser Ser Gly Gly Ala Leu Asn Phe Thr Val Gly Gly Ser
            835                     840                 845

Thr Ser Leu Asn Gly Gln Cys Glu Trp Leu Ser Arg Leu Gln Ser Gly
    850                 855                 860

Met Val Pro Asn Gln Tyr Asn Pro Leu Arg Gly Ser Val Ala Pro Gly
865                 870                 875                 880

Pro Leu Ser Thr Gln Ala Pro Ser Leu Gln His Gly Met Val Gly Pro
            885                 890                 895

Leu His Ser Ser Leu Ala Ala Ser Ala Leu Ser Gln Met Met Ser Tyr
            900                 905                 910

Gln Gly Leu Pro Ser Thr Arg Leu Ala Thr Gln Pro His Leu Val Gln
        915                 920                 925

Thr Gln Gln Val Gln Pro Gln Asn Leu Gln Met Gln Gln Gln Asn Leu
930                 935                 940

Gln Pro Ala Asn Ile Gln Gln Gln Ser Leu Gln Pro Pro Pro Pro
945                 950                 955                 960

Pro Pro Gln Pro His Leu Gly Val Ser Ala Ala Ser Gly His Leu
            965                 970                 975

Gly Arg Ser Phe Leu Ser Gly Glu Pro Ser Gln Ala Asp Val Gln Pro
            980                 985                 990

Leu Gly Pro Ser Ser Leu Ala Val His Thr Ile Leu Pro Gln Glu Ser
        995                 1000                1005

Pro Ala Leu Pro Thr Ser Leu Pro Ser Ser Leu Val Pro Pro Val Thr
    1010                1015                1020

Ala Ala Gln Phe Leu Thr Pro Pro Ser Gln His Ser Tyr Ser Ser Pro
1025                1030                1035                1040

Val Asp Asn Thr Pro Ser His Gln Leu Gln Val Pro Val Pro Val Met
            1045                1050                1055

Val Met Ile Arg Ser Ser Asp Pro Ser Lys Gly Ser Ser Ile Leu Ile
            1060                1065                1070

Glu Ala Pro Asp Ser Trp
            1075

(2) INFORMATION FOR SEQ ID NO:12:

(i) SEQUENCE CHARACTERISTICS:
        (A) LENGTH: 4268 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 2..1972

(xi) SEQUENCE DESCRIPTION: SEQ ID NO:12:

G GAG GTG GAT GTG TTA GAT GTG AAT GTC CGT GGC CCA GAT GGC TGC        46
  Glu Val Asp Val Leu Asp Val Asn Val Arg Gly Pro Asp Gly Cys
    1               5                   10                  15

ACC CCA TTG ATG TTG GCT TCT CTC CGA GGA GGC AGC TCA GAT TTG AGT     94
Thr Pro Leu Met Leu Ala Ser Leu Arg Gly Gly Ser Ser Asp Leu Ser
                20                  25                  30

GAT GAA GAT GAA GAT GCA GAG GAC TCT TCT GCT AAC ATC ATC ACA GAC    142
Asp Glu Asp Glu Asp Ala Glu Asp Ser Ser Ala Asn Ile Ile Thr Asp
            35                  40                  45

TTG GTC TAC CAG GGT GCC AGC CTC CAG GCC CAG ACA GAC CGG ACT GGT    190

| | | | | | | | | | | | | | | |
|---|---|---|---|---|---|---|---|---|---|---|---|---|---|---|
| Leu | Val | Tyr | Gln | Gly | Ala | Ser | Leu | Gln | Ala | Gln | Thr | Asp | Arg | Thr | Gly |
| | | 50 | | | | | 55 | | | | | 60 | | | |

| | | | | | | | | | | | | | | | |
|---|---|---|---|---|---|---|---|---|---|---|---|---|---|---|---|
| GAG | ATG | GCC | CTG | CAC | CTT | GCA | GCC | CGC | TAC | TCA | CGG | GCT | GAT | GCT | GCC | 238 |
| Glu | Met | Ala | Leu | His | Leu | Ala | Ala | Arg | Tyr | Ser | Arg | Ala | Asp | Ala | Ala |
| | 65 | | | | | 70 | | | | | 75 | | | | |

| AAG | CGT | CTC | CTG | GAT | GCA | GGT | GCA | GAT | GCC | AAT | GCC | CAG | GAC | AAC | ATG | 286 |
|---|---|---|---|---|---|---|---|---|---|---|---|---|---|---|---|---|
| Lys | Arg | Leu | Leu | Asp | Ala | Gly | Ala | Asp | Ala | Asn | Ala | Gln | Asp | Asn | Met |
| 80 | | | | | 85 | | | | | 90 | | | | | 95 |

| GGC | CGC | TGT | CCA | CTC | CAT | GCT | GCA | GTG | GCA | GCT | GAT | GCC | CAA | GGT | GTC | 334 |
|---|---|---|---|---|---|---|---|---|---|---|---|---|---|---|---|---|
| Gly | Arg | Cys | Pro | Leu | His | Ala | Ala | Val | Ala | Ala | Asp | Ala | Gln | Gly | Val |
| | | | | 100 | | | | | 105 | | | | | 110 | |

| TTC | CAG | ATT | CTG | ATT | CGC | AAC | CGA | GTA | ACT | GAT | CTA | GAT | GCC | AGG | ATG | 382 |
|---|---|---|---|---|---|---|---|---|---|---|---|---|---|---|---|---|
| Phe | Gln | Ile | Leu | Ile | Arg | Asn | Arg | Val | Thr | Asp | Leu | Asp | Ala | Arg | Met |
| | | | | 115 | | | | | 120 | | | | | 125 | |

| AAT | GAT | GGT | ACT | ACA | CCC | CTG | ATC | CTG | GCT | GCC | CGC | CTG | GCT | GTG | GAG | 430 |
|---|---|---|---|---|---|---|---|---|---|---|---|---|---|---|---|---|
| Asn | Asp | Gly | Thr | Thr | Pro | Leu | Ile | Leu | Ala | Ala | Arg | Leu | Ala | Val | Glu |
| | | 130 | | | | | 135 | | | | | 140 | | | |

| GGA | ATG | GTG | GCA | GAA | CTG | ATC | AAC | TGC | CAA | GCG | GAT | GTG | AAT | GCA | GTG | 478 |
|---|---|---|---|---|---|---|---|---|---|---|---|---|---|---|---|---|
| Gly | Met | Val | Ala | Glu | Leu | Ile | Asn | Cys | Gln | Ala | Asp | Val | Asn | Ala | Val |
| 145 | | | | | 150 | | | | | 155 | | | | | |

| GAT | GAC | CAT | GGA | AAA | TCT | GCT | CTT | CAC | TGG | GCA | GCT | GCT | GTC | AAT | AAT | 526 |
|---|---|---|---|---|---|---|---|---|---|---|---|---|---|---|---|---|
| Asp | Asp | His | Gly | Lys | Ser | Ala | Leu | His | Trp | Ala | Ala | Ala | Val | Asn | Asn |
| 160 | | | | | 165 | | | | | 170 | | | | | 175 |

| GTG | GAG | GCA | ACT | CTT | TTG | TTG | TTG | AAA | AAT | GGG | GCC | AAC | CGA | GAC | ATG | 574 |
|---|---|---|---|---|---|---|---|---|---|---|---|---|---|---|---|---|
| Val | Glu | Ala | Thr | Leu | Leu | Leu | Leu | Lys | Asn | Gly | Ala | Asn | Arg | Asp | Met |
| | | | | 180 | | | | | 185 | | | | | 190 | |

| CAG | GAC | AAC | AAG | GAA | GAG | ACA | CCT | CTG | TTT | CTT | GCT | GCC | CGG | GAG | GGG | 622 |
|---|---|---|---|---|---|---|---|---|---|---|---|---|---|---|---|---|
| Gln | Asp | Asn | Lys | Glu | Glu | Thr | Pro | Leu | Phe | Leu | Ala | Ala | Arg | Glu | Gly |
| | | | 195 | | | | | 200 | | | | | 205 | | |

| AGC | TAT | GAA | GCA | GCC | AAG | ATC | CTG | TTA | GAC | CAT | TTT | GCC | AAT | CGA | GAC | 670 |
|---|---|---|---|---|---|---|---|---|---|---|---|---|---|---|---|---|
| Ser | Tyr | Glu | Ala | Ala | Lys | Ile | Leu | Leu | Asp | His | Phe | Ala | Asn | Arg | Asp |
| | | 210 | | | | | 215 | | | | | 220 | | | |

| ATC | ACA | GAC | CAT | ATG | GAT | CGT | CTT | CCC | CGG | GAT | GTG | GCT | CGG | GAT | CGC | 718 |
|---|---|---|---|---|---|---|---|---|---|---|---|---|---|---|---|---|
| Ile | Thr | Asp | His | Met | Asp | Arg | Leu | Pro | Arg | Asp | Val | Ala | Arg | Asp | Arg |
| | 225 | | | | | 230 | | | | | 235 | | | | |

| ATG | CAC | CAT | GAC | ATT | GTG | CGC | CTT | CTG | GAT | GAA | TAC | AAT | GTG | ACC | CCA | 766 |
|---|---|---|---|---|---|---|---|---|---|---|---|---|---|---|---|---|
| Met | His | His | Asp | Ile | Val | Arg | Leu | Leu | Asp | Glu | Tyr | Asn | Val | Thr | Pro |
| 240 | | | | | 245 | | | | | 250 | | | | | 255 |

| AGC | CCT | CCA | GGC | ACC | GTG | TTG | ACT | TCT | GCT | CTC | TCA | CCT | GTC | ATC | TGT | 814 |
|---|---|---|---|---|---|---|---|---|---|---|---|---|---|---|---|---|
| Ser | Pro | Pro | Gly | Thr | Val | Leu | Thr | Ser | Ala | Leu | Ser | Pro | Val | Ile | Cys |
| | | | | 260 | | | | | 265 | | | | | 270 | |

| GGG | CCC | AAC | AGA | TCT | TTC | CTC | AGC | CTG | AAG | CAC | ACC | CCA | ATG | GGC | AAG | 862 |
|---|---|---|---|---|---|---|---|---|---|---|---|---|---|---|---|---|
| Gly | Pro | Asn | Arg | Ser | Phe | Leu | Ser | Leu | Lys | His | Thr | Pro | Met | Gly | Lys |
| | | | 275 | | | | | 280 | | | | | 285 | | |

| AAG | TCT | AGA | CGG | CCC | AGT | GCC | AAG | AGT | ACC | ATG | CCT | ACT | AGC | CTC | CCT | 910 |
|---|---|---|---|---|---|---|---|---|---|---|---|---|---|---|---|---|
| Lys | Ser | Arg | Arg | Pro | Ser | Ala | Lys | Ser | Thr | Met | Pro | Thr | Ser | Leu | Pro |
| | | 290 | | | | | 295 | | | | | 300 | | | |

| AAC | CTT | GCC | AAG | GAG | GCA | AAG | GAT | GCC | AAG | GGT | AGT | AGG | AGG | AAG | AAG | 958 |
|---|---|---|---|---|---|---|---|---|---|---|---|---|---|---|---|---|
| Asn | Leu | Ala | Lys | Glu | Ala | Lys | Asp | Ala | Lys | Gly | Ser | Arg | Arg | Lys | Lys |
| | | 305 | | | | | 310 | | | | | 315 | | | |

| TCT | CTG | AGT | GAG | AAG | GTC | CAA | CTG | TCT | GAG | AGT | TCA | GTA | ACT | TTA | TCC | 1006 |
|---|---|---|---|---|---|---|---|---|---|---|---|---|---|---|---|---|
| Ser | Leu | Ser | Glu | Lys | Val | Gln | Leu | Ser | Glu | Ser | Ser | Val | Thr | Leu | Ser |
| 320 | | | | | 325 | | | | | 330 | | | | | 335 |

| CCT | GTT | GAT | TCC | CTA | GAA | TCT | CCT | CAC | ACG | TAT | GTT | TCC | GAC | ACC | ACA | 1054 |
|---|---|---|---|---|---|---|---|---|---|---|---|---|---|---|---|---|
| Pro | Val | Asp | Ser | Leu | Glu | Ser | Pro | His | Thr | Tyr | Val | Ser | Asp | Thr | Thr |
| | | | | 340 | | | | | 345 | | | | | 350 | |

| TCC | TCT | CCA | ATG | ATT | ACA | TCC | CCT | GGG | ATC | TTA | CAG | GCC | TCA | CCC | AAC | 1102 |
|---|---|---|---|---|---|---|---|---|---|---|---|---|---|---|---|---|
| Ser | Ser | Pro | Met | Ile | Thr | Ser | Pro | Gly | Ile | Leu | Gln | Ala | Ser | Pro | Asn |
| | | | 355 | | | | | 360 | | | | | 365 | | |

| CCT | ATG | TTG | GCC | ACT | GCC | GCC | CCT | CCT | GCC | CCA | GTC | CAT | GCC | CAG | CAT | 1150 |
|---|---|---|---|---|---|---|---|---|---|---|---|---|---|---|---|---|

```
        Pro Met Leu Ala Thr Ala Ala Pro Pro Ala Pro Val His Ala Gln His
                370                 375                 380

GCA CTA TCT TTT TCT AAC CTT CAT GAA ATG CAG CCT TTG GCA CAT GGG              1198
Ala Leu Ser Phe Ser Asn Leu His Glu Met Gln Pro Leu Ala His Gly
        385                 390                 395

GCC AGC ACT GTG CTT CCC TCA GTG AGC CAG TTG CTA TCC CAC CAC CAC              1246
Ala Ser Thr Val Leu Pro Ser Val Ser Gln Leu Leu Ser His His His
400                 405                 410                 415

ATT GTG TCT CCA GGC AGT GGC AGT GCT GGA AGC TTG AGT AGG CTC CAT              1294
Ile Val Ser Pro Gly Ser Gly Ser Ala Gly Ser Leu Ser Arg Leu His
                    420                 425                 430

CCA GTC CCA GTC CCA GCA GAT TGG ATG AAC CGC ATG GAG GTG AAT GAG              1342
Pro Val Pro Val Pro Ala Asp Trp Met Asn Arg Met Glu Val Asn Glu
                435                 440                 445

ACC CAG TAC AAT GAG ATG TTT GGT ATG GTC CTG GCT CCA GCT GAG GGC              1390
Thr Gln Tyr Asn Glu Met Phe Gly Met Val Leu Ala Pro Ala Glu Gly
            450                 455                 460

ACC CAT CCT GGC ATA GCT CCC CAG AGC AGG CCA CCT GAA GGG AAG CAC              1438
Thr His Pro Gly Ile Ala Pro Gln Ser Arg Pro Pro Glu Gly Lys His
465                 470                 475

ATA ACC ACC CCT CGG GAG CCC TTG CCC CCC ATT GTG ACT TTC CAG CTC              1486
Ile Thr Thr Pro Arg Glu Pro Leu Pro Pro Ile Val Thr Phe Gln Leu
480                 485                 490                 495

ATC CCT AAA GGC AGT ATT GCC CAA CCA GCG GGG GCT CCC CAG CCT CAG              1534
Ile Pro Lys Gly Ser Ile Ala Gln Pro Ala Gly Ala Pro Gln Pro Gln
                500                 505                 510

TCC ACC TGC CCT CCA GCT GTT GCG GGC CCC CTG CCC ACC ATG TAC CAG              1582
Ser Thr Cys Pro Pro Ala Val Ala Gly Pro Leu Pro Thr Met Tyr Gln
            515                 520                 525

ATT CCA GAA ATG GCC CGT TTG CCC AGT GTG GCT TTC CCC ACT GCC ATG              1630
Ile Pro Glu Met Ala Arg Leu Pro Ser Val Ala Phe Pro Thr Ala Met
        530                 535                 540

ATG CCC CAG CAG GAC GGG CAG GTA GCT CAG ACC ATT CTC CCA GCC TAT              1678
Met Pro Gln Gln Asp Gly Gln Val Ala Gln Thr Ile Leu Pro Ala Tyr
    545                 550                 555

CAT CCT TTC CCA GCC TCT GTG GGC AAG TAC CCC ACA CCC CCT TCA CAG              1726
His Pro Phe Pro Ala Ser Val Gly Lys Tyr Pro Thr Pro Pro Ser Gln
560                 565                 570                 575

CAC AGT TAT GCT TCC TCA AAT GCT GCT GAG CGA ACA CCC AGT CAC AGT              1774
His Ser Tyr Ala Ser Ser Asn Ala Ala Glu Arg Thr Pro Ser His Ser
                580                 585                 590

GGT CAC CTC CAG GGT GAG CAT CCC TAC CTG ACA CCA TCC CCA GAG TCT              1822
Gly His Leu Gln Gly Glu His Pro Tyr Leu Thr Pro Ser Pro Glu Ser
            595                 600                 605

CCT GAC CAG TGG TCA AGT TCA TCA CCC CAC TCT GCT TCT GAC TGG TCA              1870
Pro Asp Gln Trp Ser Ser Ser Ser Pro His Ser Ala Ser Asp Trp Ser
        610                 615                 620

GAT GTG ACC ACC AGC CCT ACC CCT GGG GGT GCT GGA GGA GGT CAG CGG              1918
Asp Val Thr Thr Ser Pro Thr Pro Gly Gly Ala Gly Gly Gly Gln Arg
625                 630                 635

GGA CCT GGG ACA CAC ATG TCT GAG CCA CCA CAC AAC AAC ATG CAG GTT              1966
Gly Pro Gly Thr His Met Ser Glu Pro Pro His Asn Asn Met Gln Val
640                 645                 650                 655

TAT GCG TGAGAGAGTC CACCTCCAGT GTAGAGACAT AACTGACTTT TGTAAATGCT              2022
Tyr Ala

GCTGAGGAAC AAATGAAGGT CATCCGGGAG AGAAATGAAG AAATCTCTGG AGCCAGCTTC           2082

TAGAGGTAGG AAAGAGAAGA TGTTCTTATT CAGATAATGC AAGAGAAGCA ATTCGTCAGT           2142

TTCACTGGGT ATCTGCAAGG CTTATTGATT ATTCTAATCT AATAAGACAA GTTTGTGGAA           2202
```

-continued

```
ATGCAAGATG AATACAAGCC TTGGGTCCAT GTTTACTCTC TTCTATTTGG AGAATAAGAT    2262
GGATGCTTAT TGAAGCCCAG ACATTCTTGC AGCTTGGACT GCATTTTAAG CCCTGCAGGC    2322
TTCTGCCATA TCCATGAGAA GATTCTACAC TAGCGTCCTG TTGGGAATTA TGCCCTGGAA    2382
TTCTGCCTGA ATTGACCTAC GCATCTCCTC CTCCTTGGAC ATTCTTTTGT CTTCATTTGG    2442
TGCTTTTGGT TTGCACCTC  TCCGTGATTG TAGCCCTACC AGCATGTTAT AGGGCAAGAC    2502
CTTTGTGCTT TTGATCATTC TGGCCCATGA AAGCAACTTT GGTCTCCTTT CCCCTCCTGT    2562
CTTCCCGGTA TCCCTTGGAG TCTCACAAGG TTTACTTTGG TATGGTTCTC AGCACAAACC    2622
TTTCAAGTAT GTTGTTTCTT TGGAAAATGG ACATACTGTA TTGTGTTCTC CTGCATATAT    2682
CATTCCTGGA GAGAGAAGGG GAGAAGAATA CTTTCTTCA  ACAAATTTTG GGGCAGGAG    2742
ATCCCTTCAA GAGGCTGCAC CTTAATTTTT CTTGTCTGTG TGCAGGTCTT CATATAAACT    2802
TTACCAGGAA GAAGGGTGTG AGTTGTTGT  TTTCTGTGT  ATGGGCCTGG TCAGTGTAAA    2862
GTTTTATCCT TGATAGTCTA GTTACTATGA CCCTCCCCAC TTTTTAAAA  CCAGAAAAG     2922
GTTGGAATG  TTGGAATGAC CAAGAGACAA GTAACTCGT  GCAAGAGCCA GTTACCCACC    2982
CACAGGTCCC CCTACTTCCT GCCAAGCATT CCATTGACTG CCTGTATGGA ACACATTTGT    3042
CCCAGATCTG AGCATTCTAG GCCTGTTTCA CTCACTCACC CAGCATATGA AACTAGTCTT    3102
AACTGTTGAG CCTTTCCTTT CATATCCACA GAAGACACTG TCTCAAATGT TGTACCCTTG    3162
CCATTAGGA  CTGAACTTTC CTTAGCCCAA GGGACCCAGT GACAGTTGTC TTCCGTTTGT    3222
CAGATGATCA GTCTCTACTG ATTATCTTGC TGCTTAAAGG CCTGCTCACC AATCTTTCTT    3282
TCACACCGTG TGGTCCGTGT TACTGGTATA CCCAGTATGT TCTCACTGAA GACATGGACT    3342
TTATATGTTC AAGTGCAGGA ATTGGAAAGT TGGACTTGTT TTCTATGATC CAAAACAGCC    3402
CTATAAGAAG GTTGGAAAAG GAGGAACTAT ATAGCAGCCT TTGCTATTTT CTGCTACCAT    3462
TTCTTTTCCT CTGAAGCGGC CATGACATTC CCTTTGGCAA CTAACGTAGA AACTCAACAG    3522
AACATTTTCC TTTCCTAGAG TCACCTTTTA GATGATAATG GACAACTATA GACTTGCTCA    3582
TTGTTCAGAC TGATTGCCCC TCACCTGAAT CCACTCTCTG TATTCATGCT CTTGGCAATT    3642
TCTTTGACTT TCTTTTAAGG GCAGAAGCAT TTTAGTTAAT TGTAGATAAA GAATAGTTTT    3702
CTTCCTCTTC TCCTTGGGCC AGTTAATAAT TGGTCCATGG CTACACTGCA ACTTCCGTCC    3762
AGTGCTGTGA TGCCCATGAC ACCTGCAAAA TAAGTTCTGC CTGGGCATTT TGTAGATATT    3822
AACAGGTGAA TTCCCGACTC TTTTGGTTTG AATGACAGTT CTCATTCCTT CTATGGCTGC    3882
AAGTATGCAT CAGTGCTTCC CACTTACCTG ATTTGTCTGT CGGTGGCCCC ATATGGAAAC    3942
CCTGCGTGTC TGTTGGCATA ATAGTTTACA AATGGTTTTT TCAGTCCTAT CCAAATTTAT    4002
TGAACCAACA AAAATAATTA CTTCTGCCCT GAGATAAGCA GATTAAGTTT GTTCATTCTC    4062
TGCTTTATTC TCTCCATGTG GCAACATTCT GTCAGCCTCT TTCATAGTGT GCAAACATTT    4122
TATCATTCTA AATGGTGACT CTCTGCCCTT GGACCCATTT ATTATTCACA GATGGGGAGA    4182
ACCTATCTGC ATGGACCCTC ACCATCCTCT GTGCAGCACA CACAGTGCAG GGAGCCAGTG    4242
GCGATGGCGA TGACTTTCTT CCCCTG                                         4268
```

(2) INFORMATION FOR SEQ ID NO:13:

(i) SEQUENCE CHARACTERISTICS:
(A) LENGTH: 657 amino acids
(B) TYPE: amino acid
(D) TOPOLOGY: unknown (ii) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Glu | Val | Asp | Val | Leu | Asp | Val | Asn | Val | Arg | Gly | Pro | Asp | Gly | Cys | Thr |
| 1 | | | | 5 | | | | | 10 | | | | | 15 | |
| Pro | Leu | Met | Leu | Ala | Ser | Leu | Arg | Gly | Gly | Ser | Ser | Asp | Leu | Ser | Asp |
| | | | 20 | | | | | 25 | | | | 30 | | | |
| Glu | Asp | Glu | Asp | Ala | Glu | Asp | Ser | Ser | Ala | Asn | Ile | Ile | Thr | Asp | Leu |
| | | 35 | | | | | 40 | | | | | 45 | | | |
| Val | Tyr | Gln | Gly | Ala | Ser | Leu | Gln | Ala | Gln | Thr | Asp | Arg | Thr | Gly | Glu |
| | 50 | | | | | 55 | | | | | 60 | | | | |
| Met | Ala | Leu | His | Leu | Ala | Ala | Arg | Tyr | Ser | Arg | Ala | Asp | Ala | Ala | Lys |
| 65 | | | | 70 | | | | | 75 | | | | | 80 | |
| Arg | Leu | Leu | Asp | Ala | Gly | Ala | Asp | Ala | Asn | Ala | Gln | Asp | Asn | Met | Gly |
| | | | | 85 | | | | | 90 | | | | | 95 | |
| Arg | Cys | Pro | Leu | His | Ala | Ala | Val | Ala | Ala | Asp | Ala | Gln | Gly | Val | Phe |
| | | | 100 | | | | | 105 | | | | | 110 | | |
| Gln | Ile | Leu | Ile | Arg | Asn | Arg | Val | Thr | Asp | Leu | Asp | Ala | Arg | Met | Asn |
| | | 115 | | | | | 120 | | | | | 125 | | | |
| Asp | Gly | Thr | Thr | Pro | Leu | Ile | Leu | Ala | Ala | Arg | Leu | Ala | Val | Glu | Gly |
| | 130 | | | | | 135 | | | | | 140 | | | | |
| Met | Val | Ala | Glu | Leu | Ile | Asn | Cys | Gln | Ala | Asp | Val | Asn | Ala | Val | Asp |
| 145 | | | | | 150 | | | | | 155 | | | | | 160 |
| Asp | His | Gly | Lys | Ser | Ala | Leu | His | Trp | Ala | Ala | Ala | Val | Asn | Asn | Val |
| | | | | 165 | | | | | 170 | | | | | 175 | |
| Glu | Ala | Thr | Leu | Leu | Leu | Leu | Lys | Asn | Gly | Ala | Asn | Arg | Asp | Met | Gln |
| | | | 180 | | | | | 185 | | | | | 190 | | |
| Asp | Asn | Lys | Glu | Glu | Thr | Pro | Leu | Phe | Leu | Ala | Ala | Arg | Glu | Gly | Ser |
| | | 195 | | | | | 200 | | | | | 205 | | | |
| Tyr | Glu | Ala | Ala | Lys | Ile | Leu | Leu | Asp | His | Phe | Ala | Asn | Arg | Asp | Ile |
| | 210 | | | | | 215 | | | | | 220 | | | | |
| Thr | Asp | His | Met | Asp | Arg | Leu | Pro | Arg | Asp | Val | Ala | Arg | Asp | Arg | Met |
| 225 | | | | | 230 | | | | | 235 | | | | | 240 |
| His | His | Asp | Ile | Val | Arg | Leu | Leu | Asp | Glu | Tyr | Asn | Val | Thr | Pro | Ser |
| | | | | 245 | | | | | 250 | | | | | 255 | |
| Pro | Pro | Gly | Thr | Val | Leu | Thr | Ser | Ala | Leu | Ser | Pro | Val | Ile | Cys | Gly |
| | | | 260 | | | | | 265 | | | | | 270 | | |
| Pro | Asn | Arg | Ser | Phe | Leu | Ser | Leu | Lys | His | Thr | Pro | Met | Gly | Lys | Lys |
| | | 275 | | | | | 280 | | | | | 285 | | | |
| Ser | Arg | Arg | Pro | Ser | Ala | Lys | Ser | Thr | Met | Pro | Thr | Ser | Leu | Pro | Asn |
| | 290 | | | | | 295 | | | | | 300 | | | | |
| Leu | Ala | Lys | Glu | Ala | Lys | Asp | Ala | Lys | Gly | Ser | Arg | Arg | Lys | Lys | Ser |
| 305 | | | | | 310 | | | | | 315 | | | | | 320 |
| Leu | Ser | Glu | Lys | Val | Gln | Leu | Ser | Glu | Ser | Ser | Val | Thr | Leu | Ser | Pro |
| | | | | 325 | | | | | 330 | | | | | 335 | |
| Val | Asp | Ser | Leu | Glu | Ser | Pro | His | Thr | Tyr | Val | Ser | Asp | Thr | Thr | Ser |
| | | | 340 | | | | | 345 | | | | | 350 | | |
| Ser | Pro | Met | Ile | Thr | Ser | Pro | Gly | Ile | Leu | Gln | Ala | Ser | Pro | Asn | Pro |
| | | 355 | | | | | 360 | | | | | 365 | | | |
| Met | Leu | Ala | Thr | Ala | Ala | Pro | Pro | Ala | Pro | Val | His | Ala | Gln | His | Ala |
| | 370 | | | | | 375 | | | | | 380 | | | | |
| Leu | Ser | Phe | Ser | Asn | Leu | His | Glu | Met | Gln | Pro | Leu | Ala | His | Gly | Ala |
| 385 | | | | | 390 | | | | | 395 | | | | | 400 |
| Ser | Thr | Val | Leu | Pro | Ser | Val | Ser | Gln | Leu | Leu | Ser | His | His | His | Ile |
| | | | | 405 | | | | | 410 | | | | | 415 | |

| | | | | | | | | | | | | | |
|---|---|---|---|---|---|---|---|---|---|---|---|---|---|
| Val | Ser | Pro | Gly<br>420 | Ser | Gly | Ser | Ala | Gly<br>425 | Ser | Leu | Ser | Arg | Leu<br>430 | His | Pro |
| Val | Pro | Val<br>435 | Pro | Ala | Asp | Trp | Met<br>440 | Asn | Arg | Met | Glu | Val<br>445 | Asn | Glu | Thr |
| Gln | Tyr<br>450 | Asn | Glu | Met | Phe | Gly<br>455 | Met | Val | Leu | Ala | Pro<br>460 | Ala | Glu | Gly | Thr |
| His<br>465 | Pro | Gly | Ile | Ala | Pro<br>470 | Gln | Ser | Arg | Pro | Pro<br>475 | Glu | Gly | Lys | His | Ile<br>480 |
| Thr | Thr | Pro | Arg | Glu<br>485 | Pro | Leu | Pro | Pro | Ile<br>490 | Val | Thr | Phe | Gln | Leu<br>495 | Ile |
| Pro | Lys | Gly | Ser<br>500 | Ile | Ala | Gln | Pro | Ala<br>505 | Gly | Ala | Pro | Gln | Pro<br>510 | Gln | Ser |
| Thr | Cys | Pro<br>515 | Pro | Ala | Val | Ala | Gly<br>520 | Pro | Leu | Pro | Thr | Met<br>525 | Tyr | Gln | Ile |
| Pro | Glu<br>530 | Met | Ala | Arg | Leu | Pro<br>535 | Ser | Val | Ala | Phe | Pro<br>540 | Thr | Ala | Met | Met |
| Pro<br>545 | Gln | Gln | Asp | Gly | Gln<br>550 | Val | Ala | Gln | Thr | Ile<br>555 | Leu | Pro | Ala | Tyr | His<br>560 |
| Pro | Phe | Pro | Ala | Ser<br>565 | Val | Gly | Lys | Tyr | Pro<br>570 | Thr | Pro | Pro | Ser | Gln<br>575 | His |
| Ser | Tyr | Ala | Ser<br>580 | Ser | Asn | Ala | Ala | Glu<br>585 | Arg | Thr | Pro | Ser | His<br>590 | Ser | Gly |
| His | Leu | Gln<br>595 | Gly | Glu | His | Pro | Tyr<br>600 | Leu | Thr | Pro | Ser | Pro<br>605 | Glu | Ser | Pro |
| Asp | Gln<br>610 | Trp | Ser | Ser | Ser | Pro<br>615 | His | Ser | Ala | Ser | Asp<br>620 | Trp | Ser | Asp |
| Val<br>625 | Thr | Thr | Ser | Pro | Thr<br>630 | Pro | Gly | Gly | Ala | Gly<br>635 | Gly | Gly | Gln | Arg | Gly<br>640 |
| Pro | Gly | Thr | His | Met<br>645 | Ser | Glu | Pro | Pro | His<br>650 | Asn | Asn | Met | Gln | Val<br>655 | Tyr |
| Ala |

( 2 ) INFORMATION FOR SEQ ID NO:14:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:14:

| | | | | | | | | | | | | | |
|---|---|---|---|---|---|---|---|---|---|---|---|---|---|
| Glu<br>1 | Asp | Ile | Asp | Glu<br>5 | Cys | Asp | Gln | Gly | Ser<br>10 | Pro | Cys | Glu | His<br>15 | Asn | Gly |
| Ile | Cys | Val | Asn<br>20 | Thr | Pro | Gly | Ser | Tyr<br>25 | Arg | Cys | Asn | Cys | Ser<br>30 | Gln | Gly |
| Phe | Thr | Gly<br>35 | Pro | Arg | Cys | Glu | Thr<br>40 | Asn | Ile | Asn | Glu | Cys<br>45 | Glu | Ser | His |
| Pro | Cys<br>50 | Gln | Asn | Glu | Gly | Ser<br>55 | Cys | Leu | Asp | Asp | Pro<br>60 | Gly | Thr | Phe | Arg |
| Cys<br>65 | Val | Cys | Met | Pro<br>70 | Gly | Phe | Thr | Gly | Thr<br>75 | Gln | Cys | Glu |

( 2 ) INFORMATION FOR SEQ ID NO:15:

( i ) SEQUENCE CHARACTERISTICS:
        ( A ) LENGTH: 78 amino acids ( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:15:

```
Asn Asp Val Asp Glu Cys Ser Leu Gly Ala Asn Pro Cys Glu His Gly
 1               5                  10                  15

Gly Arg Cys Thr Asn Thr Leu Gly Ser Phe Gln Cys Asn Cys Pro Gln
            20                  25                  30

Gly Tyr Ala Gly Pro Arg Cys Glu Ile Asp Val Asn Glu Cys Leu Ser
        35                  40                  45

Asn Pro Cys Gln Asn Asp Ser Thr Cys Leu Asp Gln Ile Gly Glu Phe
    50                  55                  60

Gln Cys Ile Cys Met Pro Gly Tyr Glu Gly Leu Tyr Cys Glu
65                  70                  75
```

( 2 ) INFORMATION FOR SEQ ID NO:16:

( i ) SEQUENCE CHARACTERISTICS:
( A ) LENGTH: 654 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:16:

```
Thr Pro Pro Gln Gly Glu Ile Glu Ala Asp Cys Met Asp Val Asn Val
 1               5                  10                  15

Arg Gly Pro Asp Gly Phe Thr Pro Leu Met Ile Ala Ser Cys Ser Gly
            20                  25                  30

Gly Gly Leu Glu Thr Gly Asn Ser Glu Glu Glu Glu Asp Ala Ser Ala
        35                  40                  45

Asn Met Ile Ser Asp Phe Ile Gly Gln Gly Ala Gln Leu His Asn Gln
    50                  55                  60

Thr Asp Arg Thr Gly Glu Thr Ala Leu His Leu Ala Ala Arg Tyr Ala
65                  70                  75                  80

Arg Ala Asp Ala Ala Lys Arg Leu Leu Glu Ser Ser Ala Asp Ala Asn
            85                  90                  95

Val Gln Asp Asn Met Gly Arg Thr Pro Leu His Ala Ala Val Ala Ala
            100                 105                 110

Asp Ala Gln Gly Val Phe Gln Ile Leu Ile Arg Asn Arg Ala Thr Asp
        115                 120                 125

Leu Asp Ala Arg Met Phe Asp Gly Thr Thr Pro Leu Ile Leu Ala Ala
    130                 135                 140

Arg Leu Ala Val Glu Gly Met Val Glu Glu Leu Ile Asn Ala His Ala
145                 150                 155                 160

Asp Val Asn Ala Val Asp Glu Phe Gly Lys Ser Ala Leu His Trp Ala
                165                 170                 175

Ala Ala Val Asn Asn Val Asp Ala Ala Ala Val Leu Leu Lys Asn Ser
            180                 185                 190

Ala Asn Lys Asp Met Gln Asn Asn Lys Glu Glu Thr Ser Leu Phe Leu
        195                 200                 205

Ala Ala Arg Glu Gly Ser Tyr Glu Thr Ala Lys Val Leu Leu Asp His
    210                 215                 220

Tyr Ala Asn Arg Asp Ile Thr Asp His Met Asp Arg Leu Pro Arg Asp
225                 230                 235                 240
```

```
Ile Ala Gln Glu Arg Met His His Asp Ile Val His Leu Leu Asp Glu
            245                 250                 255
Tyr Asn Leu Val Lys Ser Pro Thr Leu His Asn Gly Pro Leu Gly Ala
            260                 265                 270
Thr Thr Leu Ser Pro Pro Ile Cys Ser Pro Asn Gly Tyr Met Gly Asn
            275                 280                 285
Met Lys Pro Ser Val Gln Ser Lys Lys Ala Arg Lys Pro Ser Ile Lys
    290                 295                 300
Gly Asn Gly Cys Lys Glu Ala Lys Glu Leu Lys Ala Arg Arg Lys Lys
305                 310                 315                 320
Ser Gln Asp Gly Lys Thr Thr Leu Leu Asp Ser Gly Ser Ser Gly Val
                325                 330                 335
Leu Ser Pro Val Asp Ser Leu Glu Ser Thr His Gly Tyr Leu Ser Asp
                340                 345                 350
Val Ser Ser Pro Pro Leu Met Thr Ser Pro Phe Gln Gln Ser Pro Ser
        355                 360                 365
Met Pro Leu Asn His Leu Thr Ser Met Pro Glu Ser Gln Leu Gly Met
    370                 375                 380
Asn His Ile Asn Met Ala Thr Lys Gln Glu Met Ala Ala Gly Ser Asn
385                 390                 395                 400
Arg Met Ala Phe Asp Ala Met Val Pro Arg Leu Thr His Leu Asn Ala
                405                 410                 415
Ser Ser Pro Asn Thr Ile Met Ser Asn Gly Ser Met His Phe Thr Val
                420                 425                 430
Gly Gly Ala Pro Thr Met Asn Ser Gln Cys Asp Trp Leu Ala Arg Leu
        435                 440                 445
Gln Asn Gly Met Val Gln Asn Gln Tyr Asp Pro Ile Arg Asn Gly Ile
    450                 455                 460
Gln Gln Gly Asn Ala Gln Gln Ala Gln Ala Leu Gln His Gly Leu Met
465                 470                 475                 480
Thr Ser Leu His Asn Gly Leu Pro Ala Thr Thr Leu Ser Gln Met Met
                485                 490                 495
Thr Tyr Gln Ala Met Pro Asn Thr Arg Leu Ala Asn Gln Pro His Leu
            500                 505                 510
Met Gln Ala Gln Gln Met Gln Gln Gln Gln Asn Leu Gln Leu His Gln
        515                 520                 525
Ser Met Gln Gln Gln His His Asn Ser Ser Thr Thr Ser Thr His Ile
    530                 535                 540
Asn Ser Pro Phe Cys Ser Ser Asp Ile Ser Gln Thr Asp Leu Gln Gln
545                 550                 555                 560
Met Ser Ser Asn Asn Ile His Ser Val Met Pro Gln Asp Thr Gln Ile
                565                 570                 575
Phe Ala Ala Ser Leu Pro Ser Asn Leu Thr Gln Ser Met Thr Thr Ala
                580                 585                 590
Gln Phe Leu Thr Pro Pro Ser Gln His Ser Tyr Ser Ser Pro Met Asp
        595                 600                 605
Asn Thr Pro Ser His Gln Leu Gln Val Pro Asp His Pro Phe Leu Thr
    610                 615                 620
Pro Ser Pro Glu Ser Pro Asp Gln Trp Ser Ser Ser Ser Pro His Ser
625                 630                 635                 640
Asn Met Ser Asp Trp Ser Glu Gly Ile Ser Ser Pro Pro Thr
                645                 650
```

( 2 ) INFORMATION FOR SEQ ID NO:17:

( i ) SEQUENCE CHARACTERISTICS:
        ( A ) LENGTH: 666 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:17:

```
Thr Pro Pro Gln Gly Glu Val Asp Ala Asp Cys Met Asp Val Asn Val
 1               5                  10                  15

Arg Gly Pro Asp Gly Phe Thr Pro Leu Met Ile Ala Ser Cys Ser Gly
            20                  25                  30

Gly Gly Leu Glu Thr Gly Asn Ser Glu Glu Glu Glu Asp Ala Pro Ala
        35                  40                  45

Val Ile Ser Asp Phe Ile Tyr Gln Gly Ala Ser Leu His Asn Gln Thr
 50                  55                  60

Asp Arg Thr Gly Glu Thr Ala Leu His Leu Ala Ala Arg Tyr Ser Arg
 65                  70                  75                  80

Ser Asp Ala Ala Lys Arg Leu Leu Glu Ala Ser Ala Asp Ala Asn Ile
                85                  90                  95

Gln Asp Asn Met Gly Arg Thr Pro Leu His Ala Ala Val Ser Ala Asp
                100                 105                 110

Ala Gln Gly Val Phe Gln Ile Leu Leu Arg Asn Arg Ala Thr Asp Leu
            115                 120                 125

Asp Ala Arg Met His Asp Gly Thr Thr Pro Leu Ile Leu Ala Ala Arg
130                 135                 140

Leu Ala Val Glu Gly Met Leu Glu Asp Leu Ile Asn Ser His Ala Asp
145                 150                 155                 160

Val Asn Ala Val Asp Asp Leu Gly Lys Ser Ala Leu His Trp Ala Ala
                165                 170                 175

Ala Val Asn Asn Val Asp Ala Ala Val Val Leu Leu Lys Asn Gly Ala
            180                 185                 190

Asn Lys Asp Met Gln Asn Asn Lys Glu Glu Thr Pro Leu Phe Leu Ala
        195                 200                 205

Ala Arg Glu Gly Ser Tyr Glu Thr Ala Lys Val Leu Leu Asp His Phe
210                 215                 220

Ala Asn Arg Asp Ile Thr Asp His Met Asp Arg Leu Pro Arg Asp Ile
225                 230                 235                 240

Ala Gln Glu Arg Met His His Asp Ile Val Arg Leu Leu Asp Glu Tyr
                245                 250                 255

Asn Leu Val Arg Ser Pro Gln Leu His Gly Thr Ala Leu Gly Gly Thr
            260                 265                 270

Pro Thr Leu Ser Pro Thr Leu Cys Ser Pro Asn Gly Tyr Leu Gly Asn
        275                 280                 285

Leu Lys Ser Ala Thr Gln Gly Lys Lys Ala Arg Lys Pro Ser Thr Lys
290                 295                 300

Gly Leu Ala Cys Ser Ser Lys Glu Ala Lys Asp Leu Lys Ala Arg Arg
305                 310                 315                 320

Lys Lys Ser Gln Asp Gly Lys Gly Cys Leu Leu Asp Ser Ser Ser Met
                325                 330                 335

Leu Ser Pro Val Asp Ser Leu Glu Ser Pro His Gly Tyr Leu Ser Asp
            340                 345                 350

Val Ala Ser Pro Pro Leu Pro Ser Pro Phe Gln Gln Ser Pro Ser Met
        355                 360                 365
```

| | | | | | | | | | | | | | |
|---|---|---|---|---|---|---|---|---|---|---|---|---|---|
|Pro|Leu 370|Ser|His|Leu|Pro|Gly 375|Met|Pro|Asp|Thr|His 380|Leu|Gly|Ile|Ser|
|His 385|Leu|Asn|Val|Ala|Ala 390|Lys|Pro|Glu|Met|Ala 395|Ala|Leu|Ala|Gly|Gly 400|
|Ser|Arg|Leu|Ala|Phe 405|Glu|Pro|Pro|Pro|Arg 410|Leu|Ser|His|Leu 415|Pro|
|Val|Ala|Ser|Ser 420|Ala|Ser|Thr|Val|Leu 425|Ser|Thr|Asn|Gly|Thr 430|Gly|Ala|
|Met|Asn|Phe 435|Thr|Val|Gly|Ala|Pro 440|Ala|Ser|Leu|Asn|Gly 445|Gln|Cys|Glu|
|Trp|Leu 450|Pro|Arg|Leu|Gln|Asn 455|Gly|Met|Val|Pro|Ser 460|Gln|Tyr|Asn|Pro|
|Leu 465|Arg|Pro|Gly|Val|Thr 470|Pro|Gly|Thr|Leu|Ser 475|Thr|Gln|Ala|Ala|Gly 480|
|Leu|Gln|His|Gly|Met 485|Met|Ser|Pro|Ile|His 490|Ser|Ser|Leu|Ser|Thr 495|Asn|
|Thr|Leu|Ser|Pro 500|Ile|Ile|Tyr|Gln|Gly 505|Leu|Pro|Asn|Thr|Arg 510|Leu|Ala|
|Thr|Gln|Pro 515|His|Leu|Val|Gln|Thr 520|Gln|Gln|Val|Gln|Pro 525|Gln|Asn|Leu|
|Gln|Ile 530|Gln|Pro|Gln|Asn|Leu 535|Gln|Pro|Pro|Ser|Gln 540|Pro|His|Leu|Ser|
|Val 545|Ser|Ser|Ala|Ala|Asn 550|Gly|His|Leu|Gly|Arg 555|Ser|Phe|Leu|Ser|Gly 560|
|Glu|Pro|Ser|Gln|Ala 565|Asp|Val|Gln|Pro|Leu 570|Gly|Pro|Ser|Ser|Leu 575|Pro|
|Val|His|Thr|Ile 580|Leu|Pro|Gln|Glu|Ser 585|Gln|Ala|Leu|Pro|Thr 590|Ser|Leu|
|Pro|Ser|Ser 595|Met|Val|Pro|Pro|Met 600|Thr|Thr|Thr|Gln|Phe 605|Leu|Thr|Pro|
|Pro|Ser 610|Gln|His|Ser|Tyr|Ser 615|Ser|Ser|Pro|Val|Asp 620|Asn|Thr|Pro|Ser|
|His 625|Gln|Leu|Gln|Val|Pro 630|Glu|His|Pro|Phe|Leu 635|Thr|Pro|Ser|Pro|Glu 640|
|Ser|Pro|Asp|Gln|Trp 645|Ser|Ser|Ser|Ser|Arg 650|His|Ser|Asn|Ile|Ser 655|Asp|
|Trp|Ser|Glu|Gly 660|Ile|Ser|Ser|Pro|Pro 665|Thr|

( 2 ) INFORMATION FOR SEQ ID NO:18:

( i ) SEQUENCE CHARACTERISTICS:
        ( A ) LENGTH: 681 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:18:

| | | | | | | | | | | | | | |
|---|---|---|---|---|---|---|---|---|---|---|---|---|---|
|Thr 1|Pro|Pro|Gln|Gly 5|Glu|Val|Asp|Ala|Cys 10|Met|Asp|Val|Asn 15|Val|
|Arg|Gly|Pro|Asp 20|Gly|Phe|Thr|Pro|Leu 25|Met|Ile|Ala|Ser|Cys 30|Ser|Gly|
|Gly|Gly|Leu|Glu 35|Thr|Gly|Asn|Ser|Glu 40|Glu|Glu|Glu|Asp 45|Ala|Pro|Ala|

```
Val  Ile  Ser  Asp  Phe  Ile  Tyr  Gln  Gly  Ala  Ser  Leu  His  Asn  Gln  Thr
     50                  55                       60

Asp  Arg  Thr  Gly  Glu  Thr  Ala  Leu  His  Leu  Ala  Ala  Arg  Tyr  Ser  Arg
65                       70                  75                            80

Ser  Asp  Ala  Ala  Lys  Arg  Leu  Leu  Glu  Ala  Ser  Ala  Asp  Ala  Asn  Ile
                    85                  90                       95

Gln  Asp  Asn  Met  Gly  Arg  Thr  Pro  Leu  His  Ala  Ala  Val  Ser  Ala  Asp
               100                 105                      110

Ala  Gln  Gly  Val  Phe  Gln  Ile  Leu  Ile  Arg  Asn  Arg  Ala  Thr  Asp  Leu
          115                 120                           125

Asp  Ala  Arg  Met  His  Asp  Gly  Thr  Thr  Pro  Leu  Ile  Leu  Ala  Ala  Arg
130                      135                      140

Leu  Ala  Val  Glu  Gly  Met  Leu  Glu  Asp  Leu  Ile  Asn  Ser  His  Ala  Asp
145                      150                 155                           160

Val  Asn  Ala  Val  Asp  Leu  Gly  Lys  Ser  Ala  Leu  His  Trp  Ala  Ala
                    165                 170                      175

Ala  Val  Asn  Asn  Val  Asp  Ala  Ala  Val  Val  Leu  Leu  Lys  Asn  Gly  Ala
               180                      185                      190

Asn  Lys  Asp  Met  Gln  Asn  Asn  Arg  Glu  Glu  Thr  Pro  Leu  Phe  Leu  Ala
          195                 200                      205

Ala  Arg  Glu  Gly  Ser  Tyr  Glu  Thr  Ala  Lys  Val  Leu  Leu  Asp  His  Phe
210                      215                      220

Ala  Asn  Arg  Asp  Ile  Thr  Asp  His  Met  Asp  Arg  Leu  Pro  Arg  Asp  Ile
225                      230                      235                      240

Ala  Gln  Glu  Arg  Met  His  His  Asp  Ile  Val  Arg  Leu  Leu  Asp  Glu  Tyr
               245                      250                      255

Asn  Leu  Val  Arg  Ser  Pro  Gln  Leu  His  Gly  Ala  Pro  Leu  Gly  Gly  Thr
                260                 265                      270

Pro  Thr  Leu  Ser  Pro  Pro  Leu  Cys  Ser  Pro  Asn  Gly  Tyr  Leu  Gly  Ser
          275                 280                      285

Leu  Lys  Pro  Gly  Val  Gln  Gly  Lys  Lys  Val  Arg  Lys  Pro  Ser  Ser  Lys
290                      295                      300

Gly  Leu  Ala  Cys  Gly  Ser  Lys  Glu  Ala  Lys  Asp  Leu  Lys  Ala  Arg  Arg
305                      310                      315                      320

Lys  Lys  Ser  Gln  Asp  Gly  Lys  Gly  Cys  Leu  Leu  Asp  Ser  Ser  Gly  Met
               325                      330                      335

Leu  Ser  Pro  Val  Asp  Ser  Leu  Glu  Ser  Pro  His  Gly  Tyr  Leu  Ser  Asp
               340                 345                      350

Val  Ala  Ser  Pro  Pro  Leu  Leu  Pro  Ser  Pro  Phe  Gln  Gln  Ser  Pro  Ser
          355                 360                      365

Val  Pro  Leu  Asn  His  Leu  Pro  Gly  Met  Pro  Asp  Thr  His  Leu  Gly  Ile
370                      375                      380

Gly  His  Leu  Asn  Val  Ala  Ala  Lys  Pro  Glu  Met  Ala  Ala  Leu  Gly  Gly
385                      390                      395                      400

Gly  Gly  Arg  Leu  Ala  Phe  Glu  Thr  Gly  Pro  Pro  Arg  Leu  Ser  His  Leu
               405                      410                      415

Pro  Val  Ala  Ser  Gly  Thr  Ser  Thr  Val  Leu  Gly  Ser  Ser  Ser  Gly  Gly
               420                      425                      430

Ala  Leu  Asn  Phe  Thr  Val  Gly  Gly  Ser  Thr  Ser  Leu  Asn  Gly  Gln  Cys
               435                      440                      445

Glu  Trp  Leu  Ser  Arg  Leu  Gln  Ser  Gly  Met  Val  Pro  Asn  Gln  Tyr  Asn
          450                 455                      460

Pro  Leu  Arg  Gly  Ser  Val  Ala  Pro  Gly  Pro  Leu  Ser  Thr  Gln  Ala  Pro
465                      470                      475                      480
```

```
Ser Leu Gln His Gly Met Val Gly Pro Leu His Ser Ser Leu Ala Ala
            485             490             495

Ser Ala Leu Ser Gln Met Met Ser Tyr Gln Gly Leu Pro Ser Thr Arg
            500             505             510

Leu Ala Thr Gln Pro His Leu Val Gln Thr Gln Gln Val Gln Pro Gln
            515             520             525

Asn Leu Gln Met Gln Gln Gln Asn Leu Gln Pro Ala Asn Ile Gln Gln
            530             535             540

Gln Gln Ser Leu Gln Pro Pro Pro Pro Pro Gln Pro His Leu Gly
545             550             555             560

Val Ser Ser Ala Ala Ser Gly His Leu Gly Arg Ser Phe Leu Ser Gly
                565             570             575

Glu Pro Ser Gln Ala Asp Val Gln Pro Leu Gly Pro Ser Ser Leu Ala
            580             585             590

Val His Thr Ile Leu Pro Gln Glu Ser Pro Ala Leu Pro Thr Ser Leu
            595             600             605

Pro Ser Ser Leu Val Pro Pro Val Thr Ala Ala Gln Phe Leu Thr Pro
    610             615             620

Pro Ser Gln His Ser Tyr Ser Ser Pro Val Glu Asn Thr Pro Ser His
625             630             635             640

Gln Leu Gln Val Pro Glu His Pro Phe Leu Thr Pro Ser Pro Glu Ser
            645             650             655

Pro Asp Gln Trp Ser Ser Ser Ser Pro His Ser Asn Val Ser Asp Trp
            660             665             670

Ser Glu Gly Val Ser Ser Pro Pro Thr
            675             680
```

( 2 ) INFORMATION FOR SEQ ID NO:19:

( i ) SEQUENCE CHARACTERISTICS:
      ( A ) LENGTH: 2471 amino acids
      ( B ) TYPE: amino acid
      ( C ) STRANDEDNESS: single
      ( D ) TOPOLOGY: unknown ( i i ) MOLECULE TYPE: peptide ( x i ) SEQUENCE DESCRIPTION: SEQ ID NO:19:

```
Met Pro Ala Leu Arg Pro Ala Leu Leu Trp Ala Leu Leu Ala Leu Trp
1               5               10              15

Leu Cys Cys Ala Ala Pro Ala His Ala Leu Gln Cys Arg Asp Gly Tyr
            20              25              30

Glu Pro Cys Val Asn Glu Gly Met Cys Val Thr Tyr His Asn Gly Thr
        35              40              45

Gly Tyr Cys Lys Cys Pro Glu Gly Phe Leu Gly Glu Tyr Cys Gln His
    50              55              60

Arg Asp Pro Cys Glu Lys Asn Arg Cys Gln Asn Gly Gly Thr Cys Val
65              70              75              80

Ala Gln Ala Met Leu Gly Lys Ala Thr Cys Arg Cys Ala Ser Gly Phe
            85              90              95

Thr Gly Glu Asp Cys Gln Tyr Ser Thr Ser His Pro Cys Phe Val Ser
            100             105             110

Arg Pro Cys Leu Asn Gly Gly Thr Cys His Met Leu Ser Arg Asp Thr
            115             120             125

Tyr Glu Cys Thr Cys Gln Val Gly Phe Thr Gly Lys Glu Cys Gln Trp
            130             135             140
```

-continued

| | | | | | | | | | | | | | | |
|---|---|---|---|---|---|---|---|---|---|---|---|---|---|---|
| Thr<br>145 | Asp | Ala | Cys | Leu<br>150 | Ser | His | Pro | Cys<br>155 | Ala | Asn | Gly | Ser | Thr<br>160 | Cys |
| Thr | Val | Ala | Asn | Gln<br>165 | Phe | Ser | Cys | Lys<br>170 | Cys | Leu | Thr | Gly | Phe<br>175 | Thr | Gly |
| Gln | Lys | Cys | Glu<br>180 | Thr | Asp | Val | Asn | Glu<br>185 | Cys | Asp | Ile | Pro | Gly<br>190 | His | Cys |
| Gln | His | Gly<br>195 | Gly | Thr | Cys | Leu | Asn<br>200 | Leu | Pro | Gly | Ser | Tyr<br>205 | Gln | Cys | Gln |
| Cys | Pro<br>210 | Gln | Gly | Phe | Thr | Gly<br>215 | Gln | Tyr | Cys | Asp | Ser<br>220 | Leu | Tyr | Val | Pro |
| Cys<br>225 | Ala | Pro | Ser | Pro | Cys<br>230 | Val | Asn | Gly | Gly | Thr<br>235 | Cys | Arg | Gln | Thr | Gly<br>240 |
| Asp | Phe | Thr | Phe | Glu<br>245 | Cys | Asn | Cys | Leu | Pro<br>250 | Gly | Phe | Glu | Gly | Ser<br>255 | Thr |
| Cys | Glu | Arg | Asn<br>260 | Ile | Asp | Asp | Cys | Pro<br>265 | Asn | His | Arg | Cys | Gln<br>270 | Asn | Gly |
| Gly | Val | Cys<br>275 | Val | Asp | Gly | Val | Asn<br>280 | Thr | Tyr | Asn | Cys | Arg<br>285 | Cys | Pro | Pro |
| Gln | Trp<br>290 | Thr | Gly | Gln | Phe | Cys<br>295 | Thr | Glu | Asp | Val | Asp<br>300 | Glu | Cys | Leu | Leu |
| Gln<br>305 | Pro | Asn | Ala | Cys | Gln<br>310 | Asn | Gly | Gly | Thr | Cys<br>315 | Ala | Asn | Arg | Asn | Gly<br>320 |
| Gly | Tyr | Gly | Cys | Val<br>325 | Cys | Val | Asn | Gly | Trp<br>330 | Ser | Gly | Asp | Asp | Cys<br>335 | Ser |
| Glu | Asn | Ile | Asp<br>340 | Asp | Cys | Ala | Phe | Ala<br>345 | Ser | Cys | Thr | Pro | Gly<br>350 | Ser | Thr |
| Cys | Ile | Asp | Arg<br>355 | Val | Ala | Ser | Phe | Ser<br>360 | Cys | Met | Cys | Pro | Glu<br>365 | Gly | Lys |
| Ala | Gly<br>370 | Leu | Leu | Cys | His | Leu<br>375 | Asp | Asp | Ala | Cys | Ile<br>380 | Ser | Asn | Pro | Cys |
| His<br>385 | Lys | Gly | Ala | Leu | Cys<br>390 | Asp | Thr | Asn | Pro | Leu<br>395 | Asn | Gly | Gln | Tyr | Ile<br>400 |
| Cys | Thr | Cys | Pro | Gln<br>405 | Gly | Tyr | Lys | Gly | Ala<br>410 | Asp | Cys | Thr | Glu | Asp<br>415 | Val |
| Asp | Glu | Cys | Ala<br>420 | Met | Ala | Asn | Ser | Asn<br>425 | Pro | Cys | Glu | His | Ala<br>430 | Gly | Lys |
| Cys | Val | Asn<br>435 | Thr | Asp | Gly | Ala | Phe<br>440 | His | Cys | Glu | Cys | Leu<br>445 | Lys | Gly | Tyr |
| Ala | Gly<br>450 | Pro | Arg | Cys | Glu | Met<br>455 | Asp | Ile | Asn | Glu | Cys<br>460 | His | Ser | Asp | Pro |
| Cys<br>465 | Gln | Asn | Asp | Ala | Thr<br>470 | Cys | Leu | Asp | Lys | Ile<br>475 | Gly | Gly | Phe | Thr | Cys<br>480 |
| Leu | Cys | Met | Pro | Gly<br>485 | Phe | Lys | Gly | Val | His<br>490 | Cys | Glu | Leu | Glu | Ile<br>495 | Asn |
| Glu | Cys | Gln | Ser<br>500 | Asn | Pro | Cys | Val | Asn<br>505 | Gly | Gln | Cys | Val | Asp<br>510 | Lys |
| Val | Asn | Arg<br>515 | Phe | Gln | Cys | Leu | Cys<br>520 | Pro | Pro | Gly | Phe | Thr<br>525 | Gly | Pro | Val |
| Cys | Gln | Ile<br>530 | Asp | Ile | Asp | Asp | Cys<br>535 | Ser | Ser | Thr | Pro | Cys<br>540 | Leu | Asn | Gly |
| Ala | Lys<br>545 | Cys | Ile | Asp | His | Pro<br>550 | Asn | Gly | Tyr | Glu | Cys<br>555 | Gln | Cys | Ala | Thr<br>560 |
| Gly | Phe | Thr | Gly | Val<br>565 | Leu | Cys | Glu | Glu | Asn<br>570 | Ile | Asp | Asn | Cys | Asp<br>575 | Pro |

-continued

```
Asp Pro Cys His His Gly Gln Cys Gln Asp Gly Ile Asp Ser Tyr Thr
            580             585                     590
Cys Ile Cys Asn Pro Gly Tyr Met Gly Ala Ile Cys Ser Asp Gln Ile
        595             600                 605
Asp Glu Cys Tyr Ser Ser Pro Cys Leu Asn Asp Gly Arg Cys Ile Asp
        610             615             620
Leu Val Asn Gly Tyr Gln Cys Asn Cys Gln Pro Gly Thr Ser Gly Val
625             630             635                         640
Asn Cys Glu Ile Asn Phe Asp Asp Cys Ala Ser Asn Pro Cys Ile His
                645             650             655
Gly Ile Cys Met Asp Gly Ile Asn Arg Tyr Ser Cys Val Cys Ser Pro
            660             665             670
Gly Phe Thr Gly Gln Arg Cys Asn Ile Asp Ile Asp Glu Cys Ala Ser
        675             680             685
Asn Pro Cys Arg Lys Gly Ala Thr Cys Ile Asn Gly Val Asn Gly Phe
        690             695             700
Arg Cys Ile Cys Pro Glu Gly Pro His His Pro Ser Cys Tyr Ser Gln
705             710             715                         720
Val Asn Glu Cys Leu Ser Asn Pro Cys Ile His Gly Asn Cys Thr Gly
            725             730             735
Gly Leu Ser Gly Tyr Lys Cys Leu Cys Asp Ala Gly Trp Val Gly Ile
            740             745             750
Asn Cys Glu Val Asp Lys Asn Glu Cys Leu Ser Asn Pro Cys Gln Asn
        755             760             765
Gly Gly Thr Cys Asp Asn Leu Val Asn Gly Tyr Arg Cys Thr Cys Lys
770             775             780
Lys Gly Phe Lys Gly Tyr Asn Cys Gln Val Asn Ile Asp Glu Cys Ala
785             790             795                         800
Ser Asn Pro Cys Leu Asn Gln Gly Thr Cys Phe Asp Asp Ile Ser Gly
            805             810             815
Tyr Thr Cys His Cys Val Leu Pro Tyr Thr Gly Lys Asn Cys Gln Thr
            820             825             830
Val Leu Ala Pro Cys Ser Pro Asn Pro Cys Glu Asn Ala Ala Val Cys
            835             840             845
Lys Glu Ser Pro Asn Phe Glu Ser Tyr Thr Cys Leu Cys Ala Pro Gly
850             855             860
Trp Gln Gly Gln Arg Cys Thr Ile Asp Ile Asp Glu Cys Ile Ser Lys
865             870             875                         880
Pro Cys Met Asn His Gly Leu Cys His Asn Thr Gln Gly Ser Tyr Met
            885             890             895
Cys Glu Cys Pro Pro Gly Phe Ser Gly Met Asp Cys Glu Glu Asp Ile
            900             905             910
Asp Asp Cys Leu Ala Asn Pro Cys Gln Asn Gly Gly Ser Cys Met Asp
        915             920             925
Gly Val Asn Thr Phe Ser Cys Leu Cys Leu Pro Gly Phe Thr Gly Asp
        930             935             940
Lys Cys Gln Thr Asp Met Asn Glu Cys Leu Ser Glu Pro Cys Lys Asn
945             950             955                         960
Gly Gly Thr Cys Ser Asp Tyr Val Asn Ser Tyr Thr Cys Lys Cys Gln
            965             970             975
Ala Gly Phe Asp Gly Val His Cys Glu Asn Asn Ile Asn Glu Cys Thr
            980             985             990
Glu Ser Ser Cys Phe Asn Gly Gly Thr Cys Val Asp Gly Ile Asn Ser
```

|   |   |   |   |   |   |   |   |   |   |   |   |   |   |   |
|---|---|---|---|---|---|---|---|---|---|---|---|---|---|---|
| | | | | 995 | | | | | 1000 | | | | | 1005 |
| Phe | Ser | Cys | Leu | Cys | Pro | Val | Gly | Phe | Thr | Gly | Ser | Phe | Cys | Leu | His |
| | | | | 1010 | | | | | 1015 | | | | | 1020 |
| Glu | Ile | Asn | Glu | Cys | Ser | Ser | His | Pro | Cys | Leu | Asn | Glu | Gly | Thr | Cys |
| 1025 | | | | | 1030 | | | | | 1035 | | | | | 1040 |
| Val | Asp | Gly | Leu | Gly | Thr | Tyr | Arg | Cys | Ser | Cys | Pro | Leu | Gly | Tyr | Thr |
| | | | | 1045 | | | | | 1050 | | | | | 1055 |
| Gly | Lys | Asn | Cys | Gln | Thr | Leu | Val | Asn | Leu | Cys | Ser | Arg | Ser | Pro | Cys |
| | | | 1060 | | | | | 1065 | | | | | 1070 |
| Lys | Asn | Lys | Gly | Thr | Cys | Val | Gln | Lys | Lys | Ala | Glu | Ser | Gln | Cys | Leu |
| | | | 1075 | | | | | 1080 | | | | | 1085 |
| Cys | Pro | Ser | Gly | Trp | Ala | Gly | Ala | Tyr | Cys | Asp | Val | Pro | Asn | Val | Ser |
| | | | 1090 | | | | | 1095 | | | | | 1100 |
| Cys | Asp | Ile | Ala | Ala | Ser | Arg | Arg | Gly | Val | Leu | Val | Glu | His | Leu | Cys |
| 1105 | | | | | 1110 | | | | | 1115 | | | | | 1120 |
| Gln | His | Ser | Gly | Val | Cys | Ile | Asn | Ala | Gly | Asn | Thr | His | Tyr | Cys | Gln |
| | | | | 1125 | | | | | 1130 | | | | | 1135 |
| Cys | Pro | Leu | Gly | Tyr | Thr | Gly | Ser | Tyr | Cys | Glu | Glu | Gln | Leu | Asp | Glu |
| | | | | 1140 | | | | | 1145 | | | | | 1150 |
| Cys | Ala | Ser | Asn | Pro | Cys | Gln | His | Gly | Ala | Thr | Cys | Ser | Asp | Phe | Ile |
| | | | | 1155 | | | | | 1160 | | | | | 1165 |
| Gly | Gly | Tyr | Arg | Cys | Glu | Cys | Val | Pro | Gly | Tyr | Gln | Gly | Val | Asn | Cys |
| | | | | 1170 | | | | | 1175 | | | | | 1180 |
| Glu | Tyr | Glu | Val | Asp | Glu | Cys | Gln | Asn | Gln | Pro | Cys | Gln | Asn | Gly | Gly |
| 1185 | | | | | 1190 | | | | | 1195 | | | | | 1200 |
| Thr | Cys | Ile | Asp | Leu | Val | Asn | His | Phe | Lys | Cys | Ser | Cys | Pro | Pro | Gly |
| | | | | 1205 | | | | | 1210 | | | | | 1215 |
| Thr | Arg | Gly | Leu | Leu | Cys | Glu | Glu | Asn | Ile | Asp | Asp | Cys | Ala | Arg | Gly |
| | | | | 1220 | | | | | 1225 | | | | | 1230 |
| Pro | His | Cys | Leu | Asn | Gly | Gly | Gln | Cys | Met | Asp | Arg | Ile | Gly | Gly | Tyr |
| | | | | 1235 | | | | | 1240 | | | | | 1245 |
| Ser | Cys | Arg | Cys | Leu | Pro | Gly | Phe | Ala | Gly | Glu | Arg | Cys | Glu | Gly | Asp |
| | | | | 1250 | | | | | 1255 | | | | | 1260 |
| Ile | Asn | Glu | Cys | Leu | Ser | Asn | Pro | Cys | Ser | Ser | Glu | Gly | Ser | Leu | Asp |
| 1265 | | | | | 1270 | | | | | 1275 | | | | | 1280 |
| Cys | Ile | Gln | Leu | Thr | Asn | Asp | Tyr | Leu | Cys | Val | Cys | Arg | Ser | Ala | Phe |
| | | | | 1285 | | | | | 1290 | | | | | 1295 |
| Thr | Gly | Arg | His | Cys | Glu | Thr | Phe | Val | Asp | Val | Cys | Pro | Gln | Met | Pro |
| | | | | 1300 | | | | | 1305 | | | | | 1310 |
| Cys | Leu | Asn | Gly | Gly | Thr | Cys | Ala | Val | Ala | Ser | Asn | Met | Pro | Asp | Gly |
| | | | | 1315 | | | | | 1320 | | | | | 1325 |
| Phe | Ile | Cys | Arg | Cys | Pro | Pro | Gly | Phe | Ser | Gly | Ala | Arg | Cys | Gln | Ser |
| | | | | 1330 | | | | | 1335 | | | | | 1340 |
| Ser | Cys | Gly | Gln | Val | Lys | Cys | Arg | Lys | Gly | Glu | Gln | Cys | Val | His | Thr |
| 1345 | | | | | 1350 | | | | | 1355 | | | | | 1360 |
| Ala | Ser | Gly | Pro | Arg | Cys | Phe | Cys | Pro | Ser | Pro | Arg | Asp | Cys | Glu | Ser |
| | | | | 1365 | | | | | 1370 | | | | | 1375 |
| Gly | Cys | Ala | Ser | Ser | Pro | Cys | Gln | His | Gly | Gly | Ser | Cys | His | Pro | Gln |
| | | | | 1380 | | | | | 1385 | | | | | 1390 |
| Arg | Gln | Pro | Pro | Tyr | Tyr | Ser | Cys | Gln | Cys | Ala | Pro | Pro | Phe | Ser | Gly |
| | | | | 1395 | | | | | 1400 | | | | | 1405 |
| Ser | Arg | Cys | Glu | Leu | Tyr | Thr | Ala | Pro | Pro | Ser | Thr | Pro | Pro | Ala | Thr |
| | | | | 1410 | | | | | 1415 | | | | | 1420 |

Cys Leu Ser Gln Tyr Cys Ala Asp Lys Ala Arg Asp Gly Val Cys Asp
1425                1430                1435                1440

Glu Ala Cys Asn Ser His Ala Cys Gln Trp Asp Gly Gly Asp Cys Ser
                1445                1450                1455

Leu Thr Met Glu Asn Pro Trp Ala Asn Cys Ser Ser Pro Leu Pro Cys
            1460                1465                1470

Trp Asp Tyr Ile Asn Asn Gln Cys Asp Glu Leu Cys Asn Thr Val Glu
            1475                1480                1485

Cys Leu Phe Asp Asn Phe Glu Cys Gln Gly Asn Ser Lys Thr Cys Lys
            1490                1495                1500

Tyr Asp Lys Tyr Cys Ala Asp His Phe Lys Asp Asn His Cys Asn Gln
1505                1510                1515                1520

Gly Cys Asn Ser Glu Glu Cys Gly Trp Asp Gly Leu Asp Cys Ala Ala
                1525                1530                1535

Asp Gln Pro Glu Asn Leu Ala Glu Gly Thr Leu Val Ile Val Val Leu
            1540                1545                1550

Met Pro Pro Glu Gln Leu Leu Gln Asp Ala Arg Ser Phe Leu Arg Ala
            1555                1560                1565

Leu Gly Thr Leu Leu His Thr Asn Leu Arg Ile Lys Arg Asp Ser Gln
            1570                1575                1580

Gly Glu Leu Met Val Tyr Pro Tyr Tyr Gly Glu Lys Ser Ala Ala Met
1585                1590                1595                1600

Lys Lys Gln Arg Met Thr Arg Arg Ser Leu Pro Gly Glu Gln Glu Gln
                1605                1610                1615

Glu Val Ala Gly Ser Lys Val Phe Leu Glu Ile Asp Asn Arg Gln Cys
            1620                1625                1630

Val Gln Asp Ser Asp His Cys Phe Lys Asn Thr Asp Ala Ala Ala Ala
            1635                1640                1645

Leu Leu Ala Ser His Ala Ile Gln Gly Thr Leu Ser Tyr Pro Leu Val
            1650                1655                1660

Ser Val Val Ser Glu Ser Leu Thr Pro Glu Arg Thr Gln Leu Leu Tyr
1665                1670                1675                1680

Leu Leu Ala Val Ala Val Val Ile Ile Leu Phe Ile Ile Leu Leu Gly
            1685                1690                1695

Val Ile Met Ala Lys Arg Lys Arg Lys His Gly Ser Leu Trp Leu Pro
            1700                1705                1710

Glu Gly Phe Thr Leu Arg Arg Asp Ala Ser Asn His Lys Arg Arg Glu
            1715                1720                1725

Pro Val Gly Gln Asp Ala Val Gly Leu Lys Asn Leu Ser Val Gln Val
            1730                1735                1740

Ser Glu Ala Asn Leu Ile Gly Thr Gly Thr Ser Glu His Trp Val Asp
1745                1750                1755                1760

Asp Glu Gly Pro Gln Pro Lys Lys Val Lys Ala Glu Asp Glu Ala Leu
            1765                1770                1775

Leu Ser Glu Glu Asp Asp Pro Ile Asp Arg Arg Pro Trp Thr Gln Gln
            1780                1785                1790

His Leu Glu Ala Ala Asp Ile Arg Arg Thr Pro Ser Leu Ala Leu Thr
            1795                1800                1805

Pro Pro Gln Ala Glu Gln Glu Val Asp Val Leu Asp Val Asn Val Arg
            1810                1815                1820

Gly Pro Asp Gly Cys Thr Pro Leu Met Leu Ala Ser Leu Arg Gly Gly
1825                1830                1835                1840

Ser Ser Asp Leu Ser Asp Glu Asp Glu Asp Ala Glu Asp Ser Ser Ala
            1845                1850                1855

```
Asn Ile Ile Thr Asp Leu Val Tyr Gln Gly Ala Ser Leu Gln Ala Gln
            1860                1865                1870

Thr Asp Arg Thr Gly Glu Met Ala Leu His Leu Ala Ala Arg Tyr Ser
        1875                1880                1885

Arg Ala Asp Ala Ala Lys Arg Leu Leu Asp Ala Gly Ala Asp Ala Asn
        1890                1895                1900

Ala Gln Asp Asn Met Gly Arg Cys Pro Leu His Ala Ala Val Ala Ala
1905                1910                1915                1920

Asp Ala Gln Gly Val Phe Gln Ile Leu Ile Arg Asn Arg Val Thr Asp
                1925                1930                1935

Leu Asp Ala Arg Met Asn Asp Gly Thr Thr Pro Leu Ile Leu Ala Ala
            1940                1945                1950

Arg Leu Ala Val Glu Gly Met Val Ala Glu Leu Ile Asn Cys Gln Ala
            1955                1960                1965

Asp Val Asn Ala Val Asp Asp His Gly Lys Ser Ala Leu His Trp Ala
            1970                1975                1980

Ala Ala Val Asn Asn Val Glu Ala Thr Leu Leu Leu Leu Lys Asn Gly
1985                1990                1995                2000

Ala Asn Arg Asp Met Gln Asp Asn Lys Glu Glu Thr Pro Leu Phe Leu
            2005                2010                2015

Ala Ala Arg Glu Gly Ser Tyr Glu Ala Ala Lys Ile Leu Leu Asp His
            2020                2025                2030

Phe Ala Asn Arg Asp Ile Thr Asp His Met Asp Arg Leu Pro Arg Asp
            2035                2040                2045

Val Ala Arg Asp Arg Met His His Asp Ile Val Arg Leu Leu Asp Glu
            2050                2055                2060

Tyr Asn Val Thr Pro Ser Pro Pro Gly Thr Val Leu Thr Ser Ala Leu
2065                2070                2075                2080

Ser Pro Val Ile Cys Gly Pro Asn Arg Ser Phe Leu Ser Leu Lys His
            2085                2090                2095

Thr Pro Met Gly Lys Lys Ser Arg Arg Pro Ser Ala Lys Ser Thr Met
            2100                2105                2110

Pro Thr Ser Leu Pro Asn Leu Ala Lys Glu Ala Lys Asp Ala Lys Gly
            2115                2120                2125

Ser Arg Arg Lys Lys Ser Leu Ser Glu Lys Val Gln Leu Ser Glu Ser
            2130                2135                2140

Ser Val Thr Leu Ser Pro Val Asp Ser Leu Glu Ser Pro His Thr Tyr
2145                2150                2155                2160

Val Ser Asp Thr Thr Ser Ser Pro Met Ile Thr Ser Pro Gly Ile Leu
                2165                2170                2175

Gln Ala Ser Pro Asn Pro Met Leu Ala Thr Ala Ala Pro Pro Ala Pro
            2180                2185                2190

Val His Ala Gln His Ala Leu Ser Phe Ser Asn Leu His Glu Met Gln
        2195                2200                2205

Pro Leu Ala His Gly Ala Ser Thr Val Leu Pro Ser Val Ser Gln Leu
        2210                2215                2220

Leu Ser His His His Ile Val Ser Pro Gly Ser Gly Ser Ala Gly Ser
2225                2230                2235                2240

Leu Ser Arg Leu His Pro Val Pro Val Pro Ala Asp Trp Met Asn Arg
            2245                2250                2255

Met Glu Val Asn Glu Thr Gln Tyr Asn Glu Met Phe Gly Met Val Leu
            2260                2265                2270

Ala Pro Ala Glu Gly Thr His Pro Gly Ile Ala Pro Gln Ser Arg Pro
```

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 2275 |     |     |     |     | 2280 |     |     |     | 2285 |     |
| Pro | Glu | Gly | Lys | His | Ile | Thr | Thr | Pro | Arg | Glu | Pro | Leu | Pro | Pro | Ile |
|     | 2290 |     |     |     |     | 2295 |     |     |     |     | 2300 |     |     |     |
| Val | Thr | Phe | Gln | Leu | Ile | Pro | Lys | Gly | Ser | Ile | Ala | Gln | Pro | Ala | Gly |
| 2305 |     |     |     |     | 2310 |     |     |     |     | 2315 |     |     |     |     | 2320 |
| Ala | Pro | Gln | Pro | Gln | Ser | Thr | Cys | Pro | Pro | Ala | Val | Ala | Gly | Pro | Leu |
|     |     |     |     | 2325 |     |     |     |     | 2330 |     |     |     |     | 2335 |
| Pro | Thr | Met | Tyr | Gln | Ile | Pro | Glu | Met | Ala | Arg | Leu | Pro | Ser | Val | Ala |
|     |     |     | 2340 |     |     |     |     | 2345 |     |     |     |     | 2350 |     |
| Phe | Pro | Thr | Ala | Met | Met | Pro | Gln | Gln | Asp | Gly | Gln | Val | Ala | Gln | Thr |
|     |     |     | 2355 |     |     |     |     | 2360 |     |     |     |     | 2365 |     |
| Ile | Leu | Pro | Ala | Tyr | His | Pro | Phe | Pro | Ala | Ser | Val | Gly | Lys | Tyr | Pro |
|     |     | 2370 |     |     |     |     | 2375 |     |     |     |     | 2380 |     |     |
| Thr | Pro | Pro | Ser | Gln | His | Ser | Tyr | Ala | Ser | Ser | Asn | Ala | Ala | Glu | Arg |
| 2385 |     |     |     |     | 2390 |     |     |     |     | 2395 |     |     |     |     | 2400 |
| Thr | Pro | Ser | His | Ser | Gly | His | Leu | Gln | Gly | Glu | His | Pro | Tyr | Leu | Thr |
|     |     |     |     | 2405 |     |     |     |     | 2410 |     |     |     |     | 2415 |     |
| Pro | Ser | Pro | Glu | Ser | Pro | Asp | Gln | Trp | Ser | Ser | Ser | Ser | Pro | His | Ser |
|     |     |     | 2420 |     |     |     |     | 2425 |     |     |     |     | 2430 |     |
| Ala | Ser | Asp | Trp | Ser | Asp | Val | Thr | Thr | Ser | Pro | Thr | Pro | Gly | Gly | Ala |
|     |     |     | 2435 |     |     |     |     | 2440 |     |     |     |     | 2445 |     |
| Gly | Gly | Gly | Gln | Arg | Gly | Pro | Gly | Thr | His | Met | Ser | Glu | Pro | Pro | His |
|     | 2450 |     |     |     |     | 2455 |     |     |     |     | 2460 |     |     |     |
| Asn | Asn | Met | Gln | Val | Tyr | Ala |
| 2465 |     |     |     |     | 2470 |     |

( 2 ) INFORMATION FOR SEQ ID NO:20:

( i ) SEQUENCE CHARACTERISTICS:
        ( A ) LENGTH: 2556 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:20:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Pro | Pro | Leu | Leu | Ala | Pro | Leu | Leu | Cys | Leu | Ala | Leu | Leu | Pro | Ala |
| 1   |     |     |     | 5   |     |     |     |     | 10  |     |     |     |     | 15  |     |
| Leu | Ala | Ala | Arg | Gly | Pro | Arg | Cys | Ser | Gln | Pro | Gly | Glu | Thr | Cys | Leu |
|     |     |     | 20  |     |     |     |     | 25  |     |     |     |     | 30  |     |     |
| Asn | Gly | Gly | Lys | Cys | Glu | Ala | Ala | Asn | Gly | Thr | Glu | Ala | Cys | Val | Cys |
|     |     | 35  |     |     |     |     | 40  |     |     |     |     | 45  |     |     |     |
| Gly | Gly | Ala | Phe | Val | Gly | Pro | Arg | Cys | Gln | Asp | Pro | Asn | Pro | Cys | Leu |
|     | 50  |     |     |     |     | 55  |     |     |     |     | 60  |     |     |     |     |
| Ser | Thr | Pro | Cys | Lys | Asn | Ala | Gly | Thr | Cys | His | Val | Val | Asp | Arg | Arg |
| 65  |     |     |     |     | 70  |     |     |     |     | 75  |     |     |     |     | 80  |
| Gly | Val | Ala | Asp | Tyr | Ala | Cys | Ser | Cys | Ala | Leu | Gly | Phe | Ser | Gly | Pro |
|     |     |     |     | 85  |     |     |     |     | 90  |     |     |     |     | 95  |     |
| Leu | Cys | Leu | Thr | Pro | Leu | Asp | Asn | Ala | Cys | Leu | Thr | Asn | Pro | Cys | Arg |
|     |     |     | 100 |     |     |     |     | 105 |     |     |     |     | 110 |     |     |
| Asn | Gly | Gly | Thr | Cys | Asp | Leu | Leu | Thr | Leu | Thr | Glu | Tyr | Lys | Cys | Arg |
|     |     | 115 |     |     |     |     | 120 |     |     |     |     | 125 |     |     |     |
| Cys | Pro | Pro | Gly | Trp | Ser | Gly | Lys | Ser | Cys | Gln | Gln | Ala | Asp | Pro | Cys |
|     | 130 |     |     |     |     | 135 |     |     |     |     | 140 |     |     |     |     |
| Ala | Ser | Asn | Pro | Cys | Ala | Asn | Gly | Gly | Gln | Cys | Leu | Pro | Phe | Glu | Ala |
| 145 |     |     |     |     | 150 |     |     |     |     | 155 |     |     |     |     | 160 |

```
Ser  Tyr  Ile  Cys  His  Cys  Pro  Pro  Ser  Phe  His  Gly  Pro  Thr  Cys  Arg
               165                      170                      175

Gln  Asp  Val  Asn  Glu  Cys  Gly  Gln  Lys  Pro  Arg  Leu  Cys  Arg  His  Gly
          180                      185                      190

Gly  Thr  Cys  His  Asn  Glu  Val  Gly  Ser  Tyr  Arg  Cys  Val  Cys  Arg  Ala
               195                      200                      205

Thr  His  Thr  Gly  Pro  Asn  Cys  Glu  Arg  Pro  Tyr  Val  Pro  Cys  Ser  Pro
     210                      215                      220

Ser  Pro  Cys  Gln  Asn  Gly  Gly  Thr  Cys  Arg  Pro  Thr  Gly  Asp  Val  Thr
225                      230                      235                      240

His  Glu  Cys  Ala  Cys  Leu  Pro  Gly  Phe  Thr  Gly  Gln  Asn  Cys  Glu  Glu
               245                      250                      255

Asn  Ile  Asp  Asp  Cys  Pro  Gly  Asn  Asn  Cys  Lys  Asn  Gly  Gly  Ala  Cys
               260                      265                      270

Val  Asp  Gly  Val  Asn  Thr  Tyr  Asn  Cys  Pro  Cys  Pro  Pro  Glu  Trp  Thr
          275                      280                      285

Gly  Gln  Tyr  Cys  Thr  Glu  Asp  Val  Asp  Glu  Cys  Gln  Leu  Met  Pro  Asn
     290                      295                      300

Ala  Cys  Gln  Asn  Gly  Gly  Thr  Cys  His  Asn  Thr  His  Gly  Gly  Tyr  Asn
305                      310                      315                      320

Cys  Val  Cys  Val  Asn  Gly  Trp  Thr  Gly  Glu  Asp  Cys  Ser  Glu  Asn  Ile
               325                      330                      335

Asp  Asp  Cys  Ala  Ser  Ala  Ala  Cys  Phe  His  Gly  Ala  Thr  Cys  His  Asp
               340                      345                      350

Arg  Val  Ala  Ser  Phe  Tyr  Cys  Glu  Cys  Pro  His  Gly  Arg  Thr  Gly  Leu
               355                      360                      365

Leu  Cys  His  Leu  Asn  Asp  Ala  Cys  Ile  Ser  Asn  Pro  Cys  Asn  Glu  Gly
     370                      375                      380

Ser  Asn  Cys  Asp  Thr  Asn  Pro  Val  Asn  Gly  Lys  Ala  Ile  Cys  Thr  Cys
385                      390                      395                      400

Pro  Ser  Gly  Tyr  Thr  Gly  Pro  Ala  Cys  Ser  Gln  Asp  Val  Asp  Glu  Cys
               405                      410                      415

Ser  Leu  Gly  Ala  Asn  Pro  Cys  Glu  His  Ala  Gly  Lys  Cys  Ile  Asn  Thr
               420                      425                      430

Leu  Gly  Ser  Phe  Glu  Cys  Gln  Cys  Leu  Gln  Gly  Tyr  Thr  Gly  Pro  Arg
               435                      440                      445

Cys  Glu  Ile  Asp  Val  Asn  Glu  Cys  Val  Ser  Asn  Pro  Cys  Gln  Asn  Asp
     450                      455                      460

Ala  Thr  Cys  Leu  Asp  Gln  Ile  Gly  Glu  Phe  Gln  Cys  Met  Cys  Met  Pro
465                      470                      475                      480

Gly  Tyr  Glu  Gly  Val  His  Cys  Glu  Val  Asn  Thr  Asp  Glu  Cys  Ala  Ser
               485                      490                      495

Ser  Pro  Cys  Leu  His  Asn  Gly  Arg  Cys  Leu  Asp  Lys  Ile  Asn  Glu  Phe
               500                      505                      510

Gln  Cys  Glu  Cys  Pro  Thr  Gly  Phe  Thr  Gly  His  Leu  Cys  Gln  Tyr  Asp
     515                      520                      525

Val  Asp  Glu  Cys  Ala  Ser  Thr  Pro  Cys  Lys  Asn  Gly  Ala  Lys  Cys  Leu
     530                      535                      540

Asp  Gly  Pro  Asn  Thr  Tyr  Thr  Cys  Val  Cys  Thr  Glu  Gly  Tyr  Thr  Gly
545                      550                      555                      560

Thr  His  Cys  Glu  Val  Asp  Ile  Asp  Glu  Cys  Asp  Pro  Asp  Pro  Cys  His
               565                      570                      575

Tyr  Gly  Ser  Cys  Lys  Asp  Gly  Val  Ala  Thr  Phe  Thr  Cys  Leu  Cys  Arg
```

```
                            580                        585                        590
       Pro  Gly  Tyr  Thr  Gly  His  His  Cys  Glu  Thr  Asn  Ile  Asn  Glu  Cys  Ser
                      595                        600                   605

Ser  Gln  Pro  Cys  Arg  Leu  Arg  Gly  Thr  Cys  Gln  Asp  Pro  Asp  Asn  Ala
            610                        615                   620

Tyr  Leu  Cys  Phe  Cys  Leu  Lys  Gly  Thr  Thr  Gly  Pro  Asn  Cys  Glu  Ile
       625                        630                   635                        640

Asn  Leu  Asp  Asp  Cys  Ala  Ser  Ser  Pro  Cys  Asp  Ser  Gly  Thr  Cys  Leu
                           645                        650                   655

Asp  Lys  Ile  Asp  Gly  Tyr  Glu  Cys  Ala  Cys  Glu  Pro  Gly  Tyr  Thr  Gly
                      660                        665                   670

Ser  Met  Cys  Asn  Ser  Asn  Ile  Asp  Glu  Cys  Ala  Gly  Asn  Pro  Cys  His
                 675                        680                   685

Asn  Gly  Gly  Thr  Cys  Glu  Asp  Gly  Ile  Asn  Gly  Phe  Thr  Cys  Arg  Cys
            690                        695                   700

Pro  Glu  Gly  Tyr  His  Asp  Pro  Thr  Cys  Leu  Ser  Glu  Val  Asn  Glu  Cys
       705                        710                   715                        720

Asn  Ser  Asn  Pro  Cys  Val  His  Gly  Ala  Cys  Arg  Asp  Ser  Leu  Asn  Gly
                           725                        730                   735

Tyr  Lys  Cys  Asp  Cys  Asp  Pro  Gly  Trp  Ser  Gly  Thr  Asn  Cys  Asp  Ile
                      740                        745                   750

Asn  Asn  Asn  Glu  Cys  Glu  Ser  Asn  Pro  Cys  Val  Asn  Gly  Gly  Thr  Cys
                 755                        760                   765

Lys  Asp  Met  Thr  Ser  Gly  Ile  Val  Cys  Thr  Cys  Arg  Glu  Gly  Phe  Ser
            770                        775                   780

Gly  Pro  Asn  Cys  Gln  Thr  Asn  Ile  Asn  Glu  Cys  Ala  Ser  Asn  Pro  Cys
       785                        790                   795                        800

Leu  Asn  Lys  Gly  Thr  Cys  Ile  Asp  Asp  Val  Ala  Gly  Tyr  Lys  Cys  Asn
                           805                        810                   815

Cys  Leu  Leu  Pro  Tyr  Thr  Gly  Ala  Thr  Cys  Glu  Val  Val  Leu  Ala  Pro
                      820                        825                   830

Cys  Ala  Pro  Ser  Pro  Cys  Arg  Asn  Gly  Gly  Glu  Cys  Arg  Gln  Ser  Glu
                 835                        840                   845

Asp  Tyr  Glu  Ser  Phe  Ser  Cys  Val  Cys  Pro  Thr  Ala  Gly  Ala  Lys  Gly
            850                        855                   860

Gln  Thr  Cys  Glu  Val  Asp  Ile  Asn  Glu  Cys  Val  Leu  Ser  Pro  Cys  Arg
       865                        870                   875                        880

His  Gly  Ala  Ser  Cys  Gln  Asn  Thr  His  Gly  Gly  Tyr  Arg  Cys  His  Cys
                           885                        890                   895

Gln  Ala  Gly  Tyr  Ser  Gly  Arg  Asn  Cys  Glu  Thr  Asp  Ile  Asp  Asp  Cys
                      900                        905                   910

Arg  Pro  Asn  Pro  Cys  His  Asn  Gly  Gly  Ser  Cys  Thr  Asp  Gly  Ile  Asn
                 915                        920                   925

Thr  Ala  Phe  Cys  Asp  Cys  Leu  Pro  Gly  Phe  Arg  Gly  Thr  Phe  Cys  Glu
            930                        935                   940

Glu  Asp  Ile  Asn  Glu  Cys  Ala  Ser  Asp  Pro  Cys  Arg  Asn  Gly  Ala  Asn
       945                        950                   955                        960

Cys  Thr  Asp  Cys  Val  Asp  Ser  Tyr  Thr  Cys  Thr  Cys  Pro  Ala  Gly  Phe
                           965                        970                   975

Ser  Gly  Ile  His  Cys  Glu  Asn  Asn  Thr  Pro  Asp  Cys  Thr  Glu  Ser  Ser
                      980                        985                   990

Cys  Phe  Asn  Gly  Gly  Thr  Cys  Val  Asp  Gly  Ile  Asn  Ser  Phe  Thr  Cys
                 995                       1000                  1005
```

```
Leu Cys Pro Pro Gly Phe Thr Gly Ser Tyr Cys Gln His Val Asn
    1010                1015                1020
Glu Cys Asp Ser Arg Pro Cys Leu Leu Gly Gly Thr Cys Gln Asp Gly
1025                1030                1035                1040
Arg Gly Leu His Arg Cys Thr Cys Pro Gln Gly Tyr Thr Gly Pro Asn
                1045                1050                1055
Cys Gln Asn Leu Val His Trp Cys Asp Ser Ser Pro Cys Lys Asn Gly
            1060                1065                1070
Gly Lys Cys Trp Gln Thr His Thr Gln Tyr Arg Cys Glu Cys Pro Ser
        1075                1080                1085
Gly Trp Thr Gly Leu Tyr Cys Asp Val Pro Ser Val Ser Cys Glu Val
        1090                1095                1100
Ala Ala Gln Arg Gln Gly Val Asp Val Ala Arg Leu Cys Gln His Gly
1105                1110                1115                1120
Gly Leu Cys Val Asp Ala Gly Asn Thr His His Cys Arg Cys Gln Ala
                1125                1130                1135
Gly Tyr Thr Gly Ser Tyr Cys Glu Asp Leu Val Asp Glu Cys Ser Pro
            1140                1145                1150
Ser Pro Cys Gln Asn Gly Ala Thr Cys Thr Asp Tyr Leu Gly Gly Tyr
        1155                1160                1165
Ser Cys Lys Cys Val Ala Gly Tyr His Gly Val Asn Cys Ser Glu Glu
        1170                1175                1180
Ile Asp Glu Cys Leu Ser His Pro Cys Gln Asn Gly Gly Thr Cys Leu
1185                1190                1195                1200
Asp Leu Pro Asn Thr Tyr Lys Cys Ser Cys Pro Arg Gly Thr Gln Gly
                1205                1210                1215
Val His Cys Glu Ile Asn Val Asp Asp Cys Asn Pro Pro Val Asp Pro
            1220                1225                1230
Val Ser Arg Ser Pro Lys Cys Phe Asn Asn Gly Thr Cys Val Asp Gln
        1235                1240                1245
Val Gly Gly Tyr Ser Cys Thr Cys Pro Pro Gly Phe Val Gly Glu Arg
        1250                1255                1260
Cys Glu Gly Asp Val Asn Glu Cys Leu Ser Asn Pro Cys Asp Ala Arg
1265                1270                1275                1280
Gly Thr Gln Asn Cys Val Gln Arg Val Asn Asp Phe His Cys Glu Cys
                1285                1290                1295
Arg Ala Gly His Thr Gly Arg Arg Cys Glu Ser Val Ile Asn Gly Cys
            1300                1305                1310
Lys Gly Lys Pro Cys Lys Asn Gly Gly Thr Cys Ala Val Ala Ser Asn
        1315                1320                1325
Thr Ala Arg Gly Phe Ile Cys Lys Cys Pro Ala Gly Phe Glu Gly Ala
1330                1335                1340
Thr Cys Glu Asn Asp Ala Arg Thr Cys Gly Ser Leu Arg Cys Leu Asn
1345                1350                1355                1360
Gly Gly Thr Cys Ile Ser Gly Pro Arg Ser Pro Thr Cys Leu Cys Leu
                1365                1370                1375
Gly Pro Phe Thr Gly Pro Glu Cys Gln Phe Pro Ala Ser Ser Pro Cys
            1380                1385                1390
Leu Gly Gly Asn Pro Cys Tyr Asn Gln Gly Thr Cys Glu Pro Thr Ser
        1395                1400                1405
Glu Ser Pro Phe Tyr Arg Cys Leu Cys Pro Ala Lys Phe Asn Gly Leu
        1410                1415                1420
Leu Cys His Ile Leu Asp Tyr Ser Phe Gly Gly Gly Ala Gly Arg Asp
1425                1430                1435                1440
```

```
Ile Pro Pro Pro Leu Ile Glu Glu Ala Cys Glu Leu Pro Glu Cys Gln
                1445                1450                1455
Glu Asp Ala Gly Asn Lys Val Cys Ser Leu Gln Cys Asn Asn His Ala
        1460                1465                1470
Cys Gly Trp Asp Gly Gly Asp Cys Ser Leu Asn Phe Asn Asp Pro Trp
            1475                1480                1485
Lys Asn Cys Thr Gln Ser Leu Gln Cys Trp Lys Tyr Phe Ser Asp Gly
        1490                1495                1500
His Cys Asp Ser Gln Cys Asn Ser Ala Gly Cys Leu Phe Asp Gly Phe
1505                1510                1515                1520
Asp Cys Gln Arg Ala Glu Gly Gln Cys Asn Pro Leu Tyr Asp Gln Tyr
            1525                1530                1535
Cys Lys Asp His Phe Ser Asp Gly His Cys Asp Gln Gly Cys Asn Ser
                1540                1545                1550
Ala Glu Cys Glu Trp Asp Gly Leu Asp Cys Ala Glu His Val Pro Glu
        1555                1560                1565
Arg Leu Ala Ala Gly Thr Leu Val Val Val Val Leu Met Pro Pro Glu
    1570                1575                1580
Gln Leu Arg Asn Ser Ser Phe His Phe Leu Arg Glu Leu Ser Arg Val
1585                1590                1595                1600
Leu His Thr Asn Val Val Phe Lys Arg Asp Ala His Gly Gln Gln Met
                1605                1610                1615
Ile Phe Pro Tyr Tyr Gly Arg Glu Glu Leu Arg Lys His Pro Ile
            1620                1625                1630
Lys Arg Ala Ala Glu Gly Trp Ala Ala Pro Asp Ala Leu Leu Gly Gln
        1635                1640                1645
Val Lys Ala Ser Leu Leu Pro Gly Gly Ser Glu Gly Gly Arg Arg Arg
    1650                1655                1660
Arg Glu Leu Asp Pro Met Asp Val Arg Gly Ser Ile Val Tyr Leu Glu
1665                1670                1675                1680
Ile Asp Asn Arg Gln Cys Val Gln Ala Ser Ser Gln Cys Phe Gln Ser
                1685                1690                1695
Ala Thr Asp Val Ala Ala Phe Leu Gly Ala Leu Ala Ser Leu Gly Ser
        1700                1705                1710
Leu Asn Ile Pro Tyr Lys Ile Glu Ala Val Gln Ser Glu Thr Val Glu
        1715                1720                1725
Pro Pro Pro Pro Ala Gln Leu His Phe Met Tyr Val Ala Ala Ala Ala
        1730                1735                1740
Phe Val Leu Leu Phe Phe Val Gly Cys Gly Val Leu Leu Ser Arg Lys
1745                1750                1755                1760
Arg Arg Arg Gln His Gly Gln Leu Trp Phe Pro Glu Gly Phe Lys Val
                1765                1770                1775
Ser Glu Ala Ser Lys Lys Lys Arg Arg Glu Glu Leu Gly Glu Asp Ser
        1780                1785                1790
Val Gly Leu Lys Pro Leu Lys Asn Ala Ser Asp Gly Ala Leu Met Asp
    1795                1800                1805
Asp Asn Gln Asn Glu Trp Gly Asp Glu Asp Leu Glu Thr Lys Lys Phe
1810                1815                1820
Arg Phe Glu Glu Pro Val Val Leu Pro Asp Leu Asp Asp Gln Thr Asp
1825                1830                1835                1840
His Arg Gln Trp Thr Gln Gln His Leu Asp Ala Ala Asp Leu Arg Met
            1845                1850                1855
Ser Ala Met Ala Pro Thr Pro Pro Gln Gly Glu Val Asp Ala Asp Cys
```

```
                    1860                      1865                      1870

Met Asp Val Asn Val Arg Gly Pro Asp Gly Phe Thr Pro Leu Met Ile
         1875                      1880                 1885
Ala Ser Cys Ser Gly Gly Gly Leu Glu Thr Gly Asn Ser Glu Glu Glu
    1890                      1895                 1900
Glu Asp Ala Pro Ala Val Ile Ser Asp Phe Ile Tyr Gln Gly Ala Ser
1905                      1910                 1915                 1920
Leu His Asn Gln Thr Asp Arg Thr Gly Glu Thr Ala Leu His Leu Ala
              1925                      1930                 1935
Ala Arg Tyr Ser Arg Ser Asp Ala Ala Lys Arg Leu Leu Glu Ala Ser
         1940                      1945                 1950
Ala Asp Ala Asn Ile Gln Asp Asn Met Gly Arg Thr Pro Leu His Ala
              1955                      1960                 1965
Ala Val Ser Ala Asp Ala Gln Gly Val Phe Gln Ile Leu Ile Arg Asn
    1970                      1975                 1980
Arg Ala Thr Asp Leu Asp Ala Arg Met His Asp Gly Thr Thr Pro Leu
1985                      1990                 1995                 2000
Ile Leu Ala Ala Arg Leu Ala Val Glu Gly Met Leu Glu Asp Leu Ile
              2005                      2010                 2015
Asn Ser His Ala Asp Val Asn Ala Val Asp Asp Leu Gly Lys Ser Ala
         2020                      2025                 2030
Leu His Trp Ala Ala Ala Val Asn Asn Val Asp Ala Ala Val Val Leu
         2035                      2040                 2045
Leu Lys Asn Gly Ala Asn Lys Asp Met Gln Asn Asn Arg Glu Glu Thr
         2050                      2055                 2060
Pro Leu Phe Leu Ala Ala Arg Glu Gly Ser Tyr Glu Thr Ala Lys Val
2065                      2070                 2075                 2080
Leu Leu Asp His Phe Ala Asn Arg Asp Ile Thr Asp His Met Asp Arg
                   2085                      2090                 2095
Leu Pro Arg Asp Ile Ala Gln Glu Arg Met His His Asp Ile Val Arg
              2100                      2105                 2110
Leu Leu Asp Glu Tyr Asn Leu Val Arg Ser Pro Gln Leu His Gly Ala
         2115                      2120                 2125
Pro Leu Gly Gly Thr Pro Thr Leu Ser Pro Pro Leu Cys Ser Pro Asn
    2130                      2135                 2140
Gly Tyr Leu Gly Ser Leu Lys Pro Gly Val Gln Gly Lys Lys Val Arg
2145                      2150                 2155                 2160
Lys Pro Ser Ser Lys Gly Leu Ala Cys Gly Ser Lys Glu Ala Lys Asp
              2165                      2170                 2175
Leu Lys Ala Arg Arg Lys Lys Ser Gln Asp Gly Lys Gly Cys Leu Leu
              2180                      2185                 2190
Asp Ser Ser Gly Met Leu Ser Pro Val Asp Ser Leu Glu Ser Pro His
         2195                      2200                 2205
Gly Tyr Leu Ser Asp Val Ala Ser Pro Pro Leu Leu Pro Ser Pro Phe
         2210                      2215                 2220
Gln Gln Ser Pro Ser Val Pro Leu Asn His Leu Pro Gly Met Pro Asp
2225                      2230                 2235                 2240
Thr His Leu Gly Ile Gly His Leu Asn Val Ala Ala Lys Pro Glu Met
              2245                      2250                 2255
Ala Ala Leu Gly Gly Gly Gly Arg Leu Ala Phe Glu Thr Gly Pro Pro
              2260                      2265                 2270
Arg Leu Ser His Leu Pro Val Ala Ser Gly Thr Ser Thr Val Leu Gly
              2275                      2280                 2285
```

| | | | | | | | | | | | | | | |
|---|---|---|---|---|---|---|---|---|---|---|---|---|---|---|
|Ser|Ser|Ser|Gly|Gly|Ala|Leu|Asn|Phe|Thr|Val|Gly|Gly|Ser|Thr Ser|
| |2290| | | |2295| | | |2300| | | | | |
|Leu|Asn|Gly|Gln|Cys|Glu|Trp|Leu|Ser|Arg|Leu|Gln|Ser|Gly|Met Val|
| 2305| | | | |2310| | | |2315| | | | |2320|
|Pro|Asn|Gln|Tyr|Asn|Pro|Leu|Arg|Gly|Ser|Val|Ala|Pro|Gly|Pro Leu|
| | | | |2325| | | | |2330| | | | |2335|
|Ser|Thr|Gln|Ala|Pro|Ser|Leu|Gln|His|Gly|Met|Val|Gly|Pro|Leu His|
| | | |2340| | | | |2345| | | | |2350| |
|Ser|Ser|Leu|Ala|Ala|Ser|Ala|Leu|Ser|Gln|Met|Met|Ser|Tyr|Gln Gly|
| | |2355| | | |2360| | | | |2365| | | |
|Leu|Pro|Ser|Thr|Arg|Leu|Ala|Thr|Gln|Pro|His|Leu|Val|Gln|Thr Gln|
| |2370| | | | |2375| | | | |2380| | | |
|Gln|Val|Gln|Pro|Gln|Asn|Leu|Gln|Met|Gln|Gln|Gln|Asn|Leu|Gln Pro|
|2385| | | | |2390| | | |2395| | | | |2400|
|Ala|Asn|Ile|Gln|Gln|Gln|Gln|Ser|Leu|Gln|Pro|Pro|Pro|Pro|Pro|
| | | | |2405| | | | |2410| | | | |2415|
|Gln|Pro|His|Leu|Gly|Val|Ser|Ser|Ala|Ala|Ser|Gly|His|Leu|Gly Arg|
| | | |2420| | | | |2425| | | | |2430| |
|Ser|Phe|Leu|Ser|Gly|Glu|Pro|Ser|Gln|Ala|Asp|Val|Gln|Pro|Leu Gly|
| | |2435| | | | |2440| | | | |2445| | |
|Pro|Ser|Ser|Leu|Ala|Val|His|Thr|Ile|Leu|Pro|Gln|Glu|Ser|Pro Ala|
| |2450| | | | |2455| | | | |2460| | | |
|Leu|Pro|Thr|Ser|Leu|Pro|Ser|Ser|Leu|Val|Pro|Pro|Val|Thr|Ala Ala|
|2465| | | | |2470| | | | |2475| | | | |2480|
|Gln|Phe|Leu|Thr|Pro|Pro|Ser|Gln|His|Ser|Tyr|Ser|Ser|Pro|Val Glu|
| | | | |2485| | | | |2490| | | | |2495|
|Asn|Thr|Pro|Ser|His|Gln|Leu|Gln|Val|Pro|Glu|His|Pro|Phe|Leu Thr|
| | | |2500| | | | |2505| | | | |2510| |
|Pro|Ser|Pro|Glu|Ser|Pro|Asp|Gln|Trp|Ser|Ser|Ser|Ser|Pro|His Ser|
| | |2515| | | | |2520| | | | |2525| | |
|Asn|Val|Ser|Asp|Trp|Ser|Glu|Gly|Val|Ser|Ser|Pro|Pro|Thr|Ser Met|
| |2530| | | | |2535| | | | |2540| | | |
|Gln|Ser|Gln|Ile|Ala|Arg|Ile|Pro|Glu|Ala|Phe|Lys| | | |
|2545| | | | |2550| | | | |2555| | | | |

( 2 ) INFORMATION FOR SEQ ID NO:21:

( i ) SEQUENCE CHARACTERISTICS:
        ( A ) LENGTH: 9723 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 10..7419

( x i ) SEQUENCE DESCRIPTION: SEQ ID NO:21:

```
GGAATTCCG CCC GCC CTG CGC CCC GCT CTG CTG TGG GCG CTG CTG GCG        48
          Pro Ala Leu Arg Pro Ala Leu Leu Trp Ala Leu Leu Ala
          1           5                   10

CTC TGG CTG TGC TGC GCG GCC CCC GCG CAT GCA TTG CAG TGT CGA GAT      96
Leu Trp Leu Cys Cys Ala Ala Pro Ala His Ala Leu Gln Cys Arg Asp
15                  20                  25

GGC TAT GAA CCC TGT GTA AAT GAA GGA ATG TGT GTT ACC TAC CAC AAT     144
Gly Tyr Glu Pro Cys Val Asn Glu Gly Met Cys Val Thr Tyr His Asn
30                  35                  40                  45
```

| | | | | | | | | | | | | | | | | |
|---|---|---|---|---|---|---|---|---|---|---|---|---|---|---|---|---|
| GGC | ACA | GGA | TAC | TGC | AAA | TGT | CCA | GAA | GGC | TTC | TTG | GGG | GAA | TAT | TGT | 192 |
| Gly | Thr | Gly | Tyr | Cys | Lys | Cys | Pro | Glu | Gly | Phe | Leu | Gly | Glu | Tyr | Cys | |
| | | | | 50 | | | | | 55 | | | | | 60 | | |
| CAA | CAT | CGA | GAC | CCC | TGT | GAG | AAG | AAC | CGC | TGC | CAG | AAT | GGT | GGG | ACT | 240 |
| Gln | His | Arg | Asp | Pro | Cys | Glu | Lys | Asn | Arg | Cys | Gln | Asn | Gly | Gly | Thr | |
| | | | 65 | | | | | 70 | | | | | 75 | | | |
| TGT | GTG | GCC | CAG | GCC | ATG | CTG | GGG | AAA | GCC | ACG | TGC | CGA | TGT | GCC | TCA | 288 |
| Cys | Val | Ala | Gln | Ala | Met | Leu | Gly | Lys | Ala | Thr | Cys | Arg | Cys | Ala | Ser | |
| | | 80 | | | | | 85 | | | | | 90 | | | | |
| GGG | TTT | ACA | GGA | GAG | GAC | TGC | CAG | TAC | TCA | ACA | TCT | CAT | CCA | TGC | TTT | 336 |
| Gly | Phe | Thr | Gly | Glu | Asp | Cys | Gln | Tyr | Ser | Thr | Ser | His | Pro | Cys | Phe | |
| | 95 | | | | | 100 | | | | | 105 | | | | | |
| GTG | TCT | CGA | CCC | TGC | CTG | AAT | GGC | GGC | ACA | TGC | CAT | ATG | CTC | AGC | CGG | 384 |
| Val | Ser | Arg | Pro | Cys | Leu | Asn | Gly | Gly | Thr | Cys | His | Met | Leu | Ser | Arg | |
| 110 | | | | | 115 | | | | | 120 | | | | | 125 | |
| GAT | ACC | TAT | GAG | TGC | ACC | TGT | CAA | GTC | GGG | TTT | ACA | GGT | AAG | GAG | TGC | 432 |
| Asp | Thr | Tyr | Glu | Cys | Thr | Cys | Gln | Val | Gly | Phe | Thr | Gly | Lys | Glu | Cys | |
| | | | | 130 | | | | | 135 | | | | | 140 | | |
| CAA | TGG | ACG | GAT | GCC | TGC | CTG | TCT | CAT | CCC | TGT | GCA | AAT | GGA | AGT | ACC | 480 |
| Gln | Trp | Thr | Asp | Ala | Cys | Leu | Ser | His | Pro | Cys | Ala | Asn | Gly | Ser | Thr | |
| | | | 145 | | | | | 150 | | | | | 155 | | | |
| TGT | ACC | ACT | GTG | GCC | AAC | CAG | TTC | TCC | TGC | AAA | TGC | CTC | ACA | GGC | TTC | 528 |
| Cys | Thr | Thr | Val | Ala | Asn | Gln | Phe | Ser | Cys | Lys | Cys | Leu | Thr | Gly | Phe | |
| | | 160 | | | | | 165 | | | | | 170 | | | | |
| ACA | GGG | CAG | AAA | TGT | GAG | ACT | GAT | GTC | AAT | GAG | TGT | GAC | ATT | CCA | GGA | 576 |
| Thr | Gly | Gln | Lys | Cys | Glu | Thr | Asp | Val | Asn | Glu | Cys | Asp | Ile | Pro | Gly | |
| | 175 | | | | | 180 | | | | | 185 | | | | | |
| CAC | TGC | CAG | CAT | GGT | GGC | ACC | TGC | CTC | AAC | CTG | CCT | GGT | TCC | TAC | CAG | 624 |
| His | Cys | Gln | His | Gly | Gly | Thr | Cys | Leu | Asn | Leu | Pro | Gly | Ser | Tyr | Gln | |
| 190 | | | | | 195 | | | | | 200 | | | | | 205 | |
| TGC | CAG | TGC | CCT | CAG | GGC | TTC | ACA | GGC | CAG | TAC | TGT | GAC | AGC | CTG | TAT | 672 |
| Cys | Gln | Cys | Pro | Gln | Gly | Phe | Thr | Gly | Gln | Tyr | Cys | Asp | Ser | Leu | Tyr | |
| | | | | 210 | | | | | 215 | | | | | 220 | | |
| GTG | CCC | TGT | GCA | CCC | TCA | CCT | TGT | GTC | AAT | GGA | GGC | ACC | TGT | CGG | CAG | 720 |
| Val | Pro | Cys | Ala | Pro | Ser | Pro | Cys | Val | Asn | Gly | Gly | Thr | Cys | Arg | Gln | |
| | | | 225 | | | | | 230 | | | | | 235 | | | |
| ACT | GGT | GAC | TTC | ACT | TTT | GAG | TGC | AAC | TGC | CTT | CCA | GGT | TTT | GAA | GGG | 768 |
| Thr | Gly | Asp | Phe | Thr | Phe | Glu | Cys | Asn | Cys | Leu | Pro | Gly | Phe | Glu | Gly | |
| | | 240 | | | | | 245 | | | | | 250 | | | | |
| AGC | ACC | TGT | GAG | AGG | AAT | ATT | GAT | GAC | TGC | CCT | AAC | CAC | AGG | TGT | CAG | 816 |
| Ser | Thr | Cys | Glu | Arg | Asn | Ile | Asp | Asp | Cys | Pro | Asn | His | Arg | Cys | Gln | |
| | 255 | | | | | 260 | | | | | 265 | | | | | |
| AAT | GGA | GGG | GTT | TGT | GTG | GAT | GGG | GTC | AAC | ACT | TAC | AAC | TGC | CGC | TGT | 864 |
| Asn | Gly | Gly | Val | Cys | Val | Asp | Gly | Val | Asn | Thr | Tyr | Asn | Cys | Arg | Cys | |
| 270 | | | | | 275 | | | | | 280 | | | | | 285 | |
| CCC | CCA | CAA | TGG | ACA | GGA | CAG | TTC | TGC | ACA | GAG | GAT | GTG | GAT | GAA | TGC | 912 |
| Pro | Pro | Gln | Trp | Thr | Gly | Gln | Phe | Cys | Thr | Glu | Asp | Val | Asp | Glu | Cys | |
| | | | | 290 | | | | | 295 | | | | | 300 | | |
| CTG | CTG | CAG | CCC | AAT | GCC | TGT | CAA | AAT | GGG | GGC | ACC | TGT | GCC | AAC | CGC | 960 |
| Leu | Leu | Gln | Pro | Asn | Ala | Cys | Gln | Asn | Gly | Gly | Thr | Cys | Ala | Asn | Arg | |
| | | | 305 | | | | | 310 | | | | | 315 | | | |
| AAT | GGA | GGC | TAT | GGC | TGT | GTA | TGT | GTC | AAC | GGC | TGG | AGT | GGA | GAT | GAC | 1008 |
| Asn | Gly | Gly | Tyr | Gly | Cys | Val | Cys | Val | Asn | Gly | Trp | Ser | Gly | Asp | Asp | |
| | | 320 | | | | | 325 | | | | | 330 | | | | |
| TGC | AGT | GAG | AAC | ATT | GAT | GAT | TGT | GCC | TTC | GCC | TCC | TGT | ACT | CCA | GGC | 1056 |
| Cys | Ser | Glu | Asn | Ile | Asp | Asp | Cys | Ala | Phe | Ala | Ser | Cys | Thr | Pro | Gly | |
| | 335 | | | | | 340 | | | | | 345 | | | | | |
| TCC | ACC | TGC | ATC | GAC | CGT | GTG | GCC | TCC | TTC | TCT | TGC | ATG | TGC | CCA | GAG | 1104 |
| Ser | Thr | Cys | Ile | Asp | Arg | Val | Ala | Ser | Phe | Ser | Cys | Met | Cys | Pro | Glu | |
| 350 | | | | | 355 | | | | | 360 | | | | | 365 | |

| | | | | | | | | | | | | | | | | |
|---|---|---|---|---|---|---|---|---|---|---|---|---|---|---|---|---|
| GGG | AAG | GCA | GGT | CTC | CTG | TGT | CAT | CTG | GAT | GAT | GCA | TGC | ATC | AGC | AAT | 1152 |
| Gly | Lys | Ala | Gly | Leu | Leu | Cys | His | Leu | Asp | Asp | Ala | Cys | Ile | Ser | Asn | |
| | | | 370 | | | | | 375 | | | | | | 380 | | |
| CCT | TGC | CAC | AAG | GGG | GCA | CTG | TGT | GAC | ACC | AAC | CCC | CTA | AAT | GGG | CAA | 1200 |
| Pro | Cys | His | Lys | Gly | Ala | Leu | Cys | Asp | Thr | Asn | Pro | Leu | Asn | Gly | Gln | |
| | | | 385 | | | | | 390 | | | | | 395 | | | |
| TAT | ATT | TGC | ACC | TGC | CCA | CAA | GGC | TAC | AAA | GGG | GCT | GAC | TGC | ACA | GAA | 1248 |
| Tyr | Ile | Cys | Thr | Cys | Pro | Gln | Gly | Tyr | Lys | Gly | Ala | Asp | Cys | Thr | Glu | |
| | | | 400 | | | | | 405 | | | | | 410 | | | |
| GAT | GTG | GAT | GAA | TGT | GCC | ATG | GCC | AAT | AGC | AAT | CCT | TGT | GAG | CAT | GCA | 1296 |
| Asp | Val | Asp | Glu | Cys | Ala | Met | Ala | Asn | Ser | Asn | Pro | Cys | Glu | His | Ala | |
| | 415 | | | | 420 | | | | | 425 | | | | | | |
| GGA | AAA | TGT | GTG | AAC | ACG | GAT | GGC | GCC | TTC | CAC | TGT | GAG | TGT | CTG | AAG | 1344 |
| Gly | Lys | Cys | Val | Asn | Thr | Asp | Gly | Ala | Phe | His | Cys | Glu | Cys | Leu | Lys | |
| 430 | | | | 435 | | | | | 440 | | | | | | 445 | |
| GGT | TAT | GCA | GGA | CCT | CGT | TGT | GAG | ATG | GAC | ATC | AAT | GAG | TGC | CAT | TCA | 1392 |
| Gly | Tyr | Ala | Gly | Pro | Arg | Cys | Glu | Met | Asp | Ile | Asn | Glu | Cys | His | Ser | |
| | | | 450 | | | | | 455 | | | | | 460 | | | |
| GAC | CCC | TGC | CAG | AAT | GAT | GCT | ACC | TGT | CTG | GAT | AAG | ATT | GGA | GGC | TTC | 1440 |
| Asp | Pro | Cys | Gln | Asn | Asp | Ala | Thr | Cys | Leu | Asp | Lys | Ile | Gly | Gly | Phe | |
| | | | 465 | | | | | 470 | | | | | | 475 | | |
| ACA | TGT | CTG | TGC | ATG | CCA | GGT | TTC | AAA | GGT | GTG | CAT | TGT | GAA | TTA | GAA | 1488 |
| Thr | Cys | Leu | Cys | Met | Pro | Gly | Phe | Lys | Gly | Val | His | Cys | Glu | Leu | Glu | |
| | | 480 | | | | | 485 | | | | | 490 | | | | |
| ATA | AAT | GAA | TGT | CAG | AGC | AAC | CCT | TGT | GTG | AAC | AAT | GGG | CAG | TGT | GTG | 1536 |
| Ile | Asn | Glu | Cys | Gln | Ser | Asn | Pro | Cys | Val | Asn | Asn | Gly | Gln | Cys | Val | |
| 495 | | | | | 500 | | | | | 505 | | | | | | |
| GAT | AAA | GTC | AAT | CGT | TTC | CAG | TGC | CTG | TGT | CCT | CCT | GGT | TTC | ACT | GGG | 1584 |
| Asp | Lys | Val | Asn | Arg | Phe | Gln | Cys | Leu | Cys | Pro | Pro | Gly | Phe | Thr | Gly | |
| 510 | | | | | 515 | | | | | 520 | | | | | 525 | |
| CCA | GTT | TGC | CAG | ATT | GAT | ATT | GAT | GAC | TGT | TCC | AGT | ACT | CCG | TGT | CTG | 1632 |
| Pro | Val | Cys | Gln | Ile | Asp | Ile | Asp | Asp | Cys | Ser | Ser | Thr | Pro | Cys | Leu | |
| | | | | 530 | | | | | 535 | | | | | 540 | | |
| AAT | GGG | GCA | AAG | TGT | ATC | GAT | CAC | CCG | AAT | GGC | TAT | GAA | TGC | CAG | TGT | 1680 |
| Asn | Gly | Ala | Lys | Cys | Ile | Asp | His | Pro | Asn | Gly | Tyr | Glu | Cys | Gln | Cys | |
| | | | 545 | | | | | 550 | | | | | 555 | | | |
| GCC | ACA | GGT | TTC | ACT | GGT | GTG | TTG | TGT | GAG | GAG | AAC | ATT | GAC | AAC | TGT | 1728 |
| Ala | Thr | Gly | Phe | Thr | Gly | Val | Leu | Cys | Glu | Glu | Asn | Ile | Asp | Asn | Cys | |
| | | 560 | | | | | 565 | | | | | 570 | | | | |
| GAC | CCC | GAT | CCT | TGC | CAC | CAT | GGT | CAG | TGT | CAG | GAT | GGT | ATT | GAT | TCC | 1776 |
| Asp | Pro | Asp | Pro | Cys | His | His | Gly | Gln | Cys | Gln | Asp | Gly | Ile | Asp | Ser | |
| | 575 | | | | | 580 | | | | | 585 | | | | | |
| TAC | ACC | TGC | ATC | TGC | AAT | CCC | GGG | TAC | ATG | GGC | GCC | ATC | TGC | AGT | GAC | 1824 |
| Tyr | Thr | Cys | Ile | Cys | Asn | Pro | Gly | Tyr | Met | Gly | Ala | Ile | Cys | Ser | Asp | |
| 590 | | | | | 595 | | | | | 600 | | | | | 605 | |
| CAG | ATT | GAT | GAA | TGT | TAC | AGC | AGC | CCT | TGC | CTG | AAC | GAT | GGT | CGC | TGC | 1872 |
| Gln | Ile | Asp | Glu | Cys | Tyr | Ser | Ser | Pro | Cys | Leu | Asn | Asp | Gly | Arg | Cys | |
| | | | | 610 | | | | | 615 | | | | | 620 | | |
| ATT | GAC | CTG | GTC | AAT | GGC | TAC | CAG | TGC | AAC | TGC | CAG | CCA | GGC | ACG | TCA | 1920 |
| Ile | Asp | Leu | Val | Asn | Gly | Tyr | Gln | Cys | Asn | Cys | Gln | Pro | Gly | Thr | Ser | |
| | | | 625 | | | | | 630 | | | | | 635 | | | |
| GGG | GTT | AAT | TGT | GAA | ATT | AAT | TTT | GAT | GAC | TGT | GCA | AGT | AAC | CCT | TGT | 1968 |
| Gly | Val | Asn | Cys | Glu | Ile | Asn | Phe | Asp | Asp | Cys | Ala | Ser | Asn | Pro | Cys | |
| | | 640 | | | | | 645 | | | | | 650 | | | | |
| ATC | CAT | GGA | ATC | TGT | ATG | GAT | GGC | ATT | AAT | CGC | TAC | AGT | TGT | GTC | TGC | 2016 |
| Ile | His | Gly | Ile | Cys | Met | Asp | Gly | Ile | Asn | Arg | Tyr | Ser | Cys | Val | Cys | |
| | 655 | | | | | 660 | | | | | 665 | | | | | |
| TCA | CCA | GGA | TTC | ACA | GGG | CAG | AGA | TGT | AAC | ATT | GAC | ATT | GAT | GAG | TGT | 2064 |
| Ser | Pro | Gly | Phe | Thr | Gly | Gln | Arg | Cys | Asn | Ile | Asp | Ile | Asp | Glu | Cys | |
| 670 | | | | 675 | | | | | 680 | | | | | | 685 | |

```
GCC TCC AAT CCC TGT CGC AAG GGT GCA ACA TGT ATC AAC GGT GTG AAT        2112
Ala Ser Asn Pro Cys Arg Lys Gly Ala Thr Cys Ile Asn Gly Val Asn
            690                 695                 700

GGT TTC CGC TGT ATA TGC CCC GAG GGA CCC CAT CAC CCC AGC TGC TAC        2160
Gly Phe Arg Cys Ile Cys Pro Glu Gly Pro His His Pro Ser Cys Tyr
        705                 710                 715

TCA CAG GTG AAC GAA TGC CTG AGC AAT CCC TGC ATC CAT GGA AAC TGT        2208
Ser Gln Val Asn Glu Cys Leu Ser Asn Pro Cys Ile His Gly Asn Cys
    720                 725                 730

ACT GGA GGT CTC AGT GGA TAT AAG TGT CTC TGT GAT GCA GGC TGG GTT        2256
Thr Gly Gly Leu Ser Gly Tyr Lys Cys Leu Cys Asp Ala Gly Trp Val
735                 740                 745

GGC ATC AAC TGT GAA GTG GAC AAA AAT GAA TGC CTT TCG AAT CCA TGC        2304
Gly Ile Asn Cys Glu Val Asp Lys Asn Glu Cys Leu Ser Asn Pro Cys
750                 755                 760                 765

CAG AAT GGA GGA ACT TGT GAC AAT CTG GTG AAT GGA TAC AGG TGT ACT        2352
Gln Asn Gly Gly Thr Cys Asp Asn Leu Val Asn Gly Tyr Arg Cys Thr
                770                 775                 780

TGC AAG AAG GGC TTT AAA GGC TAT AAC TGC CAG GTG AAT ATT GAT GAA        2400
Cys Lys Lys Gly Phe Lys Gly Tyr Asn Cys Gln Val Asn Ile Asp Glu
            785                 790                 795

TGT GCC TCA AAT CCA TGC CTG AAC CAA GGA ACC TGC TTT GAT GAC ATA        2448
Cys Ala Ser Asn Pro Cys Leu Asn Gln Gly Thr Cys Phe Asp Asp Ile
        800                 805                 810

AGT GGC TAC ACT TGC CAC TGT GTG CTG CCA TAC ACA GGC AAG AAT TGT        2496
Ser Gly Tyr Thr Cys His Cys Val Leu Pro Tyr Thr Gly Lys Asn Cys
    815                 820                 825

CAG ACA GTA TTG GCT CCC TGT TCC CCA AAC CCT TGT GAG AAT GCT GCT        2544
Gln Thr Val Leu Ala Pro Cys Ser Pro Asn Pro Cys Glu Asn Ala Ala
830                 835                 840                 845

GTT TGC AAA GAG TCA CCA AAT TTT GAG AGT TAT ACT TGC TTG TGT GCT        2592
Val Cys Lys Glu Ser Pro Asn Phe Glu Ser Tyr Thr Cys Leu Cys Ala
                850                 855                 860

CCT GGC TGG CAA GGT CAG CGG TGT ACC ATT GAC ATT GAC GAG TGT ATC        2640
Pro Gly Trp Gln Gly Gln Arg Cys Thr Ile Asp Ile Asp Glu Cys Ile
            865                 870                 875

TCC AAG CCC TGC ATG AAC CAT GGT CTC TGC CAT AAC ACC CAG GGC AGC        2688
Ser Lys Pro Cys Met Asn His Gly Leu Cys His Asn Thr Gln Gly Ser
        880                 885                 890

TAC ATG TGT GAA TGT CCA CCA GGC TTC AGT GGT ATG GAC TGT GAG GAG        2736
Tyr Met Cys Glu Cys Pro Pro Gly Phe Ser Gly Met Asp Cys Glu Glu
    895                 900                 905

GAC ATT GAT GAC TGC CTT GCC AAT CCT TGC CAG AAT GGA GGT TCC TGT        2784
Asp Ile Asp Asp Cys Leu Ala Asn Pro Cys Gln Asn Gly Gly Ser Cys
910                 915                 920                 925

ATG GAT GGA GTG AAT ACT TTC TCC TGC CTC TGC CTT CCG GGT TTC ACT        2832
Met Asp Gly Val Asn Thr Phe Ser Cys Leu Cys Leu Pro Gly Phe Thr
                930                 935                 940

GGG GAT AAG TGC CAG ACA GAC ATG AAT GAG TGT CTG AGT GAA CCC TGT        2880
Gly Asp Lys Cys Gln Thr Asp Met Asn Glu Cys Leu Ser Glu Pro Cys
            945                 950                 955

AAG AAT GGA GGG ACC TGC TCT GAC TAC GTC AAC AGT TAC ACT TGC AAG        2928
Lys Asn Gly Gly Thr Cys Ser Asp Tyr Val Asn Ser Tyr Thr Cys Lys
        960                 965                 970

TGC CAG GCA GGA TTT GAT GGA GTC CAT TGT GAG AAC AAC ATC AAT GAG        2976
Cys Gln Ala Gly Phe Asp Gly Val His Cys Glu Asn Asn Ile Asn Glu
    975                 980                 985

TGC ACT GAG AGC TCC TGT TTC AAT GGT GGC ACA TGT GTT GAT GGG ATT        3024
Cys Thr Glu Ser Ser Cys Phe Asn Gly Gly Thr Cys Val Asp Gly Ile
990                 995                 1000                1005
```

| | | | | | | | | | | | | | | | | |
|---|---|---|---|---|---|---|---|---|---|---|---|---|---|---|---|---|
| AAC | TCC | TTC | TCT | TGC | TTG | TGC | CCT | GTG | GGT | TTC | ACT | GGA | TCC | TTC | TGC | 3072 |
| Asn | Ser | Phe | Ser | Cys | Leu | Cys | Pro | Val | Gly | Phe | Thr | Gly | Ser | Phe | Cys | |
| | | | 1010 | | | | 1015 | | | | | 1020 | | | | |
| CTC | CAT | GAG | ATC | AAT | GAA | TGC | AGC | TCT | CAT | CCA | TGC | CTG | AAT | GAG | GGA | 3120 |
| Leu | His | Glu | Ile | Asn | Glu | Cys | Ser | Ser | His | Pro | Cys | Leu | Asn | Glu | Gly | |
| | | 1025 | | | | | 1030 | | | | | 1035 | | | | |
| ACG | TGT | GTT | GAT | GGC | CTG | GGT | ACC | TAC | CGC | TGC | AGC | TGC | CCC | CTG | GGC | 3168 |
| Thr | Cys | Val | Asp | Gly | Leu | Gly | Thr | Tyr | Arg | Cys | Ser | Cys | Pro | Leu | Gly | |
| | 1040 | | | | | 1045 | | | | | 1050 | | | | | |
| TAC | ACT | GGG | AAA | AAC | TGT | CAG | ACC | CTG | GTG | AAT | CTC | TGC | AGT | CGG | TCT | 3216 |
| Tyr | Thr | Gly | Lys | Asn | Cys | Gln | Thr | Leu | Val | Asn | Leu | Cys | Ser | Arg | Ser | |
| | 1055 | | | | | 1060 | | | | | 1065 | | | | | |
| CCA | TGT | AAA | AAC | AAA | GGT | ACT | TGT | GTT | CAG | AAA | AAA | GCA | GAG | TCC | CAG | 3264 |
| Pro | Cys | Lys | Asn | Lys | Gly | Thr | Cys | Val | Gln | Lys | Lys | Ala | Glu | Ser | Gln | |
| 1070 | | | | 1075 | | | | | 1080 | | | | | 1085 | | |
| TGC | CTA | TGT | CCA | TCT | GGA | TGG | GCT | GGT | GCC | TAT | TGT | GAC | GTG | CCC | AAT | 3312 |
| Cys | Leu | Cys | Pro | Ser | Gly | Trp | Ala | Gly | Ala | Tyr | Cys | Asp | Val | Pro | Asn | |
| | | | | 1090 | | | | | 1095 | | | | | 1100 | | |
| GTC | TCT | TGT | GAC | ATA | GCA | GCC | TCC | AGG | AGA | GGT | GTG | CTT | GTT | GAA | CAC | 3360 |
| Val | Ser | Cys | Asp | Ile | Ala | Ala | Ser | Arg | Arg | Gly | Val | Leu | Val | Glu | His | |
| | | | 1105 | | | | | 1110 | | | | | 1115 | | | |
| TTG | TGC | CAG | CAC | TCA | GGT | GTC | TGC | ATC | AAT | GCT | GGC | AAC | ACG | CAT | TAC | 3408 |
| Leu | Cys | Gln | His | Ser | Gly | Val | Cys | Ile | Asn | Ala | Gly | Asn | Thr | His | Tyr | |
| | | 1120 | | | | | 1125 | | | | | 1130 | | | | |
| TGT | CAG | TGC | CCC | CTG | GGC | TAT | ACT | GGG | AGC | TAC | TGT | GAG | GAG | CAA | CTC | 3456 |
| Cys | Gln | Cys | Pro | Leu | Gly | Tyr | Thr | Gly | Ser | Tyr | Cys | Glu | Glu | Gln | Leu | |
| | 1135 | | | | | 1140 | | | | | 1145 | | | | | |
| GAT | GAG | TGT | GCG | TCC | AAC | CCC | TGC | CAG | CAC | GGG | GCA | ACA | TGC | AGT | GAC | 3504 |
| Asp | Glu | Cys | Ala | Ser | Asn | Pro | Cys | Gln | His | Gly | Ala | Thr | Cys | Ser | Asp | |
| 1150 | | | | | 1155 | | | | | 1160 | | | | | 1165 | |
| TTC | ATT | GGT | GGA | TAC | AGA | TGC | GAG | TGT | GTC | CCA | GGC | TAT | CAG | GGT | GTC | 3552 |
| Phe | Ile | Gly | Gly | Tyr | Arg | Cys | Glu | Cys | Val | Pro | Gly | Tyr | Gln | Gly | Val | |
| | | | | 1170 | | | | | 1175 | | | | | 1180 | | |
| AAC | TGT | GAG | TAT | GAA | GTG | GAT | GAG | TGC | CAG | AAT | CAG | CCC | TGC | CAG | AAT | 3600 |
| Asn | Cys | Glu | Tyr | Glu | Val | Asp | Glu | Cys | Gln | Asn | Gln | Pro | Cys | Gln | Asn | |
| | | | 1185 | | | | | 1190 | | | | | 1195 | | | |
| GGA | GGC | ACC | TGT | ATT | GAC | CTT | GTG | AAC | CAT | TTC | AAG | TGC | TCT | TGC | CCA | 3648 |
| Gly | Gly | Thr | Cys | Ile | Asp | Leu | Val | Asn | His | Phe | Lys | Cys | Ser | Cys | Pro | |
| | | 1200 | | | | | 1205 | | | | | 1210 | | | | |
| CCA | GGC | ACT | CGG | GGC | CTA | CTC | TGT | GAA | GAG | AAC | ATT | GAT | GAC | TGT | GCC | 3696 |
| Pro | Gly | Thr | Arg | Gly | Leu | Leu | Cys | Glu | Glu | Asn | Ile | Asp | Asp | Cys | Ala | |
| | 1215 | | | | | 1220 | | | | | 1225 | | | | | |
| CGG | GGT | CCC | CAT | TGC | CTT | AAT | GGT | GGT | CAG | TGC | ATG | GAT | AGG | ATT | GGA | 3744 |
| Arg | Gly | Pro | His | Cys | Leu | Asn | Gly | Gly | Gln | Cys | Met | Asp | Arg | Ile | Gly | |
| 1230 | | | | | 1235 | | | | | 1240 | | | | | 1245 | |
| GGC | TAC | AGT | TGT | CGC | TGC | TTG | CCT | GGC | TTT | GCT | GGG | GAG | CGT | TGT | GAG | 3792 |
| Gly | Tyr | Ser | Cys | Arg | Cys | Leu | Pro | Gly | Phe | Ala | Gly | Glu | Arg | Cys | Glu | |
| | | | | 1250 | | | | | 1255 | | | | | 1260 | | |
| GGA | GAC | ATC | AAC | GAG | TGC | CTC | TCC | AAC | CCC | TGC | AGC | TCT | GAG | GGC | AGC | 3840 |
| Gly | Asp | Ile | Asn | Glu | Cys | Leu | Ser | Asn | Pro | Cys | Ser | Ser | Glu | Gly | Ser | |
| | | | 1265 | | | | | 1270 | | | | | 1275 | | | |
| CTG | GAC | TGT | ATA | CAG | CTC | ACC | AAT | GAC | TAC | CTG | TGT | GTT | TGC | CGT | AGT | 3888 |
| Leu | Asp | Cys | Ile | Gln | Leu | Thr | Asn | Asp | Tyr | Leu | Cys | Val | Cys | Arg | Ser | |
| | | 1280 | | | | | 1285 | | | | | 1290 | | | | |
| GCC | TTT | ACT | GGC | CGG | CAC | TGT | GAA | ACC | TTC | GTC | GAT | GTG | TGT | CCC | CAG | 3936 |
| Ala | Phe | Thr | Gly | Arg | His | Cys | Glu | Thr | Phe | Val | Asp | Val | Cys | Pro | Gln | |
| | 1295 | | | | | 1300 | | | | | 1305 | | | | | |
| ATG | CCC | TGC | CTG | AAT | GGA | GGG | ACT | TGT | GCT | GTG | GCC | AGT | AAC | ATG | CCT | 3984 |
| Met | Pro | Cys | Leu | Asn | Gly | Gly | Thr | Cys | Ala | Val | Ala | Ser | Asn | Met | Pro | |
| 1310 | | | | | 1315 | | | | | 1320 | | | | | 1325 | |

```
GAT GGT TTC ATT TGC CGT TGT CCC CCG GGA TTT TCC GGG GCA AGG TGC      4032
Asp Gly Phe Ile Cys Arg Cys Pro Pro Gly Phe Ser Gly Ala Arg Cys
            1330            1335                    1340

CAG AGC AGC TGT GGA CAA GTG AAA TGT AGG AAG GGG GAG CAG TGT GTG      4080
Gln Ser Ser Cys Gly Gln Val Lys Cys Arg Lys Gly Glu Gln Cys Val
        1345                1350                1355

CAC ACC GCC TCT GGA CCC CGC TGC TTC TGC CCC AGT CCC CGG GAC TGC      4128
His Thr Ala Ser Gly Pro Arg Cys Phe Cys Pro Ser Pro Arg Asp Cys
        1360                1365                1370

GAG TCA GGC TGT GCC AGT AGC CCC TGC CAG CAC GGG GGC AGC TGC CAC      4176
Glu Ser Gly Cys Ala Ser Ser Pro Cys Gln His Gly Gly Ser Cys His
        1375                1380                1385

CCT CAG CGC CAG CCT CCT TAT TAC TCC TGC CAG TGT GCC CCA CCA TTC      4224
Pro Gln Arg Gln Pro Pro Tyr Tyr Ser Cys Gln Cys Ala Pro Pro Phe
    1390                1395                1400                1405

TCG GGT AGC CGC TGT GAA CTC TAC ACG GCA CCC CCC AGC ACC CCT CCT      4272
Ser Gly Ser Arg Cys Glu Leu Tyr Thr Ala Pro Pro Ser Thr Pro Pro
                1410                1415                1420

GCC ACC TGT CTG AGC CAG TAT TGT GCC GAC AAA GCT CGG GAT GGC GTC      4320
Ala Thr Cys Leu Ser Gln Tyr Cys Ala Asp Lys Ala Arg Asp Gly Val
        1425                1430                1435

TGT GAT GAG GCC TGC AAC AGC CAT GCC TGC CAG TGG GAT GGG GGT GAC      4368
Cys Asp Glu Ala Cys Asn Ser His Ala Cys Gln Trp Asp Gly Gly Asp
        1440                1445                1450

TGT TCT CTC ACC ATG GAG AAC CCC TGG GCC AAC TGC TCC TCC CCA CTT      4416
Cys Ser Leu Thr Met Glu Asn Pro Trp Ala Asn Cys Ser Ser Pro Leu
        1455                1460                1465

CCC TGC TGG GAT TAT ATC AAC AAC CAG TGT GAT GAG CTG TGC AAC ACG      4464
Pro Cys Trp Asp Tyr Ile Asn Asn Gln Cys Asp Glu Leu Cys Asn Thr
1470                1475                1480                1485

GTC GAG TGC CTG TTT GAC AAC TTT GAA TGC CAG GGG AAC AGC AAG ACA      4512
Val Glu Cys Leu Phe Asp Asn Phe Glu Cys Gln Gly Asn Ser Lys Thr
                1490                1495                1500

TGC AAG TAT GAC AAA TAC TGT GCA GAC CAC TTC AAA GAC AAC CAC TGT      4560
Cys Lys Tyr Asp Lys Tyr Cys Ala Asp His Phe Lys Asp Asn His Cys
        1505                1510                1515

AAC CAG GGG TGC AAC AGT GAG GAG TGT GGT TGG GAT GGG CTG GAC TGT      4608
Asn Gln Gly Cys Asn Ser Glu Glu Cys Gly Trp Asp Gly Leu Asp Cys
        1520                1525                1530

GCT GCT GAC CAA CCT GAG AAC CTG GCA GAA GGT ACC CTG GTT ATT GTG      4656
Ala Ala Asp Gln Pro Glu Asn Leu Ala Glu Gly Thr Leu Val Ile Val
        1535                1540                1545

GTA TTG ATG CCA CCT GAA CAA CTG CTC CAG GAT GCT CGC AGC TTC TTG      4704
Val Leu Met Pro Pro Glu Gln Leu Leu Gln Asp Ala Arg Ser Phe Leu
1550                1555                1560                1565

CGG GCA CTG GGT ACC CTG CTC CAC ACC AAC CTG CGC ATT AAG CGG GAC      4752
Arg Ala Leu Gly Thr Leu Leu His Thr Asn Leu Arg Ile Lys Arg Asp
                1570                1575                1580

TCC CAG GGG GAA CTC ATG GTG TAC CCC TAT TAT GGT GAG AAG TCA GCT      4800
Ser Gln Gly Glu Leu Met Val Tyr Pro Tyr Tyr Gly Glu Lys Ser Ala
            1585                1590                1595

GCT ATG AAG AAA CAG AGG ATG ACA CGC AGA TCC CTT CCT GGT GAA CAA      4848
Ala Met Lys Lys Gln Arg Met Thr Arg Arg Ser Leu Pro Gly Glu Gln
        1600                1605                1610

GAA CAG GAG GTG GCT GGC TCT AAA GTC TTT CTG GAA ATT GAC AAC CGC      4896
Glu Gln Glu Val Ala Gly Ser Lys Val Phe Leu Glu Ile Asp Asn Arg
        1615                1620                1625

CAG TGT GTT CAA GAC TCA GAC CAC TGC TTC AAG AAC ACG GAT GCA GCA      4944
Gln Cys Val Gln Asp Ser Asp His Cys Phe Lys Asn Thr Asp Ala Ala
        1630                1635                1640                1645
```

```
GCA GCT CTC CTG GCC TCT CAC GCC ATA CAG GGG ACC CTG TCA TAC CCT      4992
Ala Ala Leu Leu Ala Ser His Ala Ile Gln Gly Thr Leu Ser Tyr Pro
            1650                1655                1660

CTT GTG TCT GTC GTC AGT GAA TCC CTG ACT CCA GAA CGC ACT CAG CTC      5040
Leu Val Ser Val Val Ser Glu Ser Leu Thr Pro Glu Arg Thr Gln Leu
        1665                1670                1675

CTC TAT CTC CTT GCT GTT GCT GTT GTC ATC ATT CTG TTT ATT ATT CTG      5088
Leu Tyr Leu Leu Ala Val Ala Val Val Ile Ile Leu Phe Ile Ile Leu
    1680                1685                1690

CTG GGG GTA ATC ATG GCA AAA CGA AAG CGT AAG CAT GGC TCT CTC TGG      5136
Leu Gly Val Ile Met Ala Lys Arg Lys Arg Lys His Gly Ser Leu Trp
1695                1700                1705

CTG CCT GAA GGT TTC ACT CTT CGC CGA GAT GCA AGC AAT CAC AAG CGT      5184
Leu Pro Glu Gly Phe Thr Leu Arg Arg Asp Ala Ser Asn His Lys Arg
1710                1715                1720                1725

CGT GAG CCA GTG GGA CAG GAT GCT GTG GGG CTG AAA AAT CTC TCA GTG      5232
Arg Glu Pro Val Gly Gln Asp Ala Val Gly Leu Lys Asn Leu Ser Val
            1730                1735                1740

CAA GTC TCA GAA GCT AAC CTA ATT GGT ACT GGA ACA AGT GAA CAC TGG      5280
Gln Val Ser Glu Ala Asn Leu Ile Gly Thr Gly Thr Ser Glu His Trp
        1745                1750                1755

GTC GAT GAT GAA GGG CCC CAG CCA AAG AAA GTA AAG GCT GAA GAT GAG      5328
Val Asp Asp Glu Gly Pro Gln Pro Lys Lys Val Lys Ala Glu Asp Glu
    1760                1765                1770

GCC TTA CTC TCA GAA GAA GAT GAC CCC ATT GAT CGA CGG CCA TGG ACA      5376
Ala Leu Leu Ser Glu Glu Asp Asp Pro Ile Asp Arg Arg Pro Trp Thr
1775                1780                1785

CAG CAG CAC CTT GAA GCT GCA GAC ATC CGT AGG ACA CCA TCG CTG GCT      5424
Gln Gln His Leu Glu Ala Ala Asp Ile Arg Arg Thr Pro Ser Leu Ala
1790                1795                1800                1805

CTC ACC CCT CCT CAG GCA GAG CAG GAG GTG GAT GTG TTA GAT GTG AAT      5472
Leu Thr Pro Pro Gln Ala Glu Gln Glu Val Asp Val Leu Asp Val Asn
            1810                1815                1820

GTC CGT GGC CCA GAT GGC TGC ACC CCA TTG ATG TTG GCT TCT CTC CGA      5520
Val Arg Gly Pro Asp Gly Cys Thr Pro Leu Met Leu Ala Ser Leu Arg
        1825                1830                1835

GGA GGC AGC TCA GAT TTG AGT GAT GAA GAT GAA GAT GCA GAG GAC TCT      5568
Gly Gly Ser Ser Asp Leu Ser Asp Glu Asp Glu Asp Ala Glu Asp Ser
    1840                1845                1850

TCT GCT AAC ATC ATC ACA GAC TTG GTC TAC CAG GGT GCC AGC CTC CAG      5616
Ser Ala Asn Ile Ile Thr Asp Leu Val Tyr Gln Gly Ala Ser Leu Gln
1855                1860                1865

GCC CAG ACA GAC CGG ACT GGT GAG ATG GCC CTG CAC CTT GCA GCC CGC      5664
Ala Gln Thr Asp Arg Thr Gly Glu Met Ala Leu His Leu Ala Ala Arg
1870                1875                1880                1885

TAC TCA CGG GCT GAT GCT GCC AAG CGT CTC CTG GAT GCA GGT GCA GAT      5712
Tyr Ser Arg Ala Asp Ala Ala Lys Arg Leu Leu Asp Ala Gly Ala Asp
            1890                1895                1900

GCC AAT GCC CAG GAC AAC ATG GGC CGC TGT CCA CTC CAT GCT GCA GTG      5760
Ala Asn Ala Gln Asp Asn Met Gly Arg Cys Pro Leu His Ala Ala Val
        1905                1910                1915

GCA GCT GAT GCC CAA GGT GTC TTC CAG ATT CTG ATT CGC AAC CGA GTA      5808
Ala Ala Asp Ala Gln Gly Val Phe Gln Ile Leu Ile Arg Asn Arg Val
    1920                1925                1930

ACT GAT CTA GAT GCC AGG ATG AAT GAT GGT ACT ACA CCC CTG ATC CTG      5856
Thr Asp Leu Asp Ala Arg Met Asn Asp Gly Thr Thr Pro Leu Ile Leu
1935                1940                1945

GCT GCC CGC CTG GCT GTG GAG GGA ATG GTG GCA GAA CTG ATC AAC TGC      5904
Ala Ala Arg Leu Ala Val Glu Gly Met Val Ala Glu Leu Ile Asn Cys
1950                1955                1960                1965
```

```
CAA GCG GAT GTG AAT GCA GTG GAT GAC CAT GGA AAA TCT GCT CTT CAC       5952
Gln Ala Asp Val Asn Ala Val Asp Asp His Gly Lys Ser Ala Leu His
                1970            1975            1980

TGG GCA GCT GCT GTC AAT AAT GTG GAG GCA ACT CTT TTG TTG TTG AAA       6000
Trp Ala Ala Ala Val Asn Asn Val Glu Ala Thr Leu Leu Leu Leu Lys
            1985            1990            1995

AAT GGG GCC AAC CGA GAC ATG CAG GAC AAC AAG GAA GAG ACA CCT CTG       6048
Asn Gly Ala Asn Arg Asp Met Gln Asp Asn Lys Glu Glu Thr Pro Leu
            2000            2005            2010

TTT CTT GCT GCC CGG GAG GGG AGC TAT GAA GCA GCC AAG ATC CTG TTA       6096
Phe Leu Ala Ala Arg Glu Gly Ser Tyr Glu Ala Ala Lys Ile Leu Leu
            2015            2020            2025

GAC CAT TTT GCC AAT CGA GAC ATC ACA GAC CAT ATG GAT CGT CTT CCC       6144
Asp His Phe Ala Asn Arg Asp Ile Thr Asp His Met Asp Arg Leu Pro
            2030            2035            2040            2045

CGG GAT GTG GCT CGG GAT CGC ATG CAC CAT GAC ATT GTG CGC CTT CTG       6192
Arg Asp Val Ala Arg Asp Arg Met His His Asp Ile Val Arg Leu Leu
            2050            2055            2060

GAT GAA TAC AAT GTG ACC CCA AGC CCT CCA GGC ACC GTG TTG ACT TCT       6240
Asp Glu Tyr Asn Val Thr Pro Ser Pro Pro Gly Thr Val Leu Thr Ser
            2065            2070            2075

GCT CTC TCA CCT GTC ATC TGT GGG CCC AAC AGA TCT TTC CTC AGC CTG       6288
Ala Leu Ser Pro Val Ile Cys Gly Pro Asn Arg Ser Phe Leu Ser Leu
            2080            2085            2090

AAG CAC ACC CCA ATG GGC AAG AAG TCT AGA CGG CCC AGT GCC AAG AGT       6336
Lys His Thr Pro Met Gly Lys Lys Ser Arg Arg Pro Ser Ala Lys Ser
            2095            2100            2105

ACC ATG CCT ACT AGC CTC CCT AAC CTT GCC AAG GAG GCA AAG GAT GCC       6384
Thr Met Pro Thr Ser Leu Pro Asn Leu Ala Lys Glu Ala Lys Asp Ala
2110            2115            2120            2125

AAG GGT AGT AGG AGG AAG AAG TCT CTG AGT GAG AAG GTC CAA CTG TCT       6432
Lys Gly Ser Arg Arg Lys Lys Ser Leu Ser Glu Lys Val Gln Leu Ser
            2130            2135            2140

GAG AGT TCA GTA ACT TTA TCC CCT GTT GAT TCC CTA GAA TCT CCT CAC       6480
Glu Ser Ser Val Thr Leu Ser Pro Val Asp Ser Leu Glu Ser Pro His
            2145            2150            2155

ACG TAT GTT TCC GAC ACC ACA TCC TCT CCA ATG ATT ACA TCC CCT GGG       6528
Thr Tyr Val Ser Asp Thr Thr Ser Ser Pro Met Ile Thr Ser Pro Gly
            2160            2165            2170

ATC TTA CAG GCC TCA CCC AAC CCT ATG TTG GCC ACT GCC GCC CCT CCT       6576
Ile Leu Gln Ala Ser Pro Asn Pro Met Leu Ala Thr Ala Ala Pro Pro
            2175            2180            2185

GCC CCA GTC CAT GCC CAG CAT GCA CTA TCT TTT TCT AAC CTT CAT GAA       6624
Ala Pro Val His Ala Gln His Ala Leu Ser Phe Ser Asn Leu His Glu
2190            2195            2200            2205

ATG CAG CCT TTG GCA CAT GGG GCC AGC ACT GTG CTT CCC TCA GTG AGC       6672
Met Gln Pro Leu Ala His Gly Ala Ser Thr Val Leu Pro Ser Val Ser
            2210            2215            2220

CAG TTG CTA TCC CAC CAC CAC ATT GTG TCT CCA GGC AGT GGC AGT GCT       6720
Gln Leu Leu Ser His His His Ile Val Ser Pro Gly Ser Gly Ser Ala
            2225            2230            2235

GGA AGC TTG AGT AGG CTC CAT CCA GTC CCA GTC CCA GCA GAT TGG ATG       6768
Gly Ser Leu Ser Arg Leu His Pro Val Pro Val Pro Ala Asp Trp Met
            2240            2245            2250

AAC CGC ATG GAG GTG AAT GAG ACC CAG TAC AAT GAG ATG TTT GGT ATG       6816
Asn Arg Met Glu Val Asn Glu Thr Gln Tyr Asn Glu Met Phe Gly Met
            2255            2260            2265

GTC CTG GCT CCA GCT GAG GGC ACC CAT CCT GGC ATA GCT CCC CAG AGC       6864
Val Leu Ala Pro Ala Glu Gly Thr His Pro Gly Ile Ala Pro Gln Ser
            2270            2275            2280            2285
```

| | | | | | | | | | | | | | | | |
|---|---|---|---|---|---|---|---|---|---|---|---|---|---|---|---|
| AGG | CCA | CCT | GAA | GGG | AAG | CAC | ATA | ACC | ACC | CCT | CGG | GAG | CCC | TTG | CCC | 6912
| Arg | Pro | Pro | Glu | Gly | Lys | His | Ile | Thr | Thr | Pro | Arg | Glu | Pro | Leu | Pro |
|     |     |     |     | 2290 |     |     |     |     | 2295 |     |     |     |     | 2300 |     |

CCC ATT GTG ACT TTC CAG CTC ATC CCT AAA GGC AGT ATT GCC CAA CCA  6960
Pro Ile Val Thr Phe Gln Leu Ile Pro Lys Gly Ser Ile Ala Gln Pro
            2305                2310                2315

GCG GGG GCT CCC CAG CCT CAG TCC ACC TGC CCT CCA GCT GTT GCG GGC  7008
Ala Gly Ala Pro Gln Pro Gln Ser Thr Cys Pro Pro Ala Val Ala Gly
        2320                2325                2330

CCC CTG CCC ACC ATG TAC CAG ATT CCA GAA ATG GCC CGT TTG CCC AGT  7056
Pro Leu Pro Thr Met Tyr Gln Ile Pro Glu Met Ala Arg Leu Pro Ser
        2335                2340                2345

GTG GCT TTC CCC ACT GCC ATG ATG CCC CAG CAG GAC GGG CAG GTA GCT  7104
Val Ala Phe Pro Thr Ala Met Met Pro Gln Gln Asp Gly Gln Val Ala
2350                2355                2360                2365

CAG ACC ATT CTC CCA GCC TAT CAT CCT TTC CCA GCC TCT GTG GGC AAG  7152
Gln Thr Ile Leu Pro Ala Tyr His Pro Phe Pro Ala Ser Val Gly Lys
            2370                2375                2380

TAC CCC ACA CCC CCT TCA CAG CAC AGT TAT GCT TCC TCA AAT GCT GCT  7200
Tyr Pro Thr Pro Pro Ser Gln His Ser Tyr Ala Ser Ser Asn Ala Ala
        2385                2390                2395

GAG CGA ACA CCC AGT CAC AGT GGT CAC CTC CAG GGT GAG CAT CCC TAC  7248
Glu Arg Thr Pro Ser His Ser Gly His Leu Gln Gly Glu His Pro Tyr
        2400                2405                2410

CTG ACA CCA TCC CCA GAG TCT CCT GAC CAG TGG TCA AGT TCA TCA CCC  7296
Leu Thr Pro Ser Pro Glu Ser Pro Asp Gln Trp Ser Ser Ser Ser Pro
        2415                2420                2425

CAC TCT GCT TCT GAC TGG TCA GAT GTG ACC ACC AGC CCT ACC CCT GGG  7344
His Ser Ala Ser Asp Trp Ser Asp Val Thr Thr Ser Pro Thr Pro Gly
2430                2435                2440                2445

GGT GCT GGA GGA GGT CAG CGG GGA CCT GGG ACA CAC ATG TCT GAG CCA  7392
Gly Ala Gly Gly Gly Gln Arg Gly Pro Gly Thr His Met Ser Glu Pro
        2450                2455                2460

CCA CAC AAC AAC ATG CAG GTT TAT GCG TGAGAGAGTC CACCTCCAGT         7439
Pro His Asn Asn Met Gln Val Tyr Ala
        2465                2470

GTAGAGACAT AACTGACTTT TGTAAATGCT GCTGAGGAAC AAATGAAGGT CATCCGGGAG  7499
AGAAATGAAG AAATCTCTGG AGCCAGCTTC TAGAGGTAGG AAAGAGAAGA TGTTCTTATT  7559
CAGATAATGC AAGAGAAGCA ATTCGTCAGT TTCACTGGGT ATCTGCAAGG CTTATTGATT  7619
ATTCTAATCT AATAAGACAA GTTTGTGGAA ATGCAAGATG AATACAAGCC TTGGGTCCAT  7679
GTTACTCTC TTCTATTTGG AGAATAAGAT GGATGCTTAT TGAAGCCCAG ACATTCTTGC    7739
AGCTTGGACT GCATTTTAAG CCCTGCAGGC TTCTGCCATA TCCATGAGAA GATTCTACAC  7799
TAGCGTCCTG TTGGGAATTA TGCCCTGGAA TTCTGCCTGA ATTGACCTAC GCATCTCCTC  7859
CTCCTTGGAC ATTCTTTTGT CTTCATTTGG TGCTTTTGGT TTTGCACCTC TCCGTGATTG  7919
TAGCCCTACC AGCATGTTAT AGGGCAAGAC CTTTGTGCTT TTGATCATTC TGGCCCATGA  7979
AAGCAACTTT GGTCTCCTTT CCCCTCCTGT CTTCCGGGTA TCCCTTGGAG TCTCACAAGG  8039
TTTACTTTGG TATGGTTCTC AGCACAAACC TTTCAAGTAT GTTGTTTCTT TGGAAAATGG  8099
ACATACTGTA TTGTGTTCTC CTGCATATAT CATTCCTGGA GAGAGAAGGG GAGAAGAATA  8159
CTTTTCTTCA ACAAATTTTG GGGGCAGGAG ATCCCTTCAA GAGGCTGCAC CTTAATTTTT  8219
CTTGTCTGTG TGCAGGTCTT CATATAAACT TTACCAGGAA GAAGGGTGTG AGTTTGTTGT  8279
TTTTCTGTGT ATGGGCCTGG TCAGTGTAAA GTTTTATCCT TGATAGTCTA GTTACTATGA  8339
CCCTCCCCAC TTTTTTAAAA CCAGAAAAAG GTTTGGAATG TTGGAATGAC CAAGAGACAA  8399

-continued

| | | | | | | |
|---|---|---|---|---|---|---|
| GTTAACTCGT | GCAAGAGCCA | GTTACCCACC | CACAGGTCCC | CCTACTTCCT | GCCAAGCATT | 8459 |
| CCATTGACTG | CCTGTATGGA | ACACATTTGT | CCCAGATCTG | AGCATTCTAG | GCCTGTTTCA | 8519 |
| CTCACTCACC | CAGCATATGA | AACTAGTCTT | AACTGTTGAG | CCTTTCCTTT | CATATCCACA | 8579 |
| GAAGACACTG | TCTCAAATGT | TGTACCCTTG | CCATTTAGGA | CTGAACTTTC | CTTAGCCCAA | 8639 |
| GGGACCCAGT | GACAGTTGTC | TTCCGTTTGT | CAGATGATCA | GTCTCTACTG | ATTATCTTGC | 8699 |
| TGCTTAAAGG | CCTGCTCACC | AATCTTTCTT | TCACACCGTG | TGGTCCGTGT | TACTGGTATA | 8759 |
| CCCAGTATGT | TCTCACTGAA | GACATGGACT | TTATATGTTC | AAGTGCAGGA | ATTGGAAAGT | 8819 |
| TGGACTTGTT | TTCTATGATC | CAAAACAGCC | CTATAAGAAG | GTTGGAAAAG | GAGGAACTAT | 8879 |
| ATAGCAGCCT | TTGCTATTTT | CTGCTACCAT | TTCTTTTCCT | CTGAAGCGGC | CATGACATTC | 8939 |
| CCTTTGGCAA | CTAACGTAGA | AACTCAACAG | AACATTTTCC | TTTCCTAGAG | TCACCTTTTA | 8999 |
| GATGATAATG | GACAACTATA | GACTTGCTCA | TTGTTCAGAC | TGATTGCCCC | TCACCTGAAT | 9059 |
| CCACTCTCTG | TATTCATGCT | CTTGGCAATT | TCTTTGACTT | TCTTTTAAGG | GCAGAAGCAT | 9119 |
| TTTAGTTAAT | TGTAGATAAA | GAATAGTTTT | CTTCCTCTTC | TCCTTGGGCC | AGTTAATAAT | 9179 |
| TGGTCCATGG | CTACACTGCA | ACTTCCGTCC | AGTGCTGTGA | TGCCCATGAC | ACCTGCAAAA | 9239 |
| TAAGTTCTGC | CTGGGCATTT | TGTAGATATT | AACAGGTGAA | TTCCCGACTC | TTTTGGTTTG | 9299 |
| AATGACAGTT | CTCATTCCTT | CTATGGCTGC | AAGTATGCAT | CAGTGCTTCC | CACTTACCTG | 9359 |
| ATTTGTCTGT | CGGTGGCCCC | ATATGGAAAC | CCTGCGTGTC | TGTTGGCATA | ATAGTTTACA | 9419 |
| AATGGTTTTT | TCAGTCCTAT | CCAAATTTAT | TGAACCAACA | AAAATAATTA | CTTCTGCCCT | 9479 |
| GAGATAAGCA | GATTAAGTTT | GTTCATTCTC | TGCTTTATTC | TCTCCATGTG | GCAACATTCT | 9539 |
| GTCAGCCTCT | TTCATAGTGT | GCAAACATTT | TATCATTCTA | AATGGTGACT | CTCTGCCCTT | 9599 |
| GGACCCATTT | ATTATTCACA | GATGGGGAGA | ACCTATCTGC | ATGGACCCTC | ACCATCCTCT | 9659 |
| GTGCAGCACA | CACAGTGCAG | GGAGCCAGTG | GCGATGGCGA | TGACTTTCTT | CCCCTGGGAA | 9719 |
| TTCC | | | | | | 9723 |

What is claimed is:

1. A method of screening for the presence of a malignancy characterized by an aberrant level of a Notch protein or a molecule capable of being bound by an anti-Notch antibody in a patient, comprising measuring the level of expression of a Notch protein or of a molecule capable of being bound by an anti-Notch antibody in a sample derived from the patient, in which an increase or decrease in the Notch protein or molecule in the patient sample relative to the level found in such a sample from an individual not having the malignancy indicates the presence of the malignancy in the patient.

2. A method of screening for the presence of a malignancy characterized by increased expression of a Notch protein or of a molecule capable of being bound by an anti-Notch antibody, comprising measuring the level of expression of a Notch protein or of a molecule capable of being bound by an anti-Notch antibody, in a sample containing or suspected of containing malignant cells from a patient, in which an increase in expression of a Notch protein or of a molecule capable of being bound by an anti-Notch antibody, in the sample, relative to said level found in an analogous sample of non-malignant cells indicates the presence of the malignancy in the patient.

3. The method according to claim 1 or 2 in which the malignancy is cervical cancer.

4. The method according to claim 1 or 2 in which the malignancy is breast cancer.

5. The method according to claim 1 or 2 in which the malignancy is colon cancer.

6. The method according to claim 1 or 2 in which the malignancy is selected from the group consisting of melanoma, seminoma, and lung cancer.

7. The method according to claim 1 or 2 in which the level of expression of the Notch protein or molecule is measured by a method comprising contacting the sample with an anti-Notch antibody such that immunospecific binding can occur, and measuring the amount of any immunospecific binding of the antibody that occurs.

8. A method of screening for the presence of a disease or disorder of the nervous system characterized by an aberrant level of a Notch protein or a molecule capable of being bound by an anti-Notch antibody in a patient, comprising measuring the level of expression of a Notch protein or of a molecule capable of being bound by an anti-Notch antibody in a sample derived from the patient, in which an increase or decrease in the Notch protein or molecule in the patient sample relative to the level found in such a sample from an individual not having the disease or disorder indicates the presence of the disease or disorder in the patient.

9. A method of screening for the presence of a benign dysproliferative disorder characterized by an aberrant level of a Notch protein or a molecule capable of being bound by an anti-Notch antibody in a patient, comprising measuring the level of expression of a Notch protein or of a molecule capable of being bound by an anti-Notch antibody in a sample derived from the patient, in which an increase or decrease in the Notch protein or molecule in the patient sample relative to the level found in such a sample from an individual not having the disorder indicates the presence of the disorder in the patient.

* * * * *